(12) United States Patent
Yang et al.

(10) Patent No.: US 10,442,789 B2
(45) Date of Patent: Oct. 15, 2019

(54) MODIFIED AMINO ACIDS COMPRISING TETRAZINE FUNCTIONAL GROUPS, METHODS OF PREPARATION, AND METHODS OF THEIR USE

(71) Applicant: SUTRO BIOPHARMA, INC., South San Francisco, CA (US)

(72) Inventors: Wenjin Yang, Foster City, CA (US); Qun Yin, Palo Alto, CA (US)

(73) Assignee: SUTRO BIOPHARMA, INC., South San Francisco, CA (US)

( * ) Notice: Subject to any disclaimer, the term of this patent is extended or adjusted under 35 U.S.C. 154(b) by 0 days.

(21) Appl. No.: 15/833,960

(22) Filed: Dec. 6, 2017

(65) Prior Publication Data

US 2018/0086734 A1 Mar. 29, 2018

Related U.S. Application Data

(62) Division of application No. 15/028,005, filed as application No. PCT/US2014/060169 on Oct. 10, 2014, now Pat. No. 9,840,493.

(60) Provisional application No. 61/890,118, filed on Oct. 11, 2013.

(51) Int. Cl.

| | |
|---|---|
| *C07D 257/08* | (2006.01) |
| *C07D 401/12* | (2006.01) |
| *C07D 409/12* | (2006.01) |
| *C07K 5/078* | (2006.01) |
| *C07K 16/22* | (2006.01) |
| *C07K 16/28* | (2006.01) |
| *C07K 16/40* | (2006.01) |
| *C12N 9/00* | (2006.01) |
| *C12P 21/00* | (2006.01) |
| *C12P 21/02* | (2006.01) |
| *A61K 47/64* | (2017.01) |
| *A61K 47/68* | (2017.01) |
| *A61K 47/60* | (2017.01) |

(52) U.S. Cl.
CPC ............ *C07D 401/12* (2013.01); *A61K 47/60* (2017.08); *A61K 47/64* (2017.08); *A61K 47/6803* (2017.08); *A61K 47/6811* (2017.08); *A61K 47/6849* (2017.08); *A61K 47/6851* (2017.08); *A61K 47/6855* (2017.08); *A61K 47/6871* (2017.08); *C07D 257/08* (2013.01); *C07D 409/12* (2013.01); *C07K 5/06139* (2013.01); *C07K 16/22* (2013.01); *C07K 16/28* (2013.01); *C07K 16/2833* (2013.01); *C07K 16/2878* (2013.01); *C07K 16/40* (2013.01); *C12N 9/93* (2013.01); *C12P 21/00* (2013.01); *C12P 21/02* (2013.01); *C07K 2317/24* (2013.01); *C07K 2317/40* (2013.01); *C07K 2317/50* (2013.01); *C07K 2317/526* (2013.01); *C07K 2317/567* (2013.01); *C07K 2317/76* (2013.01); *C12Y 601/01001* (2013.01)

(58) Field of Classification Search
CPC .... C07D 257/08; C07D 401/12; C07K 16/22; C07K 16/28; C07K 5/078; C07K 16/40; C12P 21/02; C12P 9/00; C12N 9/00; A61K 47/48215
USPC ......................................... 544/179; 530/300
See application file for complete search history.

(56) References Cited

U.S. PATENT DOCUMENTS

| | | | |
|---|---|---|---|
| 7,045,337 B2 | 5/2006 | Schultz et al. | |
| 7,083,970 B2 | 8/2006 | Schultz et al. | |
| 9,840,493 B2 * | 12/2017 | Yang ................... | C07D 401/12 |
| 2008/0317670 A1 | 12/2008 | Miao et al. | |
| 2009/0093405 A1 | 4/2009 | Wallen, III et al. | |
| 2015/0246893 A1 | 9/2015 | Devaraj et al. | |

FOREIGN PATENT DOCUMENTS

| | | |
|---|---|---|
| CN | 102 627 615 A | 8/2012 |
| WO | WO-2004/016778 A1 | 2/2004 |
| WO | WO-2008/066583 A2 | 6/2008 |

(Continued)

OTHER PUBLICATIONS

Blackman et al., "Tetrazine Ligation: Fast Bioconjugation Based on Inverse-Electron-Demand Diels-Aider Reactivity", *Journal of the American Chemical Society*, Oct. 15, 2008, vol. 130, No. 41, pp. 13518-13519.

(Continued)

*Primary Examiner* — Venkataraman Balasubramanian
(74) *Attorney, Agent, or Firm* — Squire Patton Boggs (LLP) US

(57) ABSTRACT

Provided herein are modified amino acids comprising a tetrazine groups according to Formula I: polypeptides, antibodies, payloads and conjugates comprising these modified amino acid residues derived from the modified amino acids, and methods of producing the polypeptides, antibodies, payloads and conjugates comprising the modified amino acid residues. The polypeptides, antibodies, payloads and conjugates are useful in methods of treatment and prevention, methods of detection and methods of diagnosis.

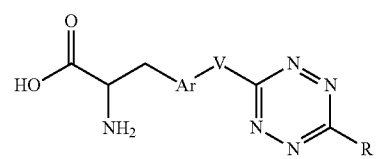

(I)

11 Claims, 3 Drawing Sheets
Specification includes a Sequence Listing.

(56) References Cited

FOREIGN PATENT DOCUMENTS

WO     WO-2014/065860 A1     5/2014

OTHER PUBLICATIONS

Chin et al., "Addition of p-Azido-L-phenylalanine to the Genetic Code of *Escherichia coli*", *Journal of the American Chemical Society*, Aug. 7, 2002, vol. 124, No. 31, pp. 9026-9027.

Communication in Cases for which no Other Form is Applicable dated Mar. 13, 2015 for Application No. PCT/US2014/060169 filed on Oct. 10, 2014, 2 pages.

Database WPI, Week 201310; *Thomson Scientific, London, GB*; AN 2012-P98574, XP002734991.

International Preliminary Report on Patentability dated Apr. 21, 2016 for Application No. PCT/US2014/060169 filed on Oct. 10, 2014, 9 pages.

International Search Report and Written Opinion dated Feb. 4, 2015 for Application No. PCT/US2014/060169 filed on Oct. 10, 2014, 14 pages.

Rostovtsev et al., "A Stepwise Huisgen Cycloaddition Process: Copper(1)-Catalyzed Regioselective "Ligation" of Azides and Terminal Alkynes", *Angew. Chew. Int. Ed.*, Jul. 15, 2002, vol. 41, No. 14, pp. 2596-2599.

Schmidt et al., "A Need for Speed: Genetic Encoding of Rapid Cycloaddition Chemistries for Protein Labelling in Living Cells"; *Chembiochem*; Jun. 29, 2012, vol. 13, No. 11, pp. 1553-1557, XP055040509.

Seitchik et al., "Genetically Encoded Tetrazine Amino Acid Directs Rapid Site-Specific In Vivo Bioorthogonal Ligation with Trans-Cyclooctenes"; *Journal of the American Chemical Society, American Chemical Society, US*; Feb. 15, 2012, vol. 134, No. 6, pp. 2898-2901, XP002733752.

Tornoe et al., "Peptidotriazoles on Solid Phase: [1,2,3]-Triazoles by Regiospecific Copper(I)-Catalyzed 1,3-Dipolar Cycloadditions of Terminal Alkynes to Azides", *J. Org. Chem.*, 2002, vol. 67, No. 9, pp. 3057-3064.

Wang et al., "Bioconjugation by Copper(I)-Catalyzed Azide-Alkyne [3 + 2] Cycloaddition", *Journal of the American Chemical Society*, Mar. 19, 2003, vol. 125, No. 11, pp. 3192-3193.

"1.2.8.4.2 Strained Alkenes in Bioconjugation," Chemistry of Bioconjugates: Synthesis, Characterization, and Biomedical Applications. Ed. R. Narain, Hoboken, John Wiley & Sons, 2014.

Torres, J. (2014) "Synthesis of Unnatural Amino Acids for Protein Labeling and Activation," retrieved from NCSU Libraries Repository Home (Accession No. 1840.16/9672); 241 pages.

\* cited by examiner

SEQUENCE LISTING

<160> NUMBER OF SEQ ID NOS: 13

<210> SEQ ID NO 1
<211> LENGTH: 449
<212> TYPE: PRT
<213> ORGANISM: Artificial Sequence
<220> FEATURE:
<223> OTHER INFORMATION: Synthetic

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu

```
                355                 360                 365
Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly

<210> SEQ ID NO 2
<211> LENGTH: 214
<212> TYPE: PRT
<213> ORGANISM: Artificial Sequence
<220> FEATURE:
<223> OTHER INFORMATION: Synthetic

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
                20                  25                  30

Val Ala Trp Tyr Gln Gln Lys Pro Gly Lys Ala Pro Lys Leu Leu Ile
                35                  40                  45

Tyr Ser Ala Ser Phe Leu Tyr Ser Gly Val Pro Ser Arg Phe Ser Gly
        50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
    210

<210> SEQ ID NO 3
<211> LENGTH: 306
<212> TYPE: PRT
<213> ORGANISM: Methanococcus jannaschii
<220> FEATURE:
<221> NAME/KEY: misc_feature
<223> OTHER INFORMATION: Wild-type tyrosyl-tRNA synthetase (TyrRS)
```

<400> SEQUENCE: 3

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Tyr
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Glu Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
130                 135                 140

Lys Val Ala Glu Val Ile Tyr Pro Ile Met Gln Val Asn Asp Ile His
145                 150                 155                 160

Tyr Leu Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305

<210> SEQ ID NO 4
<211> LENGTH: 306
<212> TYPE: PRT
<213> ORGANISM: Artificial Sequence
<220> FEATURE:
<223> OTHER INFORMATION: Synthetic: 2A2

<400> SEQUENCE: 4

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Leu
            20                  25                  30

```
Ile Gly Phe Glu Pro Ser Gly Lys Ile His Leu Gly His Tyr Leu Gln
         35                  40                  45

Ile Lys Lys Met Ile Asp Leu Gln Asn Ala Gly Phe Asp Ile Ile Ile
 50                  55                  60

Val Leu Ala Asp Leu Ala Ala Tyr Leu Asn Gln Lys Gly Glu Leu Asp
 65                  70                  75                  80

Glu Ile Arg Lys Ile Gly Asp Tyr Asn Lys Lys Val Phe Glu Ala Met
                 85                  90                  95

Gly Leu Lys Ala Lys Tyr Val Tyr Gly Ser Glu Trp Ser Leu Asp Lys
                100                 105                 110

Asp Tyr Thr Leu Asn Val Tyr Arg Leu Ala Leu Lys Thr Thr Leu Lys
            115                 120                 125

Arg Ala Arg Arg Ser Met Glu Leu Ile Ala Arg Glu Asp Glu Asn Pro
130                 135                 140

Lys Val Ala Glu Val Ile Tyr Pro Ile Met Gln Val Asn Val Ala His
145                 150                 155                 160

Tyr Val Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
        210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
                260                 265                 270

Leu Glu Ser Leu Phe Lys Asn Lys Glu Leu His Pro Met Asp Leu Lys
            275                 280                 285

Asn Ala Val Ala Glu Glu Leu Ile Lys Ile Leu Glu Pro Ile Arg Lys
290                 295                 300

Arg Leu
305

<210> SEQ ID NO 5
<211> LENGTH: 306
<212> TYPE: PRT
<213> ORGANISM: Artificial Sequence
<220> FEATURE:
<223> OTHER INFORMATION: Synthetic: 2A9

<400> SEQUENCE: 5

Met Asp Glu Phe Glu Met Ile Lys Arg Asn Thr Ser Glu Ile Ile Ser
 1               5                  10                  15

Glu Glu Glu Leu Arg Glu Val Leu Lys Lys Asp Glu Lys Ser Ala Gly
                20                  25                  30

Ile Gly Phe Glu Pro Ser Gly Lys Ile His Leu Gly His Tyr Leu Gln
         35                  40                  45

Ile Lys Lys Met Ile Asp Leu Gln Asn Ala Gly Phe Asp Ile Ile Ile
 50                  55                  60

Val Leu Ala Asp Leu Ala Ala Tyr Leu Asn Gln Lys Gly Glu Leu Asp
 65                  70                  75                  80
```

Glu Ile Arg Lys Ile Gly Asp Tyr Asn Lys Lys Val Phe Glu Ala Met
            85                  90                  95

Gly Leu Lys Ala Lys Tyr Val Tyr Gly Ser Glu Phe Ser Leu Asp Lys
            100                 105                 110

Asp Tyr Thr Leu Asn Val Tyr Arg Leu Ala Leu Lys Thr Thr Leu Lys
            115                 120                 125

Arg Ala Arg Arg Ser Met Glu Leu Ile Ala Arg Glu Asp Glu Asn Pro
130                 135                 140

Lys Val Ala Glu Val Ile Tyr Pro Ile Met Gln Val Asn Gly Ile His
145                 150                 155                 160

Tyr Ser Gly Val Asp Val Ala Val Gly Gly Met Glu Gln Arg Lys Ile
            165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
            195                 200                 205

Lys Gly Asn Phe Ile Ala Val Asp Asp Ser Pro Glu Glu Ile Arg Ala
            210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
            245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
            275                 280                 285

Asn Ala Val Ala Glu Glu Leu Ile Lys Ile Leu Glu Pro Ile Arg Lys
            290                 295                 300

Arg Leu
305

<210> SEQ ID NO 6
<211> LENGTH: 312
<212> TYPE: PRT
<213> ORGANISM: Artificial Sequence
<220> FEATURE:
<223> OTHER INFORMATION: Synthetic: PyrTetRS

<400> SEQUENCE: 6

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Gly
            20                  25                  30

Ile Gly Phe Glu Pro Ser Gly Lys Ile His Leu Gly His Tyr Leu Gln
            35                  40                  45

Ile Lys Lys Met Ile Asp Leu Gln Asn Ala Gly Phe Asp Ile Ile Ile
        50                  55                  60

Val Leu Ala Asp Leu Ala Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
            85                  90                  95

Gly Leu Lys Ala Lys Tyr Val Tyr Gly Ser Glu Phe Ser Leu Asp Lys
            100                 105                 110

Asp Tyr Thr Leu Asn Val Tyr Arg Leu Ala Leu Lys Thr Thr Leu Lys
            115                 120                 125

Arg Ala Arg Arg Ser Met Glu Leu Ile Ala Arg Glu Asp Glu Asn Pro
130                 135                 140

Lys Val Ala Glu Val Ile Tyr Pro Ile Met Gln Val Asn Gly Ile His
145                 150                 155                 160

Tyr Ser Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
                180                 185                 190

Asn Pro Val Leu Thr Gly Leu Asp Gly Glu Gly Lys Met Ser Ser Ser
                195                 200                 205

Lys Gly Asn Phe Ile Ala Val Asp Asp Ser Pro Glu Glu Ile Arg Ala
210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
                260                 265                 270

Leu Glu Ser Leu Phe Lys Asn Lys Glu Leu His Pro Met Arg Leu Lys
                275                 280                 285

Asn Ala Val Ala Glu Glu Leu Ile Lys Ile Leu Glu Pro Ile Arg Lys
                290                 295                 300

Arg Leu His His His His His His
305                 310

<210> SEQ ID NO 7
<211> LENGTH: 419
<212> TYPE: PRT
<213> ORGANISM: Methanosarcina barkeri
<220> FEATURE:
<221> NAME/KEY: misc_feature
<223> OTHER INFORMATION: Methanosarcina barkeri PylRS

<400> SEQUENCE: 7

Met Asp Lys Lys Pro Leu Asp Val Leu Ile Ser Ala Thr Gly Leu Trp
1               5                   10                  15

Met Ser Arg Thr Gly Thr Leu His Lys Ile Lys His His Glu Val Ser
                20                  25                  30

Arg Ser Lys Ile Tyr Ile Glu Met Ala Cys Gly Asp His Leu Val Val
            35                  40                  45

Asn Asn Ser Arg Ser Cys Arg Thr Ala Arg Ala Phe Arg His His Lys
        50                  55                  60

Tyr Arg Lys Thr Cys Lys Arg Cys Arg Val Ser Asp Glu Asp Ile Asn
65                  70                  75                  80

Asn Phe Leu Thr Arg Ser Thr Glu Ser Lys Asn Ser Val Lys Val Arg
                85                  90                  95

Val Val Ser Ala Pro Lys Val Lys Lys Ala Met Pro Lys Ser Val Ser
                100                 105                 110

Arg Ala Pro Lys Pro Leu Glu Asn Ser Val Ser Ala Lys Ala Ser Thr
            115                 120                 125

Asn Thr Ser Arg Ser Val Pro Ser Pro Ala Lys Ser Thr Pro Asn Ser
        130                 135                 140

Ser Val Pro Ala Ser Ala Pro Ala Pro Ser Leu Thr Arg Ser Gln Leu
145                 150                 155                 160

Asp Arg Val Glu Ala Leu Leu Ser Pro Glu Asp Lys Ile Ser Leu Asn
                165                 170                 175

```
Met Ala Lys Pro Phe Arg Glu Leu Glu Pro Glu Leu Val Thr Arg Arg
            180                 185                 190

Lys Asn Asp Phe Gln Arg Leu Tyr Thr Asn Asp Arg Glu Asp Tyr Leu
        195                 200                 205

Gly Lys Leu Glu Arg Asp Ile Thr Lys Phe Phe Val Asp Arg Gly Phe
    210                 215                 220

Leu Glu Ile Lys Ser Pro Ile Leu Ile Pro Ala Glu Tyr Val Glu Arg
225                 230                 235                 240

Met Gly Ile Asn Asn Asp Thr Glu Leu Ser Lys Gln Ile Phe Arg Val
                245                 250                 255

Asp Lys Asn Leu Cys Leu Arg Pro Met Leu Ala Pro Thr Leu Tyr Asn
            260                 265                 270

Tyr Leu Arg Lys Leu Asp Arg Ile Leu Pro Gly Pro Ile Lys Ile Phe
        275                 280                 285

Glu Val Gly Pro Cys Tyr Arg Lys Glu Ser Asp Gly Lys Glu His Leu
    290                 295                 300

Glu Glu Phe Thr Met Val Asn Phe Cys Gln Met Gly Ser Gly Cys Thr
305                 310                 315                 320

Arg Glu Asn Leu Glu Ala Leu Ile Lys Glu Phe Leu Asp Tyr Leu Glu
                325                 330                 335

Ile Asp Phe Glu Ile Val Gly Asp Ser Cys Met Val Tyr Gly Asp Thr
            340                 345                 350

Leu Asp Ile Met His Gly Asp Leu Glu Leu Ser Ser Ala Val Val Gly
        355                 360                 365

Pro Val Ser Leu Asp Arg Glu Trp Gly Ile Asp Lys Pro Trp Ile Gly
    370                 375                 380

Ala Gly Phe Gly Leu Glu Arg Leu Leu Lys Val Met His Gly Phe Lys
385                 390                 395                 400

Asn Ile Lys Arg Ala Ser Arg Ser Glu Ser Tyr Tyr Asn Gly Ile Ser
                405                 410                 415

Thr Asn Leu

<210> SEQ ID NO 8
<211> LENGTH: 76
<212> TYPE: DNA
<213> ORGANISM: M. jannaschii
<220> FEATURE:
<221> NAME/KEY: misc_feature
<223> OTHER INFORMATION: M. jannaschii opal suppressor

<400> SEQUENCE: 8
cccgccttag ttcagagggc agaacggcgg acttcaaatc cgcatggcac gggttcaaat      60
cccgtaggcg ggacca                                                     76

<210> SEQ ID NO 9
<211> LENGTH: 72
<212> TYPE: DNA
<213> ORGANISM: Methanosarcina mazei
<220> FEATURE:
<221> NAME/KEY: misc_feature
<223> OTHER INFORMATION: Methanosarcina mazei (PylRS) amber suppressor

<400> SEQUENCE: 9
ggaaacctga tcatgtagat cgaacggact ctaaatccgt tcagccgggt tagattcccg      60
gggtttccgc ca                                                         72
```

```
<210> SEQ ID NO 10
<211> LENGTH: 456
<212> TYPE: PRT
<213> ORGANISM: Artificial Sequence
<220> FEATURE:
<223> OTHER INFORMATION: Synthetic: Sequence of brentuximab heavy chain
      HC-6His

<400> SEQUENCE: 10

Gln Ile Gln Leu Gln Gln Ser Gly Pro Glu Val Val Lys Pro Gly Ala
1               5                   10                  15

Ser Val Lys Ile Ser Cys Lys Ala Ser Gly Tyr Thr Phe Thr Asp Tyr
            20                  25                  30

Tyr Ile Thr Trp Val Lys Gln Lys Pro Gly Gln Gly Leu Glu Trp Ile
        35                  40                  45

Gly Trp Ile Tyr Pro Gly Ser Gly Asn Thr Lys Tyr Asn Glu Lys Phe
    50                  55                  60

Lys Gly Lys Ala Thr Leu Thr Val Asp Thr Ser Ser Ser Thr Ala Phe
65                  70                  75                  80

Met Gln Leu Ser Ser Leu Thr Ser Glu Asp Thr Ala Val Tyr Phe Cys
                85                  90                  95

Ala Asn Tyr Gly Asn Tyr Trp Phe Ala Tyr Trp Gly Gln Gly Thr Gln
            100                 105                 110

Val Thr Val Ser Ala Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365
```

```
Val Lys Gly Phe Tyr Pro Ser Asp Ile Ala Val Glu Trp Glu Ser Asn
    370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Lys Leu Thr Val Asp Lys Ser Arg
                405                 410                 415
Trp Gln Gln Gly Asn Val Phe Ser Cys Ser Val Met His Glu Ala Leu
            420                 425                 430
His Asn His Tyr Thr Gln Lys Ser Leu Ser Leu Ser Pro Gly Lys Gly
        435                 440                 445
Gly Ser His His His His His His
    450                 455

<210> SEQ ID NO 11
<211> LENGTH: 218
<212> TYPE: PRT
<213> ORGANISM: Artificial Sequence
<220> FEATURE:
<223> OTHER INFORMATION: Synthetic: Sequence of brentuximab light chain
      LC

<400> SEQUENCE: 11

Asp Ile Val Leu Thr Gln Ser Pro Ala Ser Leu Ala Val Ser Leu Gly
1               5                   10                  15
Gln Arg Ala Thr Ile Ser Cys Lys Ala Ser Gln Ser Val Asp Phe Asp
            20                  25                  30
Gly Asp Ser Tyr Met Asn Trp Tyr Gln Gln Lys Pro Gly Gln Pro Pro
        35                  40                  45
Lys Val Leu Ile Tyr Ala Ala Ser Asn Leu Glu Ser Gly Ile Pro Ala
    50                  55                  60
Arg Phe Ser Gly Ser Gly Ser Gly Thr Asp Phe Thr Leu Asn Ile His
65                  70                  75                  80
Pro Val Glu Glu Glu Asp Ala Ala Thr Tyr Tyr Cys Gln Gln Ser Asn
                85                  90                  95
Glu Asp Pro Trp Thr Phe Gly Gly Gly Thr Lys Leu Glu Ile Lys Arg
            100                 105                 110
Thr Val Ala Ala Pro Ser Val Phe Ile Phe Pro Pro Ser Asp Glu Gln
        115                 120                 125
Leu Lys Ser Gly Thr Ala Ser Val Val Cys Leu Leu Asn Asn Phe Tyr
    130                 135                 140
Pro Arg Glu Ala Lys Val Gln Trp Lys Val Asp Asn Ala Leu Gln Ser
145                 150                 155                 160
Gly Asn Ser Gln Glu Ser Val Thr Glu Gln Asp Ser Lys Asp Ser Thr
                165                 170                 175
Tyr Ser Leu Ser Ser Thr Leu Thr Leu Ser Lys Ala Asp Tyr Glu Lys
            180                 185                 190
His Lys Val Tyr Ala Cys Glu Val Thr His Gln Gly Leu Ser Ser Pro
        195                 200                 205
Val Thr Lys Ser Phe Asn Arg Gly Glu Cys
    210                 215

<210> SEQ ID NO 12
<211> LENGTH: 462
<212> TYPE: PRT
<213> ORGANISM: Artificial Sequence
<220> FEATURE:
<223> OTHER INFORMATION: Synthetic: ANTI-CD74 HC
```

<400> SEQUENCE: 12

```
Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Asp Lys Gly Leu Glu Trp Val
            35                  40                  45

Ala Val Ile Trp Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Gly Gly Thr Leu Val Arg Gly Ala Met Tyr Gly Thr Asp Val
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
            165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
            245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
            325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
            405                 410                 415
```

-continued

```
Thr Val Asp Lys Ser Arg Trp Gln Gln Gly Asn Val Phe Ser Cys Ser
        420                 425                 430

Val Met His Glu Ala Leu His Asn His Tyr Thr Gln Lys Ser Leu Ser
        435                 440                 445

Leu Ser Pro Gly Lys Gly Gly Ser His His His His His His
        450                 455                 460

<210> SEQ ID NO 13
<211> LENGTH: 214
<212> TYPE: PRT
<213> ORGANISM: Artificial Sequence
<220> FEATURE:
<223> OTHER INFORMATION: Synthetic: ANTI-CD74 LC

<400> SEQUENCE: 13

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

MODIFIED AMINO ACIDS COMPRISING TETRAZINE FUNCTIONAL GROUPS, METHODS OF PREPARATION, AND METHODS OF THEIR USE

CROSS-REFERENCE TO RELATED APPLICATIONS

This application is a divisional application of U.S. Nonprovisional application Ser. No. 15/028,005 filed Apr. 7, 2016 which is a National Stage of International Application No. PCT/US2014/060169 filed Oct. 10, 2014, which claims the benefit of U.S. Provisional Patent Application No. 61/890,118, filed Oct. 11, 2013, the contents of which are hereby incorporated by reference in their entireties.

This application includes an electronically submitted sequence listing in .txt format. The .txt file contains a sequence listing entitled "10884300133SEQID.txt" created on Dec. 6, 2017 and is 32.8 kilo bytes in size. The sequence listing contained in this .txt file is part of the specification and is hereby incorporated by reference herein in its entirety.

FIELD

Provided herein are modified amino acids comprising a tetrazine functional group, polypeptides, antibodies, payloads and conjugates comprising modified amino acid residues derived from the modified amino acids, and methods of producing the polypeptides, antibodies, payloads and conjugates comprising the modified amino acid residues. The polypeptides, antibodies, payloads and conjugates are useful in methods of treatment and prevention, methods of detection and methods of diagnosis.

BACKGROUND

Engineered polypeptides are used widely in therapeutic and diagnostic applications. Therapeutic antibodies have been used for many years in, for example, treatment of cancer and inflammatory conditions. Therapeutic polypeptides are also used to treat and prevent blood conditions and viral infections. Diagnostic polypeptides have been used successfully to identify healthy and diseased cells and tissues in vivo.

Many polypeptides can provide targeting functionality to specific cells. The selective affinity of certain polypeptides can be used to target nearly any cell or tissue desired, for example a cell expressing an antigen. A polypeptide can carry a payload to destroy the target cell or tissue, or to slow its growth. Polypeptides have thus found use in therapy for conditions such as cancer, inflammatory diseases, autoimmune diseases and transplant rejection.

In certain applications therapeutic polypeptides are linked to molecular shields (e.g., macromolecules) to increase their half-life within an organism. For example, the attachment of polyethylene glycol (PEG) to a polypeptide can render the polypeptide non-detectable or less detectable by a patient's immune system, thereby reducing immunogenicity.

Polypeptides have also found use as diagnostics. These polypeptides can carry a label whose detection indicates the presence of a target receptor or antigen on a cell or in a tissue. These labels are typically linked to the polypeptides by covalent bonds.

To date, techniques for linking polypeptides to payloads such as molecular shields, labels, diagnostic compounds, and therapeutic compounds have been limited by their heterogeneity in degree and location of linking to the polypeptides, by their low yields and by losses in activity. These problems are particularly acute when attempting to conjugate more than one payload to a single polypeptide in a controlled manner, to produce a homogeneous product. Typical conjugation sites include random locations on polypeptide chains, e.g. random amines on amino acid residue side chains, and the N-terminus of certain polypeptide chains. In such cases, some polypeptides might be linked to a payload at one location while some polypeptides are linked to the same payload at another location, and some polypeptides might not be linked at all. If more than one payload is used, some polypeptides may be linked to a single payload, some polypeptides may be linked to all payloads, and some polypeptides may be linked to fewer than all payloads.

There is a need, therefore, for polypeptides modified at site-specific positions optimized for uniformity, yield and/or activity to further the promising use of polypeptides in, for example, therapy and diagnostics.

SUMMARY

Provided herein are modified amino acids comprising a tetrazine group, polypeptides, antibodies, payloads and conjugates comprising the modified amino acid residues derived from the modified amino acids, and methods of producing the polypeptides, antibodies, payloads and conjugates comprising modified amino acid residues. The polypeptides, antibodies, payloads and conjugates are useful in methods of treatment and prevention, methods of detection and methods of diagnosis.

In one aspect a compound according to formula I is provided:

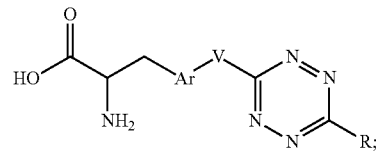

Formula I or a salt thereof, wherein:
Ar is

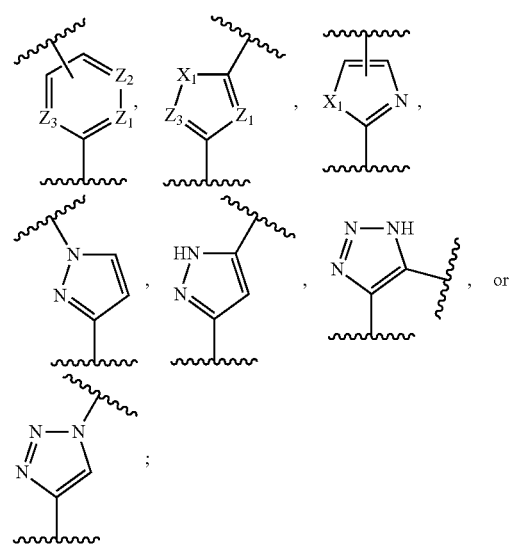

V is a single bond, lower alkylene, or —W₁—W₂—; one of W₁ and W₂ is absent or lower alkylene, and the other is —NH—, —O—, or —S—; each X₁ is independently —NH—, —O—, or —S—; one of Z₁, Z₂, and Z₃ is —CH— or —N— and the others of Z₁, Z₂, and Z₃ are each independently —CH—; and R is lower alkyl. In certain embodiments, when Ar is

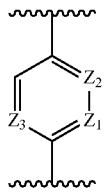

and V is —NH—, then one of Z₁, Z₂, and Z₃ is —N—.

In a further aspect, polypeptides and antibodies comprising an amino acid residue corresponding to a compound of formula I are provided. In particular embodiments, conjugates of the polypeptides and payloads are provided. In further embodiments, conjugates of the antibodies and payloads are provided.

In another aspect, an orthogonal tRNA is provided aminoacylated with an amino acid residue corresponding to a compound of formula I. In a related aspect, a method of producing a polypeptide is provided, comprising contacting a polypeptide with an orthogonal tRNA aminoacylated with an amino acid residue corresponding to a compound of formula I.

The compounds of formula I described herein can be incorporated into any polypeptide known to those of skill in the art. Such polypeptides include, but are not limited to, proteins, antibodies, antibody fragments, and enzymes.

BRIEF DESCRIPTION OF THE FIGURES

In FIG. 1, the y-axis shows fluorescence, in relative fluorescence units (RFU); "aaRS" is 2A2; "GFP" is native GFP (without K49TAG); and "negative control" is a cell-free protein synthesis reaction without a DNA template.

In FIG. 2, the y-axis shows fluorescence, in relative fluorescence units (RFU); "aaRS" is 2A9; "GFP" is native GFP (without K49TAG); and "negative control" is a cell-free protein synthesis reaction without a DNA template.

DESCRIPTION OF EXEMPLARY EMBODIMENTS

Figure 1:
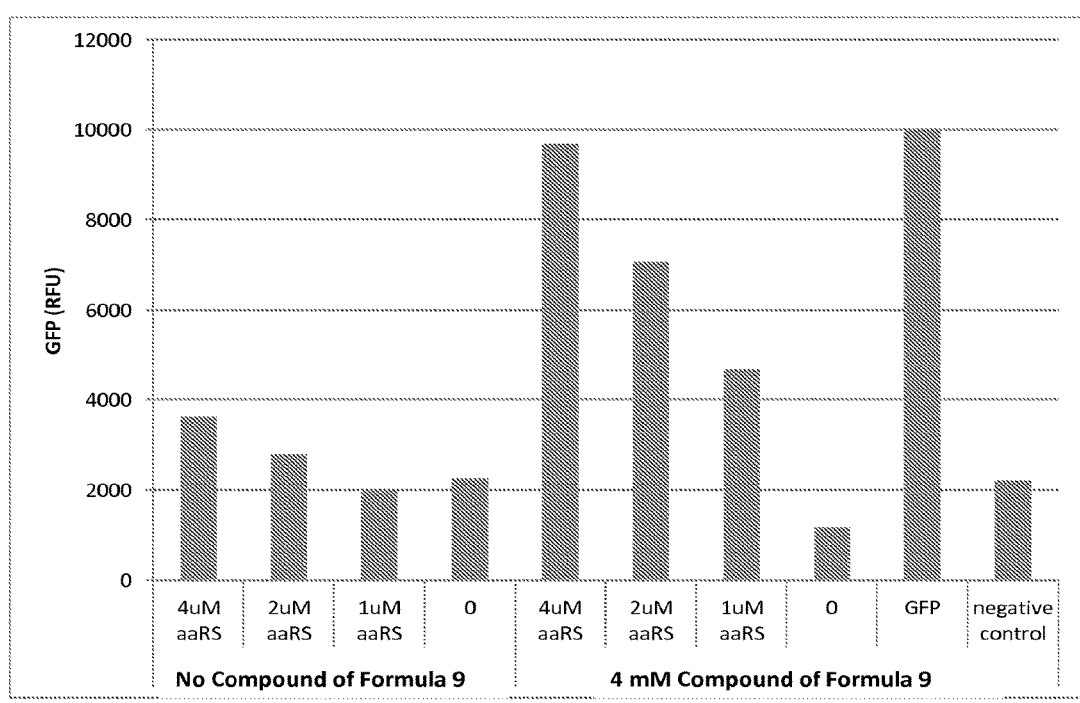
FIG. 1 provides results demonstrating that tRNA synthetase 2A2 incorporates a compound of formula 9 into a GFP polypeptide, as described in Example 4.

Provided herein are compounds of formula I, polypeptides, antibodies, payloads and conjugates comprising the amino acid residues corresponding to the compounds of formula I, and methods of producing the polypeptides, antibodies, payloads and conjugates comprising the modified amino acid residues corresponding to the compounds of formula I.

Definitions

When referring to the compounds provided herein, the following terms have the following meanings unless indicated otherwise. Unless defined otherwise, all technical and scientific terms used herein have the same meaning as is commonly understood by one of ordinary skill in the art. In the event that there is a plurality of definitions for a term herein, those in this section prevail unless stated otherwise.

The term "alkyl," as used herein, unless otherwise specified, refers to a saturated straight or branched hydrocarbon. In certain embodiments, the alkyl group is a primary, secondary, or tertiary hydrocarbon. In certain embodiments, the alkyl group includes one to ten carbon atoms, i.e., $C_1$ to $C_{10}$ alkyl. In certain embodiments, the alkyl group is selected from the group consisting of methyl, $CF_3$, $CCl_3$, $CFCl_2$, $CF_2Cl$, ethyl, $CH_2CF_3$, $CF_2CF_3$, propyl, isopropyl, butyl, isobutyl, secbutyl, t-butyl, pentyl, isopentyl, neopentyl, hexyl, isohexyl, 3-methylpentyl, 2,2-dimethylbutyl, and 2,1-dimethylbutyl. The term includes both substituted and unsubstituted alkyl groups, including halogenated alkyl groups. In certain embodiments, the alkyl group is a fluorinated alkyl group. Non-limiting examples of moieties with which the alkyl group can be substituted are selected from the group consisting of halogen (fluoro, chloro, bromo or iodo), hydroxyl, carbonyl, sulfanyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., Protective Groups in Organic Synthesis, John Wiley and Sons, Second Edition, 1991, hereby incorporated by reference.

The term "lower alkyl," as used herein, and unless otherwise specified, refers to a saturated straight or branched hydrocarbon having one to six carbon atoms, i.e., $C_1$ to $C_6$ alkyl. In certain embodiments, the lower alkyl group is a primary, secondary, or tertiary hydrocarbon. The term includes both substituted and unsubstituted moieties.

The term "cycloalkyl," as used herein, unless otherwise specified, refers to a saturated cyclic hydrocarbon. In certain embodiments, the cycloalkyl group may be a saturated, and/or bridged, and/or non-bridged, and/or a fused bicyclic group. In certain embodiments, the cycloalkyl group includes three to ten carbon atoms, i.e., $C_3$ to $C_{10}$ cycloalkyl. In some embodiments, the cycloalkyl has from 3 to 15 ($C_{3-15}$), from 3 to 10 ($C_{3-10}$), or from 3 to 7 ($C_{3-7}$) carbon atoms. In certain embodiments, the cycloalkyl group is cyclopropyl, cyclobutyl, cyclopentyl, cyclohexyl, cyclohexylmethyl, cycloheptyl, bicyclo[2.1.1]hexyl, bicyclo[2.2.1]heptyl, decalinyl or adamantyl. The term includes both substituted and unsubstituted cycloalkyl groups, including halogenated cycloalkyl groups. In certain embodiments, the cycloalkyl group is a fluorinated cycloalkyl group. Non-limiting examples of moieties with which the cycloalkyl group can be substituted are selected from the group consisting of halogen (fluoro, chloro, bromo or iodo), hydroxyl, carbonyl, sulfanyl, amino, alkylamino, arylamino, alkoxy, aryloxy, nitro, cyano, sulfonic acid, sulfate, phosphonic acid, phosphate, or phosphonate, either unprotected, or protected as necessary.

"Alkylene" refers to divalent saturated aliphatic hydrocarbon groups particularly having from one to eleven carbon atoms which can be straight-chained or branched. In certain embodiments, the alkylene group contains 1 to 10 carbon atoms. The term includes both substituted and unsubstituted moieties. This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—) and the like. The term includes halogenated alkylene groups. In certain embodiments, the alkylene group is a fluorinated alkylene group. Non-limiting examples of moieties with which the alkylene group can be substituted are selected from the group consisting of halogen (fluoro, chloro, bromo or iodo), hydroxyl, carbonyl, sulfanyl, amino, alkylamino, alkylaryl, arylamino, alkoxy, aryloxy, nitro, cyano, sulfonic acid, sulfate, phosphonic acid, phosphate, and phosphonate, either unprotected, or protected as necessary.

"Alkenyl" refers to monovalent olefinically unsaturated hydrocarbon groups, in certain embodiment, having up to about 11 carbon atoms, from 2 to 8 carbon atoms, or from 2 to 6 carbon atoms, which can be straight-chained or branched and having at least 1 or from 1 to 2 sites of olefinic unsaturation. The term includes both substituted and unsubstituted moieties. Exemplary alkenyl groups include ethenyl (i.e., vinyl, or —CH═CH$_2$), n-propenyl (—CH$_2$CH═CH$_2$), isopropenyl (—C(CH$_3$)═CH$_2$), and the like. The term includes halogenated alkenyl groups. In certain embodiments, the alkenyl group is a fluorinated alkenyl group. Non-limiting examples of moieties with which the alkenyl group can be substituted are selected from the group consisting of halogen (fluoro, chloro, bromo or iodo), hydroxyl, carbonyl, sulfanyl, amino, alkylamino, arylamino, alkoxy, aryloxy, nitro, cyano, sulfonic acid, sulfate, phosphonic acid, phosphate, or phosphonate, either unprotected, or protected as necessary.

The term "cycloalkenyl," as used herein, unless otherwise specified, refers to an unsaturated cyclic hydrocarbon. In certain embodiments, cycloalkenyl refers to mono- or multicyclic ring systems that include at least one double bond. In certain embodiments, the cycloalkenyl group may be a bridged, non-bridged, and/or a fused bicyclic group. In certain embodiments, the cycloalkyl group includes three to ten carbon atoms, i.e., $C_3$ to $C_{10}$ cycloalkyl. In some embodiments, the cycloalkenyl has from 3 to 7 ($C_{3-10}$), or from 4 to 7 ($C_{3-7}$) carbon atoms. The term includes both substituted and unsubstituted cycloalkenyl groups, including halogenated cycloalkenyl groups. In certain embodiments, the cycloalkenyl group is a fluorinated cycloalkenyl group. Non-limiting examples of moieties with which the cycloalkenyl group can be substituted are selected from the group consisting of halogen (fluoro, chloro, bromo or iodo), hydroxyl, carbonyl, sulfanyl, amino, alkylamino, arylamino, alkoxy, aryloxy, nitro, cyano, sulfonic acid, sulfate, phosphonic acid, phosphate, or phosphonate, either unprotected, or protected as necessary.

"Alkenylene" refers to divalent olefinically unsaturated hydrocarbon groups, in certain embodiments, having up to about 11 carbon atoms or from 2 to 6 carbon atoms which can be straight-chained or branched and having at least 1 or from 1 to 2 sites of olefinic unsaturation. This term is exemplified by groups such as ethenylene (—CH═CH—), the propenylene isomers (e.g., —CH═CHCH$_2$— and —C(CH$_3$)═CH— and —CH═C(CH$_3$)—) and the like. The term includes both substituted and unsubstituted alkenylene groups, including halogenated alkenylene groups. In certain embodiments, the alkenylene group is a fluorinated alkenylene group. Non-limiting examples of moieties with which the alkenylene group can be substituted are selected from the group consisting of halogen (fluoro, chloro, bromo or iodo), hydroxyl, carbonyl, sulfanyl, amino, alkylamino, arylamino, alkoxy, aryloxy, nitro, cyano, sulfonic acid, sulfate, phosphonic acid, phosphate, or phosphonate, either unprotected, or protected as necessary.

"Alkynyl" refers to acetylenically unsaturated hydrocarbon groups, in certain embodiments, having up to about 11 carbon atoms or from 2 to 6 carbon atoms which can be straight-chained or branched and having at least 1 or from 1 to 2 sites of alkynyl unsaturation. Non-limiting examples of alkynyl groups include acetylenic, ethynyl (—C≡CH), propargyl (—CH$_2$C≡CH), and the like. The term includes both substituted and unsubstituted alkynyl groups, including halogenated alkynyl groups. In certain embodiments, the alkynyl group is a fluorinated alkynyl group. Non-limiting examples of moieties with which the alkynyl group can be substituted are selected from the group consisting of halogen (fluoro, chloro, bromo or iodo), hydroxyl, carbonyl, sulfanyl, amino, alkylamino, arylamino, alkoxy, aryloxy, nitro, cyano, sulfonic acid, sulfate, phosphonic acid, phosphate, or phosphonate, either unprotected, or protected as necessary.

The term "aryl," as used herein, and unless otherwise specified, refers to phenyl, biphenyl or naphthyl. The term includes both substituted and unsubstituted moieties. An aryl group can be substituted with any described moiety, including, but not limited to, one or more moieties selected from the group consisting of halogen (fluoro, chloro, bromo or iodo), alkyl, haloalkyl, hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., *Protective Groups in Organic Synthesis*, John Wiley and Sons, Second Edition, 1991.

"Alkoxy" refers to the group —OR' where R' is alkyl or cycloalkyl. Alkoxy groups include, by way of example, methoxy, ethoxy, n-propoxy, isopropoxy, n-butoxy, tert-butoxy, sec-butoxy, n-pentoxy, n-hexoxy, 1,2-dimethylbutoxy, and the like.

"Alkoxycarbonyl" refers to a radical —C(O)-alkoxy where alkoxy is as defined herein.

"Amino" refers to the radical —NH$_2$.

"Carboxyl" or "carboxy" refers to the radical —C(O)OH.

The term "alkylamino" or "arylamino" refers to an amino group that has one or two alkyl or aryl substituents, respectively. In certain embodiments, the alkyl substituent is lower alkyl. In some embodiments, the alkyl or lower alkyl is unsubstituted.

"Halogen" or "halo" refers to chloro, bromo, fluoro or iodo.

"Thioalkoxy" refers to the group —SR' where R' is alkyl or cycloalkyl.

The term "heterocyclyl" or "heterocyclic" refers to a monovalent monocyclic non-aromatic ring system and/or multicyclic ring system that contains at least one non-aromatic ring, wherein one or more of the non-aromatic ring atoms are heteroatoms independently selected from O, S, or N; and the remaining ring atoms are carbon atoms. In certain embodiments, the heterocyclyl or heterocyclic group has from 3 to 20, from 3 to 15, from 3 to 10, from 3 to 8, from 4 to 7, or from 5 to 6 ring atoms. Heterocyclyl groups are bonded to the rest of the molecule through the non-aromatic ring. In certain embodiments, the heterocyclyl is a monocyclic, bicyclic, tricyclic, or tetracyclic ring system, which may include a fused or bridged ring system, and in which the nitrogen or sulfur atoms may be optionally oxidized, the nitrogen atoms may be optionally quaternized, and some rings may be partially or fully saturated, or aromatic. The heterocyclyl may be attached to the main structure at any heteroatom or carbon atom which results in the creation of a stable compound. Examples of such heterocyclic radicals include, but are not limited to, azepinyl, benzodioxanyl, benzodioxolyl, benzopyranonyl, benzopyranonyl, benzopyranyl, benzotetrahydrofuranyl, benzotetrahydrothienyl, benzothiopyranyl, benzoxazinyl, β-carbolinyl, chromanyl, chromonyl, cinnolinyl, coumarinyl, decahydroisoquinolinyl, dihydrobenzisothiazinyl, dihydrobenzisoxazinyl, dihydrofuryl, dihydroisoindolyl, dihydropyranyl, dihydropyrazolyl, dihydropyrazinyl, dihydropyridinyl, dihydropyrimidinyl, dihydropyrrolyl, dioxolanyl, 1,4-dithianyl, furanonyl, imidazolidinyl, imidazolinyl, indolinyl, isobenzotetrahydrofuranyl, isobenzotetrahydrothienyl, isochromanyl, isocoumarinyl, isoindolinyl, isothiazolidinyl, isoxazolidinyl, morpholinyl, octahydroindolyl, octahydroisoindolyl, oxazolidinonyl, oxazolidinyl, oxiranyl, piperazinyl, piperidinyl, 4-piperidonyl, pyrazolidinyl, pyrazolinyl, pyrrolidinyl, pyrrolinyl, quinuclidinyl, tetrahydrofuryl, tetrahydroisoquinolinyl, tetrahydropyranyl, tetrahydrothienyl, thiamorpholinyl, thiazolidinyl, tetrahydroquinolinyl, and 1,3,5-trithianyl. In certain embodiments, heterocyclic may also be optionally substituted as described herein.

The term "heteroaryl" refers to refers to a monovalent monocyclic aromatic group and/or multicyclic aromatic group that contain at least one aromatic ring, wherein at least one aromatic ring contains one or more heteroatoms independently selected from O, S and N in the ring. Heteroaryl groups are bonded to the rest of the molecule through the aromatic ring. Each ring of a heteroaryl group can contain one or two O atoms, one or two S atoms, and/or one to four N atoms, provided that the total number of heteroatoms in each ring is four or less and each ring contains at least one carbon atom. In certain embodiments, the heteroaryl has from 5 to 20, from 5 to 15, or from 5 to 10 ring atoms. Examples of monocyclic heteroaryl groups include, but are not limited to, furanyl, imidazolyl, isothiazolyl, isoxazolyl, oxadiazolyl, oxadiazolyl, oxazolyl, pyrazinyl, pyrazolyl, pyridazinyl, pyridyl, pyrimidinyl, pyrrolyl, thiadiazolyl, thiazolyl, thienyl, tetrazolyl, triazinyl and triazolyl. Examples of bicyclic heteroaryl groups include, but are not limited to, benzofuranyl, benzimidazolyl, benzoisoxazolyl, benzopyranyl, benzothiadiazolyl, benzothiazolyl, benzothienyl, benzotriazolyl, benzoxazolyl, furopyridyl, imidazopyridinyl, imidazothiazolyl, indolizinyl, indolyl, indazolyl, isobenzofuranyl, isobenzothienyl, isoindolyl, isoquinolinyl, isothiazolyl, naphthyridinyl, oxazolopyridinyl, phthalazinyl, pteridinyl, purinyl, pyridopyridyl, pyrrolopyridyl, quinolinyl, quinoxalinyl, quinazolinyl, thiadiazolopyrimidyl, and thienopyridyl. Examples of tricyclic heteroaryl groups include, but are not limited to, acridinyl, benzindolyl, carbazolyl, dibenzofuranyl, perimidinyl, phenanthrolinyl, phenanthridinyl, phenarsazinyl, phenazinyl, phenothiazinyl, phenoxazinyl and xanthenyl. In certain embodiments, heteroaryl may also be optionally substituted as described herein.

The term "alkylaryl" refers to an aryl group with an alkyl substituent. The term "aralkyl" or "arylalkyl" refers to an alkyl group with an aryl substituent.

The term "protecting group" as used herein and unless otherwise defined refers to a group that is added to an oxygen, nitrogen or phosphorus atom to prevent its further reaction or for other purposes. A wide variety of oxygen and nitrogen protecting groups are known to those skilled in the art of organic synthesis.

"Pharmaceutically acceptable salt" refers to any salt of a compound provided herein which retains its biological properties and which is not toxic or otherwise undesirable for pharmaceutical use. Such salts may be derived from a variety of organic and inorganic counter-ions well known in the art. Such salts include, but are not limited to: (1) acid addition salts formed with organic or inorganic acids such as hydrochloric, hydrobromic, sulfuric, nitric, phosphoric, sulfamic, acetic, trifluoroacetic, trichloroacetic, propionic, hexanoic, cyclopentylpropionic, glycolic, glutaric, pyruvic, lactic, malonic, succinic, sorbic, ascorbic, malic, maleic, fumaric, tartaric, citric, benzoic, 3-(4-hydroxybenzoyl)benzoic, picric, cinnamic, mandelic, phthalic, lauric, methanesulfonic, ethanesulfonic, 1,2-ethane-disulfonic, 2-hydroxyethanesulfonic, benzenesulfonic, 4-chlorobenzenesulfonic, 2-naphthalenesulfonic, 4-toluenesulfonic, camphoric, camphorsulfonic, 4-methylbicyclo[2.2.2]-oct-2-ene-1-carboxylic, glucoheptonic, 3-phenylpropionic, trimethylacetic, tert-butylacetic, lauryl sulfuric, gluconic, benzoic, glutamic, hydroxynaphthoic, salicylic, stearic, cyclohexylsulfamic, quinic, muconic acid and the like acids; or (2) base addition salts formed when an acidic proton present in the parent compound either (a) is replaced by a metal ion, e.g., an alkali metal ion, an alkaline earth ion or an aluminum ion, or alkali metal or alkaline earth metal hydroxides, such as sodium, potassium, calcium, magnesium, aluminum, lithium, zinc, and barium hydroxide, ammonia or (b) coordinates with an organic base, such as aliphatic, alicyclic, or aromatic organic amines, such as ammonia, methylamine, dimethylamine, diethylamine, picoline, ethanolamine, diethanolamine, triethanolamine, ethylenediamine, lysine, arginine, ornithine, choline, N,N'-dibenzylethylene-diamine, chloroprocaine, diethanolamine, procaine, N-benzylphenethylamine, N-methylglucamine piperazine, tris(hydroxymethyl)-aminomethane, tetramethylammonium hydroxide, and the like.

Pharmaceutically acceptable salts further include, by way of example only and without limitation, sodium, potassium, calcium, magnesium, ammonium, tetraalkylammonium and the like, and when the compound contains a basic functionality, salts of non-toxic organic or inorganic acids, such as hydrohalides, e.g. hydrochloride and hydrobromide, sulfate, phosphate, sulfamate, nitrate, acetate, trifluoroacetate, trichloroacetate, propionate, hexanoate, cyclopentylpropionate, glycolate, glutarate, pyruvate, lactate, malonate, succinate, sorbate, ascorbate, malate, maleate, fumarate, tartarate, citrate, benzoate, 3-(4-hydroxybenzoyl)benzoate, picrate, cinnamate, mandelate, phthalate, laurate, methanesulfonate (mesylate), ethanesulfonate, 1,2-ethane-disulfonate, 2-hydroxyethanesulthnate, benzenesulfonate (besylate), 4-chlorobenzenesulfonate, 2-naphthalenesulfonate, 4-toluenesulfonate, camphorate, camphorsulfonate, 4-methylbicyclo[2.2.2]-oct-2-ene-1-carboxylate, glucoheptonate, 3-phenylpropionate, trimethylacetate, tert-butylacetate, lauryl sulfate, gluconate, benzoate, glutamate, hydroxynaphthoate, salicylate, stearate, cyclohexylsulfamate, quinate, muconate and the like.

The term "acyl" or "O-linked ester" refers to a group of the formula C(O)R', wherein R' is alkyl or cycloalkyl (including lower alkyl), carboxylate reside of amino acid, aryl including phenyl, alkaryl, arylalkyl including benzyl, alkoxyalkyl including methoxymethyl, aryloxyalkyl such as phenoxymethyl; or substituted alkyl (including lower alkyl), aryl including phenyl optionally substituted with chloro, bromo, fluoro, iodo, $C_1$ to $C_4$ alkyl or $C_1$ to $C_4$ alkoxy, sulfonate esters such as alkyl or arylalkyl sulphonyl including methanesulfonyl, the mono, di or triphosphate ester, trityl or monomethoxy-trityl, substituted benzyl, alkaryl, arylalkyl including benzyl, alkoxyalkyl including methoxymethyl, aryloxyalkyl such as phenoxymethyl. Aryl groups in the esters optimally comprise a phenyl group. In particular, acyl groups include acetyl, trifluoroacetyl, methylacetyl, cyclpropylacetyl, propionyl, butyryl, hexanoyl, heptanoyl, octanoyl, neo-heptanoyl, phenylacetyl, 2-acetoxy-2-phenylacetyl, diphenylacetyl, α-methoxy-α-trifluoromethyl-phenylacetyl, bromoacetyl, 2-nitro-benzeneacetyl, 4-chloro-benzeneacetyl, 2-chloro-2,2-diphenylacetyl, 2-chloro-2-phenylacetyl, trimethylacetyl, chlorodifluoroacetyl, perfluoroacetyl, fluoroacetyl, bromodifluoroacetyl, methoxyacetyl, 2-thiopheneacetyl, chloro sulfonylacetyl, 3-methoxyphenylacetyl, phenoxyacetyl, tert-butylacetyl, trichloroacetyl, monochloro-acetyl, dichloro-acetyl, 7H-dodecafluoro-heptano yl, perfluoro-heptanoyl, 7H-dodeca-fluoroheptanoyl, 7-chlorododecafluoro-heptanoyl, 7-chloro-dodecafluoro-heptanoyl, 7H-dodecafluoro-heptanoyl, 7H-dodeca-fluoroheptanoyl, nona-fluoro-3,6-dioxa-heptanoyl, nonafluoro-3,6-dioxaheptanoyl, perfluoroheptanoyl, methoxybenzoyl, methyl 3-amino-5-phenylthiophene-2-carboxyl, 3,6-dichloro-2-methoxy-benzoyl, 4-(1,1,2,2-tetrafluoro-ethoxy)-benzoyl, 2-bromo-propionyl, omega-aminocapryl, decanoyl, n-pentadecanoyl, stearyl, 3-cyclopentyl-propionyl, 1-benzene-carboxyl, 0-acetylmandelyl, pivaloyl acetyl, 1-adamantane-carboxyl, cyclohexane-carboxyl, 2,6-pyridinedicarboxyl, cyclopropane-carboxyl, cyclobutane-carboxyl, perfluorocyclohexyl carboxyl, 4-methylbenzoyl, chloromethyl isoxazolyl carbonyl, perfluorocyclohexyl carboxyl, crotonyl, 1-methyl-1H-indazole-3-carbonyl, 2-propenyl, isovaleryl, 1-pyrrolidin-ecarbonyl, 4-phenylbenzyl.

The term "amino acid" refers to naturally occurring and synthetic α, β γ or δ amino acids, and includes but is not limited to, amino acid residues found in proteins, i.e. glycine, alanine, valine, leucine, isoleucine, methionine, phenylalanine, tryptophan, proline, serine, threonine, cysteine, tyrosine, asparagine, glutamine, aspartate, glutamate, lysine, arginine and histidine. In certain embodiments, the amino acid is in the L-configuration. Alternatively, the amino acid can be a derivative of alanyl, valinyl, leucinyl, isoleuccinyl, prolinyl, phenylalaninyl, tryptophanyl, methioninyl, glycinyl, serinyl, threoninyl, cysteinyl, tyrosinyl, asparaginyl, glutaminyl, aspartoyl, glutaroyl, lysinyl, argininyl, histidinyl, β-alanyl, β-valinyl, β-leucinyl, β-isoleuccinyl, β-prolinyl, β-phenylalaninyl, β-tryptophanyl, β-methioninyl, β-glycinyl, β-serinyl, β-threoninyl, β-cysteinyl, β-tyrosinyl, β-asparaginyl, β-glutaminyl, β-aspartoyl, β-glutaroyl, β-lysinyl, β-argininyl or β-histidinyl.

The terms "polypeptide," "peptide" and "protein" are used interchangeably herein to refer to a polymer of amino acid residues. That is, a description directed to a polypeptide applies equally to a description of a peptide and a description of a protein, and vice versa. The terms apply to polymers of naturally occurring amino acid residues as well as polymers in which one or more amino acid residues is a modified amino acid residue. Additionally, such "polypeptides," "peptides" and "proteins" include amino acid residue chains of any length, including full length proteins, wherein the amino acid residues are linked by covalent peptide bonds.

The term "substantially free of" or "substantially in the absence of" with respect to a chemical composition refers to a chemical composition that includes at least 85% or 90% by weight, in certain embodiments 95%, 98%, 99% or 100% by weight, of the designated chemical.

Similarly, the term "isolated" with respect to a chemical composition refers to a chemical composition that includes at least 85%, 90%, 95%, 98%, 99% to 100% by weight, of the chemical, the remainder comprising other species or enantiomers.

"Solvate" refers to a compound provided herein or a salt thereof, that further includes a stoichiometric or non-stoichiometric amount of solvent bound by non-covalent intermolecular forces. Where the solvent is water, the solvate is a hydrate.

"Isotopic composition" refers to the amount of each isotope present for a given atom, and "natural isotopic composition" refers to the naturally occurring isotopic composition or abundance for a given atom. Atoms containing their natural isotopic composition may also be referred to herein as "non-enriched" atoms. Unless otherwise designated, the atoms of the compounds recited herein are meant to represent any stable isotope of that atom. For example, unless otherwise stated, when a position is designated specifically as "H" or "hydrogen," the position is understood to have hydrogen at its natural isotopic composition.

"Isotopic enrichment" refers to the percentage of incorporation of an amount of a specific isotope at a given atom in a molecule in the place of that atom's natural isotopic abundance. For example, deuterium enrichment of 1% at a given position means that 1% of the molecules in a given sample contain deuterium at the specified position. Because the naturally occurring distribution of deuterium is about 0.0156%, deuterium enrichment at any position in a compound synthesized using non-enriched starting materials is about 0.0156%. The isotopic enrichment of the compounds provided herein can be determined using conventional analytical methods known to one of ordinary skill in the art, including mass spectrometry and nuclear magnetic resonance spectroscopy.

"Isotopically enriched" refers to an atom having an isotopic composition other than the natural isotopic composition of that atom. "Isotopically enriched" may also refer to a compound containing at least one atom having an isotopic composition other than the natural isotopic composition of that atom.

As used herein, "alkyl," "cycloalkyl," "alkenyl," "cycloalkenyl," "alkynyl," "aryl," "alkoxy," "alkoxycarbonyl," "amino," "carboxyl," "alkylamino," "arylamino," "thioalkyoxy," "heterocyclyl," "heteroaryl," "alkylheterocyclyl," "alkylheteroaryl," "acyl," "aralkyl," "alkaryl," "purine," "pyrimidine," "carboxyl" and "amino acid" groups optionally comprise deuterium at one or more positions where hydrogen atoms are present, and wherein the deuterium composition of the atom or atoms is other than the natural isotopic composition.

Also as used herein, "alkyl," "cycloalkyl," "alkenyl," "cycloalkenyl," "alkynyl," "aryl," "alkoxy," "alkoxycarbonyl," "carboxyl," "alkylamino," "arylamino," "thioalkyoxy," "heterocyclyl," "heteroaryl," "alkylheterocyclyl," "alkylheteroaryl," "acyl," "aralkyl," "alkaryl," "purine," "pyrimidine," "carboxyl" and "amino acid" groups optionally comprise carbon-13 at an amount other than the natural isotopic composition.

As used herein, $EC_{50}$ refers to a dosage, concentration or amount of a particular test compound that elicits a dose-dependent response at 50% of maximal expression of a particular response that is induced, provoked or potentiated by the particular test compound.

As used herein, the $IC_{50}$ refers to an amount, concentration or dosage of a particular test compound that achieves a 50% inhibition of a maximal response in an assay that measures such response.

As used herein, the terms "subject" and "patient" are used interchangeably herein. The terms "subject" and "subjects" refer to an animal, such as a mammal including a non-primate (e.g., a cow, pig, horse, cat, dog, rat, and mouse) and a primate (e.g., a monkey such as a cynomolgous monkey, a chimpanzee and a human), and for example, a human.

As used herein, the terms "therapeutic agent" and "therapeutic agents" refer to any agent(s) which can be used in the treatment or prevention of a disorder or one or more symptoms thereof. In certain embodiments, the term "therapeutic agent" includes a compound provided herein. In certain embodiments, a therapeutic agent is an agent which is known to be useful for, or has been or is currently being used for the treatment or prevention of a disorder or one or more symptoms thereof.

"Therapeutically effective amount" refers to an amount of a compound or composition that, when administered to a subject for treating a disease, is sufficient to effect such treatment for the disease. A "therapeutically effective amount" can vary depending on, inter alia, the compound, the disease and its severity, and the age, weight, etc., of the subject to be treated.

"Treating" or "treatment" of any disease or disorder refers, in certain embodiments, to ameliorating a disease or disorder that exists in a subject. In some embodiments, "treating" or "treatment" includes amelidrating at least one physical parameter, which may be indiscernible by the subject. In certain embodiments, "treating" or "treatment" includes modulating the disease or disorder, either physically (e.g., stabilization of a discernible symptom) or physiologically (e.g., stabilization of a physical parameter) or both. In some embodiments, "treating" or "treatment" includes delaying the onset of the disease or disorder.

As used herein, the terms "prophylactic agent" and "prophylactic agents" as used refer to any agent(s) which can be used in the prevention of a disorder or one or more symptoms thereof. In certain embodiments, the term "prophylactic agent" includes a compound provided herein. In certain other embodiments, the term "prophylactic agent" does not refer a compound provided herein. For example, a prophylactic agent is an agent which is known to be useful for, or has been or is currently being used to prevent or impede the onset, development, progression and/or severity of a disorder.

As used herein, the phrase "prophylactically effective amount" refers to the amount of a therapy (e.g., prophylactic agent) which is sufficient to result in the prevention or reduction of the development, recurrence or onset of one or more symptoms associated with a disorder, or to enhance or improve the prophylactic effect(s) of another therapy (e.g., another prophylactic agent).

The term "substantially pure" with respect to a composition comprising a modified amino acid residue refers to a composition that includes at least 80, 85, 90 or 95% by weight or, in certain embodiments, 95, 98, 99 or 100% by weight, e.g. dry weight, of the modified amino acid residue relative to the remaining portion of the composition. The weight percentage can be relative to the total weight of protein in the composition or relative to the total weight of modified amino acid residues in the composition. Purity can be determined by techniques apparent to those of skill in the art.

The term "antibody" refers to any macromolecule that would be recognized as an antibody by those of skill in the art. Antibodies share common properties including binding to an antigen and a structure comprising at least one polypeptide chain with a region or regions substantially similar to a polypeptide encoded by any of the immunoglobulin genes recognized by those of skill in the art. The immunoglobulin genes include, but are not limited to, the κ, λ, α, γ (IgG1, IgG2, IgG3, and IgG4), δ, ε and μ constant region genes, as well as the immunoglobulin variable region genes (e.g., IGHV, IGHD, IGHJ, IGLV, IGKV, IGLJ, and IGKJ genes). The term includes full-length antibodies and antibody fragments recognized by those of skill in the art, and variants thereof.

The term "antibody fragment" refers to any form of an antibody other than the full-length form. Antibody fragments herein include antibodies that are smaller components that exist within full-length antibodies, and antibodies that have been engineered. Antibody fragments include but are not limited to Fv, Fc, Fab, and (Fab)$_2$, single chain Fv (scFv), domain antibodies (dAbs), diabodies, triabodies, tetrabodies, bifunctional hybrid antibodies, CDR1, CDR2, CDR3, combinations of CDR's, variable regions, framework regions, constant regions, and the like (Maynard & Georgiou, 2000, *Annu. Rev. Biomed. Eng.* 2:339-76; Hudson, 1998, *Curr. Opin. Biotechnol.* 9:395-402).

The term "immunoglobulin (Ig)" refers to a protein consisting of one or more polypeptides substantially encoded by one or more of the immunoglobulin genes, or a protein substantially identical thereto in amino acid residue sequence. Immunoglobulins include but are not limited to antibodies. Immunoglobulins may have a number of structural forms, including but not limited to full-length antibodies, antibody fragments, and individual immunoglobulin domains including but not limited to $V_H$, $D_H$, $J_H$, $C_H$ (e.g., Cγ1, Cγ2, Cγ3), $V_L$, $J_L$, and $C_L$ (e.g., $V_\kappa$ and $V_\lambda$).

The term "immunoglobulin (Ig) domain" refers to a protein domain consisting of a polypeptide substantially encoded by an immunoglobulin gene. Ig domains include but are not limited to $V_H$, $D_H$, $J_H$, $C_H$ (e.g., Cγ1, Cγ2, Cγ3), $V_L$, $J_L$, and $C_L$ (e.g., $V_\kappa$ and $V_\lambda$).

The term "variable region" of an antibody refers to a polypeptide or polypeptides composed of the $V_H$ immunoglobulin domain, the $V_L$ immunoglobulin domain, or the $V_H$ and $V_L$ immunoglobulin domains. Variable region may refer to this or these polypeptides in isolation, or as a fragment (e.g., as an Fv fragment or as an scFv fragment), as this region in the context of a larger antibody fragment, or as this region in the context of a full-length antibody or an alternative, non-antibody scaffold molecule.

The term "variable" refers to the fact that certain portions of the variable domains differ extensively in sequence among antibodies and are responsible for the binding specificity of each particular antibody for its particular antigen. However, the variability is not evenly distributed through the variable domains of antibodies. It is concentrated in six segments called complementarity determining regions (CDRs). Three of these CDRs are located in the light chain variable domain and three in the heavy chain variable domain. The conserved portions of the variable domains are called the framework regions (FR). The variable domains of native heavy and light chains each comprise four FR regions, largely adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the antigen binding site of antibodies (see Kabat et al., Sequences of Proteins of Immunological Interest, 5th Ed. Public Health Service, National Institutes of Health, Bethesda, Md. (1991)).

The constant domains are typically not directly involved in the binding of an antibody to an antigen, but exhibit various effector functions. Depending on the amino acid residue sequence of the constant region of the heavy chains, antibodies can be assigned to different classes. There are five major classes of immunoglobulins: IgA, IgD, IgE, IgG and IgM, and several of these may be further divided into subclasses (isotypes), e.g. IgG1, IgG2, IgG3, and IgG4; IgA1 and IgA2. The heavy chain constant regions that correspond to the different classes of immunoglobulins are also called α, δ, ε, γ and μ respectively. Of the various human immunoglobulin classes, only human IgG1, IgG2, IgG3 and IgM are known to activate complement.

The term "conjugate" generally refers to a moiety comprising a modified amino acid residue, as described herein, attached to a payload. The term "payload" generally refers to a moiety that is attached (or "conjugated") to a modified amino acid residue, as described herein. For example, a conjugate may comprise a polypeptide or an antibody comprising a modified amino acid residue attached to a payload. A payload may be a small molecule or a macromolecule. In some embodiments, the payload is a bioactive molecule including, but not limited to, a protein, a peptide, a nucleic active or a hybrid thereof. In some embodiments, the payload is a polymer such as polyethylene glycol. In some embodiments, the payload is a therapeutic agent, such as a drug. In some embodiments, the payload is a label that can recognize and bind to specific targets, such as a payload that is useful for detection or diagnosis. In some embodiments, the payload is connected to a modified amino acid residue via a linker. In some embodiments, the payload is directly connected to a modified amino acid residue without a linker.

The term "variant protein sequence" refers to a protein sequence that has one or more residues that differ in amino acid residue identity from another similar protein sequence. Said similar protein sequence may be the natural wild type protein sequence, or another variant of the wild type sequence. Variants include proteins that have one or more amino acid residue insertions, deletions or substitutions. Variants also include proteins that have one or more post-translationally modified amino acid residues.

The term "parent antibody" refers to an antibody that is modified according to the description provided herein. The modification can be physical, i.e., chemically or biochemically replacing or modifying one or more amino acid residues of the parent antibody to yield an antibody within the scope of the present description. The modification can also be conceptual, i.e., using the sequence of one or more polypeptide chains of the parent antibody to design an antibody comprising one or more site-specific modified amino acid residues according to the present description. Parent antibodies can be naturally occurring antibodies or antibodies designed or developed in a laboratory. Parent antibodies can also be artificial or engineered antibodies, e.g., chimeric or humanized antibodies.

The term "conservatively modified variant" refers to a protein that differs from a related protein by conservative substitutions in the amino acid residue sequence. One of skill in the art will recognize that individual substitutions, deletions or additions to a peptide, polypeptide, or protein sequence which alters, adds or deletes a single amino acid residue or a small percentage of amino acid residues in the encoded sequence is a "conservatively modified variant" where the alteration results in the substitution of an amino acid residue with a chemically similar amino acid residue. Conservative substitution tables providing functionally similar amino acids are well known in the art. Such conservatively modified variants are in addition to and do not exclude polymorphic variants, interspecies homologs, and alleles.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M).

See, e.g., Creighton, *Proteins: Structures and Molecular Properties*, W H Freeman & Co.; 2nd edition (December 1993).

The terms "identical" or "identity," in the context of two or more polypeptide sequences, refer to two or more sequences or subsequences that are the same. Sequences are "substantially identical" if they have a percentage of amino acid residues or nucleotides that are the same (i.e., about 60% identity, optionally about 65%, about 70%, about 75%, about 80%, about 85%, about 90%, about 95%, about 96%, about 97%, about 98%, about 99%, about 99.5%, or about 99.9% identity over a specified region), when compared and aligned for maximum correspondence over a comparison window, or designated region as measured using one of the following sequence comparison algorithms or by manual alignment and visual inspection. The identity can exist over a region that is at least about 50 amino acid residues or nucleotides in length, over a region that is about 10-17 residues in length (e.g., the approximate length of CDRL1), over a region that is about 7 residues in length (e.g., the approximate length of CDRL2), over a region that is about 7-11 residues in length (e.g., the approximate length of CDRL3), over a region that is about 10-12 residues in length (e.g., the approximate length of CDRH1), over a region that is about 16-19 residues in length (e.g., the approximate length of CDRH2), over a region that is about 3-35 residues in length (e.g., the approximate length of CDRH3), or over a region that is 75-100 amino acid residues or nucleotides in length, or, where not specified, across the entire sequence or a polypeptide. In the case of antibodies, identity can be measured outside the variable CDRs. Identity can also be measured within the entirety of the heavy or light chains, or within the variable regions of the heavy or light chains. Optimal alignment of sequences for comparison can be conducted by methods including, but not limited to, the local homology algorithm of Smith and Waterman (1970) Adv. Appl. Math. 2:482c, the homology alignment algorithm of Needleman and Wunsch (1970) J. Mol. Biol. 48:443, the search for similarity method of Pearson and Lipman (1988) Proc. Nat'l. Acad. Sci. USA 85:2444, computerized implementations of these algorithms (GAP, BESTFIT, FASTA, and TFASTA in the Wisconsin Genetics Software Package, Genetics Computer Group, 575 Science Dr., Madison, Wis.); or by manual alignment and visual inspection (see, e.g., Ausubel et al., Current Protocols in Molecular Biology (1995 supplement)).

Examples of algorithms that are suitable for determining percent sequence identity and sequence similarity include the BLAST and BLAST 2.0 algorithms, which are described in Altschul et al. (1977) Nuc. Acids Res. 25:3389-3402, and Altschul et al. (1990) J. Mol. Biol. 215:403-410, respectively. Software for performing BLAST analyses is publicly available through the National Center for Biotechnology Information. The BLAST algorithm parameters W, T, and X determine the sensitivity and speed of the alignment. The BLASTN program (fui nucleotide sequences) uses as defaults a wordlength (W) of 11, an expectation (E) or 10, M=5, N=−4 and a comparison of both strands. For amino acid residue sequences, the BLASTP program uses as defaults a wordlength of 3, and expectation (E) of 10, and the BLOSUM62 scoring matrix (see Henikoff and Henikoff (1989) Proc. Natl. Acad. Sci. USA 89:10915) alignments (B) of 50, expectation (E) of 10, M=5, N=−4, and a comparison of both strands. The BLAST algorithm is typically performed with the "low complexity" filter turned off. In some embodiments, the BLAST algorithm is typically performed with the "low complexity" filter turned on.

The BLAST algorithm also performs a statistical analysis of the similarity between two sequences (see, e.g., Karlin and Altschul (1993) Proc. Natl. Acad. Sci. USA 90:5873-5787). One measure of similarity provided by the BLAST algorithm is the smallest sum probability (P(N)), which provides an indication of the probability by which a match between two nucleotide or amino acid residue sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

The term "amino acid" refers to naturally occurring and non-naturally occurring amino acids, as well as amino acids such as proline, amino acid analogs and amino acid mimetics that function in a manner similar to naturally occurring amino acids.

Naturally encoded amino acids are the proteinogenic amino acids known to those of skill in the art. They include the 20 common amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine) and the less common pyrrolysine and selenocysteine. Naturally encoded amino acids include post-translational variants of the 22 naturally occurring amino acids such as prenylated amino acids, isoprenylated amino acids, myrisoylated amino acids, palmitoylated amino acids, N-linked glycosylated amino acids, O-linked glycosylated amino acids, phosphorylated amino acids and acylated amino acids.

The term "modified amino acid" refers to an amino acid that is not a proteinogenic amino acid, or a post-translationally modified variant thereof. In particular, the term refers to an amino acid that is not one of the 20 common amino acids or pyrrolysine or selenocysteine, or post-translationally modified variants thereof.

The term "strained alkene" refers to a molecule comprising an alkene moiety that is capable of reacting with tetrazine in a tetrazine ligation. Exemplary tetrazine ligations are described in Blackman et al., 2008, *J. Am. Chem. Soc.* 130:13518-13519. Examples include trans-cyclooctenes and norbornenes. Useful compounds include, but are not limited to, trans-cyclooctene, (E)-cyclooct-4-enol, (E)-cyclooct-4-enyl 2,5-dioxo-1-pyrrolidinyl carbonate, 5-norbornene-2-acetic acid succinimidyl ester, and 5-norbornene-2-endo-acetic acid.

Compounds

Provided herein are compounds according to formula I:

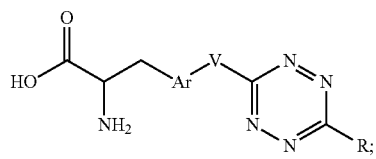

Formula I or a salt thereof, wherein Ar is:

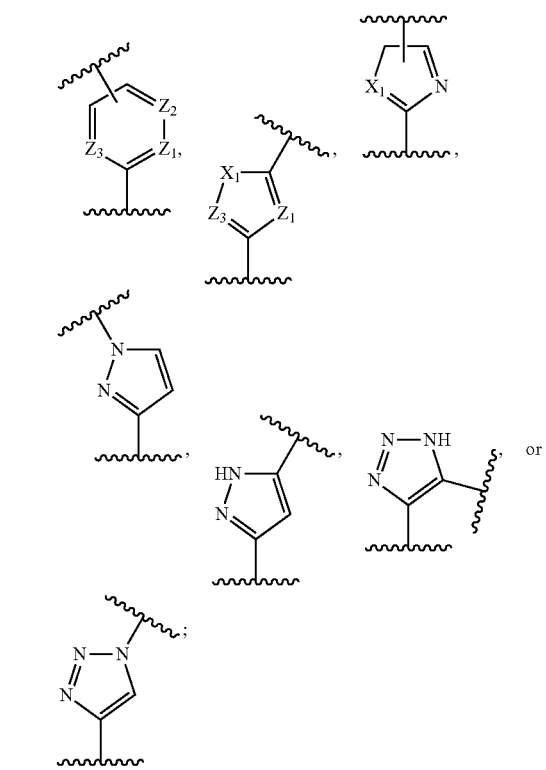

V is a single bond, lower alkylene, or —$W_1$—$W_2$—; one of $W_1$ and $W_2$ is absent or lower alkylene, and the other is —NH—, —O—, or —S—; each $X_1$ is independently —NH—, —O—, or —S—; one of $Z_1$, $Z_2$, and $Z_3$ is —CH— or —N— and the others of $Z_1$, $Z_2$, and $Z_3$ are each independently —CH—; and R is lower alkyl. In certain embodiments, when Ar is

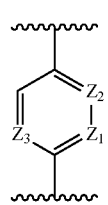

and V is —NH—, then one of $Z_1$, $Z_2$, and $Z_3$ is —N—. In certain embodiments, V is a single bond, —NH—, or —$CH_2$NH—.

In certain embodiments, Ar is

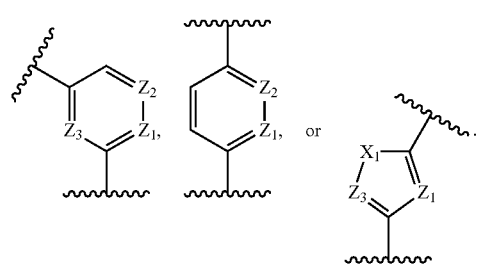

and $Z_1$, $Z_2$, $Z_3$ and $X_1$ are as defined in the context of formula I. In certain embodiments according to this paragraph, V is —$W_1$—$W_2$—; one of $W_1$ and $W_2$ is absent or —$CH_2$—, and the other is —NH—, —O—, or —S—. In certain embodiments according to this paragraph, V is a single bond, —NH—, or —$CH_2$NH—. In certain embodiments according to this paragraph, $Z_1$ is N. In certain embodiments according to this paragraph, $Z_2$ is N. In certain embodiments according to this paragraph, $Z_3$ is N. In certain embodiments according to this paragraph, $Z_1$ is CH, $Z_3$ is CH and $X_1$ is S.

In certain embodiments, Ar is

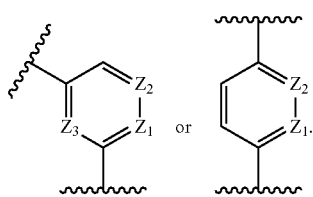

and $Z_1$, $Z_2$, and $Z_3$ are as defined in the context of formula I. In certain embodiments according to this paragraph, V is —$W_1$—$W_2$—; one of $W_1$ and $W_2$ is absent or —$CH_2$—, and the other is —NH—, —O—, or —S—. In certain embodiments according to this paragraph, V is a single bond, —NH—, or —$CH_2$NH—. In certain embodiments according to this paragraph, $Z_1$ is N. In certain embodiments according to this paragraph, $Z_2$ is N. In certain embodiments according to this paragraph, $Z_3$ is N.

In certain embodiments, Ar is

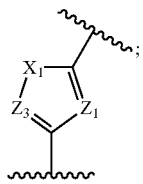

and $Z_1$, $Z_3$ and $X_1$ are as defined in the context of formula I. In certain embodiments according to this paragraph, V is —$W_1$—$W_2$—; one of $W_1$ and $W_2$ is absent or —$CH_2$—, and the other is —NH—, —O—, or —S—. In certain embodiments according to this paragraph, V is a single bond, —NH—, or —$CH_2$NH—. In certain embodiments according to this paragraph, $Z_1$ is N. In certain embodiments according to this paragraph, $Z_3$ is N. In certain embodiments according to this paragraph, $Z_1$ is CH, $Z_3$ is CH and $X_1$ is S.

In an embodiment, a compound according to formula Ia is provided:

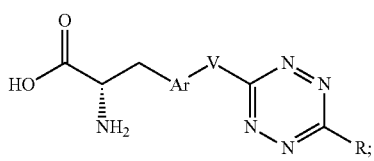

Formula Ia where Ar, V, and R are defined in the context of formula I.

In an embodiment, compounds of either of formulas I and Ia are provided wherein V is a single bond. In another embodiment, compounds of either of formulas I and Ia are provided wherein V is —NH—. In another embodiment, compounds of either of formulas I and Ia are provided wherein V is —$CH_2$NH—.

In an embodiment, a compound according to formula II is provided:

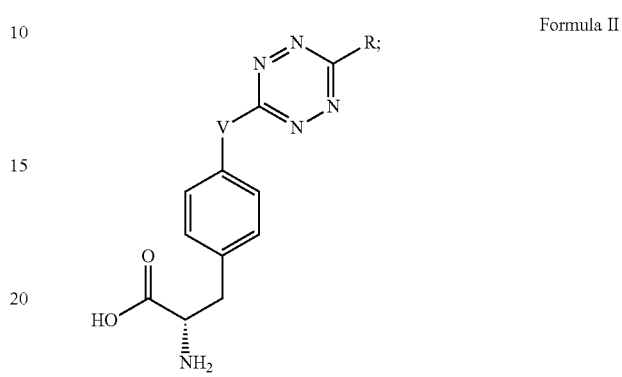

Formula II or a salt thereof, wherein V and R are as defined in Formula I. In certain embodiments according to this paragraph, V is —$W_1$—$W_2$—; one of $W_1$ and $W_2$ is absent or —$CH_2$—, and the other is —NH—, —O—, or —S—. In certain embodiments, V is a single bond, —NH—, or —$CH_2$NH—. In certain embodiments, V is a single bond or —$CH_2$NH—; and R is methyl.

In an embodiment, a compound according to formula III is provided:

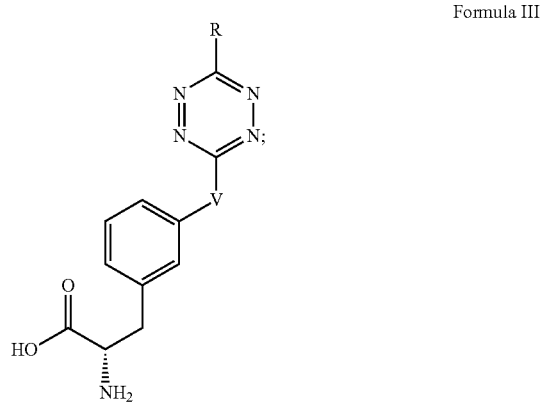

Formula III or a salt thereof, wherein V and R are as defined in Formula I. In certain embodiments according to this paragraph, V is —$W_1$—$W_2$—; one of $W_1$ and $W_2$ is absent or —$CH_2$—, and the other is —NH—, —O—, or —S—. In certain embodiments, V is a single bond, —NH—, or —$CH_2$NH—. In certain embodiments, V is a single bond, —NH—, or —$CH_2$NH—; and R is methyl.

In an embodiment, a compound according to formula IV is provided:

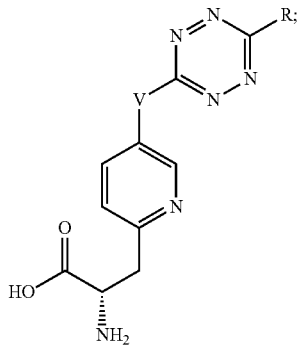

Formula IV or a salt thereof, wherein V and R are as defined in Formula I. In certain embodiments according to this paragraph, V is —$W_1$—$W_2$—; one of $W_1$ and $W_2$ is absent or —$CH_2$—, and the other is —NH—, —O—, or —S—. In certain embodiments, V is a single bond, —NH—, or —$CH_2$NH—. In certain embodiments, V is a single bond, —NH—, or —$CH_2$NH—; and R is methyl.

In an embodiment, a compound according to formula V is provided:

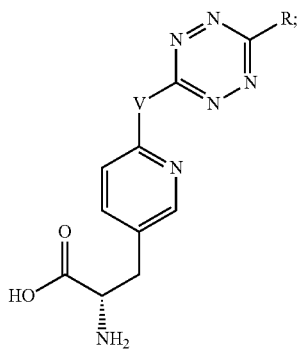

Formula V or a salt thereof, wherein V and R are as defined in Formula I. In certain embodiments according to this paragraph, V is —$W_1$—$W_2$—; one of $W_1$ and $W_2$ is absent or —$CH_2$—, and the other is —NH—, —O—, or —S—. In certain embodiments, V is a single bond, —NH—, or —$CH_2$NH—. In certain embodiments, V is a single bond, —NH—, or —$CH_2$NH—; and R is methyl.

In an embodiment, a compound according to formula VI is provided:

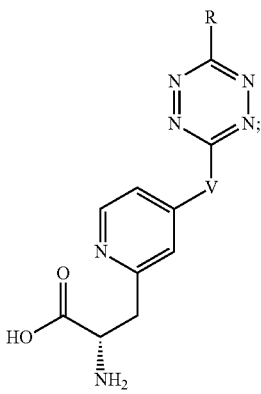

Formula VI or a salt thereof, wherein V and R are as defined in Formula I. In certain embodiments according to this paragraph, V is —$W_1$—$W_2$—; one of $W_1$ and $W_2$ is absent or —$CH_2$—, and the other is —NH—, —O—, or —S—. In certain embodiments, V is a single bond, —NH—, or —$CH_2$NH—. In certain embodiments, V is a single bond, —NH—, or —$CH_2$NH—; and R is methyl.

In an embodiment, a compound according to formula Vii is provided:

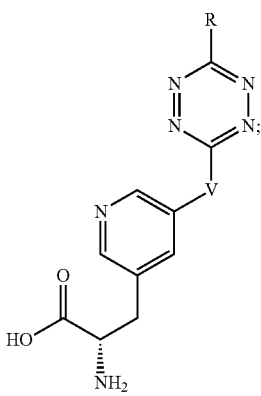

Formula VII or a salt thereof, wherein V and R are as defined in Formula I. In certain embodiments according to this paragraph, V is —$W_1$—$W_2$—; one of $W_1$ and $W_2$ is absent or —$CH_2$—, and the other is —NH—, —O—, or —S—. In certain embodiments, V is a single bond, —NH—, or —$CH_2$NH—. In certain embodiments, V is a single bond, —NH—, or —$CH_2$NH—; and R is methyl.

In an embodiment, a compound according to formula VIII is provided:

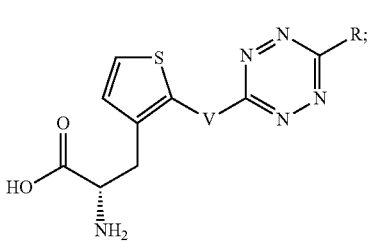

Formula VIII or a salt thereof, wherein V and R are as defined in Formula I. In certain embodiments according to this paragraph, V is —$W_1$—$W_2$—; one of $W_1$ and $W_2$ is absent or —$CH_2$—, and the other is —NH—, —O—, or —S—. In certain embodiments, V is a single bond, —NH—, or —$CH_2$NH—. In certain embodiments, V is a single bond, —NH—, or —$CH_2$NH—; and R is methyl.

In an embodiment, a compound according to formula IX is provided:

Formula IX

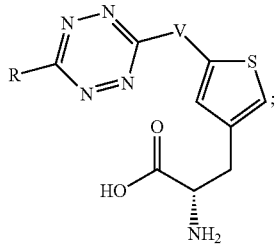

or a salt thereof, wherein V and R are as defined in Formula I. In certain embodiments according to this paragraph, V is —$W_1$—$W_2$—; one of $W_1$ and $W_2$ is absent or —$CH_2$—, and the other is —NH—, —O—, or —S—. In certain embodiments, V is a single bond, —NH—, or —$CH_2$NH—. In certain embodiments, V is a single bond, —NH—, or —$CH_2$NH—; and R is methyl.

In an embodiment, a compound according to any of formulas 1-10 is provided:

(1)

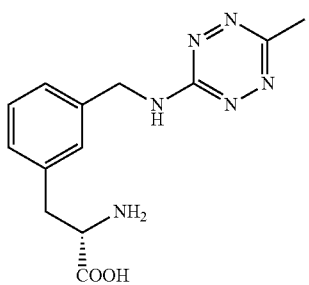

(2)

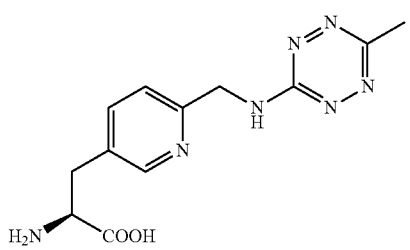

(3)

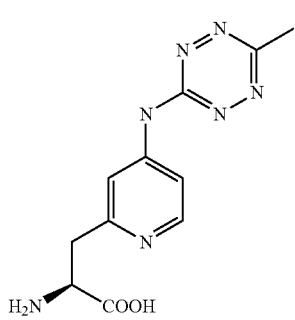

(4)

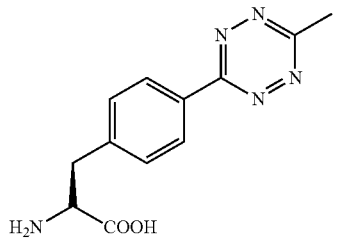

(5)

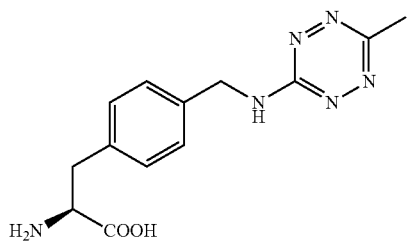

(6)

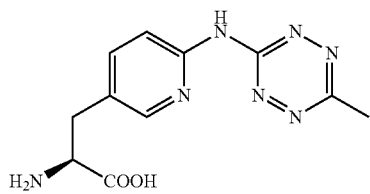

(7)

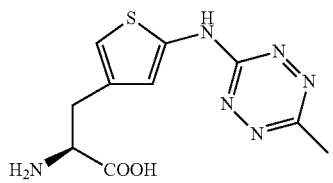

(8)

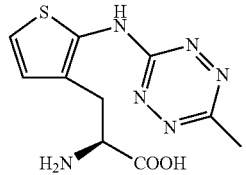

(9)

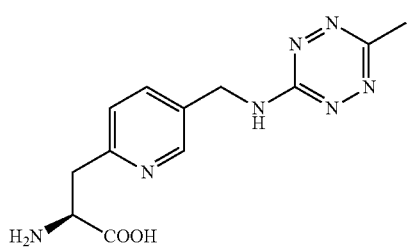

(10)

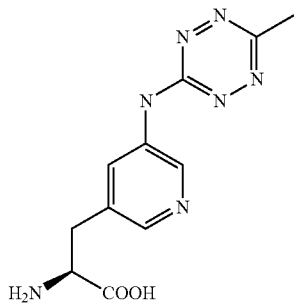

or a salt thereof.

In an embodiment, a polypeptide is provided comprising an amino acid residue corresponding to a compound of formula I, Ia, II, III, IV, V, VI, VII, VIII, IX, or 1-10. In an embodiment, a conjugate is provided comprising a polypeptide comprising an amino acid residue corresponding to a compound of formula I, Ia, II, III, IV, V, VI, VII, VIII, IX, or 1-10. linked to a payload and optionally comprising a linking moiety between the polypeptide and the payload.

In an embodiment, an antibody is provided comprising an amino acid residue corresponding to a compound of formula I, Ia, II, III, IV, V, VI, VII, VIII, IX, or 1-10. In an embodiment, a conjugate is provided comprising an antibody comprising an amino acid residue corresponding to a compound of formula I, Ia, II, III, IV, V, VI, VII, VIII, IX, or 1-10. linked to a payload and optionally comprising a linking moiety between the antibody and the payload.

In an embodiment, an orthogonal tRNA is provided aminoacylated with an amino acid residue corresponding to a compound of formula I, Ia, II, III, IV, V, VI, VII, VIII, IX, or 1-10. In a related embodiment, a method of producing a polypeptide is provided, comprising contacting a polypeptide with an orthogonal tRNA aminoacylated with an amino acid residue corresponding to a compound of formula I, Ia, II, III, IV, V, VI, VII, VIII, IX, or 1-10 under conditions suitable for incorporating the amino acid residue into the polypeptide. In an aspect, the orthogonal tRNA base pairs with a codon that is not normally associated with an amino acid. In another aspect, the contacting occurs in a reaction mixture which comprises a tRNA synthetase capable of aminoacylating the orthogonal tRNA with a compound of formula I, Ia, II, III, IV, V, VI, VII, VIII, IX, or 1-10.

In certain embodiments, a polypeptide comprising a modified amino acid residue is provided according to any of the following formulas, where Ar, V and R are as defined in the context of formula I:

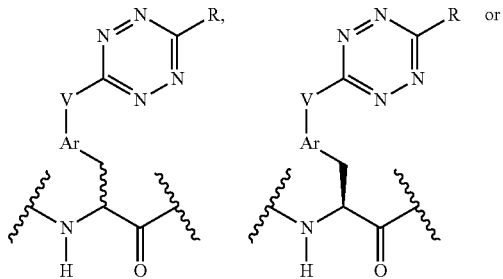

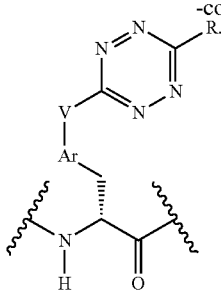

Those of skill in the art will recognize that proteins are generally comprised of L-amino acid residues. However, with modified amino acids, the present methods and compositions provide the practitioner with the ability to use L-, D- or racemic modified amino acids. In certain embodiments, the modified amino acids described herein include D-versions of the natural amino acids and racemic versions of the natural amino acids.

Tetrazine Ligation with Modified Amino Acids Comprising Tetrazine Functional Groups Modification of amino acids to incorporate tetrazine functional groups enables selective and efficient reaction of the modified amino acids with compounds comprising strained alkenes. These reactions are selective in that the reactive groups—the tetrazines and the strained alkenes—are not reactive with the functional groups of the naturally occurring amino acids or with other well-known reactive groups. Further, the reactions can be carried out in complex environments such as cell extracts, in vitro protein synthesis reaction mixtures and the like.

The reaction between tetrazine and a strained alkene is known as the "tetrazine ligation." It is believed that the tetrazine and strained alkene react in an inverse-demand Diels-Alder reaction followed by a retro-Diels-Alder reaction that links the tetrazine to the strained alkene. The reaction is specific, with little to no cross-reactivity with functional groups that occur on biomolecules. The reaction may be carried out under mild conditions, for example at room temperature and without a catalyst.

Useful strained alkenes include trans-cyclooctenes and norbornenes described herein. Useful modified amino acids comprising tetrazine functional groups include compounds according to any of formulas I, Ia, II, III, IV, V, VI, VII, VIII, IX, or 1-10 described herein, and polypeptides comprising residues corresponding to the compounds.

In some embodiments, modified amino acids comprising tetrazine functional groups are used in conjunction with modified amino acids comprising other functional groups. In some embodiments, the modified amino acid comprising a tetrazine functional group is a modified amino acid according to any of formulas I, Ia, II, III, IV, V, VI, VII, VIII, IX, or 1-10. This approach may be used, for example, to produce polypeptides or antibodies comprising modified amino acid residues with two or more different types of functional groups. In some embodiments, the polypeptides or antibodies comprise modified amino acids with three or more different types of functional groups.

Useful additional functional groups for additional modified amino acids include carbonyls, thiols, azides, alkynes, and other functional groups deemed suitable by those of skill in the art.

In advantageous embodiments, provided are polypeptides comprising one or more of the modified amino acids comprising tetrazine moieties, described herein, along with one or more other modified amino acids comprising an azide moiety. This combination of reactive amino acids facilitates two, independent reactions at specific sites on the polypeptide. A molecule comprising a strained alkene can selectively react with the one or more tetrazine moieties. Another molecule comprising an alkyne group can react with the one or more azide moieties. Advantageously, there can be little or no cross-reaction between the tetrazine ligations and the azide-alkyne condensations.

Incorporation of both tetrazine and azide functionality into a single polypeptide enables, for example, controlled conjugation of more than one payload molecule to the polypeptide chain. For example, in some embodiments, a first payload comprises a strained alkene functional group, enabling reaction with amino acid residues comprising tetrazine, while a second payload comprises an alkyne functional group, enabling reaction with amino acid residues comprising azide. Further payloads, comprising additional functional groups may also be used. The functional groups carried by such further payloads may react with any other suitable functional group, such as a functional group on a further modified amino acid residue or a natural amino acid residue.

The reaction between an azido functional group and an alkyne, to form a triazole, is known as the Huisgen cycloaddition. It is believed that the azido and alkyne groups react in a 1,3-dipolar cycloaddition reaction to form a 1,2,3-triazolylene moiety which links the azido group to the alkyne. The reaction may be carried out at room temperature under aqueous conditions by the addition of Cu(II) (including but not limited to, in the form of a catalytic amount of $CuSO_4$) in the presence of a reducing agent for reducing Cu(II) to Cu(I), in situ, in catalytic amount. See, e.g., Wang, Q., et al., J. Am. Chem. Soc. 125, 3192-3193 (2003); Tornoe, C. W., et al., J. Org. Chem. 67:3057-3064 (2002); Rostovtsev, et al., Angew. Chem. Int. Ed. 41:2596-2599 (2002). Exemplary reducing agents include, including but are not limited to, ascorbate, metallic copper, quinine, hydroquinone, vitamin K, glutathione, cysteine, $Fe^{2+}$, $Co^{2+}$, and an applied electric potential. In addition to the Huisgen cycloaddition reaction, the azide functional group can be reacted selectively with a payload moiety comprising an aryl ester and an aryl phosphine moiety to generate an amide linkage. See Saxon and Bertozzi, Science 287:2007-2010 (2000). The azide functional group can also be reacted selectively with a payload moiety comprising a thioester and an aryl phosphine moiety to generate an amide linkage.

Modification of amino acids to incorporate azide functional groups therefore enables selective and efficient reaction of the modified amino acids with molecules comprising alkynes, aryl esters and thioesters. Examples of modified amino acids comprising azide functional groups include p-azido-phenylalanine (See Chin et al., J. Am. Chem. Soc. 124:9026-9027 (2002)), as well as compounds according to any of formulas AI, A1-A30 or A40, as shown below. Such compounds may be prepared, for example, according to methods provided in PCT/US2013/057677, which is incorporated by reference in its entirety.

In certain embodiments, the modified amino acid is a compound according to formula AI:

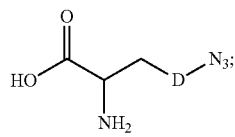

Formula AI or a salt thereof, wherein: D is —Ar—$W_3$— or —$W_1$—$Y_1$—C(O)—$Y_2$—$W_2$—; Ar is

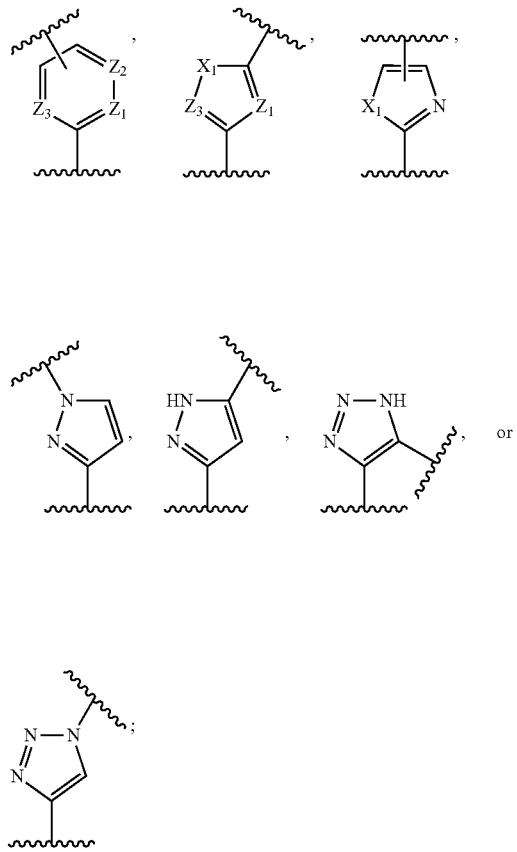

each of $W_1$, $W_2$, and $W_3$ is independently a single bond or lower alkylene; each $X_1$ is independently —NH—, —O—, or each $Y_1$ is independently a single bond, —NH—, or —O—; each $Y_2$ is independently a single bond, —NH—, —O—, or an N-linked or C-linked pyrrolidinylene; and one of $Z_1$, $Z_2$, and $Z_3$ is —N— and the others of $Z_1$, $Z_2$, and $Z_3$ are independently —CH—. In certain embodiments, provided are polypeptides comprising modified tetrazine residues, provided herein, along with residues according to one of the following:

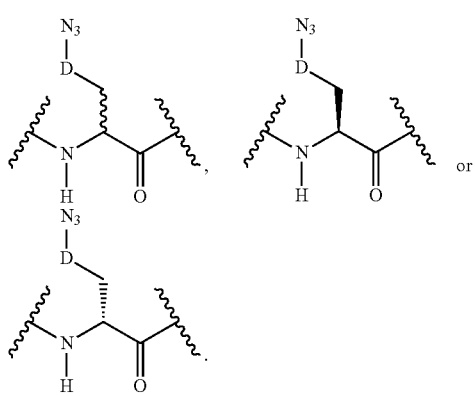

where D is as described above.

In some embodiments, the modified amino acid is a compound according to formula A1-A30 or A40:
(A1)
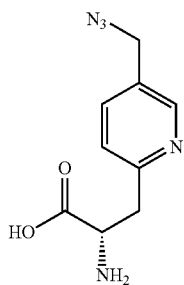
(A2)
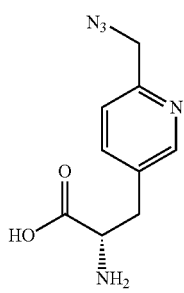
(A3)
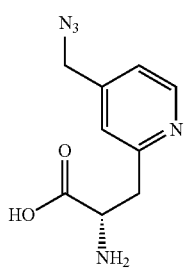
(A4)
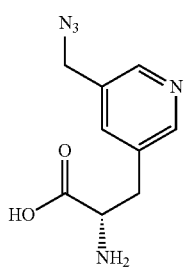
(A5)
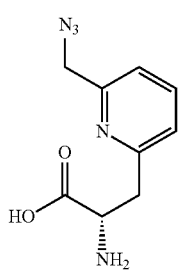
(A6)
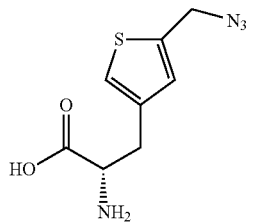
(A7)
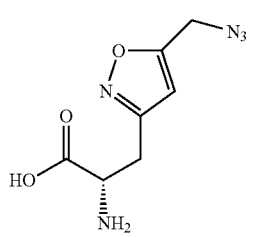
(A8)
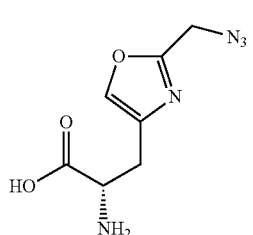
(A9)
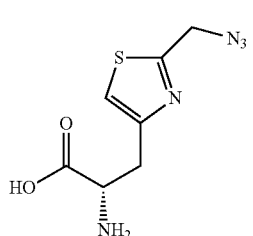
(A10)
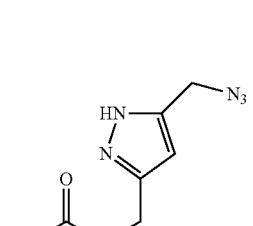
(A11)
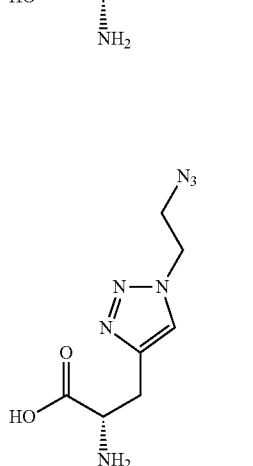

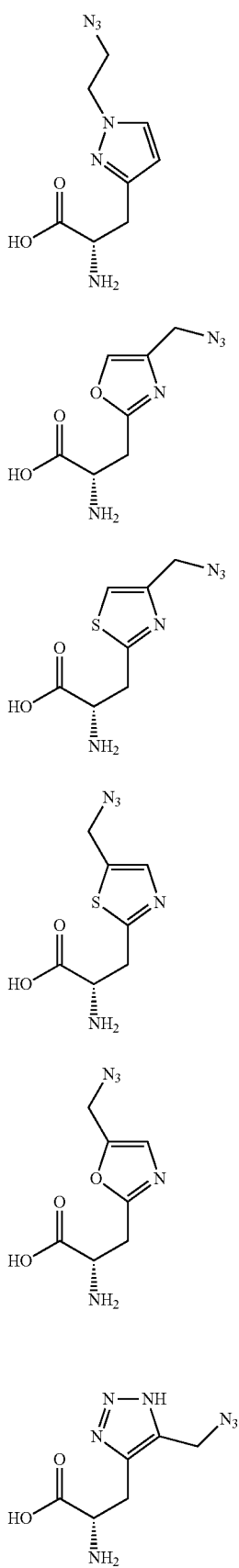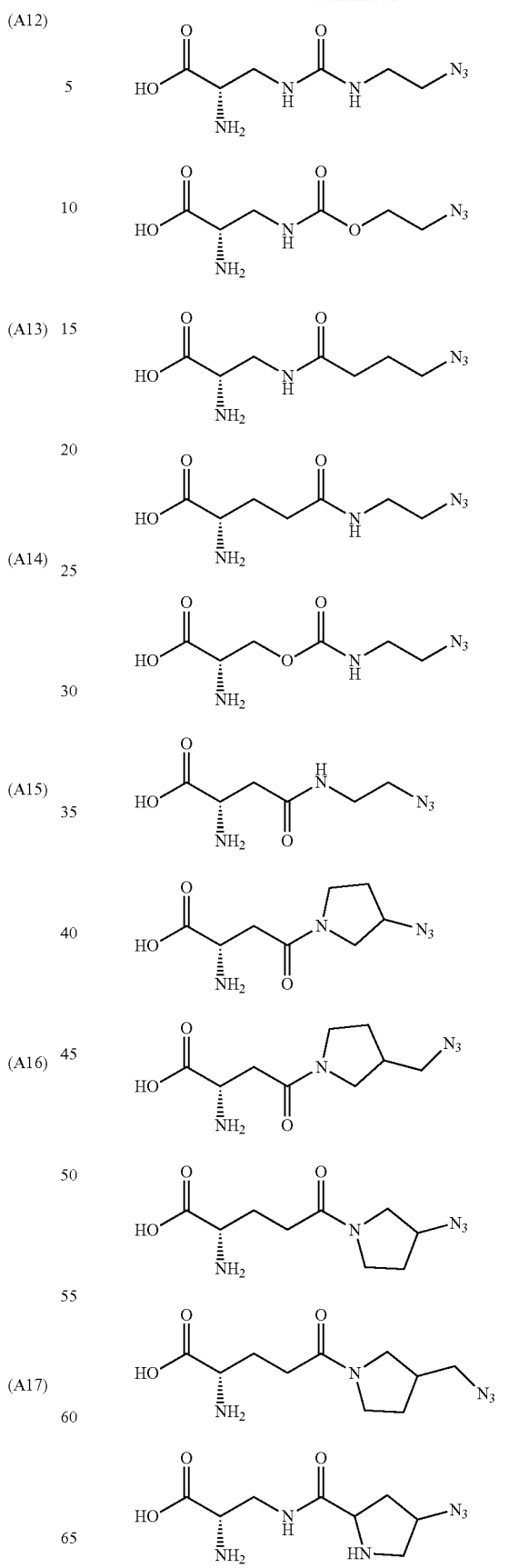

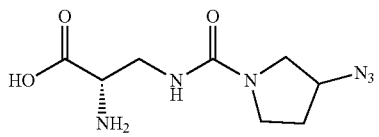
(A29)

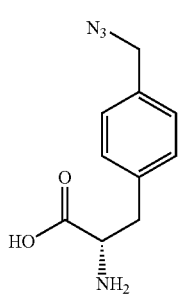
(A30)

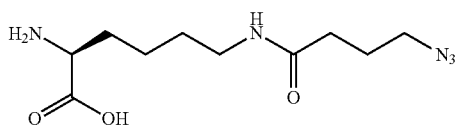
(A40)

In some embodiments, provided herein are polypeptides comprising modified tetrazine residues, provided herein, along with residues corresponding to any of the modified amino acids p-azido-phenylalanine, A1-A30 or A40.

Polypeptides

Provided herein are polypeptides comprising one or more modified amino acid residues at site-specific positions in an amino acid residue sequence of at least one polypeptide chain. In an embodiment, the compositions are antibodies comprising one or more modified amino acid residues at site-specific positions in the amino acid sequence of at least one polypeptide chain.

In certain embodiments, a polypeptide comprises at least one tetrazine-comprising amino acid residue as described herein. In certain embodiments, a polypeptide comprises at least two tetrazine-comprising amino acid residues as described herein. In certain embodiments, a polypeptide comprises at least three tetrazine-comprising amino acid residues as described herein.

In certain embodiments, a polypeptide comprises at least one tetrazine-comprising amino acid residue as described herein and at least one azide-comprising amino acid residue. In certain embodiments, a polypeptide comprises at least two tetrazine-comprising amino acid residues as described herein and at least one azide-comprising amino acid residue. In certain embodiments, a polypeptide comprises at least two tetrazine-comprising amino acid residues as described herein and at least two azide-comprising amino acid residues. In certain embodiments, a polypeptide comprises at least three tetrazine-comprising amino acid residues as described herein and at least one azide-comprising amino acid residue. In certain embodiments, a polypeptide comprises at least three tetrazine-comprising amino acid residues as described herein and at least two azide-comprising amino acid residues. In certain embodiments, a polypeptide comprises at least three tetrazine-comprising amino acid residues as described herein and at least three azide-comprising amino acid residues.

The polypeptide can share high sequence identity with any polypeptide recognized by those of skill in the art, i.e. a parent polypeptide. In certain embodiments, the amino acid residue sequence of the polypeptide is identical to the amino acid residue sequence of the parent polypeptide, other than the modified amino acid residues at site-specific positions. In further embodiments, the polypeptide provided herein can have one or more insertions, deletions or mutations relative to the parent polypeptide in addition to the one or more modified amino acid residues at the site-specific positions. In certain embodiments, the polypeptide provided herein can have a unique primary sequence, so long as it would be recognized as a polypeptide by those of skill in the art. In certain aspects of this embodiment, the polypeptide is an antibody.

The compositions and methods described herein provide for the incorporation of at least one modified amino acid residue into a polypeptide. In some embodiments, at least two modified amino acid residues are incorporated into a polypeptide. In some embodiments, at least three modified amino acids residues are incorporated into a polypeptide. In some embodiments, at least four modified amino acid residues are incorporated into a polypeptide. In some embodiments, at least five modified amino acid residues are incorporated into a polypeptide. In some embodiments, at least six modified amino acid residues are incorporated into a polypeptide. The modified amino acid residues may be present at any location on the polypeptide, including any terminal position or any internal position of the polypeptide. Preferably, the modified amino acid residue does not destroy the activity and/or the tertiary structure of the polypeptide relative to the homologous naturally-occurring polypeptide, unless such destruction of the activity and/or tertiary structure was one of the purposes of incorporating the modified amino acid residue into the polypeptide. Further, the incorporation of the modified amino acid residue into the polypeptide may modify to some extent the activity (e.g., manipulating the therapeutic effectiveness of the polypeptide, improving the safety profile of the polypeptide, adjusting the pharmacokinetics, pharmacologics and/or pharmacodynamics of the polypeptide (e.g., increasing water solubility, bioavailability, increasing serum half-life, increasing therapeutic half-life, modulating immunogenicity, modulating biological activity, or extending the circulation time), providing additional functionality to the polypeptide, incorporating a tag, label or detectable signal into the polypeptide, easing the isolation properties of the polypeptide, and any combination of the aforementioned modifications) and/or tertiary structure of the polypeptide relative to the homologous naturally-occurring polypeptide without fully causing destruction of the activity and/or tertiary structure. Such modifications of the activity and/or tertiary structure are often one of the goals of effecting such incorporations, although the incorporation of the modified amino acid residue into the polypeptide may also have little effect on the activity and/or tertiary structure of the polypeptide relative to the homologous naturally-occurring polypeptide. Correspondingly, polypeptides comprising modified amino acid residues, compositions comprising polypeptides with modified amino acid residues, methods for making such polypeptides and polypeptide compositions, methods for purifying, isolating, and characterizing such polypeptides and polypeptide compositions, and methods for using such polypeptides and polypeptide compositions are considered within the scope of the present disclosure. Further, the polypeptides comprising modified amino acid residues described herein may also be ligated to other polypeptides (including, by way of example, a polypeptide comprising modified amino acid residues or a naturally-occurring polypeptide).

The methods, compositions, strategies and techniques described herein are not limited to a particular type, class or family of polypeptides or proteins. Indeed, virtually any polypeptide may include at least one modified amino acid residue derived from the modified amino acids described herein. By way of example only, the polypeptide can be homologous to a therapeutic protein selected from the group consisting of: alpha-1 antitrypsin, angiostatin, antihemolytic factor, antibody, apolipoprotein, apoprotein, atrial natriuretic factor, atrial natriuretic polypeptide, atrial peptide, C—X—C chemokine, T39765, NAP-2, ENA-78, gro-a, gro-b, gro-c, IP-10, GCP-2, NAP-4, SDF-1, PF4, MIG, calcitonin, c-kit ligand, cytokine, CC chemokine, monocyte chemoattractant protein-1, monocyte chemoattractant protein-2, monocyte chemoattractant protein-3, monocyte inflammatory protein-1 alpha, monocyte inflammatory protein-1β, RANTES, 1309, R83915, R91733, HCC1, T58847, D31065, T64262, CD40, CD40 ligand, c-kit ligand, collagen, colony stimulating factor (CSF), complement factor 5a, complement inhibitor, complement receptor 1, cytokine, epithelial neutrophil activating peptide-78, MIP-16, MCP-1, epidermal growth factor (EGF), epithelial neutrophil activating peptide, erythropoietin (EPO), exfoliating toxin, Factor IX, Factor VII, Factor VIII, Factor X, fibroblast growth factor (FGF), fibrinogen, fibronectin, four-helical bundle protein, G-CSF, GLP-1, GM-CSF, glucocerebrosidase, gonadotropin, growth factor, growth factor receptor, GRF, hedgehog protein, hemoglobin, hepatocyte growth factor (hGF), hirudin, human growth hormone (hGH), human serum albumin, ICAM-1, ICAM-1 receptor, LFA-1, LFA-1 receptor, insulin, insulin-like growth factor (IGF), IGF-1, IGF-II, interferon (IFN), IFN-β, IFN-γ, interleukin (IL), IL-1, IL-2, IL-3, IL-4, IL-5, IL-6, IL-7, IL-8, IL-9, IL-10, IL-11, IL-12, keratinocyte growth factor (KGF), lactoferrin, leukemia inhibitory factor, luciferase, neurturin, neutrophil inhibitory factor (NIF), oncostatin M, osteogenic protein, oncogene product, paracitonin, parathyroid hormone, PD-ECSF, PDGF, peptide hormone, pleiotropin, protein A, protein G, PTH, pyrogenic exotoxin A, pyrogenic exotoxin B, pyrogenic exotoxin C, PYY, relaxin, renin, SCF, small biosynthetic protein, soluble complement receptor I, soluble I-CAM 1, soluble interleukin receptor, soluble TNF receptor, somatomedin, somatostatin, somatotropin, streptokinase, superantigens, staphylococcal enterotoxin, SEA, SEB, SECT, SEC2, SEC3, SED, SEE, steroid hormone receptor, superoxide dismutase, toxic shock syndrome toxin, thymosin alpha 1, tissue plasminogen activator, tumor growth factor (TGF), tumor necrosis factor, tumor necrosis factor alpha, tumor necrosis factor beta, tumor necrosis factor receptor (TNFR), VLA-4 protein, VCAM-1 protein, vascular endothelial growth factor (VEGF), urokinase, mos, ras, raf, met, p53, tat, fos, myc, jun, myb, rel, estrogen receptor, progesterone receptor, testosterone receptor, aldosterone receptor, LDL receptor, and corticosterone. In a related or further embodiment, the polypeptide comprising a modified amino acid residue may also be homologous to any polypeptide member of the growth hormone supergene family.

In certain embodiments, the modified amino acid residue can be at any position within the polypeptide, for example, at the N-terminus, at the C-terminus, or within the polypeptide. In advantageous embodiments, the modified amino acid residue is positioned at select locations in a polypeptide. These locations are identified as providing optimum sites for substitution with a modified amino acid residue. Each site is capable of bearing a modified amino acid residue with optimum structure, function and/or methods for producing the polypeptide.

In certain embodiments, a site-specific position for substitution provides a polypeptide that is stable. Stability can be measured by any technique apparent to those of skill in the art.

In certain embodiments, a site-specific position for substitution provides a polypeptide that is has optimal functional properties. For instance, the polypeptide can show little or no loss of binding affinity for its target compared to a polypeptide without the site-specific modified amino acid residue. In certain embodiments, the polypeptide can show enhanced binding compared to a polypeptide without the site-specific modified amino acid residue. In certain aspects of this embodiment, the polypeptide is an antibody and the target is an antigen.

In certain embodiments, a site-specific position for substitution provides a polypeptide that can be made advantageously. For instance, in certain embodiments, the polypeptide shows advantageous properties in its methods of synthesis, for example as discussed herein. In certain embodiments, the polypeptide can show little or no loss in yield in production compared to a polypeptide without the site-specific modified amino acid residue. In certain embodiments, the polypeptide can show enhanced yield in production compared to a polypeptide without the site-specific modified amino acid residue. In certain embodiments, the polypeptide can show little or no loss of tRNA suppression, for example as described herein, compared to a polypeptide without the site-specific modified amino acid residue. In certain embodiments, the polypeptide can show enhanced tRNA suppression, for example as described herein, in production compared to a polypeptide without the site-specific modified amino acid residue. In certain aspects of this embodiment, the polypeptide is an antibody.

In certain embodiments, a site-specific position for substitution provides a polypeptide that has advantageous solubility. In certain embodiments, the polypeptide can show little or no loss in solubility compared to a polypeptide without the site-specific modified amino acid residue. In certain embodiments, the polypeptide can show enhanced solubility compared to a polypeptide without the site-specific modified amino acid residue. In certain aspects of this embodiment, the polypeptide is an antibody.

In certain embodiments, a site-specific position for substitution provides a polypeptide that has advantageous expression. In certain embodiments, the polypeptide can show little or no loss in expression compared to a polypeptide without the site-specific modified amino acid residue. In certain embodiments, the polypeptide can show enhanced expression compared to a polypeptide without the site-specific modified amino acid residue. In certain aspects of this embodiment, the polypeptide is an antibody.

In certain embodiments, a site-specific position for substitution provides a polypeptide that has advantageous folding. In certain embodiments, the polypeptide can show little or no loss in proper folding compared to a polypeptide without the site-specific modified amino acid residue. In certain embodiments, the polypeptide can show enhanced folding compared to a polypeptide without the site-specific modified amino acid residue. In certain aspects of this embodiment, the polypeptide is an antibody.

In certain embodiments, a site-specific position for substitution provides a polypeptide that is capable of advantageous conjugation. As described herein, several modified amino acid residues have side chains or functional groups that facilitate conjugation of the polypeptide to one or more agents, either directly or via a linker. In certain embodiments, the polypeptide can show enhanced conjugation efficiency compared to a polypeptide without the same or other modified amino acid residues at other positions. In certain embodiments, the polypeptide can show enhanced conjugation yield compared to a polypeptide without the same or other modified amino acid residues at other positions. In certain embodiments, the polypeptide can show enhanced conjugation specificity compared to a polypeptide without the same or other modified amino acid residues at other positions. In certain aspects of this embodiment, the polypeptide is an antibody.

In certain embodiments, further provided herein are conservatively modified variants of the polypeptides described herein. Conservatively modified variants of a polypeptide include one or more insertions, deletions or substitutions that do not disrupt the structure and/or function of the polypeptide when evaluated by one of skill in the art. In certain embodiments, conservatively modified variants include 20 or fewer amino acid residue insertions, deletions or substitutions. In certain embodiments, conservatively modified variants include 15 or fewer amino acid residue insertions, deletions or substitutions. In certain embodiments, conservatively modified variants include 10 or fewer amino acid residue insertions, deletions or substitutions. In certain embodiments, conservatively modified variants include 9 or fewer amino acid residue insertions, deletions or substitutions. In certain embodiments, conservatively modified variants include 8 or fewer amino acid residue insertions, deletions or substitutions. In certain embodiments, conservatively modified variants include 7 or fewer amino acid residue insertions, deletions or substitutions. In certain embodiments, conservatively modified variants include 6 or fewer amino acid residue insertions, deletions or substitutions. In certain embodiments, conservatively modified variants include 5 or fewer amino acid residue insertions, deletions or substitutions. In certain embodiments, conservatively modified variants include 4 or fewer amino acid residue insertions, deletions or substitutions. In certain embodiments, conservatively modified variants include 3 or fewer amino acid residue insertions, deletions or substitutions. In certain embodiments, conservatively modified variants include 2 or fewer amino acid residue insertions, deletions or substitutions. In certain embodiments, conservatively modified variants include 1 amino acid residue insertion, deletion or substitution. In particular embodiments the substitutions are conservative, substituting an amino acid residue within the same class, as described herein. In particular embodiments, the polypeptide is an antibody.

In certain embodiments, the polypeptides can be modified to modulate structure, stability and/or activity. In such embodiments, the modifications can be conservative or non-conservative. The modifications need only be suitable to the practitioner carrying out the methods and using the compositions described herein. In certain embodiments where the polypeptide is an antibody, the modifications decrease but do not eliminate antigen binding affinity. In certain embodiments where the polypeptide is an antibody, the modifications increase antigen binding affinity. In certain embodiments, the modifications enhance structure or stability of the polypeptide. In certain embodiments, the modifications reduce but do not eliminate structure or stability of the polypeptide. In certain embodiments, modified variants include 20 or fewer amino acid residue insertions, deletions or substitutions. In certain embodiments, modified variants include 15 or fewer amino acid residue insertions, deletions or substitutions. In certain embodiments, modified variants include 10 or fewer amino acid residue insertions, deletions or substitutions. In certain embodiments, modified variants include 9 or fewer amino acid residue insertions, deletions or substitutions. In certain embodiments, modified variants include 8 or fewer amino acid residue insertions, deletions or substitutions. In certain embodiments, modified variants include 7 or fewer amino acid residue insertions, deletions or substitutions. In certain embodiments, modified variants include 6 or fewer amino acid residue insertions, deletions or substitutions. In certain embodiments, modified variants include 5 or fewer amino acid residue insertions, deletions or substitutions. In certain embodiments, modified variants include 4 or fewer amino acid residue insertions, deletions or substitutions. In certain embodiments, modified variants include 3 or fewer amino acid residue insertions, deletions or substitutions. In certain embodiments, modified variants include 2 or fewer amino acid residue insertions, deletions or substitutions. In certain embodiments, modified variants include 1 amino acid residue insertion, deletion or substitution.

Also within the scope are post-translationally modified variants. Any of the polypeptides provided herein can be post-translationally modified in any manner recognized by those of skill in the art. Typical post-translational modifications for polypeptides include interchain disulfide bonding, intrachain disulfide bonding, N-linked glycosylation and proteolysis. Also provided herein are other post-translationally modified polypeptides having modifications such as phosphorylation, O-linked glycosylation, methylation, acetylation, lipidation, GPI anchoring, myristoylation and prenylation. The post-translational modification can occur during production, in vivo, in vitro or otherwise. In certain embodiments, the post-translational modification can be an intentional modification by a practitioner, for instance, using the methods provided herein. In particular embodiments, the polypeptide is an antibody.

Further included are polypeptides fused to further peptides or polypeptides. Exemplary fusions include, but are not limited to, e.g., a methionyl polypeptide in which a methionine is linked to the N-terminus of the polypeptide resulting from the recombinant expression, fusions for the purpose of purification (including but not limited to, to poly-histidine or affinity epitopes), fusions for the purpose of linking to other biologically active molecules, fusions with serum albumin binding peptides, and fusions with serum proteins such as serum albumin. The polypeptides may comprise protease cleavage sequences, reactive groups, polypeptide-binding domains (including but not limited to, FLAG or poly-His) or other affinity based sequences (including but not limited to e.g., GST). The polypeptides may also comprise linked molecules (including but not limited to, biotin) that improve detection (including but not limited to, GFP), purification or other features of the polypeptide. In certain embodiments, the polypeptides comprise a C-terminal affinity sequence that facilitates purification of full length polypeptides. In certain embodiments, such C-terminal affinity sequence is a poly-His sequence, e.g., a 6-His sequence. In particular embodiments, the polypeptide is an antibody.

Also provided herein are polypeptides that are conjugated to one or more conjugation moieties. The conjugation moiety can be any conjugation moiety deemed useful to one of skill in the art. For instance, the conjugation moiety can be a polymer, such as polyethylene glycol, that can improve the stability of the polypeptide in vitro or in vivo. The conjugation moiety can have therapeutic activity, thereby yielding a polypeptide-drug conjugate. The conjugation moiety can be a payload that is harmful to target cells. The conjugation moiety can be a label useful for detection or diagnosis. In certain embodiments, the conjugation moiety is linked to the polypeptide via a direct covalent bond. In certain embodiments, the conjugation moiety is linked to the polypeptide via a linker. In advantageous embodiments, the conjugation moiety or the linker is attached via one of the modified amino acid residues of the polypeptide. Exemplary conjugation moieties and linkers are described herein. In certain embodiments, the conjugation moiety is linked to the polypeptide via a non-covalent interaction. In particular embodiments, the polypeptide is an antibody.

The parent polypeptide can be any polypeptide known to those of skill in the art, or later discovered, without limitation. In particular embodiments, the polypeptide is an antibody. The parent polypeptide may be substantially encoded by a polypeptide gene or polypeptide genes from any organism, including but not limited to humans, mice, rats, rabbits, chickens, camels, llamas, dromedaries, monkeys, particularly mammals and particularly human and particularly mice and rats. In one embodiment, the parent polypeptide may be fully human, obtained for example from a patient or subject, by using transgenic mice or other animals (see Bruggemann & Taussig, 1997, Curr. Opin. Biotechnol. 8:455-458 for antibody examples) or human polypeptide libraries coupled with selection methods (see Griffiths & Duncan, 1998, Curr. Opin. Biotechnol. 9:102-108 for antibody examples). The parent polypeptide may be from any source, including artificial or naturally occurring. For example, a parent polypeptide can be an engineered polypeptide, including but not limited to chimeric polypeptides and humanized polypeptides (see Clark, 2000, Immunol. Today 21:397-402 for antibody examples) or derived from a combinatorial library. In addition, the parent polypeptide may be an engineered variant of a polypeptide that is substantially encoded by one or more natural polypeptide genes. In some embodiments, the parent polypeptide is a polypeptide that has been identified by affinity maturation.

Parent polypeptides can be any polypeptide known in the art or any polypeptide developed by those of skill in the art without limitation. Antibody examples include, but are not limited to anti-TNF antibody (U.S. Pat. No. 6,258,562), anti-IL-12 and/or anti-IL-12p40 antibody (U.S. Pat. No. 6,914,128); anti-IL-18 antibody (U.S. Patent Publication No. 2005/0147610), anti-05, anti-CBL, anti-CD147, anti-gp120, anti-VLA-4, anti-CD11a, anti-CD18, anti-VEGF, anti-CD40L, anti CD-40 (e.g., see PCT Publication No. WO 2007/124299) anti-Id, anti-ICAM-1, anti-CXCL13, anti-CD2, anti-EGFR, anti-TGF-β2, anti-HGF, anti-cMet, anti DLL-4, anti-NPR1, anti-PLGF, anti-ErbB3, anti-E-selectin, anti-Fact VII, anti-Her2/neu, anti-F gp, anti-CD11/18, anti-CD14, anti-ICAM-3, anti-RON, anti-SOST, anti CD-19, anti-CD80 (e.g., see PCT Publication No. WO 2003/039486, anti-CD4, anti-CD3, anti-CD23, anti-β2-integrin, anti-α4β7, anti-CD52, anti-HLA DR, anti-CD22 (e.g., see U.S. Pat. No. 5,789,554), anti-CD20, anti-MIF, anti-CD64 (FcR), anti-TCR α and/or β, anti-CD2, anti-Hep B, anti-CA 125, anti-EpCAM, anti-gp120, anti-CMV, anti-gpIIbIIIa, anti-IgE, anti-CD25, anti-CD33, anti-HLA, anti-IGF1,2, anti-IGFR, anti-VNRintegrin, anti-IL-1α, anti-IL-1β, anti-IL-1 receptor, anti-IL-2 receptor, anti-IL-4, anti-IL-4 receptor, anti-IL5, anti-IL-5 receptor, anti-IL-6, anti-IL-8, anti-IL-9, anti-IL-13, anti-IL-13 receptor, anti-IL-17, anti-IL-6R, anti-RANKL, anti-NGF, anti-DKK, anti-αVβ3, anti-IL-17A, anti-IL23p19 and anti-IL-23 (see Presta, L. G. (2005) J. Allergy Clin. Immunol. 116: 731-6).

Parent polypeptides may also be selected from various therapeutic polypeptides approved for use, in clinical trials, or in development for clinical use. Antibody examples of such therapeutic polypeptides include, but are not limited to, rituximab (Rituxan®, IDEC/Genentech/Roche) (see, for example, U.S. Pat. No. 5,736,137), a chimeric anti-CD20 antibody approved to treat Non-Hodgkin's lymphoma; HuMax-CD20, an anti-CD20 currently being developed by Genmab, an anti-CD20 antibody described in U.S. Pat. No. 5,500,362, AME-133 (Applied Molecular Evolution), hA20 (Immunomedics, Inc.), HumaLYM (Intracel), and PRO70769 (PCT Application No. PCT/US2003/040426), trastuzumab (Herceptin®, Genentech) (see, for example, U.S. Pat. No. 5,677,171), a humanized anti-Her2/neu antibody approved to treat breast cancer; pertuzumab (rhuMab-2C4, Omnitarg®), currently being developed by Genentech; an anti-Her2 antibody (U.S. Pat. No. 4,753,894; cetuximab (Erbitux®, Imclone) (U.S. Pat. No. 4,943,533; PCT Publication No. WO 96/40210), a chimeric anti-EGFR antibody in clinical trials for a variety of cancers; ABX-EGF (U.S. Pat. No. 6,235,883), currently being developed by Abgenix-Immunex-Amgen; HuMax-EGFr (U.S. Pat. No. 7,247,301), currently being developed by Genmab; 425, EMD55900, EMD62000, and EMD72000 (Merck KGaA) (U.S. Pat. No. 5,558,864; Murthy, et al. (1987) Arch. Biochem. Biophys. 252(2): 549-60; Rodeck, et al. (1987) J. Cell. Biochem. 35(4): 315-20; Kettleborough, et al. (1991) Protein Eng. 4(7): 773-83); ICR62 (Institute of Cancer Research) (PCT Publication No. WO 95/20045; Modjtahedi, et al. (1993) J. Cell. Biophys. 22(1-3): 129-46; Modjtahedi, et al. (1993) Br. J. Cancer 67(2): 247-53; Modjtahedi, et al. (1996) Br. J. Cancer 73(2): 228-35; Modjtahedi, et al. (2003) Int. J. Cancer 105(2): 273-80); TheraCIM hR3 (YM Biosciences, Canada and Centro de Immunologia Molecular, Cuba (U.S. Pat. No. 5,891,996; U.S. Pat. No. 6,506,883; Mateo, et al. (1997) Immunotechnol. 3(1): 71-81); mAb-806 (Ludwig Institute for Cancer Research, Memorial Sloan-Kettering) (Jungbluth, et al. (2003) Proc. Natl. Acad. Sci. USA. 100(2): 639-44); KSB-102 (KS Biomedix); MR1-1 (IVAX, National Cancer Institute) (PCT Publication No. WO 01/62931A2); and $SC_{100}$ (Scancell) (PCT Publication No. WO 01/88138); alemtuzumab (Campath®, Millenium), a humanized mAb currently approved for treatment of B-cell chronic lymphocytic leukemia; muromonab-CD3 (Orthoclone OKT3®), an anti-CD3 antibody developed by Ortho Biotech/Johnson & Johnson, ibritumomab tiuxetan (Zevalin®), an anti-CD20 antibody developed by IDEC/Schering AG, gemtuzumab ozogamicin (Mylotarg®), an anti-CD33 (p67 protein) antibody developed by Celltech/Wyeth, alefacept (Amevive®), an anti-LFA-3 Fc fusion developed by Biogen), abciximab (ReoPro®), developed by Centocor/Lilly, basiliximab (Simulect®), developed by Novartis, palivizumab (Synagis®), developed by Medimmune, infliximab (Remicade®), an anti-TNFα antibody developed by Centocor, adalimumab (Humira®), an anti-TNFα antibody developed by Abbott, Humicade®, an anti-TNFα antibody developed by Celltech, golimumab (CNTO-148), a fully human TNF antibody developed by Centocor, etanercept (Enbrel®), an p75 TNF receptor Fc fusion developed by Immunex/Amgen, Ienercept, an p55TNF receptor Fc fusion previously developed by Roche, ABX-CBL, an anti-CD147 antibody being developed by Abgenix, ABX-IL8, an anti-IL8 antibody being developed by Abgenix, ABX-MA1, an anti-MUC18 antibody being developed by Abgenix, Pemtumomab (R1549, 90Y-muHMFG1), an anti-MUC1 in development by Antisoma, Therex (R1550), an anti-MUC1 antibody being developed by Antisoma, AngioMab (AS1405), being developed by Antisoma, HuBC-1, being developed by Antisoma, Thioplatin (AS1407) being developed by Antisoma, Antegren® (natalizumab), an anti-α-4-β-1 (VLA-4) and α-4-β-7 antibody being developed by Biogen, VLA-1 mAb, an anti-VLA-1 integrin antibody being developed by Biogen, LTBR mAb, an anti-lymphotoxin beta receptor (LTBR) antibody being developed by Biogen, CAT-152, an anti-TGF-β antibody being developed by Cambridge Antibody Technology, ABT 874 (J695), an anti-IL-12 p40 antibody being developed by Abbott, CAT-192, an anti-TGFβ1 antibody being developed by Cambridge Antibody Technology and Genzyme, CAT-213, an anti-Eotaxinl antibody being developed by Cambridge Antibody Technology, LymphoStat-B® an anti-Blys antibody being developed by Cambridge Antibody Technology and Human Genome Sciences Inc., TRAIL-R1 mAb, an anti-TRAIL-R1 antibody being developed by Cambridge Antibody Technology and Human Genome Sciences, Inc., Avastin® bevacizumab, rhuMAb-VEGF), an anti-VEGF antibody being developed by Genentech, an anti-HER receptor family antibody being developed by Genentech, Anti-Tissue Factor (ATF), an anti-Tissue Factor antibody being developed by Genentech, Xolair® (Omalizumab), an anti-IgE antibody being developed by Genentech, Raptiva® (Efalizumab), an anti-CD11a antibody being developed by Genentech and Xoma, MLN-02 Antibody (formerly LDP-02), being developed by Genentech and Millenium Pharmaceuticals, HuMax CD4, an anti-CD4 antibody being developed by Genmab, HuMax-1L15, an anti-1L15 antibody being developed by Genmab and Amgen, HuMax-Inflam, being developed by Genmab and Medarex, HuMax-Cancer, an anti-Heparanase I antibody being developed by Genmab and Medarex and Oxford GcoSciences, HuMax-Lymphoma, being developed by Genmab and Amgen, HuMax-TAC, being developed by Genmab, IDEC-131, and anti-CD40L antibody being developed by IDEC Pharmaceuticals, IDEC-151 (Clenoliximab), an anti-CD4 antibody being developed by IDEC Pharmaceuticals, IDEC-114, an anti-CD80 antibody being developed by IDEC Pharmaceuticals, IDEC-152, an anti-CD 23 being developed by IDEC Pharmaceuticals, anti-macrophage migration factor (MIF) antibodies being developed by IDEC Pharmaceuticals, BEC2, an anti-idiotypic antibody being developed by Imclone, IMC-1C11, an anti-KDR antibody being developed by Imclone, $DC_{101}$, an anti-flk-1 antibody being developed by Imclone, anti-VE cadherin antibodies being developed by Imclone, CEA-Cide® (Iabetuzumab), an anti-carcinoembryonic antigen (CEA) antibody being developed by Immunomedics, LymphoCide® (Epratuzumab), an anti-CD22 antibody being developed by Immunomedics, AFP-Cide, being developed by Immunomedics, MyelomaCide, being developed by Immunomedics, LkoCide, being developed by Immunomedics, ProstaCide, being developed by Immunomedics, MDX-010, an anti-CTLA4 antibody being developed by Medarex, MDX-060, an anti-CD30 antibody being developed by Medarex, MDX-070 being developed by Medarex, MDX-018 being developed by Medarex, Osidem® (IDM-1), and anti-Her2 antibody being developed by Medarex and Immuno-Designed Molecules, HuMax®-CD4, an anti-CD4 antibody being developed by Medarex and Genmab, HuMax-IL15, an anti-IL15 antibody being developed by Medarex and Genmab, CNTO 148, an anti-TNFα antibody being developed by Medarex and Centocor/J&J, CNTO 1275, an anti-cytokine antibody being developed by Centocor/J&J, MOR101 and MOR102, anti-intercellular adhesion molecule-1 (ICAM-1) (CD54) antibodies being developed by MorphoSys, MOR201, an anti-fibroblast growth factor receptor 3 (FGFR-3) antibody being developed by MorphoSys, Nuvion® (visilizumab), an anti-CD3 antibody being developed by Protein Design Labs, HuZAF®, an anti-gamma interferon antibody being developed by Protein Design Labs, Anti-α5β1 Integrin, being developed by Protein Design Labs, anti-IL-12, being developed by Protein Design Labs, ING-1, an anti-Ep-CAM antibody being developed by Xoma, Xolair® (Omalizumab) a humanized anti-IgE antibody developed by Genentech and Novartis, and MLN01, an anti-Beta2 integrin antibody being developed by Xoma. In some embodiments, the therapeutics include KRN330 (Kirin); huA33 antibody (A33, Ludwig Institute for Cancer Research); CNTO 95 (alpha V integrins, Centocor); MEDI-522 (αVβ3integrin, Medimmune); volociximab (αVβ1 integrin, Biogen/PDL); Human mAb 216 (B cell glycosolated epitope, NCl); BITE MT103 (bispecific CD19×CD3, Medimmune); 4G7×H22 (Bispecific BcellxFcγR1, Medarex/Merck KGa); rM28 (Bispecific CD28×MAPG, EP Patent No. EP1444268); MDX447 (EMD 82633) (Bispecific CD64×EGFR, Medarex); Catumaxomab (removab) (Bispecific EpCAMx anti-CD3, Trion/Fres); Ertumaxomab (bispecific HER2/CD3, Fresenius Biotech); oregovomab (OvaRex) (CA-125, ViRexx); Rencarex® (WX G250) (carbonic anhydrase IX, Wilex); CNTO 888 (CCL2, Centocor); $TRC_{105}$ (CD105 (endoglin), Tracon); BMS-663513 (CD137 agonist, Brystol Myers Squibb); MDX-1342 (CD19, Medarex); Siplizumab (MEDI-507) (CD2, Medimmune); Ofatumumab (Humax-CD20) (CD20, Genmab); Rituximab (Rituxan) (CD20, Genentech); veltuzumab (hA20) (CD20, Immunomedics); Epratuzumab (CD22, Amgen); lumiliximab (IDEC 152) (CD23, Biogen); muromonab-CD3 (CD3, Ortho); HuM291 (CD3 fc receptor, PDL Biopharma); HeFi-1, CD30, NCl); MDX-060 (CD30, Medarex); MDX-1401 (CD30, Medarex); SGN-30 (CD30, Seattle Genentics); SGN-33 (Lintuzumab) (CD33, Seattle Genentics); Zanolimumab (HuMax-CD4) (CD4, Genmab); HCD122 (CD40, Novartis); SGN-40 (CD40, Seattle Genentics); Campathlh (Alemtuzumab) (CD52, Genzyme); MDX-1411 (CD70, Medarex); hLL1 (EPB-1) (CD74.38, Immunomedics); Galiximab (IDEC-144) (CD80, Biogen); MT293 (TRC093/D93) (cleaved collagen, Tracon); HuLuc63 (CS1, PDL Pharma); ipilimumab (MDX-010) (CTLA4, Brystol Myers Squibb); Tremelimumab (Ticilimumab, CP-675,2) (CTLA4, Pfizer); HGS-ETR1 (Mapatumumab) (DR4TRAIL-R1 agonist, Human Genome Science/Glaxo Smith Kline); AMG-655 (DR5, Amgen); Apomab (DR5, Genentech); CS-1008 (DR5, Daiichi Sankyo); HGS-ETR2 (lexatumumab) (DR5TRAIL-R2 agonist, HGS); Cetuximab (Erbitux) (EGFR, Imclone); IMC-11F8, (EGFR, Imclone); Nimotuzumab (EGFR, YM Bio); Panitumumab (Vectabix) (EGFR, Amgen); Zalutumumab (HuMaxEGFr) (EGFR, Genmab); CDX-110 (EGFRvIII, AVANT Immunotherapeutics); adecatumumab (MT201) (Epcam, Merck); edrecolomab (Panorex, 17-1A) (Epcam, Glaxo/Centocor); MORAb-003 (folate receptor a, Morphotech); KW-2871 (ganglioside GD3, Kyowa); MORAb-009 (GP-9, Morphotech); CDX-1307 (MDX-1307) (hCGb, Celldex); Trastuzumab (Herceptin) (HER2, Celldex); Pertuzumab (rhuMAb 2C4) (HER2 (DI), Genentech); apolizumab (HLA-DR β chain, PDL Pharma); AMG-479 (IGF-1R, Amgen); anti-IGF-1R R1507 (IGF1-R, Roche); CP 751871 (IGF1-R, Pfizer); IMC-A12 (IGF1-R, Imclone); BIIB022 (IGF-1R, Biogen); Mik-β-1 (IL-2Rb (CD122), Hoffman LaRoche); CNTO 328 (IL6, Centocor); Anti-KIR (1-7F9) (Killer cell Ig-like Receptor (KIR), Novo); Hu3S193 (Lewis (y), Wyeth, Ludwig Institute of Cancer Research); hCBE-11 (LTβR, Biogen); HuHMFG1 (MUC1, Antisoma/NC1); RAV12 (N-linked carbohydrate epitope, Raven); CAL (parathyroid hormone-related protein (PTH-rP), University of California); CT-011 (PD1, CureTech); MDX-1106 (ono-4538) (PD1, Medarex/Ono); MAb CT-011 (PD1, Curetech); IMC-3G3 (PDGFRa, Imclone); bavituximab (phosphatidylserine, Peregrine); huJ591 (PSMA, Cornell Research Foundation); muJ591 (PSMA, Cornell Research Foundation); $GC_{1008}$ (TGFb (pan) inhibitor (IgG4), Genzyme); Infliximab (Remicade) (TNFa, Centocor); A27.15 (transferrin receptor, Salk Institute, INSERN WO 2005/111082); E2.3 (transferrin receptor, Salk Institute); Bevacizumab (Avastin) (VEGF, Genentech); HuMV833 (VEGF, Tsukuba Research Lab, PCT Publication No. WO/2000/034337, University of Texas); IMC-18F1 (VEGFR1, Imclone); IMC-1121 (VEGFR2, Imclone).

In certain embodiments, the polypeptides provided herein comprise one modified amino acid residue at a site-specific position. In certain embodiments, the polypeptides provided herein comprise two modified amino acid residues at site-specific positions. In certain embodiments, the polypeptides provided herein comprise three modified amino acid residues at site-specific positions. In certain embodiments, the polypeptides provided herein comprise more than three modified amino acid residues at site-specific positions.

Antibodies

In certain embodiments, provided herein are antibodies comprising one or more polypeptides that comprise one or more modified amino acid residues described herein. In certain embodiments, the antibody is a heterotetramer comprising two identical light (L) chains and two identical heavy (H) chains. In some embodiments, incorporation of different light chains and/or heavy chains may be used to produce antibodies with more than one specificity (e.g., bispecificity). Thus, in certain embodiments, the antibody comprises two different light chains and a single heavy chain. In some embodiments, the antibody comprises two different heavy chains and a single light chain. In some embodiments the antibody comprises two different light chains and two different heavy chains.

Each light chain can be linked to a heavy chain by a disulfide bond. Each heavy chain can be linked to the other heavy chain by one or more disulfide bonds. Each heavy chain and each light chain can also have one or more intrachain disulfide bonds. As is known to those of skill in the art, each heavy chain typically comprises a variable domain ($V_H$) followed by a number of constant domains. Each light chain typically comprises a variable domain ($V_L$) and a constant domain. As is known to those of skill in the art, antibodies typically have selective affinity for their target molecules, i.e. antigens.

The antibodies provided herein can have any polypeptide form known to those of skill in the art. They can be full-length or fragments. Exemplary full length antibodies include IgA, IgA1, IgA2, IgD, IgE, IgG, IgG1, IgG2, IgG3, IgG4, and IgM. Exemplary fragments include Fv, Fab, Fc, sFv, and other fragments known in the art and discussed herein.

The one or more modified amino acid residues can be located at selected site-specific positions in at least one polypeptide chain of an antibody. The polypeptide chain can be any polypeptide chain of the antibody without limitation, including either light chain or either heavy chain. The site-specific position can be in any domain of the antibody, including any variable domain and any constant domain.

Examples of Site-Specific Positions for Substitution: Heavy Chains

In this disclosure, the Kabat or Chothia numbering system is used to refer to amino acid residues in positions 117 or less of a heavy chain or heavy chain variable region, and positions 107 or less of a light chain or light chain variable region. As is customary in the art, the EU numbering system is used to refer to amino acid residues in positions 118 or greater of a heavy chain and positions 108 or greater of a light chain.

The site-specific positions for substituting can be described with any polypeptide nomenclature system known to those of skill in the art, including the Kabat or Chothia numbering systems, the EU numbering system, or by reference to an amino acid residue or nucleotide sequence (e.g., by reference to SEQ ID NO:1 or SEQ ID NO:2, representing an exemplary heavy chain and an exemplary light chain, respectively). Table 1 provides the correspondence between Kabat, Chothia, and EU residue numbers, and the residue numbers in SEQ ID NO:1 and SEQ ID NO: 2. The term "minus 1", when referring to Kabat or Chothia numbers, refers to an amino acid residue that directly precedes the first (i.e., H001 or L001) residue of the heavy chain or the light chain. Residue "minus 1" may occur, for example, in a sequence that is part of a leader sequence that is N-terminal to the heavy chain or light chain. Such leader sequences may be naturally occurring or engineered.

In an embodiment wherein the polypeptide is an antibody, the site-specific positions are selected from heavy chain residues H005, H023, H042, H065, H074, and H084 according to the Kabat or Chothia numbering schemes; and residues H118, H119, H132, H134, H135, H136, H137, H138, H139, H155, H160, H162, H165, H172, H174, H176, H177, H191, H194, H219, H238, H239, H241, H243, H246, H262, H264, H265, H267, H268, H269, H270, H271, H272, H274, H275, H278, H280, H281, H282, H283, H286, H289, H292, H293, H294, H295, H296, H297, H298, H299, H300, H301, H303, H305, H317, H320, H324, H326, H327, H329, H330, H332, H333, H334, H335, H337, H339, H340, H344, H355, H356, H358, H359, H360, H375, H383, H384, H386, H389, H392, H398, H420, H421, H436, and H438 according to the EU numbering scheme (see Table 2, "SSHC-1" and the corresponding positions of the representative heavy chain polypeptide according to SEQ ID NO:1). Specifically provided herein are antibodies comprising one or more modified amino acid residues at one or more of these positions; antibodies comprising one or more modified amino acid residues at two or more of these positions; antibodies comprising one or more modified amino acid residues at three or more of these positions; antibodies comprising two or more modified amino acid residues at one or more of these positions; antibodies comprising two or more modified amino acid residues at two or more of these positions; antibodies comprising two or more modified amino acid residues at three or more of these positions; antibodies comprising three or more modified amino acid residues at one or more of these positions; antibodies comprising three or more modified amino acid residues at two or more of these positions; and antibodies comprising three or more modified amino acid residues at three or more of these positions.

In certain embodiments, the site-specific positions are selected from Kabat or Chothia heavy chain residues H005, H023, H074, and H084; and EU heavy chain residues H118, H119, H132, H134, H135, H136, H137, H139, H160, H162, H165, H172, H191, H194, H239, H241, H246, H267, H268, H269, H270, H271, H272, H274, H275, H280, H281, H282, H283, H286, H289, H292, H293, H294, H295, H296, H297, H298, H299, H300, H301, H303, H305, H317, H320, H324, H326, H327, H329, H330, H332, H333, H334, H335, H337, H339, H340, H344, H355, H359, H375, H386, H389, H392, H398, H420, H421, and H438 (see Table 2, "SSHC-2" and the corresponding positions of the representative heavy chain polypeptide according to SEQ ID NO:1). Specifically provided herein are antibodies comprising one or more modified amino acid residues at one or more of these positions; antibodies comprising one or more modified amino acid residues at two or more of these positions; antibodies comprising one or more modified amino acid residues at three or more of these positions; antibodies comprising two or more modified amino acid residues at one or more of these positions; antibodies comprising two or more modified amino acid residues at two or more of these positions; antibodies comprising two or more modified amino acid residues at three or more of these positions; antibodies comprising three or more modified amino acid residues at one or more of these positions; antibodies comprising three or more modified amino acid residues at two or more of these positions; and antibodies comprising three or more modified amino acid residues at three or more of these positions.

In certain embodiments, the site-specific positions are selected from Kabat or Chothia heavy chain residues H005 and H084; and EU heavy chain residues H118, H132, H136, H239, H293, H334, H355, H359, and H389 (see Table 2, "SSHC-3" and the corresponding positions of the representative heavy chain polypeptide according to SEQ ID NO:1). Specifically provided herein are antibodies comprising one or more modified amino acid residues at one or more of these positions; antibodies comprising one or more modified amino acid residues at two or more of these positions; antibodies comprising one or more modified amino acid residues at three or more of these positions; antibodies comprising two or more modified amino acid residues at one or more of these positions; antibodies comprising two or more modified amino acid residues at two or more of these positions; antibodies comprising two or more modified amino acid residues at three or more of these positions; antibodies comprising three or more modified amino acid residues at one or more of these positions; antibodies comprising three or more modified amino acid residues at two or more of these positions; and antibodies comprising three or more modified amino acid residues at three or more of these positions.

In certain embodiments, the site-specific positions are selected from Kabat or Chothia heavy chain residues H023 and H074; and EU heavy chain residues H119, H134, H135, H137, H139, H160, H162, H165, H172, H191, H194, H241, H246, H267, H268, H269, H270, H271, H272, H274, H275, H280, H281, H282, H283, H286, H289, H292, H294, H295, H296, H297, H298, H299, H300, H301, H303, H305, H317, H320, H324, H326, H327, H329, H330, H332, H333, H335, H337, H339, H340, H344, H355, H375, H386, H392, H398, H420, H421, and H438 (see Table 2, "SSHC-4" and the corresponding positions of the representative heavy chain polypeptide according to SEQ ID NO:1). Specifically provided herein are antibodies comprising one or more modified amino acid residues at one or more of these positions; antibodies comprising one or more modified amino acid residues at two or more of these positions; antibodies comprising one or more modified amino acid residues at three or more of these positions; antibodies comprising two or more modified amino acid residues at one or more of these positions; antibodies comprising two or more modified amino acid residues at two or more of these positions; antibodies comprising two or more modified amino acid residues at three or more of these positions; antibodies comprising three or more modified amino acid residues at one or more of these positions; antibodies comprising three or more modified amino acid residues at two or more of these positions; and antibodies comprising three or more modified amino acid residues at three or more of these positions.

In certain embodiments, provided herein are antibodies comprising one or more modified amino acid residues at one or more positions selected from Kabat or Chothia residues H042 and H065; and EU residues H138, H155, H174, H176, H177, H219, H238, H243, H262, H264, H265, H278, H356, H358, H360, H383, H384 and H436 (see Table 2, "SSHC-5" and the corresponding positions of the representative heavy chain polypeptide according to SEQ ID NO:1). Specifically provided herein are antibodies comprising one or more modified amino acid residues at one or more of these positions; antibodies comprising one or more modified amino acid residues at two or more of these positions; antibodies comprising one or more modified amino acid residues at three or more of these positions; antibodies comprising two or more modified amino acid residues at one or more of these positions; antibodies comprising two or more modified amino acid residues at two or more of these positions; antibodies comprising two or more modified amino acid residues at three or more of these positions; antibodies comprising three or more modified amino acid residues at one or more of these positions; antibodies comprising three or more modified amino acid residues at two or more of these positions; and antibodies comprising three or more modified amino acid residues at three or more of these positions.

In certain embodiments, provided herein are antibodies comprising one or more modified amino acid residues at one or more positions selected from EU residues corresponding to H292, H293, H294, H295, H296, H297, H298, H299, H300, H301, H303, and H305 (see Table 2, "SSHC-6" and the corresponding positions of the representative heavy chain polypeptide according to SEQ ID NO:1). Specifically provided herein are antibodies comprising one or more modified amino acid residues at one or more of these positions; antibodies comprising one or more modified amino acid residues at two or more of these positions; antibodies comprising one or more modified amino acid residues at three or more of these positions; antibodies comprising two or more modified amino acid residues at one or more of these positions; antibodies comprising two or more modified amino acid residues at two or more of these positions; antibodies comprising two or more modified amino acid residues at three or more of these positions; antibodies comprising three or more modified amino acid residues at one or more of these positions; antibodies comprising three or more modified amino acid residues at two or more of these positions; and antibodies comprising three or more modified amino acid residues at three or more of these positions.

In certain embodiments, provided herein are antibodies comprising one or more modified amino acid residues at one or more positions selected from Kabat or Chothia residues corresponding to H019, H025, H040, H052, H071, and H117; and EU residues corresponding to H119, H124, H139, H183, H193, H224, H225, and H407 (see Table 2, "SSHC-7" and the corresponding positions of the representative heavy chain polypeptide according to SEQ ID NO:1). Specifically provided herein are antibodies comprising one or more modified amino acid residues at one or more of these positions; antibodies comprising one or more modified amino acid residues at two or more of these positions; antibodies comprising one or more modified amino acid residues at three or more of these positions; antibodies comprising two or more modified amino acid residues at one or more of these positions; antibodies comprising two or more modified amino acid residues at two or more of these positions; antibodies comprising two or more modified amino acid residues at three or more of these positions; antibodies comprising three or more modified amino acid residues at one or more of these positions; antibodies comprising three or more modified amino acid residues at two or more of these positions; and antibodies comprising three or more modified amino acid residues at three or more of these positions.

In certain embodiments, provided herein are antibodies comprising one or more modified amino acid residues at one or more positions selected from Kabat or Chothia residues corresponding to H019, H025, H040, H052, and H070; and EU residues corresponding to H119, H121, H136, H180, H190, H222, H241, and H404 (see Table 2, "SSHC-8" and the corresponding positions of the representative heavy chain polypeptide according to SEQ ID NO:1). Specifically provided herein are antibodies comprising one or more modified amino acid residues at one or more of these positions; antibodies comprising one or more modified amino acid residues at two or more of these positions; antibodies comprising one or more modified amino acid residues at three or more of these positions; antibodies comprising two or more modified amino acid residues at one or more of these positions; antibodies comprising two or more modified amino acid residues at two or more of these positions; antibodies comprising two or more modified amino acid residues at three or more of these positions; antibodies comprising three or more modified amino acid residues at one or more of these positions; antibodies comprising three or more modified amino acid residues at two or more of these positions; and antibodies comprising three or more modified amino acid residues at three or more of these positions.

In certain embodiments, provided herein are antibodies comprising one or more modified amino acid residues at one or more positions selected from Kabat or Chothia residues corresponding to H025 and H040; and EU residues corresponding to H119, H121, H136, H180, H190, H222, H241, and H404 (see Table 2, "SSHC-9" and the corresponding positions of the representative heavy chain polypeptide according to SEQ ID NO:1). Specifically provided herein are antibodies comprising one or more modified amino acid residues at one or more of these positions; antibodies comprising one or more modified amino acid residues at two or more of these positions; antibodies comprising one or more modified amino acid residues at three or more of these positions; antibodies comprising two or more modified amino acid residues at one or more of these positions; antibodies comprising two or more modified amino acid residues at two or more of these positions; antibodies comprising two or more modified amino acid residues at three or more of these positions; antibodies comprising three or more modified amino acid residues at one or more of these positions; antibodies comprising three or more modified amino acid residues at two or more of these positions; and antibodies comprising three or more modified amino acid residues at three or more of these positions.

In certain embodiments, provided herein are antibodies comprising one or more modified amino acid residues at one or more positions selected from EU residues corresponding to H121, H136, H180, H241, and H404 (see Table 2, "SSHC-10" and the corresponding positions of the representative heavy chain polypeptide according to SEQ ID NO:1). Specifically provided herein are antibodies comprising one or more modified amino acid residues at one or more of these positions; antibodies comprising one or more modified amino acid residues at two or more of these positions; antibodies comprising one or more modified amino acid residues at three or more of these positions; antibodies comprising two or more modified amino acid residues at one or more of these positions; antibodies comprising two or more modified amino acid residues at two or more of these positions; antibodies comprising two or more modified amino acid residues at three or more of these positions; antibodies comprising three or more modified amino acid residues at one or more of these positions; antibodies comprising three or more modified amino acid residues at two or more of these positions; and antibodies comprising three or more modified amino acid residues at three or more of these positions.

In certain embodiments, provided herein are antibodies comprising one or more modified amino acid residues at one or more positions selected from Kabat or Chothia residues corresponding to H019, H025, H040, H052, H070, and H110; and EU residues corresponding to H119, H121, H136, H180, H190, H221, H222, and H404 (see Table 2, "SSHC-11" and the corresponding positions of the representative heavy chain polypeptide according to SEQ ID NO:1). Specifically provided herein, are antibodies comprising one or more modified amino acid residues at one or more of these positions; antibodies comprising one or more modified amino acid residues at two or more of these positions; antibodies comprising one or more modified amino acid residues at three or more of these positions; antibodies comprising two or more modified amino acid residues at one or more of these positions; antibodies comprising two or more modified amino acid residues at two or more of these positions; antibodies comprising two or more modified amino acid residues at three or more of these positions; antibodies comprising three or more modified amino acid residues at one or more of these positions; antibodies comprising three or more modified amino acid residues at two or more of these positions; and antibodies comprising three or more modified amino acid residues at three or more of these positions.

In certain embodiments, provided herein are antibodies comprising one or more modified amino acid residues at one or more positions selected from Kabat or Chothia residues corresponding to H005, H023, H042, H065, H074, and H084; and EU residues corresponding to 1-1118, H119, H132, H134, H135, H136, H137, H138, H139, H155, H160, H162, H165, H172, H174, H176, H177, H191, H194, H219, H238, H239, H241, H243, H246, H262, H264, H265, H267, H268, H269, H270, H271; H272, H274, H275, H278, H280, H281, H282, H283, H286, H289, H292, H293, H294, H295, H296, H297, H298, H299, H300, H301, H303, H305, H317, H320, H324, H326, H327, H329, H330, H332, H333, H334, H335, H337, H339, H340, H342, H344, H355, H356, H358, H359, H360, H375, H383, H384, H386, H389, H392, H398, H404, H420, H421, H436, and H438 (see Table 2, "SSHC-12" and the corresponding positions of the representative heavy chain polypeptide according to SEQ ID NO:1). Specifically provided herein are antibodies comprising one or more modified amino acid residues at one or more of these positions; antibodies comprising one or more modified amino acid residues at two or more of these positions; antibodies comprising one or more modified amino acid residues at three or more of these positions; antibodies comprising two or more modified amino acid residues at one or more of these positions; antibodies comprising two or more modified amino acid residues at two or more of these positions; antibodies comprising two or more modified amino acid residues at three or more of these positions; antibodies comprising three or more modified amino acid residues at one or more of these positions; antibodies comprising three or more modified amino acid residues at two or more of these positions; and antibodies comprising three or more modified amino acid residues at three or more of these positions.

In certain embodiments, provided herein are antibodies comprising one or more modified amino acid residues at one or more positions selected from Kabat or Chothia residues corresponding to H005, H023, H074, and H084; and EU residues corresponding to H118, H119, H132, H134, H135, H136, H137, H139, H160, H162, H165, H172, H191, H194, H239, H241, H246, H267, H268, H269, H270, H271, H272, H274, H275, H280, H281, H282, H283, H286, H289, H292, H293, H294, H295, H296, H297, H298, H299, H300, H301, H303, H305, H317, H320, H324, H326, H327, H329, H330, H332, H333, H334, H335, H337, H339, H340, H342, H344, H355, H359, H375, H386, H389, H392, H398, H404, H420, H421, and H438 (see Table 2, "SSHC-13" and the corresponding positions of the representative heavy chain polypeptide according to SEQ ID NO:1). Specifically provided herein are antibodies comprising one or more modified amino acid residues at one or more of these positions; antibodies comprising one or more modified amino acid residues at two or more of these positions; antibodies comprising one or more modified amino acid residues at three or more of these positions; antibodies comprising two or more modified amino acid residues at one or more of these positions; antibodies comprising two or more modified amino acid residues at two or more of these positions; antibodies comprising two or more modified amino acid residues at three or more of these positions; antibodies comprising three or more modified amino acid residues at one or more of these positions; antibodies comprising three or more modified amino acid residues at two or more of these positions; and antibodies comprising three or more modified amino acid residues at three or more of these positions.

In certain embodiments, provided herein are antibodies comprising one or more modified amino acid residues at one or more positions selected from Kabat or Chothia residues corresponding to H023 and H074; and EU residues corresponding to H119, H134, H135, H137, H139, H160, H162, H165, H172, H191, H194, H241, H246, H267, H268, H269, H270, H271, H272, H274, H275, H280, H281, H282, H283, H286, H289, H292, H294, H295, H296, H297, H298, H299, H300, H301, H303, H305, H317, H320, H324, H326, H327, H329, H330, H332, H333, H335, H337, H339, H340, H342, H344, H355, H375, H386, H392, H398, H404, H420, H421, and H438 (see Table 2, "SSHC-14" and the corresponding positions of the representative heavy chain polypeptide according to SEQ ID NO:1). Specifically provided herein are antibodies comprising one or more modified amino acid residues at one or more of these positions; antibodies comprising one or more modified amino acid residues at two or more of these positions; antibodies comprising one or more modified amino acid residues at three or more of these positions; antibodies comprising two or more modified amino acid residues at one or more of these positions; antibodies comprising two or more modified amino acid residues at two or more of these positions; antibodies comprising two or more modified amino acid residues at three or more of these positions; antibodies comprising three or more modified amino acid residues at one or more of these positions; antibodies comprising three or more modified amino acid residues at two or more of these positions; and antibodies comprising three or more modified amino acid residues at three or more of these positions.

In certain embodiments, provided herein are antibodies comprising one or more modified amino acid residues at one or more positions selected from Kabat or Chothia residues corresponding to H042 and H065; and EU residues corresponding to H138, H155, H174, H176, H177, H219, H238, H243, H262, H264, H265, H278, H342, H356, H358, H360, H383, H404, H384 and H436 (see Table 2, "SSHC-15" and the corresponding positions of the representative heavy chain polypeptide according to SEQ ID NO:1). Specifically provided herein are antibodies comprising one or more modified amino acid residues at one or more of these positions; antibodies comprising one or more modified amino acid residues at two or more of these positions; antibodies comprising one or more modified amino acid residues at three or more of these positions; antibodies comprising two or more modified amino acid residues at one or more of these positions; antibodies comprising two or more modified amino acid residues at two or more of these positions; antibodies comprising two or more modified amino acid residues at three or more of these positions; antibodies comprising three or more modified amino acid residues at one or more of these positions; antibodies comprising three or more modified amino acid residues at two or more of these positions; and antibodies comprising three or more modified amino acid residues at three or more of these positions.

In certain embodiments, provided herein are antibodies comprising one or more modified amino acid residues at one or more positions selected from Kabat or Chothia residues corresponding to H005 and H084; and EU residues corresponding to H118, H132, H136, H239, H293, H334, H342, H355, H359, H389, and H404 (see Table 2, "SSHC-16" and the corresponding positions of the representative heavy chain polypeptide according to SEQ ID NO:1). Specifically provided herein are antibodies comprising one or more modified amino acid residues at one or more of these positions; antibodies comprising one or more modified amino acid residues at two or more of these positions; antibodies comprising one or more modified amino acid residues at three or more of these positions; antibodies comprising two or more modified amino acid residues at one or more of these positions; antibodies comprising two or more modified amino acid residues at two or more of these positions; antibodies comprising two or more modified amino acid residues at three or more of these positions; antibodies comprising three or more modified amino acid residues at one or more of these positions; antibodies comprising three or more modified amino acid residues at two or more of these positions; and antibodies comprising three or more modified amino acid residues at three or more of these positions.

In certain embodiments, provided herein are antibodies comprising one or more modified amino acid residues at one or more positions selected from Kabat or Chothia residues corresponding to H005, H023, and H084; and EU residues corresponding to H118, H119, H132, H134, H136, H137, H160, H162, H172, H239, H241, H267, H269, H270, H271, H272, H282, H286, H292, H293, H296, H298, H329, H330, H334, H335, H340, H342, H355, H359, H386, H389, H404, H420, H421, and H438 (see Table 2, "SSHC-17" and the corresponding positions of the representative heavy chain polypeptide according to SEQ ID NO:1). Specifically provided herein are antibodies comprising one or more modified amino acid residues at one or more of these positions; antibodies comprising one or more modified amino acid residues at two or more of these positions; antibodies comprising one or more modified amino acid residues at three or more of these positions; antibodies comprising two or more modified amino acid residues at one or more of these positions; antibodies comprising two or more modified amino acid residues at two or more of these positions; antibodies comprising two or more modified amino acid residues at three or more of these positions; antibodies comprising three or more modified amino acid residues at one or more of these positions; antibodies comprising three or more modified amino acid residues at two or more of these positions; and antibodies comprising three or more modified amino acid residues at three or more of these positions.

In certain embodiments, provided herein are antibodies comprising one or more modified amino acid residues at one or more positions selected from Kabat or Chothia residues corresponding to H023 and H084; and EU residues corresponding to H118, H119, H135, H136, H137, H160, H161, H162, H164, H195, H197, H219, H282, H289, H296, H330, H335, H361, H400, H404, H422, H440, H260, H267, H268, H272, H274, H292, H293, H297, H298, H303, H305, H332, H333, H334, H340, H341, H342, H343, H355, H362, H386, H392, H404, H424, H438, H442 and H443 (see Table 2, "SSHC-18" and the corresponding positions of the representative heavy chain polypeptide according to SEQ ID NO:1). Specifically provided herein are antibodies comprising one or more modified amino acid residues at one or more of these positions; antibodies comprising one or more modified amino acid residues at two or more of these positions; antibodies comprising one or more modified amino acid residues at three or more of these positions; antibodies comprising two or more modified amino acid residues at one or more of these positions; antibodies comprising two or more modified amino acid residues at two or more of these positions; antibodies comprising two or more modified amino acid residues at three or more of these positions; antibodies comprising three or more modified amino acid residues at one or more of these positions; antibodies comprising three or more modified amino acid residues at two or more of these positions; and antibodies comprising three or more modified amino acid residues at three or more of these positions.

In certain embodiments, provided herein are antibodies comprising one or more modified amino acid residues at one or more positions selected from Kabat or Chothia residues corresponding to H023 and H084; and EU residues corresponding to H118, H119, H135, H116, H137, H160, H161, H162, H164, H195, H197, H219, H282, H296, H335, H361, H422, H440, H267, H272, H274, H293, H297, H298, H303, H305, H334, H340, H341, H342, H343, H355, H362, H392, H404, H424, H438, H442 and H443 (see Table 2, "SSHC-19" and the corresponding positions of the representative heavy chain polypeptide according to SEQ ID NO:1). Specifically provided herein are antibodies comprising one or more modified amino acid residues at one or more of these positions; antibodies comprising one or more modified amino acid residues at two or more of these positions; antibodies comprising one or more modified amino acid residues at three or more of these positions; antibodies comprising two or more modified amino acid residues at one or more of these positions; antibodies comprising two or more modified amino acid residues at two or more of these positions; antibodies comprising two or more modified amino acid residues at three or more of these positions; antibodies comprising three or more modified amino acid residues at one or more of these positions; antibodies comprising three or more modified amino acid residues at two or more of these positions; and antibodies comprising three or more modified amino acid residues at three or more of these positions.

In certain embodiments, provided herein are antibodies comprising one or more modified amino acid residues at one or more positions selected from Kabat or Chothia residues corresponding to H023 and H084; and EU residues corresponding to H118, H119, H135, H136, H137, H160, H161, H162, H195, H197, H219, H282, H296, H422, H440, H267, H272, H293, H297, H298, H303, H305, H334, H340, H341, H342, H355, H392, H404, H424, H438, H442 and H443 (see Table 2, "SSHC-20" and the corresponding positions of the representative heavy chain polypeptide according to SEQ ID NO:1). Specifically provided herein are antibodies comprising one or more modified amino acid residues at one or more of these positions; antibodies comprising one or more modified amino acid residues at two or more of these positions; antibodies comprising one or more modified amino acid residues at three or more of these positions; antibodies comprising two or more modified amino acid residues at one or more of these positions; antibodies comprising two or more modified amino acid residues at two or more of these positions; antibodies comprising two or more modified amino acid residues at three or more of these positions; antibodies comprising three or more modified amino acid residues at one or more of these positions; antibodies comprising three or more modified amino acid residues at two or more of these positions; and antibodies comprising three or more modified amino acid residues at three or more of these positions.

In certain embodiments, provided herein are antibodies comprising one or more modified amino acid residues at one or more positions selected from Kabat or Chothia residues corresponding to H023 and H084; and EU residues corresponding to H118, H119, H135, H136, H160, H162, H195, H219, H282, H296, H267, H293, H297, H298, H303, H305, H334, H340, H341, H392, H438, and H442 (see Table 2, "SSHC-21" and the corresponding positions of the representative heavy chain polypeptide according to SEQ ID NO:1). Specifically provided herein are antibodies comprising one or more modified amino acid residues at one or more of these positions; antibodies comprising one or more modified amino acid residues at two or more of these positions; antibodies comprising one or more modified amino acid residues at three or more of these positions; antibodies comprising two or more modified amino acid residues at one or more of these positions; antibodies comprising two or more modified amino acid residues at two or more of these positions; antibodies comprising two or more modified amino acid residues at three or more of these positions; antibodies comprising three or more modified amino acid residues at one or more of these positions; antibodies comprising three or more modified amino acid residues at two or more of these positions; and antibodies comprising three or more modified amino acid residues at three or more of these positions.

In certain embodiments, provided herein are antibodies comprising one or more modified amino acid residues at one or more positions selected from Kabat or Chothia residues corresponding to H003, H007, H014, H016, H019, H025, H040, H042, H043, H051, H052, H053, H056, H070, H082A, H098, H100, H110, and H112; and EU residues corresponding to H121, H180, H184, H190, H192, H214, H216, H221, H222, H225, H227, H230, H231, H232, and H236 (see Table 2, "SSHC-22" and the corresponding positions of the representative heavy chain polypeptide according to SEQ ID NO:1). Specifically provided herein are antibodies comprising one or more modified amino acid residues at one or more of these positions; antibodies comprising one or more modified amino acid residues at two or more of these positions; antibodies comprising one or more modified amino acid residues at three or more of these positions; antibodies comprising two or more modified amino acid residues at one or more of these positions; antibodies comprising two or more modified amino acid residues at two or more of these positions; antibodies comprising two or more modified amino acid residues at three or more of these positions; antibodies comprising three or more modified amino acid residues at one or more of these positions; antibodies comprising three or more modified amino acid residues at two or more of these positions; and antibodies comprising three or more modified amino acid residues at three or more of these positions.

In certain embodiments, provided herein are antibodies comprising one or more modified amino acid residues at one or more positions selected from Kabat or Chothia residues corresponding to H003, H007, H014, H016, H019, H025, H040, H042, H043, H052, H053, H056, H070, H082A, H100, H110, and H112; and EU residues corresponding to H121, H180, H190, H192, H214, H216, H221, H222, H225, H227, H230, H231, H232, and H236 (see Table 2, "SSHC-23" and the corresponding positions of the representative heavy chain polypeptide according to SEQ ID NO:1). Specifically provided herein are antibodies comprising one or more modified amino acid residues at one or more of these positions; antibodies comprising one or more modified amino acid residues at two or more of these positions; antibodies comprising one or more modified amino acid residues at three or more of these positions; antibodies comprising two or more modified amino acid residues at one or more of these positions; antibodies comprising two or more modified amino acid residues at two or more of these positions; antibodies comprising two or more modified amino acid residues at three or more of these positions; antibodies comprising three or more modified amino acid residues at one or more of these positions; antibodies comprising three or more modified amino acid residues at two or more of these positions; and antibodies comprising three or more modified amino acid residues at three or more of these positions.

In certain embodiments, provided herein are antibodies comprising one or more modified amino acid residues at one or more positions selected from Kabat or Chothia residues corresponding to H003, H007, H014, H016, H019, H025, H040, H042, H043, H052, H070, H082A, H100, H110, and H112; and EU residues corresponding to H121, H180, H190, H192, H214, H216, H221, H222, H225, H227, H230, H231, H232, and H236 (see Table 2, "SSHC-24" and the corresponding positions of the representative heavy chain polypeptide according to SEQ ID NO:1). Specifically provided herein are antibodies comprising one or more modified amino acid residues at one or more of these positions; antibodies comprising one or more modified amino acid residues at two or more of these positions; antibodies comprising one or more modified amino acid residues at three or more of these positions; antibodies comprising two or more modified amino acid residues at one or more of these positions; antibodies comprising two or more modified amino acid residues at two or more of these positions; antibodies comprising two or more modified amino acid residues at three or more of these positions; antibodies comprising three or more modified amino acid residues at one or more of these positions; antibodies comprising three or more modified amino acid residues at two or more of these positions; and antibodies comprising three or more modified amino acid residues at three or more of these positions.

In certain embodiments, provided herein are antibodies comprising one or more modified amino acid residues at one or more positions selected from Kabat or Chothia residues corresponding to H007, H014, H019, H025, H040, H043, H052, H070, H100, H110, and H112; and EU residues corresponding to H121, H180, H214, H216, H222, H227, H230, H231, H232, and H236 (see Table 2, "SSHC-25" and the corresponding positions of the representative heavy chain polypeptide according to SEQ ID NO:1). Specifically provided herein are antibodies comprising one or more modified amino acid residues at one or more of these positions; antibodies comprising one or more modified amino acid residues at two or more of these positions; antibodies comprising one or more modified amino acid residues at three or more of these positions; antibodies comprising two or more modified amino acid residues at one or more of these positions; antibodies comprising two or more modified amino acid residues at two or more of these positions; antibodies comprising two or more modified amino acid residues at three or more of these positions; antibodies comprising three or more modified amino acid residues at one or more of these positions; antibodies comprising three or more modified amino acid residues at two or more of these positions; and antibodies comprising three or more modified amino acid residues at three or more of these positions.

In certain embodiments, provided herein are antibodies comprising one or more modified amino acid residues at one or more positions selected from Kabat or Chothia residues corresponding to H019, H025, H051, H070, H098, H110, and H112; and EU residues corresponding to H121, H136, H180, H187, H190, H214, H216, H221, and H222 (see Table 2, "SSHC-26" and the corresponding positions of the representative heavy chain polypeptide according to SEQ ID NO:1). Specifically provided herein are antibodies comprising one or more modified amino acid residues at one or more of these positions; antibodies comprising one or more modified amino acid residues at two or more of these positions; antibodies comprising one or more modified amino acid residues at three or more of these positions; antibodies comprising two or more modified amino acid residues at one or more of these positions; antibodies comprising two or more modified amino acid residues at two or more of these positions; antibodies comprising two or more modified amino acid residues at three or more of these positions; antibodies comprising three or more modified amino acid residues at one or more of these positions; antibodies comprising three or more modified amino acid residues at two or more of these positions; and antibodies comprising three or more modified amino acid residues at three or more of these positions.

In certain embodiments, provided herein are antibodies comprising one or more modified amino acid residues at one or more positions selected from Kabat or Chothia residues corresponding to H019, H025, H051, H070, H077, H079, H098, H110, and H112; and EU residues corresponding to H121, H136, H180, H187, H190, H214, H216, H221, and H222 (see Table 2, "SSHC-27" and the corresponding positions of the representative heavy chain polypeptide according to SEQ ID NO:1). Specifically provided herein are antibodies comprising one or more modified amino acid residues at one or more of these positions; antibodies comprising one or more modified amino acid residues at two or more of these positions; antibodies comprising one or more modified amino acid residues at three or more of these positions; antibodies comprising two or more modified amino acid residues at one or more of these positions; antibodies comprising two or more modified amino acid residues at two or more of these positions; antibodies comprising two or more modified amino acid residues at three or more of these positions; antibodies comprising three or more modified amino acid residues at one or more of these positions; antibodies comprising three or more modified amino acid residues at two or more of these positions; and antibodies comprising three or more modified amino acid residues at three or more of these positions.

Examples of Site-Specific Positions for Substitution: Light Chains

In certain embodiments, the site-specific positions are selected from Kabat or Chothia light chain residues L007 and L022; and EU light chain residue L152 (see Table 3, "SSLC-1" and the corresponding positions of the representative light chain polypeptide according to SEQ 1D NO:2). Specifically provided herein are antibodies comprising one or more modified amino acid residues at one or more of these positions; antibodies comprising one or more modified amino acid residues at two or more of these positions; antibodies comprising one or more modified amino acid residues at three or more of these positions; antibodies comprising two or more modified amino acid residues at one or more of these positions; antibodies comprising two or more modified amino acid residues at two or more of these positions; antibodies comprising two or more modified amino acid residues at three or more of these positions; antibodies comprising three or more modified amino acid residues at one or more of these positions; antibodies comprising three or more modified amino acid residues at two or more of these positions; and antibodies comprising three or more modified amino acid residues at three or more of these positions.

In certain embodiments, the site-specific positions are selected from Kabat or Chothia light chain residues L043, L049, L056, L057, L060, L067, and L068; and EU light chain residues L109, L112, L114, L144, L153, L156, L157, L168, L184, L202, L203, and L206 (see Table 3, "SSLC-2" and the corresponding positions of the representative light chain polypeptide according to SEQ ID NO:2). Specifically provided herein are antibodies comprising one or more modified amino acid residues at one or more of these positions; antibodies comprising one or more modified amino acid residues at two or more of these positions; antibodies comprising one or more modified amino acid residues at three or more of these positions; antibodies comprising two or more modified amino acid residues at one or more of these positions; antibodies comprising two or more modified amino acid residues at two or more of these positions; antibodies comprising two or more modified amino acid residues at three or more of these positions; antibodies comprising three or more modified amino acid residues at one or more of these positions; antibodies comprising three or more modified amino acid residues at two or more of these positions; and antibodies comprising three or more modified amino acid residues at three or more of these positions.

In certain embodiments, the site-specific positions are selected from Kabat or Chothia light chain residues L043, L049, L056, L057, L060, L067, and L068; and EU light chain residues L109, L112, L114, L144, L153, L156, L168, L184, L202, and L203 (see Table 3, "SSLC-3" and the corresponding positions of the representative light chain polypeptide according to SEQ ID NO:2). Specifically provided herein are antibodies comprising one or more modified amino acid residues at one or more of these positions; antibodies comprising one or more modified amino acid residues at two or more of these positions; antibodies comprising one or more modified amino acid residues at three or more of these positions; antibodies comprising two or more modified amino acid residues at one or more of these positions; antibodies comprising two or more modified amino acid residues at two or more of these positions; antibodies comprising two or more modified amino acid residues at three or more of these positions; antibodies comprising three or more modified amino acid residues at one or more of these positions; antibodies comprising three or more modified amino acid iesidues al two or more of these positions; and antibodies comprising three or more modified amino acid residues at three or more of these positions.

In certain embodiments, the site-specific positions are selected from Kabat or Chothia light chain residues L043, L049, L056, L057, L060, L067, and L068; and EU light chain residues L109, L144, L153, L156, L184, L202, and L203 (see Table 3, "SSLC-4" and the corresponding positions of the representative light chain polypeptide according to SEQ ID NO:2). Specifically provided herein are antibodies comprising one or more modified amino acid residues at one or more of these positions; antibodies comprising one or more modified amino acid residues at two or more of these positions; antibodies comprising one or more modified amino acid residues at three or more of these positions; antibodies comprising two or more modified amino acid residues at one or more of these positions; antibodies comprising two or more modified amino acid residues at two or more of these positions; antibodies comprising two or more modified amino acid residues at three or more of these positions; antibodies comprising three or more modified amino acid residues at one or more of these positions; antibodies comprising three or more modified amino acid residues at two or more of these positions; and antibodies comprising three or more modified amino acid residues at three or more of these positions.

In certain embodiments, the site-specific positions are selected from Kabat or Chothia light chain residues L049, L056, L057, L060, and L067; and EU light chain residues L109, L153, L202, and L203 (see Table 3, "SSLC-5" and the corresponding positions of the representative light chain polypeptide according to SEQ ID NO:2). Specifically provided herein are antibodies comprising one or more modified amino acid residues at one or more of these positions; antibodies comprising one or more modified amino acid residues at two or more of these positions; antibodies comprising one or more modified amino acid residues at three or more of these positions; antibodies comprising two or more modified amino acid residues at one or more of these positions; antibodies comprising two or more modified amino acid residues at two or more of these positions; antibodies comprising two or more modified amino acid residues at three or more of these positions; antibodies comprising three or more modified amino acid residues at one or more of these positions; antibodies comprising three or more modified amino acid residues at two or more of these positions; and antibodies comprising three or more modified amino acid residues at three or more of these positions.

In certain embodiments, the site-specific positions are selected from Kabat or Chothia light chain residues minus 1, L003, L005, L007, L008, L009, L010, L016, L017, L018, L020, L022, L026, L027, L045, L058, L063, L065, L066, L070, L077, L079, and L107; and EU light chain residues L138, L142, L143, L152, L171, L182, L188, L199, and L201 (see Table 3, "SSLC-6" and the corresponding positions of the representative light chain polypeptide according to SEQ ID NO:2). Specifically provided herein are antibodies comprising one or more modified amino acid residues at one or more of these positions; antibodies comprising one or more modified amino acid residues at two or more of these positions; antibodies comprising one or more modified amino acid residues at three or more of these positions; antibodies comprising two or more modified amino acid residues at one or more of these positions; antibodies comprising two or more modified amino acid residues at two or more of these positions; antibodies comprising two or more modified amino acid residues at three or more of these positions; antibodies comprising three or more modified amino acid residues at one or more of these positions; antibodies comprising three or more modified amino acid residues at two or more of these positions; and antibodies comprising three or more modified amino acid residues at three or more of these positions.

In certain embodiments, the site-specific positions are selected from Kabat or Chothia light chain residues minus 1, L003, L005, L007, L008, L009, L010, L016, L017, L018, L020, L022, L026, L027, L045, L058, L063, L065, L066, L070, L077, L079, and L107; and EU light chain residues L142, L143, L152, L171, L182, L188, L199, and L201 (see Table 3, "SSLC-7" and the corresponding positions of the representative light chain polypeptide according to SEQ ID NO:2). Specifically provided herein are antibodies comprising one or more modified amino acid residues at one or more of these positions; antibodies comprising one or more modified amino acid residues at two or more of these positions; antibodies comprising one or more modified amino acid residues at three or more of these positions; antibodies comprising two or more modified amino acid residues at one or more of these positions; antibodies comprising two or more modified amino acid residues at two or more of these positions; antibodies comprising two or more modified amino acid residues at three or more of these positions; antibodies comprising three or more modified amino acid residues at one or more of these positions; antibodies comprising three or more modified amino acid residues at two or more of these positions; and antibodies comprising three or more modified amino acid residues at three or more of these positions.

In certain embodiments, the site-specific positions are selected from Kabat or Chothia light chain residues minus 1, L003, L005, L007, L008, L009, L016, L017, L018, L020, L022, L026, L027, L045, L058, L063, L065, L066, L070, L077, L079, and L107; and EU light chain residues L142, L152, L171, L182, L188, and L199 (see Table 3, "SSLC-8" and the corresponding positions of the representative light chain polypeptide according to SEQ ID NO:2). Specifically provided herein are antibodies comprising one or more modified amino acid residues at one or more of these positions; antibodies comprising one or more modified amino acid residues at two or more of these positions; antibodies comprising one or more modified amino acid residues at three or more of these positions; antibodies comprising two or more modified amino acid residues at one or more of these positions; antibodies comprising two or more modified amino acid residues at two or more of these positions; antibodies comprising two or more modified amino acid residues at three or more of these positions; antibodies comprising three or more modified amino acid residues at one or more of these positions; antibodies comprising three or more modified amino acid residues at two or more of these positions; and antibodies comprising three or more modified amino acid residues at three or more of these positions.

In certain embodiments, the site-specific positions are selected from Kabat or Chothia light chain residues minus 1, L005, L007, L008, L016, L017, L018, L020, L022, L027, L045, L058, L063, L077, L079, and L107; and EU light chain residues L142, L152, L182, L188, and L199 (see Table 3, "SSLC-9" and the corresponding positions of the representative light chain polypeptide according to SEQ ID NO:2). Specifically provided herein are antibodies comprising one or more modified amino acid residues at one or more of these positions; antibodies comprising one or more modified amino acid residues at two or more of these positions; antibodies comprising one or more modified amino acid residues at three or more of these positions; antibodies comprising two or more modified amino acid residues at one or more of these positions; antibodies comprising two or more modified amino acid residues at two or more of these positions; antibodies comprising two or more modified amino acid residues at three or more of these positions; antibodies comprising three or more modified amino acid residues at one or more of these positions; antibodies comprising three or more modified amino acid residues at two or more of these positions; and antibodies comprising three or more modified amino acid residues at three or more of these positions.

In certain embodiments, the site-specific positions are selected from Kabat or Chothia light chain residues minus 1, L016, and L063; and EU light chain residue L199 (see Table 3, "SSLC-10" and the corresponding positions of the representative light chain polypeptide according to SEQ ID NO:2). Specifically provided herein are antibodies comprising one or more modified amino acid residues at one or more of these positions; antibodies comprising one or more modified amino acid residues at two or more of these positions; antibodies comprising one or more modified amino acid residues at three or more of these positions; antibodies comprising two or more modified amino acid residues at one or more of these positions; antibodies comprising two or more modified amino acid residues at two or more of these positions; antibodies comprising two or more modified amino acid residues at three or more of these positions; antibodies comprising three or more modified amino acid residues at one or more of these positions; antibodies comprising three or more modified amino acid residues at two or more of these positions; and antibodies comprising three or more modified amino acid residues at three or more of these positions.

In certain embodiments, the site-specific positions are selected from Kabat or Chothia light chain residues minus 1, L007, L008, L014, L016, L022, L063, and L070; and EU light chain residues L138, L142, L143 and L152 (see Table 3, "SSLC-11" and the corresponding positions of the representative light chain polypeptide according to SEQ ID NO:2). Specifically provided herein are antibodies comprising one or more modified amino acid residues at one or more of these positions; antibodies comprising one or more modified amino acid residues at two or more of these positions; antibodies comprising one or more modified amino acid residues at three or more of these positions; antibodies comprising two or more modified amino acid residues at one or more of these positions; antibodies comprising two or more modified amino acid residues at two or more of these positions; antibodies comprising two or more modified amino acid residues at three or more of these positions; antibodies comprising three or more modified amino acid residues at one or more of these positions; antibodies comprising three or more modified amino acid residues at two or more of these positions; and antibodies comprising three or more modified amino acid residues at three or more of these positions.

In certain embodiments, the site-specific positions are selected from Kabat or Chothia light chain residues minus 1, L007, L008, L016, L022, L063, and L070; and EU light chain residues L138, L142, L143, L152 and L201 (see Table 3, "SSLC-12" and the corresponding positions of the representative light chain polypeptide according to SEQ ID NO:2). Specifically provided herein are antibodies comprising one or more modified amino acid residues at one or more of these positions; antibodies comprising one or more modified amino acid residues at two or more of these positions; antibodies comprising one or more modified amino acid residues at three or more of these positions; antibodies comprising two or more modified amino acid residues at one or more of these positions; antibodies comprising two or more modified amino acid residues at two or more of these positions; antibodies comprising two or more modified amino acid residues at three or more of these positions; antibodies comprising three or more modified amino acid residues at one or more of these positions; antibodies comprising three or more modified amino acid residues at two or more of these positions; and antibodies comprising three or more modified amino acid residues at three or more of these positions.

In certain embodiments, the site-specific positions are selected from Kabat or Chothia light chain residues minus 1, L003, L005, L007, L008, L009, L010, L016, L017, L018, L020, L022, L026, L027, L045, L058, L063, L065, L066, L070, L077, L079, and L107; and EU light chain residues L138, L142, L143, L152, L171, L182, L188, L199, and L201 (see Table 3, "SSLC-13" and the corresponding positions of the representative light chain polypeptide according to SEQ ID NO:2). Specifically provided herein are antibodies comprising one or more modified amino acid residues at one or more of these positions; antibodies comprising one or more modified amino acid residues at two or more of these positions; antibodies comprising one or more modified amino acid residues at three or more of these positions; antibodies comprising two or more modified amino acid residues at one or more of these positions; antibodies comprising two or more modified amino acid residues at two or more of these positions; antibodies comprising two or more modified amino acid residues at three or more of these positions; antibodies comprising three or more modified amino acid residues at one or more of these positions; antibodies comprising three or more modified amino acid residues at two or more of these positions; and antibodies comprising three or more modified amino acid residues at three or more of these positions.

In certain embodiments, the site-specific positions are selected from Kabat or Chothia light chain residues minus 1, L003, L005, L007, L008, LOO 9, L016, L017, L018, L020, L022, L026, L027, L045, L058, L063, L065, L066, L070, L077, L079, and L107; and EU light chain residues L142, L152, L171, L182, L188, and L199 (see Table 3, "SSLC-14" and the corresponding positions of the representative light chain polypeptide according to SEQ ID NO:2). Specifically provided herein are antibodies comprising one or more modified amino acid residues at one or more of these positions; antibodies comprising one or more modified amino acid residues at two or more of these positions; antibodies comprising one or more modified amino acid residues at three or more of these positions; antibodies comprising two or more modified amino acid residues at one or more of these positions; antibodies comprising two or more modified amino acid residues at two or more of these positions; antibodies comprising two or more modified amino acid residues at three or more of these positions; antibodies comprising three or more modified amino acid residues at one or more of these positions; antibodies comprising three or more modified amino acid residues at two or more of these positions; and antibodies comprising three or more modified amino acid residues at three or more of these positions.

In certain embodiments, the site-specific positions are selected from Kabat or Chothia light chain residues minus 1, L005, L007, L008, L016, L017, L018, L020, L022, L027, L045, L058, L063, L077, L079, and L107; and EU light chain residues L142, L152, L182, L188, and L199 (see Table 3, "SSLC-15" and the corresponding positions of the representative light chain polypeptide according to SEQ ID NO:2). Specifically provided herein are antibodies comprising one or more modified amino acid residues at one or more of these positions; antibodies comprising one or more modified amino acid residues at two or more of these positions; antibodies comprising one or more modified amino acid residues at three or more of these positions; antibodies comprising two or more modified amino acid residues at one or more of these positions; antibodies comprising two or more modified amino acid residues at two or more of these positions; antibodies comprising two or more modified amino acid residues at three or more of these positions; antibodies comprising three or more modified amino acid residues at one or more of these positions; antibodies comprising three or more modified amino acid residues at two or more of these positions; and antibodies comprising three or more modified amino acid residues at three or more of these positions.

In certain embodiments, the site-specific positions are selected from Kabat or Chothia light chain residues minus 1, L016 and L063; and EU light chain residue L199 (see Table 3, "SSLC-16" and the corresponding positions of the representative light chain polypeptide according to SEQ ID NO:2). Specifically provided herein are antibodies comprising one or more modified amino acid residues at one or more of these positions; antibodies comprising one or more modified amino acid residues at two or more of these positions; antibodies comprising one or more modified amino acid residues at three or more of these positions; antibodies comprising two or more modified amino acid residues at one or more of these positions; antibodies comprising two or more modified amino acid residues at two or more of these positions; antibodies comprising two or more modified amino acid residues at three or more of these positions; antibodies comprising three or more modified amino acid residues at one or more of these positions; antibodies comprising three or more modified amino acid residues at two or more of these positions; and antibodies comprising three or more modified amino acid residues at three or more of these positions.

In certain embodiments, the site-specific positions are selected from Kabat or Chothia light chain residues minus 1, L007, L008, L014, L016, L022, L063, and L070; and EU light chain residues L138, L142, L143 and L152 (see Table 3, "SSLC-17" and the corresponding positions of the representative light chain polypeptide according to SEQ ID NO:2). Specifically provided herein are antibodies comprising one or more modified amino acid residues at one or more of these positions; antibodies comprising one or more modified amino acid residues at two or more of these positions; antibodies comprising one or more modified amino acid residues at three or more of these positions; antibodies comprising two or more modified amino acid residues at one or more of these positions; antibodies comprising two or more modified amino acid residues at two or more of these positions; antibodies comprising two or more modified amino acid residues at three or more of these positions; antibodies comprising three or more modified amino acid residues at one or more of these positions; antibodies comprising three or more modified amino acid residues at two or more of these positions; and antibodies comprising three or more modified amino acid residues at three or more of these positions.

In certain embodiments, the site-specific positions are selected from Kabat or Chothia light chain residues minus 1, L007, L008, L016, 22, L063, and L070; and EU light chain residues L138, L142, L143, L152, and L201 (see Table 3, "SSLC-18" and the corresponding positions of the representative light chain polypeptide according to SEQ ID NO:2). Specifically provided herein are antibodies comprising one or more modified amino acid residues at one or more of these positions; antibodies comprising one or more modified amino acid residues at two or more of these positions; antibodies comprising one or more modified amino acid residues at three or more of these positions; antibodies comprising two or more modified amino acid residues at one or more of these positions; antibodies comprising two or more modified amino acid residues at two or more of these positions; antibodies comprising two or more modified amino acid residues at three or more of these positions; antibodies comprising three or more modified amino acid residues at one or more of these positions; antibodies comprising three or more modified amino acid residues at two or more of these positions; and antibodies comprising three or more modified amino acid residues at three or more of these positions.

In certain embodiments, the site-specific positions are selected from Kabat or Chothia light chain residues L043, L049, L056, L057, L060, L067, and L068; and EU light chain residues L109, L112, L114, L144, L153, L156, L157, L168, L184, L202, L203, and L206 (see Table 3, "SSLC-19" and the corresponding positions of the representative light chain polypeptide according to SEQ ID NO:2). Specifically provided herein are antibodies comprising one or more modified amino acid residues at one or more of these positions; antibodies comprising one or more modified amino acid residues at two or more of these positions; antibodies comprising one or more modified amino acid residues at three or more of these positions; antibodies comprising two or more modified amino acid residues at one or more of these positions; antibodies comprising two or more modified amino acid residues at two or more of these positions; antibodies comprising two or more modified amino acid residues at three or more of these positions; antibodies comprising three or more modified amino acid residues at one or more of these positions; antibodies comprising three or more modified amino acid residues at two or more of these positions; and antibodies comprising three or more modified amino acid residues at three or more of these positions.

In certain embodiments, the site-specific positions are selected from Kabat or Chothia light chain residues L043, L049, L056, L057, L060, L067, and L068; and EU light chain residues L109, L112, L144, L153, L156, L168, L184, L202, and L203 (see Table 3, "SSLC-20" and the corresponding positions of the representative light chain polypeptide according to SEQ ID NO:2). Specifically provided herein are antibodies comprising one or more modified amino acid residues at one or more of these positions; antibodies comprising one or more modified amino acid residues at two or more of these positions; antibodies comprising one or more modified amino acid residues at three or more of these positions; antibodies comprising two or more modified amino acid residues at one or more of these positions; antibodies comprising two or more modified amino acid residues at two or more of these positions; antibodies comprising two or more modified amino acid residues at three or more of these positions; antibodies comprising three or more modified amino acid residues at one or more of these positions; antibodies comprising three or more modified amino acid residues at two or more of these positions; and antibodies comprising three or more modified amino acid residues at three or more of these positions.

In certain embodiments, the site-specific positions are selected from Kabat or Chothia light chain residues L043, L049, L056, L057, L060, L067, and L068; and EU light chain residues L109, L144, L153, L156, L184, L202, and L203 (see Table 3, "SSLC-21" and the corresponding positions of the representative light chain polypeptide according to SEQ ID NO:2). Specifically provided herein are antibodies comprising one or more modified amino acid residues at one or more of these positions; antibodies comprising one or more modified amino acid residues at two or more of these positions; antibodies comprising one or more modified amino acid residues at three or more of these positions; antibodies comprising two or more modified amino acid residues at one or more of these positions; antibodies comprising two or more modified amino acid residues at two or more of these positions; antibodies comprising two or more modified amino acid residues at three or more of these positions; antibodies comprising three or more modified amino acid residues at one or more of these positions; antibodies comprising three or more modified amino acid residues at two or more of these positions; and antibodies comprising three or more modified amino acid residues at three or more of these positions.

In certain embodiments, the site-specific positions are selected from Kabat or Chothia light chain residues L049, L056, L057, L060, and L067; and EU light chain residues L109, L153, L202, and L203 (see Table 3, "SSLC-22" and the corresponding positions of the representative light chain polypeptide according to SEQ ID NO:2). Specifically provided herein are antibodies comprising one or more modified amino acid residues at one or more of these positions; antibodies comprising one or more modified amino acid residues at two or more of these positions; antibodies comprising one or more modified amino acid residues at three or more of these positions; antibodies comprising two or more modified amino acid residues at one or more of these positions; antibodies comprising two or more modified amino acid residues at two or more of these positions; antibodies comprising two or more modified amino acid residues at three or more of these positions; antibodies comprising three or more modified amino acid residues at one or more of these positions; antibodies comprising three or more modified amino acid residues at two or more of these positions; and antibodies comprising three or more modified amino acid residues at three or more of these positions.

Examples of Site-Specific Positions for Substitution: Heavy and Light Chains

Specifically contemplated is every site-specific heavy chain modification described herein with every site-specific light chain modification described herein.

In some embodiments, the site-specific positions are selected from Kabat or Chothia heavy chain residues H019, H025, H040, H052, H071, and H117; and EU heavy chain residues H119, H124, H139, H183, H193, H224, H225, and H407 (see Table 2, "SSHC-7" and the corresponding positions of the representative heavy chain polypeptide according to SEQ ID NO:1) and Kabat or Chothia light chain residues L007 and L022; and EU light chain residue L152 (see Table 3, "SSLC-1" and the corresponding positions of the representative light chain polypeptide according to SEQ ID NO:2). In some embodiments, at least one of these positions is modified in the heavy chain and at least one of these positions is modified in the light chain. In some embodiments, at least two of these positions are modified in the heavy chain and at least one of these positions is modified in the light chain. In some embodiments, at least one of these positions is modified in the heavy chain and at least two of these positions are modified in the light chain.

In some embodiments, the site-specific positions are selected from Kabat or Chothia heavy chain residues H019, H025, H040, H052, and H070; and EU heavy chain residues H119, H121, H136, H180, H190, H222, H241, and H404 (see Table 2, "SSHC-8" and the corresponding positions of the representative heavy chain polypeptide according to SEQ ID NO:1) and Kabat or Chothia light chain residues L007 and L022; and EU light chain residue L152 (see Table 3, "SSLC-1" and the corresponding positions of the representative light chain polypeptide according to SEQ ID NO:2). In some embodiments, at least one of these positions is modified in the heavy chain and at least one of these positions is modified in the light chain. In some embodiments, at least two of these positions are modified in the heavy chain and at least one of these positions is modified in the light chain. In some embodiments, at least one of these positions is modified in the heavy chain and at least two of these positions are modified in the light chain.

In some embodiments, the site-specific positions are selected from Kabat or Chothia heavy chain residues H025 and H040; and EU heavy chain residues H119, H121, H136, H180, H190, H222, H241, and H404 (see Table 2, "SSHC-9" and the corresponding positions of the representative heavy chain polypeptide according to SEQ ID NO:1) and Kabat or Chothia light chain residues L007 and L022; and EU light chain residue L152 (see Table 3, "SSLC-1" and the corresponding positions of the representative light chain polypeptide according to SEQ ID NO:2). In some embodiments, at least one of these positions is modified in the heavy chain and at least one of these positions is modified in the light chain. In some embodiments, at least two of these positions are modified in the heavy chain and at least one of these positions is modified in the light chain. In some embodiments, at least one of these positions is modified in the heavy chain and at least two of these positions are modified in the light chain.

In some embodiments, the site-specific positions are selected from EU heavy chain residues H121, H136, H180, H241, and H404 (see Table 2, "SSHC-10" and the corresponding positions of the representative heavy chain polypeptide according to SEQ ID NO:1) and Kabat or Chothia light chain residues L007 and L022; and EU light chain residue L152 (see Table 3, "SSLC-1" and the corresponding positions of the representative light chain polypeptide according to SEQ ID NO:2). In some embodiments, at least one of these positions is modified in the heavy chain and at least one of these positions is modified in the light chain. In some embodiments, at least two of these positions are modified in the heavy chain and at least one of these positions is modified in the light chain. In some embodiments, at least one of these positions is modified in the heavy chain and at least two of these positions are modified in the light chain.

In some embodiments, the site-specific positions are selected from Kabat or Chothia heavy chain residues H019, H025, H040, H052, H070, and H110; and EU heavy chain residues H119, H121, H136, H180, H190, H221, H222, and H404 (see Table 2, "SSHC-11" and the corresponding positions of the representative heavy chain polypeptide according to SEQ ID NO:1) and Kabat or Chothia light chain residues L007 and L022; and EU light chain residue L152 (see Table 3, "SSLC-1" and the corresponding positions of the representative light chain polypeptide according to SEQ ID NO:2). In some embodiments, at least one of these positions is modified in the heavy chain and at least one of these positions is modified in the light chain. In some embodiments, at least two of these positions are modified in the heavy chain and at least one of these positions is modified in the light chain. In some embodiments, at least one of these positions is modified in the heavy chain and at least two of these positions are modified in the light chain.

In certain embodiments, provided herein are antibodies comprising a polypeptide chain having at least 70%, 80%, 90%, 95%, or 99% homology to SEQ ID NO:1 and having one or more modified amino acid residues at sites selected from Kabat or Chothia heavy chain residues H019, H025, H040, H052, and H070; and EU heavy chain residues H119, H121, H136, H180, H190, H222, H241, and H404 (see Table 2, "SSHC-8"). Specifically provided herein are antibodies comprising one or more modified amino acid residues at one or more of these positions; antibodies comprising one or more modified amino acid residues at two or more of these positions; antibodies comprising one or more modified amino acid residues at three or more of these positions; antibodies comprising two or more modified amino acid residues at one or more of these positions; antibodies comprising two or more modified amino acid residues at two or more of these positions; antibodies comprising two or more modified amino acid residues at three or more of these positions; antibodies comprising three or more modified amino acid residues at one or more of these positions; antibodies comprising three or more modified amino acid residues at two or more of these positions; and antibodies comprising three or more modified amino acid residues at three or more of these positions.

In certain embodiments, provided herein are antibodies comprising a polypeptide chain having at least 70%, 80%, 90%, 95%, or 99% homology to SEQ ID NO:2 and having one or more modified amino acid residues at sites selected from Kabat or Chothia light chain residues L007 and L022; and EU light chain residue L152 (see Table 3, "SSLC-1"). Specifically provided herein are antibodies comprising one or more modified amino acid residues at one or more of these positions; antibodies comprising one or more modified amino acid residues at two or more of these positions; antibodies comprising one or more modified amino acid residues at all three of these positions; antibodies comprising two or more modified amino acid residues at one or more of these positions; antibodies comprising two or more modified amino acid residues at two Or more of these positions; antibodies comprising two or more modified amino acid residues at all three of these positions; antibodies comprising three modified amino acid residues at one or more of these positions; antibodies comprising three modified amino acid residues at two or more of these positions; and antibodies comprising three modified amino acid residues at all three of these positions.

In certain embodiments, each modified amino acid residue is independently at a specific site selected from the group consisting of optimally substitutable positions of any polypeptide chain of the antibody. In certain embodiments, the antibodies comprise two or more site-specific modified amino acid residues in a single light chain polypeptide. In certain embodiments, the antibodies comprise two or more site-specific modified amino acid residues in a single heavy chain polypeptide. In certain embodiments, the antibodies comprise at least one site-specific modified amino acid residue in a light chain polypeptide and at least one site-specific modified amino acid residue in a heavy chain polypeptide.

In certain embodiments, the antibodies comprise at least one site-specific modified amino acid residue in a light chain polypeptide and at least one site-specific modified amino acid residue in each of two heavy chain polypeptides. In certain embodiments, the antibodies comprise at least one site-specific modified amino acid residue in each of two light chain polypeptides and at least one site-specific modified amino acid residue in a heavy chain polypeptide. In certain embodiments, the antibodies comprise at least one site-specific modified amino acid residue in each of two light chain polypeptides and at least one site-specific modified amino acid residue in each of two heavy chain polypeptides.

In certain embodiments, the antibodies comprise three or more, four or more, five or more, or six or more site-specific modified amino acid residues. In certain embodiments, the antibodies comprise two to six modified amino acid residues. In certain embodiments, the antibodies comprise three to six modified amino acid residues. In certain embodiments, the antibodies comprise four to six modified amino acid residues. In certain embodiments, the antibodies comprise five to six modified amino acid residues.

The antibody can have any form recognized by those of skill in the art. The antibody can comprise a single polypeptide chain—a single heavy chain or a single light chain. The antibody can also form multimers that will be recognized by those of skill in the art including homodimers, heterodimers, homomultimers, and heteromultimers. These multimers can be linked or unlinked. Useful linkages include interchain disulfide bonds typical for polypeptide molecules. The multimers can also be linked by other amino acid residues, including modified amino acid residues derived from the modified amino acids described herein. The antibody can be an immunoglobulin such as of any class or subclass including IgA, IgA1, IgA2, IgD, IgE, IgG, IgG1, IgG2, IgG3, IgG4 and IgM. The antibody can be of the form of any antibody fragment including Fv, Fc, Fab, and (Fab')$_2$ and scFv.

A parent antibody can have affinity to any antigen known to those of skill in the art, or later discovered. Virtually any substance may be an antigen for a parent antibody, or an antibody of the present description. Examples of useful antigens include, but are not limited to, alpha-1 antitrypsin, angiostatin, antihemolytic factor, polypeptides, apolipoprotein, apoprotein, atrial natriuretic factor, atrial natriuretic polypeptide, atrial peptides, C—X—C chemokines (e.g., T39765, NAP-2, ENA-78, Gro-a, Gro-b, Gro-c, IP-10, GCP-2, NAP-4, SDF-1, PF4, MIG), calcitonin, CC chemokines (e.g., monocyte chemoattractant protein-1, monocyte chemoattractant protein-2, monocyte chemoattractant protein-3, monocyte inflammatory protein-1 alpha, monocyte inflammatory protein-1 beta, RANTES, 1309, R83915, R91733, HCC1, T58847, D31065, T64262), CD40 ligand, C-kit ligand, collagen, colony stimulating factor (CSF), complement factor 5a, complement inhibitor, complement receptor 1, cytokines, (e.g., epithelial neutrophil activating peptide-78, GRO/MGSA, GRO, GRO, MIP-1, MIP-1, MCP-1), epidermal growth factor (EGF), erythropoietin ("EPO"), exfoliating toxins A and B, factor IX, factor VII, factor VIII, factor X, fibroblast growth factor (FGF), fibrinogen, fibronectin, G-CSF, GM-CSF, glucocerebrosidase, gonadotropin, growth factors, hedgehog proteins (e.g., Sonic, Indian, Desert), hemoglobin, hepatocyte growth factor (HGF), hirudin, human serum albumin, insulin, insulin-like growth factor (IGF), interferons (e.g., IFN-α, IFN-, IFN-γ), interleukins (e.g., IL-1, IL-2, IL-3, IL-4, IL-5, IL-6, IL-7, IL-8, IL-9, IL-10, IL-11, IL-12, etc.), keratinocyte growth factor (KGF), lactoferrin, leukemia inhibitory factor, luciferase, neurturin, neutrophil inhibitory factor (NIF), oncostatin M, osteogenic protein, parathyroid hormone, PD-ECSF, PDGF, peptide hormones (e.g., human growth hormone), pleiotropin, protein A, protein G, pyrogenic exotoxins A, B, and C, relaxin, renin, SCF, soluble complement receptor 1, soluble I-CAM 1, soluble interleukin receptors (IL-1, 2, 3, 4, 5, 6, 7, 9, 10, 11, 12, 13, 14, 15), soluble TNF receptor, somatomedin, somatostatin, somatotropin, streptokinase, superantigens, i.e., staphylococcal enterotoxins (SEA, SEB, SEC1, SEC2, SEC3, SED, SEE), superoxide dismutase, toxic shock syndrome toxin (TSST-1), thymosin alpha 1, tissue plasminogen activator, tumor necrosis factor (TNF β), tumor necrosis factor receptor (TNFR), tumor necrosis factor-alpha (TNFα), vascular endothelial growth factor (VEGF), urokinase and others. These antigens can be obtained by methods known to those of skill in the art, for example, from commercial sources or from published polypeptide or polynucleotide sequences (e.g. Genbank).

Additional antigens include, but are not limited to, transcriptional and expression activators. Exemplary transcriptional and expression activators include genes and proteins that modulate cell growth, differentiation, regulation, or the like. Expression and transcriptional activators are found in prokaryotes, viruses, and eukaryotes, including fungi, plants, and animals, including mammals, providing a wide range of therapeutic targets. It will be appreciated that expression and transcriptional activators regulate transcription by many mechanisms, e.g., by binding to receptors, stimulating a signal transduction cascade, regulating expression of transcription factors, binding to promoters and enhancers, binding to proteins that bind to promoters and enhancers, unwinding DNA, splicing pre-mRNA, polyadenylating RNA, and degrading RNA. Antigens include, but are not limited to, expression activators such as cytokines, inflammatory molecules, growth factors, their receptors, and oncogene products, e.g., interleukins (e.g., IL-1, IL-2, IL-8, etc.), interferons, FGF, IGF-I, IGF-II, FGF, PDGF, TNF, TGF-α, TGF-β, EGF, KGF, SCF/c-Kit, CD40L/CD40, VLA-4VCAM-1, ICAM-1/LFA-1, and hyalurin/CD44; signal transduction molecules and corresponding oncogene products, e.g., Mos, Ras, Raf, and Met; and transcriptional activators and suppressors, e.g., p53, Tat, Fos, Myc, Jun, Myb, Rel, and steroid hormone receptors such as those for estrogen, progesterone, testosterone, aldosterone, the LDL receptor ligand and corticosterone.

Antigens may also include, but are not limited to, proteins from infectious fungi, e.g., *Aspergillus, Candida* species; bacteria, particularly *E. coli*, which serves a model for pathogenic bacteria, as well as medically important bacteria such as Staphylococci (e.g., *aureus*), or Streptococci (e.g., *pneumoniae*); protozoa such as sporozoa (e.g., Plasmodia), rhizopods (e.g., *Entamoeba*) and *flagellates* (*Trypanosoma, Leishmania, Trichomonas, Giardia*, etc.); viruses such as (+) RNA viruses (examples include Poxviruses e.g., vaccinia; picornaviruses, e.g. polio; Togaviruses, e.g., rubella; flaviviruses, e.g., HCV; and coronaviruses), (−) RNA viruses (e.g., Rhabdoviruses, e.g., VSV; Paramyxovimses, e.g., RSV; Orthomyxovimses, e.g., influenza; Bunyaviruses; and Arenaviruses), dsDNA viruses (Reoviruses, for example), RNA to DNA viruses, i.e., Retroviruses, e.g., HIV and HTLV, and certain DNA to RNA viruses such as hepatitis B.

Antigens may be enzymes including, but not limited to, amidases, amino acid racemases, acylases, dehalogenases, dioxygenases, diarylpropane peroxidases, epimerases, epoxide hydrolases, esterases, isomerases, kinases, glucose isomerases, glycosidases, glycosyl transferases, haloperoxidases, monooxygenases (e.g., p450s), lipases, lignin peroxidases, nitrile hydratases, nitrilases, proteases, phosphatases, subtilisins, transaminase, and nucleases.

Agriculturally related proteins such as insect resistance proteins (e.g., the Cry proteins), starch and lipid production enzymes, plant and insect toxins, toxin-resistance proteins, mycotoxin detoxification proteins, plant growth enzymes (e.g., ribulose 1,5-bisphosphate carboxylase/oxygenase, "RUBISCO"), lipoxygenase (LOX), and phosphoenolpyruvate (PEP) carboxylase may also be antigens.

For example, the antigen may be a disease-associated molecule, such as tumor surface antigen such as B-cell idiotypes, CD20 on malignant B cells, CD33 on leukemic blasts, and HER2/neu on breast cancer. Alternatively, the antigen may be a growth factor receptor. Examples of the growth factors include, but are not limited to, epidermal growth factors (EGFs), transferrin, insulin-like growth factor, transforming growth factors (TGFs), interleukin-1, and interleukin-2. For example, a high expression of EGF receptors has been found in a wide variety of human epithelial primary tumors. TGF-α has been found to mediate an autocrine stimulation pathway in cancer cells. Several murine monoclonal antibodies have been demonstrated to be able to bind EGF receptors, block the binding of ligand to EGF receptors, and inhibit proliferation of a variety of human cancer cell lines in culture and in xenograft models. Mendelsohn and Baselga (1995) Antibodies to growth factors and receptors, in Biologic Therapy of Cancer, 2nd Ed., J B Lippincott, Philadelphia, pp. 607-623. Thus, antibodies may be used to treat a variety of cancers.

The antigen may also be cell surface protein or receptor associated with coronary artery disease such as platelet glycoprotein IIb/IIIa receptor, autoimmune diseases such as CD4, CAMPATH-1 and lipid A region of the gram-negative bacterial lipopolysaccharide. Humanized antibodies against CD4 have been tested in clinical trials in the treatment of patients with mycosis fungoides, generalized postular psoriasis, severe psoriasis, and rheumatoid arthritis. Antibodies against lipid A region of the gram-negative bacterial lipopolysaccharide have been tested clinically in the treatment of septic shock. Antibodies against CAMPATH-1 have also been tested clinically in the treatment of against refractory rheumatoid arthritis. Thus, antibodies provided herein may be used to treat a variety of autoimmune diseases.

Useful antigens also include proteins or peptides associated with human allergic diseases, such as inflammatory mediator proteins, e.g. interleukin-1 (IL-1), tumor necrosis factor (TNF), leukotriene receptor and 5-lipoxygenase, and adhesion molecules such as V-CAM/VLA-4. In addition, IgE may also serve as the antigen because IgE plays pivotal role in type I immediate hypersensitive allergic reactions such as asthma. Studies have shown that the level of total serum IgE tends to correlate with severity of diseases, especially in asthma. Burrows et al. (1989) "Association of asthma with serum IgE levels and skin-test reactivity to allergens" New Engl. L. Med. 320:271-277. Thus, antibodies selected against IgE may be used to reduce the level of IgE or block the binding of IgE to mast cells and basophils in the treatment of allergic diseases without having substantial impact on normal immune functions.

The antigen may also be a viral surface or core protein which may serve as an antigen to trigger an immune response of the infected host. Examples of these viral proteins include, but are not limited to, glycoproteins (or surface antigens, e.g., GP120 and GP41) and capsid proteins (or structural proteins, e.g., P24 protein); surface antigens or core proteins of hepatitis A, B, C, D or E virus (e.g. small hepatitis B surface antigen (SHBsAg) of hepatitis B virus and the core proteins of hepatitis C virus, NS3, NS4 and NS5 antigens); glycoprotein (G-protein) or the fusion protein (F-protein) of respiratory syncytial virus (RSV); surface and core proteins of herpes simplex virus HSV-1 and HSV-2 (e.g., glycoprotein D from HSV-2).

The antigen may also be a mutated tumor suppressor gene product that has lost its tumor-suppressing function and may render the cells more susceptible to cancer. Tumor suppressor genes are genes that function to inhibit the cell growth and division cycles, thus preventing the development of neoplasia. Mutations in tumor suppressor genes cause the cell to ignore one or more of the components of the network of inhibitory signals, overcoming the cell cycle check points and resulting in a higher rate of controlled cell growth-cancer. Examples of the tumor suppressor genes include, but are not limited to, DPC-4, NF-1, NF-2, RB, p53, WT1, BRCA1 and BRCA2. DPC-4 is involved in pancreatic cancer and participates in a cytoplasmic pathway that inhibits cell division. NF-1 codes for a protein that inhibits Ras, a cytoplasmic inhibitory protein. NF-1 is involved in neurofibroma and pheochromocytomas of the nervous system and myeloid leukemia. NF-2 encodes a nuclear protein that is involved in meningioma, schwanoma, and ependymoma of the nervous system. RB codes for the pRB protein, a nuclear protein that is a major inhibitor of cell cycle. RB is involved in retinoblastoma as well as bone, bladder, small cell lung and breast cancer. p53 codes for p53 protein that regulates cell division and can induce apoptosis. Mutation and/or inaction of p53 is found in a wide ranges of cancers. WT1 is involved in Wilms tumor of the kidneys. BRCA1 is involved in breast and ovarian cancer, and BRCA2 is involved in breast cancer. Thus, antibodies may be used to block the interactions of the gene product with other proteins or biochemicals in the pathways of tumor onset and development.

The antigen may be a CD molecule including but not limited to, CD1a, CD1b, CD1c, CD1d, CD2, CD3γ, CD3δ, CD3ε, CD4, CD5, CD6, CD7, CD8α, CD8β, CD9, CD10, CD11a, CD11b, CD11c, CDw12, CD13, CD14, CD15, CD15s, CD16a, CD16b, CD18, CD19, CD20, CD21, CD22, CD23, CD24, CD25, CD26, CD27, CD28, CD29, CD30, CD31, CD32, CD33, CD34, CD35, CD36, CD37, CD38, CD39, CD40, CD41, CD42a, CD42b, CD42c, CD42d, CD43, CD44, CD45, CD45R, CD46, CD47, CD48, CD49a, CD49b, CD49c, CD49d, CD49e, CD49f, CD50, CD51, CD52, CD53, CD54, CD55, CD56, CD57, CD58, CD59, CDw60, CD61, CD62E, CD62L, CD62P, CD63, CD64, CD65, CD66a, CD66b, CD66c, CD66d, CD66e, CD66f, CD67, CD68, CD69, CDw70, CD71, CD72, CD73, CD74, CDw75, CDw76, CD77, CD79a, CD79r3, CD80, CD81, CD82, CD83, CD84, CD85, CD86, CD87, CD88, CD89, CD90, CD91, CDw92, CD93, CD94, CD95, CD96, CD97, CD98, CD99, CD100, CD101, CD102, CD103, CD104, CD105, CD106, CD107a, CD107b, CDw108, CDw109, CD110-113, CD114, CD115, CD116, CD117, CD118, CD119, CD120a, CD120b, CD121a, CD121b, CD122, CD123, CDw124, CD125, CD126, CDw127, CDw128a, CDw128b, CD129, CDw130, CD131, CD132, CD133, CD134, CD135, CD136, CDw137, CD138, CD139, CD140a, CD140b, CD141, CD142, CD143, CD144, CDw145, CD146, CD147, CD148, CDw149, CD150, CD151, CD152, CD153, CD154, CD155, CD156, CD157, CD158a, CD158b, CD161, CD162, CD163, CD164, CD165, CD166, and TCR4. The antigen may be VEGF, VEGF receptor, EGFR, Her2, TNFa, TNFRI receptor, GPIIb/IIIa, IL-2Rα chain, IL-2R β chain, RSV F protein, α4 integrin, IgE, IgE receptor, digoxin, carpet viper venom, complement C5, OPGL, CA-125 tumor antigen, Staphylococci proteins, *Staphylococcus epidermidis* proteins, *Staphylococcus aureus* proteins, proteins involved Staphylococcal infection (including but not limited to, *Staphylococcus aureus* and *Staphylococcus epidermidis*), IL-6 receptor, CTLA-4, RSV, Tac subunit of IL-2 receptor, IL-5, and EpCam. The antigen may be a fragment of a molecule.

In some embodiments, the parent antibodies are multispecific antibodies. Any suitable multispecific antibody may be used, including a bispecific antibody. Examples of useful bispecific parent antibodies include, but are not limited to, those with one antibody directed against a tumor cell antigen and the other antibody directed against a cytotoxic trigger molecule such as anti-FcγRI/anti-CD 15, anti-p185$^{HER2}$/FcγRIII (CD16), anti-CD3/anti-malignant B-cell (1D10), anti-CD3/anti-p185$^{HER2}$, anti-CD3/anti-p97, anti-CD3/anti-renal cell carcinoma, anti-CD3/anti-OVCAR-3, anti-CD3/L-D1 (anti-colon carcinoma), anti-CD3/anti-melanocyte stimulating hormone analog, anti-EGF receptor/anti-CD3, anti-CD3/anti-CAMA1, anti-CD3/anti-CD19, anti-CD3/MoV18, anti-neural cell adhesion molecule (NCAM)/anti-CD3, anti-folate binding protein (FBP)/anti-CD3, anti-pan carcinoma associated antigen (AMOC-31)/anti-CD3; bispecific antibodies with one antibody which binds specifically to a tumor antigen and another antibody which binds to a toxin such as anti-saporin/anti-Id-1, anti-CD22/anti-saporin, anti-CD7/anti-saporin, anti-CD38/anti-saporin, anti-CEA/anti-ricin A chain, anti-interferon-α (IFN-α)/anti-hybridoma idiotype, anti-CEA/anti-vinca alkaloid; bispecific antibodies for converting enzyme activated prodrugs such as anti-CD30/anti-alkaline phosphatase (which catalyzes conversion of mitomycin phosphate prodrug to mitomycin alcohol); bispecific antibodies which can be used as fibrinolytic agents such as anti-fibrin/anti-tissue plasminogen activator (tPA), anti-fibrin/anti-urokinase-type plasminogen activator (uPA); bispecific antibodies for targeting immune complexes to cell surface receptors such as anti-low density lipoprotein (LDL)/anti-Fc receptor (e.g. FcγRI, FcγRII or FcγRIII); bispecific antibodies for use in therapy of infectious diseases such as anti-CD3/anti-herpes simplex virus (HSV), anti-T-cell receptor:CD3 complex/anti-influenza, anti-FcγR/anti-HIV; bispecific antibodies for tumor detection in vitro or in vivo such as anti-CEA/anti-EOTUBE, anti-CEA/anti-DPTA, anti-anti-p185$^{HER2}$/anti-hapten; bispecific antibodies as vaccine adjuvants (see Fanger, M W et al., Crit Rev Immunol. 1992; 12(34):101-24, which is incorporated by reference herein); and bispecific antibodies as diagnostic tools such as anti-rabbit IgG/anti-ferritin, anti-horse radish peroxidase (HRP)/anti-hormone, anti-somatostatin/anti-substance P, anti-HRP/anti-FITC, anti-CEA/anti-β-galactosidase (see Nolan, O et R. O'Kennedy, Biochim Biophys Acta. 1990 Aug. 1; 1040(1):1-11, which is incorporated by reference herein). Examples of trispecific antibodies include anti-CD3/anti-CD4/anti-CD37, anti-CD3/anti-CD5/anti-CD37 and anti-CD3/anti-CD8/anti-CD37.

Linkers and Payloads

One of skill in the art can use the reactive groups described herein to link the polypeptides or antibodies to any molecular entity capable of forming a covalent bond with a modified amino acid described herein, or a modified amino acid residue derived from such a modified amino acid. Such linking can be performed directly or indirectly via a linker. Thus, provided herein are conjugates comprising a polypeptide comprising an amino acid residue corresponding to a compound of formula I, Ia, II, III, IV, V, VI, VII, VIII, IX, or 1-10 linked to a payload and optionally comprising a linking moiety between the polypeptide and the payload.

Useful linkers include those described herein. In certain embodiments, the linker is any divalent or multivalent linker known to those of skill in the art. Generally, the linker is capable of forming covalent bonds with the payload moiety and a modified amino acid or a modified amino acid residue. Useful divalent linkers include a bond, alkylene, substituted alkylene, heteroalkylene, substituted heteroalkylene, arylene, substituted arylene, heteroarlyene and substituted heteroarylene. In certain embodiments, the linker is $C_{1-10}$ alkylene or $C_{1-10}$ heteroalkylene.

The payload can be any molecular entity that one of skill in the art might desire to conjugate to the polypeptide. In certain embodiments, the payload is a therapeutic moiety. In such embodiment, the polypeptide conjugate can be used to target the therapeutic moiety to its molecular target. In certain embodiments, the payload is a labeling moiety. In such embodiments, the polypeptide conjugate can be used to detect binding of the polypeptide to its target. In certain embodiments, the payload is a cytotoxic moiety. In such embodiments, the conjugate can be used target the cytotoxic moiety to a diseased cell, for example a cancer cell, to initiate destruction or elimination of the cell. Conjugates comprising other payloads apparent to those of skill in the art are within the scope of the conjugates described herein.

In certain embodiments, a conjugate can have a payload selected from the group consisting of a label, a dye, a polymer, a water-soluble polymer, polyethylene glycol, a derivative of polyethylene glycol, a photocrosslinker, a cytotoxic compound, a radionuclide, a drug, an affinity label, a photoaffinity label, a reactive compound, a resin, a second protein or polypeptide or polypeptide analog, an antibody or antibody fragment, a metal chelator, a cofactor, a fatty acid, a carbohydrate, a polynucleotide, a DNA, a RNA, an antisense polynucleotide, a peptide, a water-soluble dendrimer, a cyclodextrin, an inhibitory ribonucleic acid, a biomaterial, a nanoparticle, a spin label, a fluorophore, a metal-containing moiety, a radioactive moiety, a novel functional group, a group that covalently or noncovalently interacts with other molecules, a photocaged moiety, a photoisomerizable moiety, biotin, a derivative of biotin, a biotin analogue, a moiety incorporating a heavy atom, a chemically cleavable group, a photocleavable group, an elongated side chain, a carbon-linked sugar, a redox-active agent, an amino thioacid, a toxic moiety, an isotopically labeled moiety, a biophysical probe, a phosphorescent group, a chemiluminescent group, an electron dense group, a magnetic group, an intercalating group, a chromophore, an energy transfer agent, a biologically active agent, a detectable label, a small molecule, or any combination thereof. In an embodiment, the payload is a label, a dye, a polymer, a cytotoxic compound, a radionuclide, a drug, an affinity label, a resin, a protein, a polypeptide, a polypeptide analog, an antibody, antibody fragment, a metal chelator, a cofactor, a fatty acid, a carbohydrate, a polynucleotide, a DNA, a RNA, a peptide, a fluorophore, or a carbon-linked sugar. In certain embodiments, the payload is a label, a dye, a polymer, a drug, an antibody, antibody fragment, a DNA, a RNA, or a peptide.

Useful drug payloads include any cytotoxic, cytostatic or immunomodulatory agent. Useful classes of cytotoxic or immunomodulatory agents include, for example, antitubulin agents, auristatins, DNA minor groove binders, DNA replication inhibitors, alkylating agents (e.g., platinum complexes such as cis-platin, mono(platinum), bis(platinum) and tri-nuclear platinum complexes and carboplatin), anthracyclines, antibiotics, antifolates, antimetabolites, calmodulin inhibitors, chemotherapy sensitizers, duocarmycins, etoposides, fluorinated pyrimidines, ionophores, lexitropsins, maytansinoids, nitrosoureas, platinols, pore-forming compounds, purine antimetabolites, puromycins, radiation sensitizers, rapamycins, steroids, taxanes, topoisomerase inhibitors, vinca alkaloids, or the like.

Individual cytotoxic or immunomodulatory agents include, for example, an androgen, anthramycin (AMC), asparaginase, 5-azacytidine, azathioprine, bleomycin, busulfan, buthionine sulfoximine, calicheamicin, calicheamicin derivatives, camptothecin, carboplatin, carmustine (BSNU), CC-1065, chlorambucil, cisplatin, colchicine, cyclophosphamide, cytarabine, cytidine arabinoside, cytochalasin B, dacarbazine, dactinomycin (formerly actinomycin), daunorubicin, decarbazine, DM1, DM4, docetaxel, doxorubicin, etoposide, an estrogen, 5-fluordeoxyuridine, 5-fluorouracil, gemcitabine, gramicidin D, hydroxyurea, idarubicin, ifosfamide, irinotecan, lomustine (CCNU), maytansine, mechlorethamine, melphalan, 6-mercaptopurine, methotrexate, mithramycin, mitomycin C, mitoxantrone, nitroimidazole, paclitaxel, palytoxin, plicamycin, procarbizine, rhizoxin, streptozotocin, tenoposide, 6-thioguanine, thioTEPA, topotecan, vinblastine, vincristine, vinorelbine, VP-16 and VM-26.

In some embodiments, suitable cytotoxic agents include, for example, DNA minor groove binders (e.g., enediynes and lexitropsins, a CBI compound; see also U.S. Pat. No. 6,130,237), duocarmycins, taxanes (e.g., paclitaxel and docetaxel), puromycins, vinca alkaloids, CC-1065, SN-38, topotecan, morpholino-doxorubicin, rhizoxin, cyanomorpholino-doxorubicin, echinomycin, combretastatin, netropsin, epothilone A and B, estramustine, cryptophycins, cemadotin, maytansinoids, discodermolide, eleutherobin, and mitoxantrone.

In some embodiments, the payload is an anti-tubulin agent. Examples of anti-tubulin agents include, but are not limited to, taxanes (e.g., Taxol® (paclitaxel), Taxotere® (docetaxel)), T67 (Tularik) and vinca alkyloids (e.g., vincristine, vinblastine, vindesine, and vinorelbine). Other anti-tubulin agents include, for example, baccatin derivatives, taxane analogs, epothilones (e.g., epothilone A and B), nocodazole, colchicine and colcimid, estramustine, cryptophycins, cemadotin, maytansinoids, combretastatins, discodermolide, and eleutherobin.

In certain embodiments, the cytotoxic agent is a maytansinoid, another group of anti-tubulin agents. For example, in specific embodiments, the maytansinoid can be maytansine or DM-1 (ImmunoGen, Inc.; see also Chari et al., 1992, Cancer Res. 52:127-131).

In some embodiments, the payload is an auristatin, such as auristatin E or a derivative thereof. For example, the auristatin E derivative can be an ester formed between auristatin E and a keto acid. For example, auristatin E can be reacted with paraacetyl benzoic acid or benzoylvaleric acid to produce AEB and AEVB, respectively. Other typical auristatin derivatives include AFP, MMAF, and MMAE. The synthesis and structure of auristatin derivatives are described in U.S. Patent Application Publication Nos. 2003-0083263, 2005-0238649 and 2005-0009751; International Patent Publication No. WO 04/010957, International Patent Publication No. WO 02/088172, and U.S. Pat. Nos. 6,323,315; 6,239,104; 6,034,065; 5,780,588; 5,665,860; 5,663,149; 5,635,483; 5,599,902; 5,554,725; 5,530,097; 5,521,284; 5,504,191; 5,410,024; 5,138,036; 5,076,973; 4,986,988; 4,978,744; 4,879,278; 4,816,444; and 4,486,414.

In some embodiments, the payload is not a radioisotope. In some embodiments, the payload is not radioactive.

In some embodiments, the payload is an antimetabolite. The antimetabolite can be, for example, a purine antagonist (e.g., azothioprine or mycophenolate mofetil), a dihydrofolate reductase inhibitor (e.g., methotrexate), acyclovir, gangcyclovir, zidovudine, vidarabine, ribavarin, azidothymidine, cytidine arabinoside, amantadine, dideoxyuridine, iododeoxyuridine, poscarnet, or trifluridine.

In other embodiments, the payload is tacrolimus, cyclosporine, FU506 or rapamycin. In further embodiments, the drug is aldesleukin, alemtuzumab, alitretinoin, allopurinol, altretamine, amifostine, anastrozole, arsenic trioxide, bexarotene, bexarotene, calusterone, capecitabine, celecoxib, cladribine, darbepoetin alfa, denileukin diftitox, dexrazoxanc, dromostanolone propionate, epirubicin, epoetin alfa, estramustine, exemestane, filgrastim, floxuridine, fludarabine, fulvestrant, gemcitabine, gemtuzumab ozogamicin (MYLOTARG), goserelin, idarubicin, ifosfamide, imatinib mesylate, interferon alfa-2a, irinotecan, letrozole, leucovorin, levamisole, meclorethamine or nitrogen mustard, megestrol, mesna, methotrexate, methoxsalen, mitomycin C, mitotane, nandrolone phenpropionate, oprelvekin, oxaliplatin, pamidronate, pegademase, pegaspargase, pegfilgrastim, pentostatin, pipobroman, plicamycin, porfimer sodium, procarbazine, quinacrine, rasburicase, Rituximab, sargramostim, streptozocin, tamoxifen, temozolomide, teniposide, testolactone, thioguanine, toremifene, tositumomab, trastuzumab (HERCEPTIN), tretinoin, uracil mustard, valrubicin, vinblastine, vincristine, vinorelbine or zoledronate.

In some embodiments, the payload is an immunomodulatory agent. The immunomodulatory agent can be, for example, gangcyclovir, etanercept, tacrolimus, cyclosporine, rapamycin, cyclophosphamide, azathioprine, mycophenolate mofetil or methotrexate. Alternatively, the immunomodulatory agent can be, for example, a glucocorticoid (e.g., cortisol or aldosterone) or a glucocorticoid analogue (e.g., prednisone or dexamethasone).

In some embodiments, the immunomodulatory agent is an anti-inflammatory agent, such as arylcarboxylic derivatives, pyrazole-containing derivatives, oxicam derivatives and nicotinic acid derivatives. Classes of anti-inflammatory agents include, for example, cyclooxygenase inhibitors, 5-lipoxygenase inhibitors, and leukotriene receptor antagonists.

Suitable cyclooxygenase inhibitors include meclofenamic acid, mefenamic acid, carprofen, diclofenac, diflunisal, fenbufen, fenoprofen, indomethacin, ketoprofen, nabumetone, sulindac, tenoxicam and tolmetin.

Suitable lipoxygenase inhibitors include redox inhibitors (e.g., catechol butane derivatives, nordihydroguaiaretic acid (NDGA), masoprocol, phenidone, Ianopalen, indazolinones, naphazatrom, benzofuranol, alkylhydroxylamine), and non-redox inhibitors (e.g., hydroxythiazoles, methoxyalkylthiazoles, benzopyrans and derivatives thereof, methoxytetrahydropyran, boswellic acids and acetylated derivatives of boswellic acids, and quinolinemethoxyphenylacetic acids substituted with cycloalkyl radicals), and precursors of redox inhibitors.

Other suitable lipoxygenase inhibitors include antioxidants (e.g., phenols, propyl gallate, flavonoids and/or naturally occurring substrates containing flavonoids, hydroxylated derivatives of the flavones, flavonol, dihydroquercetin, luteolin, galangin, orobol, derivatives of chalcone, 4,2',4'-trihydroxychalcone, ortho-aminophenols, N-hydroxyureas, benzofuranols, ebselen and species that increase the activity of the reducing selenoenzymes), iron chelating agents (e.g., hydroxamic acids and derivatives thereof, N-hydroxyureas, 2-benzyl-1-naphthol, catechols, hydroxylamines, carnosol trolox C, catechol, naphthol, sulfasalazine, zyleuton, 5-hydroxyanthranilic acid and 4-(omega-arylalkyl)phenylalkanoic acids), imidazole-containing compounds (e.g., ketoconazole and itraconazole), phenothiazines, and benzopyran derivatives.

Yet other suitable lipoxygenase inhibitors include inhibitors of eicosanoids (e.g., octadecatetraenoic, eicosatetraenoic, docosapentaenoic, eicosahexaenoic and docosahexaenoic acids and esters thereof, PGE1 (prostaglandin E1), PGA2 (prostaglandin A2), viprostol, 15-mo nohydroxyeicosatetraenoic, 15-monohydroxy-eicosatrienoic and 15-monohydroxyeicosapentaenoic acids, and leukotrienes B5, C5 and D5), compounds interfering with calcium flows, phenothiazines, diphenylbutylamines, verapamil, fuscoside, curcumin, chlorogenic acid, caffeic acid, 5,8,11,14-eicosatetrayenoic acid (ETYA), hydroxyphenylretinamide, ionapalen, esculin, diethylcarbamazine, phenantroline, baicalein, proxicromil, thioethers, diallyl sulfide and di-(1-propenyl) sulfide.

Leukotriene receptor antagonists include calcitriol, ontazolast, Bayer Bay-x-1005, Ciba-Geigy CGS-25019C, ebselen, Leo Denmark ETH-615, Lilly LY-293111, Ono ONO-4057, Terumo TMK-688, Boehringer Ingleheim BI-RM-270, Lilly LY 213024, Lilly LY 264086, Lilly LY 292728, Ono ONO LB457, Pfizer 105696, Perdue Frederick PF 10042, Rhone-Poulenc Rorer RP 66153, SmithKline Beecham SB-201146, SmithKline Beecham SB-201993, SmithKline Beecham SB-209247, Searle SC-53228, Sumitamo SM 15178, American Home Products WAY 121006, Bayer Bay-o-8276, Warner-Lambert CI-987, Warner-Lambert CI-987BPC-15LY 223982, Lilly LY 233569, Lilly LY-255283, MacroNex MNX-160, Merck and Co. MK-591, Merck and Co. MK-886, Ono ONO-LB-448, Purdue Frederick PF-5901, Rhone-Poulenc Rorer RG14893, Rhone-Poulenc Rorer RP 66364, Rhone-Poulenc Rorer RP 69698, Shionoogi S-2474, Searle SC-41930, Searle SC-50505, Searle SC-51146, Searle SC-52798, SmithKline Beecham SK&F-104493, Leo Denmark SR-2566, Tanabe T-757 and Teijin TEI-1338.

Other useful drug payloads include chemical compounds useful in the treatment of cancer. Examples of chemotherapeutic agents include Erlotinib (TARCEVA®. Genentech/OS1 Pharm.), Bortezomib (VELCADE®, Millennium Pharm.), Fulvestrant (FASLODEX®, AstraZeneca), Sutent (SU11248, Pfizer), Letrozole (FEMARA®, Novartis), Imatinib mesylate (GLEEVEC®, Novartis), PTK787/ZK 222584 (Novartis), Oxaliplatin (Eloxatin®, Sanofi), 5-FU (5-fluorouracil), Leucovorin, Rapamycin (Sirolimus, RAPAMUNE®, Wyeth), Lapatinib (TYKERB®, GSK572016, Glaxo Smith Kline), Lonafarnib (SCH 66336), Sorafenib (BAY43-9006, Bayer Labs), and Gefitinib (IRESSA®, AstraZeneca), AG1478, AG1571 (SU 5271; Sugen), alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin γ11 and calicheamicin omegall (Angew Chem. Intl. Ed. Engl. (1994) 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamniprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® (paclitaxel; Bristol-Myers Squibb Oncology, Princeton, N.J.), ABRAXANE®

(Cremophor-free), albumin-engineered nanoparticle formulations of paclitaxel (American Pharmaceutical Partners, Schaumberg, Ill.), and TAXOTERE® (doxetaxel; Rhone-Poulenc Rorer, Antony, France); chloranmbucil; GEMZAR® (gemcitabine); 6-thioguanine; mercaptopurine; methotrexate; platinum analogs such as cisplatin and carboplatin; vinblastine; etoposide (VP-16); ifosfamide; mitoxantrone; vincristine; NAVELBINE® (vinorelbine); novantrone; teniposide; edatrexate; daunomycin; aminopterin; capecitabine (XELODA®); ibandronate; CPT-11; topoisomerase inhibitor RFS 2000; difluoromethylornithine (DMFO); retinoids such as retinoic acid; and pharmaceutically acceptable salts, acids and derivatives of any of the above.

Other useful payloads include: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxo lane nucleoside cytosine analog); (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-α, Ralf and H-Ras; (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN® rIL-2; a topoisomerase 1 inhibitor such as LURTOTECAN®; ABARELIX® rmRH; (ix) anti-angiogenic agents such as bevacizumab (AVASTIN®, Genentech); and (x) pharmaceutically acceptable salts, acids and derivatives of any of the above. Other anti-angiogenic agents include MMP-2 (matrix-metalloproteinase 2) inhibitors, MMP-9 (matrix-metalloproteinase 9) inhibitors, COX-II (cyclooxygenase II) inhibitors, and VEGF receptor tyrosine kinase inhibitors. Examples of such useful matrix metalloproteinase inhibitors that can be used in combination with the present compounds/compositions are described in WO 96/33172, WO 96/27583, EP 818442, EP 1004578, WO 98/07697, WO 98/03516, WO 98/34918, WO 98/34915, WO 98/33768, WO 98/30566, EP 606,046, EP 931,788, WO 90/05719, WO 99/52910, WO 99/52889, WO 99/29667, WO 99/07675, EP 945864, U.S. Pat. No. 5,863,949, 5,861,510, and EP 780,386, all of which are incorporated herein in their entireties by reference. Examples of VEGF receptor tyrosine kinase inhibitors include 4-(4-bromo-2-fluoroanilino)-6-methoxy-7-(1-methylpiperidin-4-ylmethoxy)quinazoline (ZD6474; Example 2 within WO 01/32651), 4-(4-fluoro-2-methylindol-5-yloxy)-6-methoxy-7-(3-pyrrolidin-1-ylpropoxy)quinazoline (AZD2171; Example 240 within WO 00/47212), vatalanib (PTK787; WO 98/35985) and SU11248 (sunitinib; WO 01/60814), and compounds such as those disclosed in PCT Publication Nos. WO 97/22596, WO 97/30035, WO 97/32856, and WO 98/13354).

In certain embodiments, the payload is an antibody or an antibody fragment. In certain embodiments, the payload antibody or fragment can be encoded by any of the immunoglobulin genes recognized by those of skill in the art. As described in more detail elsewhere in this disclosure, the immunoglobulin genes include, but are not limited to, the κ, λ, α, γ (IgG1, IgG2, IgG3, and IgG4), δ, ε and μ constant region genes, as well as the immunoglobulin variable region genes. The term includes full-length antibody and antibody fragments recognized by those of skill in the art, and variants thereof. Exemplary fragments include but are not limited to Fv, Fc, Fab, and (Fab')$_2$, single chain Fv (scFv), diabodies, triabodies, tetrabodies, bifunctional hybrid polypeptides, CDR1, CDR2, CDR3, combinations of CDR's, variable regions, framework regions, constant regions, and the like.

In certain embodiments, the payload is one or more water-soluble polymers. A wide variety of macromolecular polymers and other molecules can be linked to the polypeptides described herein to modulate biological properties of the polypeptide, and/or provide new biological properties to the polypeptide. These macromolecular polymers can be linked to the polypeptide via a naturally encoded amino acid or residue, via a modified amino acid or residue, or any functional substituent of a natural or modified amino acid or residue of either, or any substituent or functional group added to a natural or modified amino acid or residue. The molecular weight of the polymer may be of a wide range, including but not limited to, between about 100 Da and about 100,000 Da or more.

The polymer selected may be water soluble so that a protein to which it is attached is more soluble or stable, or both, in an aqueous environment, such as a physiological environment. The polymer may be branched or unbranched. Preferably, for therapeutic use of the end-product preparation, the polymer will be pharmaceutically acceptable.

The water soluble polymer may be any structural form including but not limited to linear, forked or branched. Typically, the water soluble polymer is a poly(alkylene glycol), such as poly(ethylene glycol) (PEG), but other water soluble polymers can also be employed. By way of example, PEG is used to describe certain embodiments.

PEG is a well-known, water soluble polymer that is commercially available or can be prepared by ring-opening polymerization of ethylene glycol according to methods well known in the art (Sandler and Karo, Polymer Synthesis, Academic Press, New York, Vol. 3, pages 138-161). The term "PEG" is used broadly to encompass any polyethylene glycol molecule, without regard to size or to modification at an end of the PEG, and can be represented as linked to a polypeptide by the formula: XO—(CH$_2$CH$_2$O)$_n$—CH$_2$CH$_2$—Y where n is 2 to 10,000 and X is H or a terminal modification, including but not limited to, a C$_{1-4}$ alkyl, and Y is a group capable of forming a bond with the polypeptide.

In some cases, a PEG terminates on one end with hydroxy or methoxy, i.e., X is H or CH$_3$ ("methoxy PEG"). Alternatively, the PEG can terminate with a reactive group, thereby forming a bifunctional polymer. Typical reactive groups can include those reactive groups that are commonly used to react with the functional groups found in the 20 common amino acids (including but not limited to, maleimide groups, activated carbonates (including but not limited to, p-nitrophenyl ester), activated esters (including but not limited to, N-hydroxysuccinimide, p-nitrophenyl ester) and aldehydes) as well as functional groups that are inert to the 20 common amino acids but that react specifically with complementary functional groups present in modified amino acids (including, but not limited to, tetrazine groups, strained alkene groups, azide groups, and alkyne groups).

The other end of the PEG, which is shown in the above formula by Y, will attach either directly or indirectly to a polypeptide via a naturally-occurring or modified amino acid residue. For instance, Y may be an amide, carbamate or urea capable of forming a linkage to an amine group (including but not limited to, the epsilon amine of lysine or the N-terminus) of the polypeptide. Alternatively, Y may be a maleimide capable of forming a linkage to a thiol group (including but not limited to, the thiol group of cysteine). In particular embodiments, Y may be a strained alkene capable of forming a linkage to a tetrazine group on a modified amino acid such as those described herein. In further embodiments, Y may be a tetrazine group capable of forming a linkage to a strained alkene group present in a modified amino acid residue. Y may also be an alkyne group capable of forming a linkage to an azide group of a modified amino acid residue, or an azide group capable of forming a linkage to an alkyne group of a modified amino acid residue.

PEG of any suitable molecular mass may be used, including but not limited to, from about 100 Daltons (Da) to 100,000 Da or more as desired (including but not limited to, sometimes 0.1-50 kDa or 10-40 kDa). Branched chain PEGs, including but not limited to, PEG molecules with each chain having a MW ranging from 1-100 kDa (including but not limited to, 1-50 kDa or 5-20 kDa) can also be used. A wide range of PEG molecules are described in, including but not limited to, the Shearwater Polymers, Inc. catalog, Nektar Therapeutics catalog, incorporated herein by reference.

If the modified amino acid or residue comprises a tetrazine, then the PEG will typically contain a strained alkene. Alternatively, if the modified amino acid or residue comprises a strained alkene, such as trans-cyclooctene or norbornene, then the PEG will typically contain a tetrazine. In preferred embodiments, the modified amino acid or residue comprises the tetrazine and the PEG comprises the strained alkene. In preferred embodiments, the tetrazine functionality is provided on a modified amino acid as described herein.

As described above, other modified amino acids or residues may also be used to enable specific conjugation of different payloads. For example, if at least one modified amino acid or residue comprises an azide, then a PEG will typically contain either an alkyne moiety to effect formation of the [3+2] cycloaddition product or an activated PEG species (i.e., ester, carbonate) containing a phosphine group to effect formation of the amide linkage. Alternatively, if the modified amino acid or residue comprises an alkyne, then a PEG will typically contain an azide moiety to effect formation of the [3+2] Huisgen cycloaddition product.

If the modified amino acid or residue comprises a carbonyl group, the PEG will typically comprise a potent nucleophile (including but not limited to, a hydrazide, hydrazine, hydroxylamine, or semicarbazide functionality) in order to effect formation of corresponding hydrazone, oxime, and semicarbazone linkages, respectively.

In certain embodiments, the payload is a strained alkene-containing polymer comprising a water soluble polymer backbone having an average molecular weight from about 800 Da to about 100,000 Da. The polymer backbone of the water-soluble polymer can be poly(ethylene glycol). However, it should be understood that a wide variety of water soluble polymers including but not limited to poly(ethylene) glycol and other related polymers, including poly(dextran) and poly(propylene glycol), are also suitable for use and that the use of the term PEG or poly(ethyleneglycol) is intended to encompass and include all such molecules. The term PEG includes, but is not limited to, poly(ethylene glycol) in any of its forms, including bifunctional PEG, multiarmed PEG, derivatized PEG, forked PEG, branched PEG, pendent PEG (i.e. PEG or related polymers having one or more functional groups pendent to the polymer backbone), or PEG with degradable linkages therein.

In certain embodiments, the proportion of polyethylene glycol molecules to polypeptide molecules will vary, as will their concentrations in the reaction mixture. In general, the optimum ratio (in terms of efficiency of reaction in that there is minimal excess unreacted protein or polymer) may be determined by the molecular weight of the polyethylene glycol selected and on the number of available reactive groups available. As relates to molecular weight, typically the higher the molecular weight of the polymer, the fewer number of polymer molecules which may be attached to the protein. Similarly, branching of the polymer should be taken into account when optimizing these parameters. Generally, the higher the molecular weight (or the more branches) the higher the polymer:protein ratio.

The polymer backbone can be linear or branched. Branched polymer backbones are generally known in the art. Typically, a branched polymer has a central branch core moiety and a plurality of linear polymer chains linked to the central branch core. PEG is commonly used in branched forms that can be prepared by addition of ethylene oxide to various polyols, such as glycerol, glycerol oligomers, pentaerythritol and sorbitol. The central branch moiety can also be derived from several amino acids, such as lysine. The branched poly(ethylene glycol) can be represented in general form as $R(-PEG-OH)_m$ in which R is derived from a core moiety, such as glycerol, glycerol oligomers, or pentaerythritol, and m represents the number of arms. Multi-armed PEG molecules, such as those described in U.S. Pat. Nos. 5,932,462 5,643,575; 5,229,490; 4,289,872; U.S. Pat. Appl. 2003/0143596; WO 96/21469; and WO 93/21259, each of which is incorporated by reference herein in its entirety, can also be used as the polymer backbone.

Branched PEG can also be in the form of a forked PEG represented by $PEG(-YCHZ_2)_n$, where Y is a linking group and Z is an activated terminal group linked to CH by a chain of atoms of defined length.

Yet another branched form, the pendant PEG, has reactive groups, such as carboxyl, along the PEG backbone rather than at the end of PEG chains.

In addition to these forms of PEG, the polymer can also be prepared with weak or degradable linkages in the backbone. For example, PEG can be prepared with ester linkages in the polymer backbone that are subject to hydrolysis. As shown herein, this hydrolysis results in cleavage of the polymer into fragments of lower molecular weight: -PEG-$CO_2$—PEG-+$H_2O \rightarrow$ PEG-$CO_2$H+HO-PEG- It is understood by those skilled in the art that the term poly(ethylene glycol) or PEG represents or includes all the forms known in the art including but not limited to those disclosed herein.

Many other polymers are also suitable for use. In some embodiments, polymer backbones that are water-soluble, with from 2 to about 300 termini, are particularly. Examples of suitable polymers include, but are not limited to, other poly(alkylene glycols), such as poly(propylene glycol) ("PPG"), copolymers thereof (including but not limited to copolymers of ethylene glycol and propylene glycol), terpolymers thereof, mixtures thereof, and the like. Although the molecular weight of each chain of the polymer backbone can vary, it is typically in the range of from about 800 Da to about 100,000 Da, often from about 6,000 Da to about 80,000 Da.

Those of ordinary skill in the art will recognize that the foregoing list for substantially water soluble backbones is by no means exhaustive and is merely illustrative, and that all polymeric materials having the qualities described herein are contemplated as being suitable for use.

In some embodiments the polymer derivatives are "multi-functional", meaning that the polymer backbone has at least two termini, and possibly as many as about 300 termini, functionalized or activated with a functional group. Multi-functional polymer derivatives include, but are not limited to, linear polymers having two termini, each terminus being bonded to a functional group which may be the same or different.

The term "protected" refers to the presence of a protecting group or moiety that prevents reaction of the chemically reactive functional group under certain reaction conditions. The protecting group will vary depending on the type of chemically reactive group being protected. For example, if the chemically reactive group is an amine or a hydrazide, the protecting group can be selected from the group of tert-butyloxycarbonyl (t-Boc) and 9-fluorenylmethoxycarbonyl (Fmoc). If the chemically reactive group is a thiol, the protecting group can be orthopyridyldisulfide. If the chemically reactive group is a carboxylic acid, such as butanoic or propionic acid, or a hydroxyl group, the protecting group can be benzyl or an alkyl group such as methyl, ethyl, or tert-butyl. Other protecting groups known in the art may also be used.

Specific examples of terminal functional groups in the literature include, but are not limited to, N-succinimidyl carbonate (see e.g., U.S. Pat. Nos. 5,281,698, 5,468,478), amine (see, e.g., Buckmann et al. Makromol. Chem. 182: 1379 (1981), Zaplipsky et al. Eur. Polym. J. 19:1177 (1983)), hydrazide (See, e.g., Andresz et al. Makromol. Chem. 179:301 (1978)), succinimidyl propionate and succinimidyl butanoate (see, e.g., Olson et al. in Poly(ethylene glycol) Chemistry & Biological Applications, pp. 170-181, Harris & Zaplipsky Eds., ACS, Washington, D.C., 1997; see also U.S. Pat. No. 5,672,662), succinimidyl succinate (See, e.g., Abuchowski et al. Cancer Biochem. Biophys. 7:175 (1984) and Joppich et al. Macrolol. Chem. 180:1381 (1979), succinimidyl ester (see, e.g., U.S. Pat. No. 4,670,417), benzotriazole carbonate (see, e.g., U.S. Pat. No. 5,650,234), glycidyl ether (see, e.g., Pitha et al. Eur. J Biochem. 94:11 (1979), Elling et al., Biotech. Appl. Biochem. 13:354 (1991), oxycarbonylimidazole (see, e.g., Beauchamp, et al., Anal. Biochem. 131:25 (1983), Tondelli et al. J. Controlled Release 1:251 (1985)), p-nitrophenyl carbonate (see, e.g., Veronese, et al., Appl. Biochem. Biotech., 11: 141 (1985); and Sartore et al., Appl. Biochem. Biotech., 27:45 (1991)), aldehyde (see, e.g., Harris et al. J. Polym. Sci. Chem. Ed. 22:341 (1984), U.S. Pat. No. 5,824,784, 5,252,714), maleimide (see, e.g., Goodson et al. Bio/Technology 8:343 (1990), Romani et al. in Chemistry of Peptides and Proteins 2:29 (1984)), and Kogan, Synthetic Comm. 22:2417 (1992)), orthopyridyl-disulfide (see, e.g., Woghiren, et al. Bioconj. Chem. 4:314(1993)), acrylol (see, e.g., Sawhney et al., Macromolecules, 26:581 (1993)), vinylsulfone (see, e.g., U.S. Pat. No. 5,900,461). All of the above references and patents are incorporated herein by reference.

In certain embodiments, polymer derivatives comprise a polymer backbone having the structure: X—$CH_2CH_2O$—($CH_2CH_2O$)$_n$$CH_2CH_2$—ZZ, wherein: X is a functional group as described herein, n is about 20 to about 4000, and ZZ is a moiety comprising a strained alkene. In some embodiments, the polymer derivatives comprise a polymer backbone having the structure: X—$CH_2CH_2O$—($CH_2CH_2O$)$_m$$CH_2CH_2$—O—($CH_2$)$_m$—W—ZZ wherein: W is an aliphatic or aromatic linker moiety comprising between 1-10 carbon atoms, n is about 20 to about 4000, X is a functional group as described herein, m is between 1 and 10, and ZZ is a moiety comprising a strained alkene. Examples of suitable functional groups include, but are not limited to, hydroxyl, protected hydroxyl, acetal, alkenyl, amine, aminooxy, protected amine, protected hydrazide, protected thiol, carboxylic acid, protected carboxylic acid, maleimide, dithiopyridine, and vinylpyridine, and ketone.

In some embodiments, the polymer derivatives comprise a polymer backbone having the structure: X—$CH_2CH_2O$—($CH_2CH_2O$)$_n$—$CH_2CH_2$—$O_n$—($CH_2$)$_n$—Y, wherein: Y is a moiety comprising a strained alkene; X is a functional group as described herein; n is about 20 to about 4000; and m is between 1 and 10. Specific examples of each of the heterobifunctional PEG polymers are shown herein.

In some embodiments, a strained alkene-terminal PEG derivative will have the following structure: RO—($CH_2CH_2O$)$_n$—O—($CH_2$)$_m$—Y where Y is a moiety comprising a strained alkene, R is a simple alkyl (methyl, ethyl, propyl, etc.), m is 2-10 and n is 100-1,000 (i.e., average molecular weight is between 5-40 kDa).

In some embodiments, a strained alkene-terminal PEG derivative will have the following structure: RO—($CH_2CH_2O$)$_n$—O—($CH_2$)$_m$—NH—C(O)—($CH_2$)$_p$—Y, where Y is a moiety comprising a strained alkene, R is a simple alkyl (methyl, ethyl, propyl, etc.), m is 2-10, p is 2-10 and n is 100 1,000.

Strained alkene-containing PEG derivatives can be prepared by a variety of methods known in the art and/or disclosed herein. In a method for preparation of a strained alkene-containing polymer derivative, a linking agent bearing a strained alkene functionality is contacted with a payload moiety, wherein the linking agent bears a chemical functionality that will react selectively with a chemical functionality on the PEG polymer, to form a strained alkene-containing polymer derivative product wherein the strained alkene is separated from the polymer backbone by a linking group. Useful PEGs comprising strained alkenes can be obtained from commercial sources, e.g. Jena Biosciences, or prepared according to published techniques, e.g. Aimetti et al., 2009, Biomaterials 30:6048-6054.

An exemplary reaction scheme is shown here: X-PEG-M+N-linker-Y→PG-X-PEG-linker-Y wherein: Y is a moiety comprising a strained alkene, PEG is poly(ethylene glycol) and X is a capping group such as alkoxy or a functional group as described herein; and M is a functional group that is not reactive with the strained alkene functionality but that will react efficiently and selectively with the N functional group. Examples of suitable functional groups include, but are not limited to, M being a carboxylic acid, carbonate or active ester if N is an amine; M being a ketone if N is a hydrazide or aminooxy moiety; M being a leaving group if N is a nucleophile.

In one method for the preparation of a strained alkene-containing PEG derivative, a water soluble polymer backbone having an average molecular weight from about 800 Da to about 100,000 Da, the polymer backbone having a first terminus bonded to a first functional group and a second terminus bonded to a suitable nucleophilic group, is reacted with a compound that bears both a strained alkene functionality and a leaving group that is suitable for reaction with the nucleophilic group on the PEG. When the PEG polymer bearing the nucleophilic moiety and the molecule bearing the leaving group are combined, the leaving group undergoes a nucleophilic displacement and is replaced by the nucleophilic moiety, affording the desired strained alkene-containing polymer: X-PEG-Nu+L-A-C→X-PEG-Nu-A-Y, where Y is a moiety comprising a strained alkene.

As shown, in some embodiments, a preferred polymer backbone for use in the reaction has the formula X-PEG-Nu, wherein PEG is poly(ethylene glycol), Nu is a nucleophilic moiety and X is a functional group that does not react with Nu, L or the strained alkene functionality.

Examples of Nu include, but are not limited to, amine, alkoxy, aryloxy, sulfhydryl, imino, carboxylate, hydrazide, aminoxy groups that would react primarily via a SN2-type mechanism. Additional examples of Nu groups include those functional groups that would react primarily via an nucleophilic addition reaction. Examples of L groups include chloride, bromide, iodide, mesylate, tresylate, and tosylate and other groups expected to undergo nucleophilic displacement as well as ketones, aldehydes, thioesters, olefins, alpha-beta unsaturated carbonyl groups, carbonates and other electrophilic groups expected to undergo addition by nucleophiles.

In certain embodiments, A is an aliphatic linker of between 1-10 carbon atoms or a substituted aryl ring of between 6-14 carbon atoms. X is a functional group which does not react with strained alkene groups and L is a suitable leaving group.

In another method for preparation of the strained alkene-containing polymer derivatives, a PEG polymer having an average molecular weight from about 800 Da to about 100,000 Da, bearing either a protected functional group or a capping agent at one terminus and a suitable leaving group at the other terminus is contacted by an activated molecule comprising a strained alkene.

Purification of the crude products may be accomplished by known methods including, but are not limited to, precipitation of the product followed by chromatography, if necessary.

A more specific example is the case of PEG diamine, in which one of the amines is protected by a protecting group moiety such as tert-butyl-Boc and the resulting monoprotected PEG diamine is reacted with a linking moiety that bears the strained alkene functionality: BocHN-PEG-NH$_2$+ HO$_2$C—(CH$_2$)$_3$—[ZZ], where ZZ is a moiety comprising a strained alkene. In this instance, the amine group can be coupled to the carboxylic acid group using a variety of activating agents such as thionyl chloride or carbodiimide reagents and N-hydroxysuccinimide or N-hydroxybenzotriazole to create an amide bond between the monoamine PEG derivative and the strained alkene-bearing linker moiety. After successful formation of the amide bond, the resulting N-tert-butyl-Boc-protected derivative can be used directly to modify bioactive molecules or it can be further elaborated to install other useful functional groups. For instance, the N-t-Boc group can be hydrolyzed by treatment with strong acid to generate an omega-amino-PEG derivative. The resulting amine can be used as a synthetic handle to install other useful functionality such as maleimide groups, activated disulfides, activated esters and so forth for the creation of valuable heterobifunctional reagents.

In certain embodiments, the polymer derivative has the structure: X-A-PAY—B—Y, where Y is a moiety comprising a strained alkene; B is a linking moiety, which may be present or absent; PAY is a payload moiety; A is a linking moiety, which may be present or absent and which may be the same as B or different; and X is a second functional group.

Examples of a linking moiety for A and B include, but are not limited to, a multiply-functionalized alkyl group containing up to 18, and more preferably between 1-10 carbon atoms. A heteroatom such as nitrogen, oxygen or sulfur may be included with the alkyl chain. The alkyl chain may also be branched at a heteroatom. Other examples of a linking moiety for A and B include, but are not limited to, a multiply functionalized aryl group, containing up to 10 and more preferably 5-6 carbon atoms. The aryl group may be substituted with one more carbon atoms, nitrogen, oxygen, or sulfur atoms. Other examples of suitable linking groups include those linking groups described in U.S. Pat. Nos. 5,932,462 and 5,643,575 and U.S. Pat. Appl. Publication 2003/0143596, each of which is incorporated by reference herein. Those of ordinary skill in the art will recognize that the foregoing list for linking moieties is by no means exhaustive and is intended to be merely illustrative, and that a wide variety of linking moieties having the qualities described herein are contemplated to be useful.

Examples of suitable functional groups for use as X include hydroxyl, protected hydroxyl, alkoxyl, active ester, such as N-hydroxysuccinimidyl esters and 1-benzotriazolyl esters, active carbonate, such as N-hydroxysuccinimidyl carbonates and 1-benzotriazolyl carbonates, acetal, aldehyde, aldehyde hydrates, alkenyl, acrylate, methacrylate, acrylamide, active sulfone, amine, aminooxy, protected amine, hydrazide, protected hydrazide, protected thiol, carboxylic acid, protected carboxylic acid, isocyanate, isothiocyanate, maleimide, vinylsulfone, dithiopyridine, vinylpyridine, iodoacetamide, epoxide, glyoxals, diones, mesylates, tosylates, and tresylate, alkene, ketone, and acetylene. As would be understood, the selected X moiety should be compatible with the strained alkene group so that reaction with the strained alkene group does not occur. The strained alkene-containing polymer derivatives may be homobifunctional, meaning that the second functional group (i.e., X) is also an strained alkene moiety, or heterobifunctional, meaning that the second functional group is a different functional group.

Water soluble polymers can be linked to the polypeptides. The water soluble polymers may be linked via a modified amino acid residue incorporated in the polypeptides or any functional group or substituent of a modified or naturally encoded amino acid residue, or any functional group or substituent added to a modified or naturally encoded amino acid residue. In an embodiment, the modified amino acid residue is a modified amino acid residue as described herein. Alternatively, the water soluble polymers are linked to an antigen-binding antibody incorporating a modified amino acid residue via a naturally-occurring amino acid residue (including but not limited to, cysteine, lysine or the amine group of the N-terminal residue). In some cases, the polypeptides comprise 1, 2, 3, 4, 5, 6, 7, 8, 9, 10 modified amino acid residues, wherein one or more modified amino acid residues are linked to water soluble polymer(s) (including but not limited to, PEG and/or oligosaccharides). In some cases, the polypeptides further comprise 1, 2, 3, 4, 5, 6, 7, 8, 9, 10, or more naturally-encoded amino acid residues linked to water soluble polymers. In some cases, the polypeptides comprise one or more modified amino acid residues linked to water soluble polymers and one or more naturally-occurring amino acid residues linked to water soluble polymers. In some embodiments, the water soluble polymers enhance the serum half-life of the polypeptides relative to the unconjugated form.

The number of water soluble polymers linked to a polypeptide (i.e., the extent of PEGylation or glycosylation) can be adjusted to provide an altered (including but not limited to, increased or decreased) pharmacologic, pharmacokinetic or pharmacodynamic characteristic such as in vivo half-life. In some embodiments, the half-life of a polypeptide is increased at least about 10, 20, 30, 40, 50, 60, 70, 80, 90 percent, 2-fold, 5-fold, 10-fold, 50-fold, or at least about 100-fold over an unmodified polypeptide.

The degree and sites at which water soluble polymer(s) are linked to the polypeptides can modulate the binding of the polypeptides to an antigen or receptor.

PEGylation (i.e., addition of any water soluble polymer) of polypeptides containing a modified amino acid residue, such as a tetrazine-comprising amino acid residue, is carried out by any convenient method. For example, a polypeptide may be PEGylated with a strained alkene-terminated PEG derivative. Briefly, an excess of solid PEG-Y, wherein Y is a moiety comprising a strained alkene, is added, with stirring, to an aqueous solution of a polypeptide comprising an amino acid residue comprising a tetrazine functional group (such as a modified amino acid described herein), at room temperature. Typically, the aqueous solution is buffered with a buffer having a $pK_a$ near the pH at which the reaction is to be carried out (generally about pH 4-10). Examples of suitable buffers for PEGylation at pH 7.5, for instance, include, but are not limited to, HEPES, phosphate, borate, TRIS-HCl, EPPS, and TES. The pH is continuously monitored and adjusted if necessary. The reaction is typically allowed to continue for between about 1-48 hours.

The reaction products are subsequently subjected to hydrophobic interaction chromatography to separate the PEGylated polypeptide variants from free PEG-Y and any high-molecular weight complexes of the PEGylated polypeptide which may form when unblocked PEG is activated at both ends of the molecule, thereby crosslinking polypeptide variant molecules. The conditions during hydrophobic interaction chromatography are such that free PEG-Y flows through the column, while any crosslinked PEGylated polypeptide variant complexes elute after the desired forms, which contain one polypeptide variant molecule conjugated to one or more PEG groups. Suitable conditions vary depending on the relative sizes of the cross-linked complexes versus the desired conjugates and are readily determined by those skilled in the art. The eluent containing the desired conjugates is concentrated by ultrafiltration and desalted by diafiltration.

If necessary, the PEGylated polypeptide obtained from the hydrophobic chromatography can be purified further by one or more procedures known to those skilled in the art including, but are not limited to, affinity chromatography; anion- or cation-exchange chromatography (using, including but not limited to, DEAE SEPHAROSE); chromatography on silica; reverse phase HPLC; gel filtration (using, including but not limited to, SEPHADEX G-75); hydrophobic interaction chromatography; size-exclusion chromatography, metal-chelate chromatography; ultrafiltration/diafiltration; ethanol precipitation; ammonium sulfate precipitation; chromatofocusing; displacement chromatography; electrophoretic procedures (including but not limited to preparative isoelectric focusing), differential solubility (including but not limited to ammonium sulfate precipitation), or extraction. Apparent molecular weight may be estimated by GPC by comparison to globular protein standards (PROTEIN PURIFICATION METHODS, A PRACTICAL APPROACH (Harris & Angal, Eds.) IRL Press 1989, 293-306). The purity of the polypeptide-PEG conjugate can be assessed by proteolytic degradation (including but not limited to, trypsin cleavage) followed by mass spectrometry analysis. Pepinsky B., et al., J. Pharmcol. & Exp. Ther. 297(3):1059-66 (2001).

A water soluble polymer linked to an amino acid residue of a polypeptide can be further derivatized or substituted without limitation.

In certain embodiments, a polypeptide comprising a tetrazine-containing amino acid residue is modified with a branched PEG derivative that contains a terminal strained alkene moiety, with each chain of the branched PEG having a MW ranging from 10-40 kDa and, more preferably, from 5-20 kDa. For instance, in some embodiments, the strained alkene-terminal PEG derivative will have the following structure: $[RO-(CH_2CH_2O)_n-O-(CH_2)_2-NH-C(O)]_2CH(CH_2)_m-X-(CH_2)_pY$ where Y is a moiety comprising a strained alkene, R is a simple alkyl (methyl, ethyl, propyl, etc.), m is 2-10, p is 2-10, and n is 100-1,000, and X is optionally an O, N, S or carbonyl group (C=O), or not present.

Useful exemplary PEG molecules that may be linked to polypeptides, as well as PEGylation methods include those described in, e.g., U.S. Patent Publication Nos. 2004/0001838; 2002/0052009; 2003/0162949; 2004/0013637; 2003/0228274; 2003/0220447; 2003/0158333; 2003/0143596; 2003/0114647; 2003/0105275; 2003/0105224; 2003/0023023; 2002/0156047; 2002/0099133; 2002/0086939; 2002/0082345; 2002/0072573; 2002/0052430; 2002/0040076; 2002/0037949; 2002/0002250; 2001/0056171; 2001/0044526; 2001/0027217; 2001/0021763; U.S. Pat. Nos. 6,646,110; 5,824,778; 5,476,653; 5,219,564; 5,629,384; 5,736,625; 4,902,502; 5,281,698; 5,122,614; 5,473,034; 5,516,673; 5,382,657; 6,552,167; 6,610,281; 6,515,100; 6,461,603; 6,436,386; 6,214,966; 5,990,237; 5,900,461; 5,739,208; 5,672,662; 5,446,090; 5,808,096; 5,612,460; 5,324,844; 5,252,714; 6,420,339; 6,201,072; 6,451,346; 6,306,821; 5,559,213; 5,612,460; 5,747,646; 5,834,594; 5,849,860; 5,980,948; 6,004,573; 6,129,912; WO 97/32607, EP 229,108, EP 402,378, WO 92/16555, WO 94/04193, WO 94/14758, WO 94/17039, WO 94/18247, WO 94/28024, WO 95/00162, WO 95/11924, WO95/13090, WO 95/33490, WO 96/00080, WO 97/18832, WO 98/41562, WO 98/48837, WO 99/32134, WO 99/32139, WO 99/32140, WO 96/40791, WO 98/32466, WO 95/06058, EP 439 508, WO 97/03106, WO 96/21469, WO 95/13312, EP 921 131, WO 98/05363, EP 809 996, WO 96/41813, WO 96/07670, EP 605 963, EP 510 356, EP 400 472, EP 183 503 and EP 154 316, which are incorporated by reference herein. Any of the PEG molecules described herein may be used in any form, including but not limited to, single chain, branched chain, multiarm chain, single functional, bi-functional, multi-functional, or any combination thereof.

In certain embodiments, the polypeptides can be linked to the payloads with one or more linkers capable of reacting with the modified amino acid residue. The one or more linkers can be any linkers apparent to those of skill in the art. The term "linker" is used herein to refer to groups or bonds that normally are formed as the result of a chemical reaction and typically are covalent linkages. Hydrolytically stable linkages means that the linkages are substantially stable in water and do not react with water at useful pH values, including but not limited to, under physiological conditions for an extended period of time, perhaps even indefinitely.

Hydrolytically unstable or degradable linkages mean that the linkages are degradable in water or in aqueous solutions, including for example, blood. Enzymatically unstable or degradable linkages mean that the linkage can be degraded by one or more enzymes. As understood in the art, PEG and related polymers may include degradable linkages in the polymer backbone or in the linker group between the polymer backbone and one or more of the terminal functional groups of the polymer molecule. For example, ester linkages formed by the reaction of PEG carboxylic acids or activated PEG carboxylic acids with alcohol groups on a biologically active agent generally hydrolyze under physiological conditions to release the agent. Other hydrolytically degradable linkages include, but are not limited to, carbonate linkages; imine linkages resulted from reaction of an amine and an aldehyde; phosphate ester linkages formed by reacting an alcohol with a phosphate group; hydrazone linkages which are reaction product of a hydrazide and an aldehyde; acetal linkages that are the reaction product of an aldehyde and an alcohol; orthoester linkages that are the reaction product of a formate and an alcohol; peptide linkages formed by an amine group, including but not limited to, at an end of a polymer such as PEG, and a carboxyl group of a peptide; and oligonucleotide linkages formed by a phosphoramidite group, including but not limited to, at the end of a polymer, and a 5' hydroxyl group of an oligonucleotide. Branched linkers may be used in polypeptides. A number of different cleavable linkers are known to those of skill in the art. See U.S. Pat. Nos. 4,618,492; 4,542,225, and 4,625,014. The mechanisms for release of an agent from these linker groups include, for example, irradiation of a photolabile bond and acid-catalyzed hydrolysis. U.S. Pat. No. 4,671,958, for example, includes a description of immunoconjugates comprising linkers which are cleaved at the target site in vivo by the proteolytic enzymes of the patient's complement system. The length of the linker may be predetermined or selected depending upon a desired spatial relationship between the polypeptide and the molecule linked to it. In view of the large number of methods that have been reported for attaching a variety of radiodiagnostic compounds, radiotherapeutic compounds, drugs, toxins, and other agents to polypeptides one skilled in the art will be able to determine a suitable method for attaching a given agent to a polypeptide Any hetero- or homo-bifunctional linker can be used to link the payload to the polypeptide or antibody. The linker may have a wide range of molecular weight or molecular length. Larger or smaller molecular weight linkers may be used to provide a desired spatial relationship or conformation between the polypeptide and the linked entity. Linkers having longer or shorter molecular length may also be used to provide a desired space or flexibility between the polypeptide and the linked entity. Similarly, a linker having a particular shape or conformation may be utilized to impart a particular shape or conformation to the polypeptide or the linked entity, either before or after the polypeptide reaches its target. The functional groups present on each end of the linker may be selected to modulate the release of a polypeptide or a payload under desired conditions. This optimization of the spatial relationship between the polypeptide and the linked entity may provide new, modulated, or desired properties to the molecule.

In some embodiments, provided herein water-soluble bifunctional linkers that have a dumbbell structure that includes: a) a tetrazine, a strained alkene, or a carbonyl-containing moiety on at least a first end of a polymer backbone; and b) at least a second functional group on a second end of the polymer backbone. The second functional group can be the same or different as the first functional group. The second functional group, in some embodiments, is not reactive with the first functional group. In some embodiments, water-soluble compounds that comprise at least one arm of a branched molecular structure are provided. For example, the branched molecular structure can be a dendritic structure.

Polypeptide Compositions

Polypeptides described herein can be formulated into compositions using methods available in the art and those disclosed herein. Any of the compounds disclosed herein can be provided in the appropriate pharmaceutical composition and be administered by a suitable route of administration.

In certain embodiments, the polypeptide compositions provided herein further comprise a pharmaceutically acceptable carrier. The carrier can be a diluent, excipient, or vehicle with which the pharmaceutical composition is administered. Such pharmaceutical carriers can be sterile liquids, such as water and oils, including those of petroleum, animal, vegetable or synthetic origin, such as peanut oil, soybean oil, mineral oil, sesame oil and the like. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in E. W. Martin, 1990, Remington's Pharmaceutical Sciences, Mack Publishing Co.

In some embodiments, the pharmaceutical composition is provided in a form suitable for administration to a human subject. In some embodiments, the pharmaceutical composition will contain a prophylactically or therapeutically effective amount of the polypeptide together with a suitable amount of carrier so as to provide the form for proper administration to the patient. The formulation should suit the mode of administration.

In some embodiments, the pharmaceutical composition is provided in a form suitable for intravenous administration. Typically, compositions suitable for intravenous administration are solutions in sterile isotonic aqueous buffer. Where necessary, the composition may also include a solubilizing agent and a local anesthetic such as lignocaine to ease pain at the site of the injection. Such compositions, however, may be administered by a route other than intravenous administration.

In particular embodiments, the pharmaceutical composition is suitable for subcutaneous administration. In particular embodiments, the pharmaceutical composition is suitable for intramuscular administration.

Components of the pharmaceutical composition can be supplied either separately or mixed together in unit dosage form, for example, as a dry lyophilized powder or water free concentrate. Where the composition is to be administered by infusion, it can be dispensed with an infusion bottle containing sterile pharmaceutical grade water or saline. Where the composition is administered by injection, an ample of sterile water for injection or saline can be provided so that the ingredients may be mixed prior to administration.

In some embodiments, the pharmaceutical composition is supplied as a dry sterilized lyophilized powder that is capable of being reconstituted to the appropriate concentration for administration to a subject. In some embodiments, polypeptides are supplied as a water free concentrate. In some embodiments, the polypeptide is supplied as a dry sterile lyophilized powder at a unit dosage of at least 0.5 mg, at least 1 mg, at least 2 mg, at least 3 mg, at least 5 mg, at least 10 mg, at least 15 mg, at least 25 mg, at least 30 mg, at least 35 mg, at least 45 mg, at least 50 mg, at least 60 mg, or at least 75 mg.

In certain embodiments, the pharmaceutical composition is supplied in liquid form. In some embodiments, the pharmaceutical composition is provided in liquid form and is substantially free of surfactants and/or inorganic salts. In some embodiments, the polypeptide is supplied as in liquid form at a unit dosage of at least 0.1 mg/ml, at least 0.5 mg/ml, at least 1 mg/ml, at least 2.5 mg/ml, at least 3 mg/ml, at least 5 mg/ml, at least 8 mg/ml, at least 10 mg/ml, at least 15 mg/ml, at least 25 mg/ml, at least 30 mg/ml, or at least 60 mg/ml.

In some embodiments, the pharmaceutical composition is formulated as a salt form. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

In therapeutic use, the practitioner will determine the posology most appropriate according to a preventive or curative treatment and according to the age, weight, stage of the infection and other factors specific to the subject to be treated. In certain embodiments, doses are from about 1 to about 1000 mg per day for an adult, or from about 5 to about 250 mg per day or from about 10 to 50 mg per day for an adult. In certain embodiments, doses are from about 5 to about 400 mg per day or 25 to 200 mg per day per adult. In certain embodiments, dose rates of from about 50 to about 500 mg per day are also contemplated.

Methods of Use for Therapy or Prophylaxis

Certain polypeptides provided herein can be used for the treatment or prevention of any disease or condition deemed suitable to the practitioner of skill in the art. Generally, a method of treatment or prevention encompasses the administration of a therapeutically or prophylactically effective amount of the polypeptide or polypeptide composition to a subject in need thereof to treat or prevent the disease or condition.

A therapeutically effective amount of the polypeptide or composition is an amount that is effective to reduce the severity, the duration and/or the symptoms of a particular disease or condition. The amount of the polypeptide or composition that will be therapeutically effective in the prevention, management, treatment and/or amelioration of a particular disease can be determined by standard clinical techniques. The precise amount of the polypeptide or composition to be administered with depend, in part, on the route of administration, the seriousness of the particular disease or condition, and should be decided according to the judgment of the practitioner and each subject's circumstances.

In some embodiments, the effective amount of the polypeptide provided herein is between about 0.025 mg/kg and about 1000 mg/kg body weight of a human subject. In certain embodiments, the polypeptide is administered to a human subject at an amount of about 1000 mg/kg body weight or less, about 950 mg/kg body weight or less, about 900 mg/kg body weight or less, about 850 mg/kg body weight or less, about 800 mg/kg body weight or less, about 750 mg/kg body weight or less, about 700 mg/kg body weight or less, about 650 mg/kg body weight or less, about 600 mg/kg body weight or less, about 550 mg/kg body weight or less, about 500 mg/kg body weight or less, about 450 mg/kg body weight or less, about 400 mg/kg body weight or less, about 350 mg/kg body weight or less, about 300 mg/kg body weight or less, about 250 mg/kg body weight or less, about 200 mg/kg body weight or less, about 150 mg/kg body weight or less, about 100 mg/kg body weight or less, about 95 mg/kg body weight or less, about 90 mg/kg body weight or less, about 85 mg/kg body weight or less, about 80 mg/kg body weight or less, about 75 mg/kg body weight or less, about 70 mg/kg body weight or less, or about 65 mg/kg body weight or less.

In some embodiments, the effective amount of polypeptide provided herein is between about 0.025 mg/kg and about 60 mg/kg body weight of a human subject. In some embodiments, the effective amount of a polypeptide of the pharmaceutical composition provided herein is about 0.025 mg/kg or less, about 0.05 mg/kg or less, about 0.10 mg/kg or less, about 0.20 mg/kg or less, about 0.40 mg/kg or less, about 0.80 mg/kg or less, about 1.0 mg/kg or less, about 1.5 mg/kg or less, about 3 mg/kg or less, about 5 mg/kg or less, about 10 mg/kg or less, about 15 mg/kg or less, about 20 mg/kg or less, about 25 mg/kg or less, about 30 mg/kg or less, about 35 mg/kg or less, about 40 mg/kg or less, about 45 mg/kg or less, about 50 mg/kg or about 60 mg/kg or less.

The pharmaceutical composition of the method can be administered using any method known to those skilled in the art. For example, the pharmaceutical composition can be administered intramuscularly, intradermally, intraperitoneally, intravenously, subcutaneously administration, or any combination thereof. In some embodiments, the pharmaceutical composition is administered subcutaneously. In some embodiments, the composition is administered intravenously. In some embodiments, the composition is administered intramuscularly.

Methods of Use for Detection or Diagnosis

The polypeptides provided herein can be used for the detection of any target or for the diagnosis of any disease or condition deemed suitable to the practitioner of skill in the art. The methods encompass detecting the binding of a polypeptide to a target in an appropriate location, e.g., the appropriate body, tissue, or cell. In the methods, the formation of a complex between the polypeptide and target can be detected by any method known to those of skill in the art. Examples include assays that use secondary reagents for detection, ELISA's and immunoprecipitation and agglutination assays. A detailed description of these assays is, for example, given in Harlow and Lane, Polypeptides: A Laboratory Manual (Cold Spring Harbor Laboratory, New York 1988 555-612, WO96/13590 to Maertens and Stuyver, Zrein et al. (1998) and WO96/29605.

For in situ diagnosis, the polypeptide may be administered to a subject by methods known in the art such as, for example, intravenous, intranasal, intraperitoneal, intracerebral, intraarterial injection such that a specific binding between a polypeptide with an epitopic region on the amyloid protein may occur. The polypeptide/target complex may conveniently be detected through a label attached to the polypeptide or any other art-known method of detection.

Further provided herein are kits for detection or diagnosis. Exemplary kits comprise one or more polypeptides provided herein along with one or more reagents useful for detecting a complex between the one or more polypeptides and their targets.

Preparation of Polypeptides Comprising a Modified Amino Acid Residues

The polypeptides described herein can be prepared by any technique apparent to those of skill in the art without limitation. Useful techniques for preparation include in vivo synthesis, for example with modified tRNA and tRNA synthetase, cell-free synthesis, for example with modified tRNA and tRNA synthetase, solid phase polypeptide synthesis and liquid phase polypeptide synthesis. Exemplary techniques are described in this section and in the examples herein. In particular embodiments, the polypeptide is an antibody or antibody fragment.

In certain embodiments, a variant of the aminoacyl tRNA synthetase provided in SEQ ID NO: 3 is used to catalyze the attachment of a non-natural amino acid to a compatible tRNA. Variants of the aminoacyl tRNA synthetase of SEQ ID NO: 3 are particularly advantageous when utilizing amino acids comprising tetrazine functional groups, such as those provided in any of formulas I, Ia, II, III, IV, V, VI, VII, VIII, IX, and (1)-(10). In certain embodiments, a variant of SEQ ID NO: 3 with the following mutations, designated "2A2", may be particularly advantageous for use with a non-natural amino acid of formula 9: Y32L, L65V, H70A, F108W, Q109S, D158V, I159A, and L162V (SEQ ID NO: 4). In some embodiments, a variant of SEQ ID NO: 3 with the following mutations, designated "2A9", may be particularly advantageous for use with a non-natural amino acid of formula 6: Y32G, L65V, H70A, Q109S, D158G, and L162S (SEQ ID NO: 5). Other aminoacyl tRNA synthetases that may be useful with the compounds of the invention include the mtaF synthetase disclosed in Seitchik et al., J. Am. Chem. Soc., 2012, 134:2898-2901 (incorporated by reference in its entirety) and other variants of SEQ ID NO: 3. Variants of SEQ ID NO: 3 may be made by mutagenesis and screened to identify mutant synthetases that act on any non-natural amino acid of interest. Such mutagenesis may be completely random, or may be deterministic with respect to the location of the mutation(s) and/or the residue(s) allowed to occur at a particular portion of the synthetase polypeptide sequence. Examples of methods for random mutagenesis of synthetases may be found in Seitchik et al., cited above and incorporated by reference in its entirety.

In certain methods, the polypeptide is translated and/or transcribed from one or more polynucleotides encoding the polypeptide. Accordingly, provided herein are polynucleotides capable of encoding the polypeptides having one or more modified amino acid residues at site-specific positions in one or more polypeptide chains. In certain embodiments, the polynucleotides comprise a codon not normally associated with an amino acid at the polynucleotide position corresponding to the site-specific polypeptide position for the modified amino acid residue. Examples of such codons include stop codons, 4 bp codons, 5 bp codons, and the like. The reaction mixture typically comprises a tRNA synthetase capable of making tRNAs that complement (suppress) said codon. These suppressor tRNAs are linked to the modified amino acids to facilitate their incorporation into the polypeptide at the site of the suppressor codon.

The polypeptides can be prepared by techniques known to those of skill in the art for expressing polynucleotides to incorporate modified amino acid residues into site specific positions of a polypeptide. Such techniques are described, for example, in U.S. Pat. Nos. 7,045,337 and 7,083,970, in U.S. Published Patent Application Nos. US 2008/0317670, US 2009/0093405, US 2010/0093082, US 2010/0098630, US 2008/0085277 and in international patent publication nos. WO 2004/016778 A1 and WO 2008/066583 A2, the contents of which are hereby incorporated by reference in their entireties.

In certain embodiments, a polypeptide can be prepared in a cell-free reaction mixture comprising at least one orthogonal tRNA aminoacylated with a modified amino acid residue, where the orthogonal tRNA base pairs with a codon that is not normally associated with an amino acid residue, e.g. a stop codon; a 4 bp codon, etc. The reaction mixture also comprises a tRNA synthetase capable of aminoacylating the orthogonal tRNA with a modified amino acid. One tRNA synthetase that can be used is shown as SEQ ID NO:55 and 56 in US Patent Publication No. 2008/0233611. Wild-type tyrosyl M janashcii tRNA may also be used. Usually the orthogonal tRNA synthetase, which is susceptible to degradation by proteases present in bacterial cell extracts, is exogenously synthesized and added to the reaction mix prior to initiation of polypeptide synthesis. The orthogonal tRNA may be synthesized in the bacterial cells from which the cell extract is obtained, may be synthesized de novo during the polypeptide synthesis reaction, or may be exogenously added to the reaction mix.

In certain embodiments, components that affect modified amino acid residue insertion and protein insertion or folding are optionally added to the reaction mixture. Such components include elevated concentrations of translation factors to minimize the effect of release factor 1 and 2 and to further optimize orthogonal component concentrations. Protein chaperones (Dsb System of oxidoreductases and isomerases, GroES, GroEL, DNAJ, DNAK, Skp, etc.) may be exogenously added to the reaction mixture or may be overexpressed in the source cells used to prepare the cell extract The reactions may utilize a large scale reactor, small scale, or may be multiplexed to perform a plurality of simultaneous syntheses. Continuous reactions will use a feed mechanism to introduce a flow of reagents, and may isolate the end-product as part of the process. Batch systems are also of interest, where additional reagents may be introduced to prolong the period of time for active synthesis. A reactor may be run in any mode such as batch, extended batch, semi-batch, semi-continuous, fed-batch and continuous, and which will be selected in accordance with the application purpose. The reactions may be of any volume, either in a small scale, usually at least about 1 µl and not more than about 15 µl, or in a scaled up reaction, where the reaction volume is at least about 15 µl, usually at least about 50 µl, more usually at least about 100 µl, and may be 500 µl, 1000 µl, or greater. In principle, reactions may be conducted at any scale as long as sufficient oxygen (or other electron acceptor) is supplied when needed.

Useful methods for synthesis where at least one modified amino acid residue is introduced into the polypeptide strand during elongation include but are not limited to: (I) addition of exogenous purified orthogonal synthetase, modified amino acid, and orthogonal tRNA to the cell-free reaction, (II) addition of exogenous purified orthogonal synthetase and modified amino acid to the reaction mixture, but with orthogonal tRNA transcribed during the cell-free reaction, (III) addition of exogenous purified orthogonal synthetase and modified amino acid to the reaction mixture, but with orthogonal tRNA synthesized by the cell extract source organism. In certain embodiments, the orthogonal components are driven by regulatable promoters, so that synthesis levels can be controlled although other measures may be used such as controlling the level of the relevant DNA templates by addition or specific digestion.

In certain embodiments, tRNA synthetase is exogenously synthesized and added to the cell-free reaction mix. In certain embodiments, the reaction mix is prepared from bacterial cells in which ompT has been inactivated or is naturally inactive. OmpT is believed to degrade components of the reaction mixture including tRNA synthetase.

In addition to the above components such as cell-free extract, genetic template, and amino acids, materials specifically required for protein synthesis may be added to the reaction. These materials include salts, folinic acid, cyclic AMP, inhibitors for protein or nucleic acid degrading enzymes, inhibitors or regulators of protein synthesis, adjusters of oxidation/reduction potential(s), non-denaturing surfactants, buffer components, spermine, spermidine, putrescine, etc.

The salts preferably include potassium, magnesium, and ammonium salts (e.g. of acetic acid or glutamic acid). One or more of such salts may have an alternative amino acid as a counter anion. There is an interdependence among ionic species for optimal concentration. These ionic species are typically optimized with regard to protein production. When changing the concentration of a particular component of the reaction medium, that of another component may be changed accordingly. For example, the concentrations of several components such as nucleotides and energy source compounds may be simultaneously adjusted in accordance with the change in those of other components. Also, the concentration levels of components in the reactor may be varied over time. The adjuster of oxidation/reduction potential may be dithiothreitol, ascorbic acid, glutathione and/or their oxidized forms.

In certain embodiments, the reaction can proceed in a dialysis mode, in a diafiltration batch mode, in a fed-batch mode of in a semi-continuous operation mode. In certain embodiments, a feed solution can be supplied to the reactor through a membrane or through an injection unit. Synthesized polypeptide can accumulate in the reactor followed by isolation or purification after completion of the system operation. Vesicles containing the polypeptide may also be continuously isolated, for example by affinity adsorption from the reaction mixture either in situ or in a circulation loop as the reaction fluid is pumped past the adsorption matrix.

During protein synthesis in the reactor, the protein isolating means for selectively isolating the desired protein may include a unit packed with particles coated with polypeptide molecules or other molecules for adsorbing the synthesized, desired protein. Preferably, the protein isolating means comprises two columns for alternating use.

The resulting polypeptide can be purified or isolated by standard techniques. Exemplary techniques are provided in the examples herein.

Assay Methods

Polypeptides can be assayed for their expected activity, or for a new activity, according to any assay apparent to those of skill in the art. The resulting polypeptide can be assayed for activity in a functional assay or by quantitating the amount of protein present in a non-functional assay, e.g. immunostaining, ELISA, quantitation on Coomasie or silver stained gel, etc., and determining the ratio of biologically active protein to total protein.

The amount of protein produced in a translation reaction can be measured in various fashions. One method relies on the availability of an assay which measures the activity of the particular protein being translated. An example of an assay for measuring protein activity is a luciferase assay system, or chloramphenicol acetyl transferase assay system. These assays measure the amount of functionally active protein produced from the translation reaction. Activity assays will not measure full length protein that is inactive due to improper protein folding or lack of other post translational modifications necessary for protein activity.

Another method of measuring the amount of protein produced in coupled in vitro transcription and translation reactions is to perform the reactions using a known quantity of radiolabeled amino acid such as $^{35}$S-methionine, $^{3}$H-leucine or $^{14}$C-leucine and subsequently measuring the amount of radiolabeled amino acid residue incorporated into the newly translated protein. Incorporation assays will measure the amount of radiolabeled amino acid residues in all proteins produced in an in vitro translation reaction including truncated protein products. The radiolabeled protein may be further separated on a protein gel, and by autoradiography confirmed that the product is the proper size and that secondary protein products have not been produced.

Preparation of Modified Amino Acids

The compounds provided herein can be prepared, isolated or obtained by any method apparent to those of skill in the art. Compounds provided herein can be prepared according to the General Preparation Scheme provided herein. Reaction conditions, steps and reactants not provided in the General Preparation Scheme would be apparent to, and known by, those skilled in the art. Exemplary methods of making the compounds are provided in the Examples below.

General Preparation Scheme 1

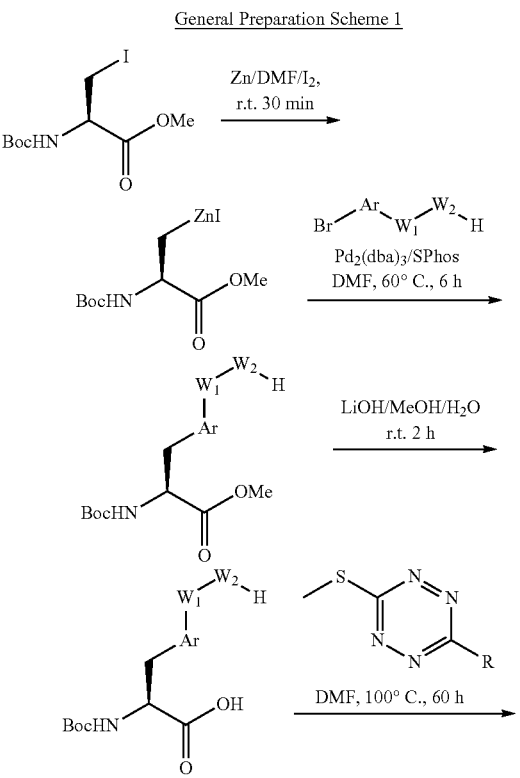

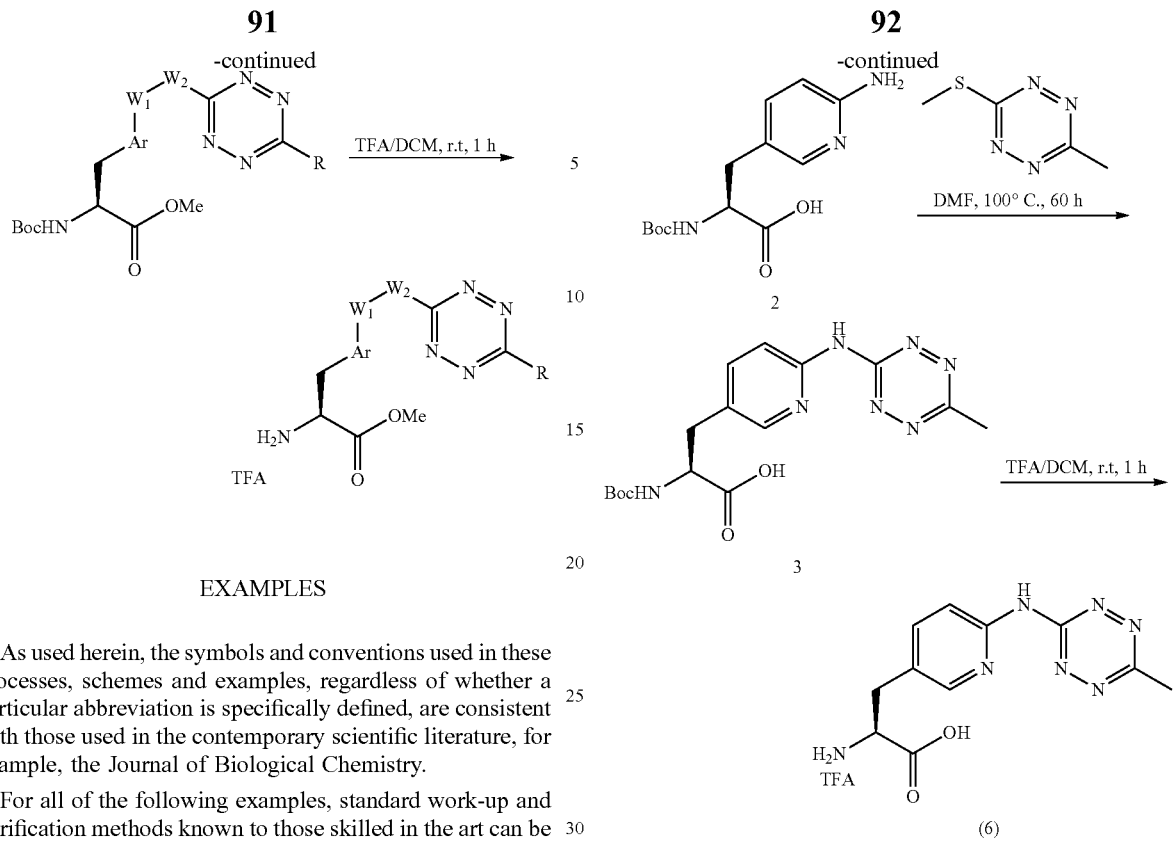

EXAMPLES

As used herein, the symbols and conventions used in these processes, schemes and examples, regardless of whether a particular abbreviation is specifically defined, are consistent with those used in the contemporary scientific literature, for example, the Journal of Biological Chemistry.

For all of the following examples, standard work-up and purification methods known to those skilled in the art can be utilized. Unless otherwise indicated, all temperatures are expressed in ° C. (degrees Centigrade). All methods are conducted at room temperature unless otherwise noted.

Example 1: Preparation of the Compound of Formula (6)

The compound of formula (6) was prepared according to the following scheme and protocols.

Preparation of Compound 1

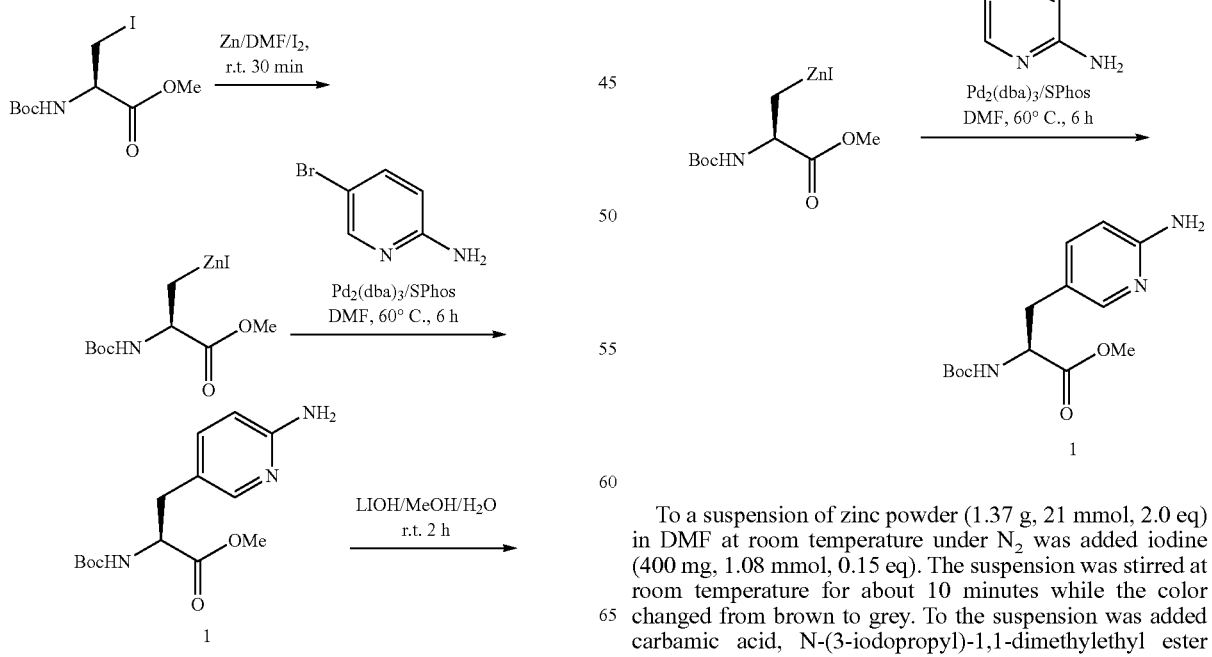

To a suspension of zinc powder (1.37 g, 21 mmol, 2.0 eq) in DMF at room temperature under $N_2$ was added iodine (400 mg, 1.08 mmol, 0.15 eq). The suspension was stirred at room temperature for about 10 minutes while the color changed from brown to grey. To the suspension was added carbamic acid, N-(3-iodopropyl)-1,1-dimethylethyl ester (3.45 g, 10.5 mmol, 1.0 eq) along with iodine (400 mg, 1.08 mmol, 0.15 eq). The reaction mixture was allowed to stir at room temperature for 30 minutes (heat produced from the reaction can be observed) and cooled to room temperature to give a crude zinc reagent, which was used for the next step without further purification.

A mixture of the 2-aminyl-5-bromopyridine (2.2 g, 12.6 mmol, 1.2 eq), Pd$_2$(dba)$_3$ (292 mg, 0.318 mmol, 0.025 eq) and 2-dicyclohexylphosphino-2',6'-dimethoxybiphenyl, SPhos (0.52 g, 1.27 mmol, 0.1 eq) in a Schlenk tube in anhydrous DMF (5 mL) under N$_2$ was stirred at room temperature for 5 min. The above prepared zinc reagent (1.0 eq) suspension was added into the mixture under N$_2$. The reaction was heated to 60° C. for 6 hours. It was cooled to room temperature and filtered through a pad of Celite. The filtrate was concentrated and purified by a silica gel column (DCM:MeOH=9:1) to give compound 1 and 2-aminyl-5-bromopyridine (could not be separated at this stage).

Preparation of Compound 2

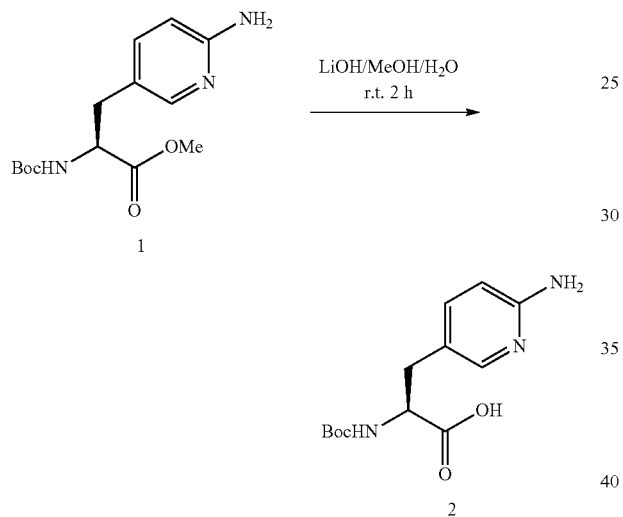

To a mixture of compound 1 (containing 2-aminyl-5-bromopyridine) in a mixed solvent of THF (5 mL) and MeOH (10 mL) was added aqueous LiOH (800 mg, 19 mmol, 5.0 eq, in 10 mL of water). The mixture was stirred at room temperature for 2 hours. The solvent was removed and the residue was purified by a silica gel column (DCM:MeOH:Et$_3$N, 9:1:1) to give product 2 (1.4 g, 37% two-steps) as a triethylamine salt.

Preparation of Compound 3

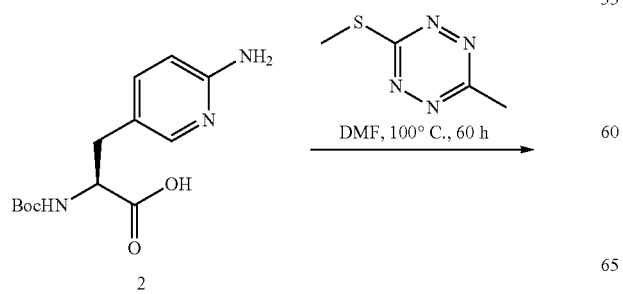

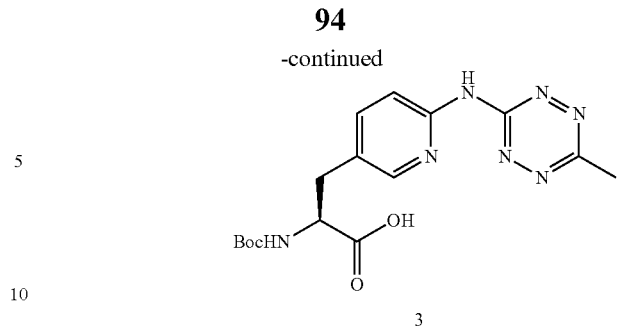

To a triethylamine salt of 2 (1.4 g, 3.66 mmol, 1.0 eq) in DMF (10.0 mL) was added 4-methyltetrazine methyl sulfide (1.56 g, 11.0 mmol, 3.0 eq) in a sealed tube. The tube was heated to 100° C. for 60 hours. The reaction mixture was cooled and purified by prep-HPLC to give product 3 (480 mg, 35%).

Preparation of the Compound Offormula (6)

Compound 3 (190 mg, 0.51 mmol) was dissolved in 20% TFA in DCM (8 mL) and stirred at room temperature for 1 hour. The solvent was removed under reduced pressure, and the residue was re-dissolved in water, frozen and lyophilized to give a compound of formula (6) (240 mg, 78%, TFA salts) as red solid. LC-MS (ESI): 276 (M+1), 274 (M−1). $^1$H NMR (300 MHz, CD$_3$OD) δ 8.29 (s, 1H), 8.04 (d, J=7.8 Hz, 1H), 7.91 (dd, J=7.8 Hz, 2.4 Hz, 1H), 4.33 (t, 1H), 3.25-3.34 (m, 2H), 2.91 (s, 3H).

Example 2: Preparation of the Compound of Formula (31

Preparation of Compound 4

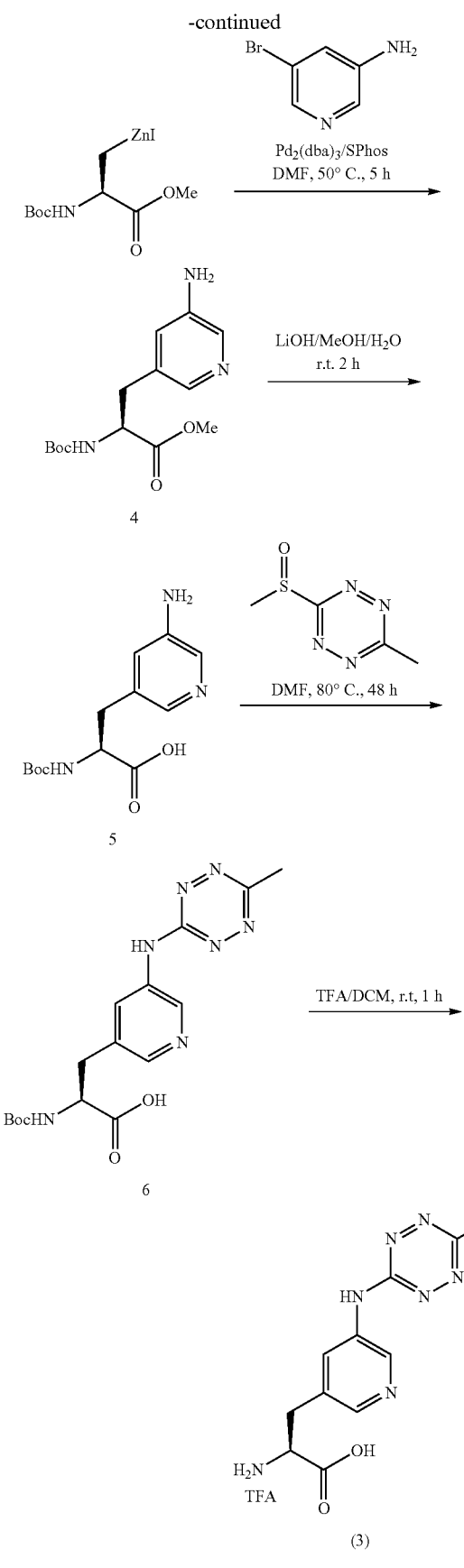

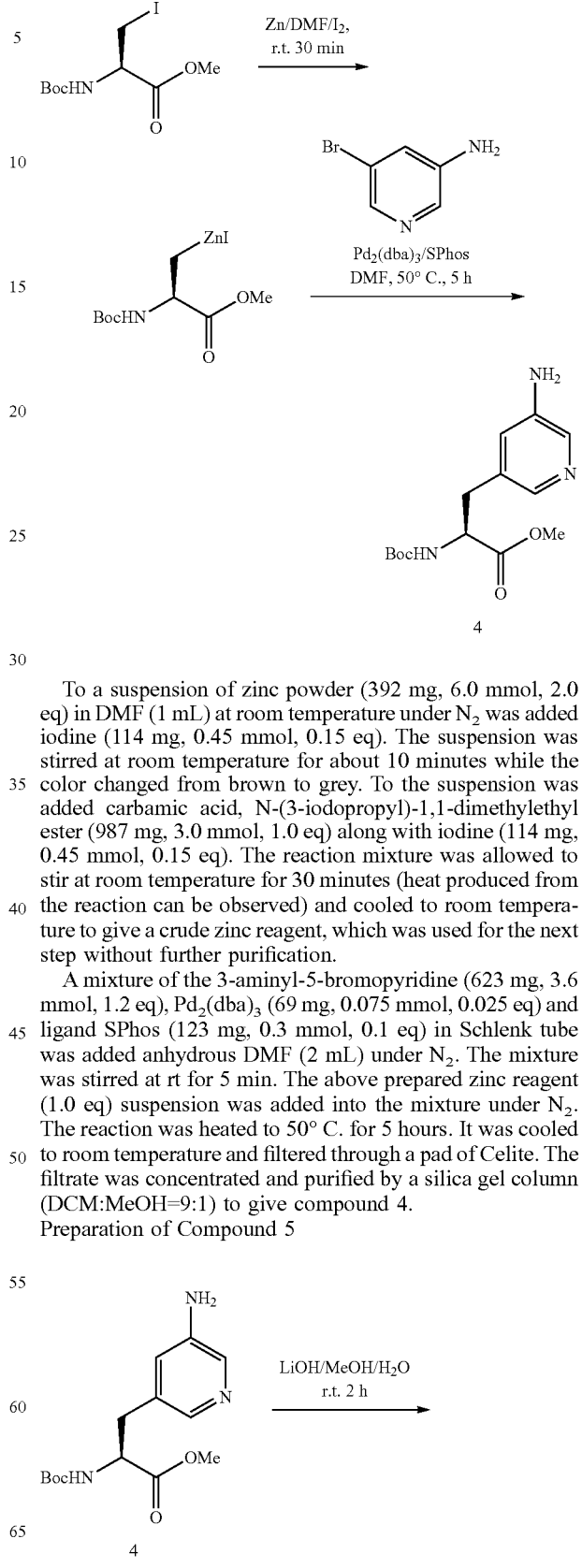

To a suspension of zinc powder (392 mg, 6.0 mmol, 2.0 eq) in DMF (1 mL) at room temperature under $N_2$ was added iodine (114 mg, 0.45 mmol, 0.15 eq). The suspension was stirred at room temperature for about 10 minutes while the color changed from brown to grey. To the suspension was added carbamic acid, N-(3-iodopropyl)-1,1-dimethylethyl ester (987 mg, 3.0 mmol, 1.0 eq) along with iodine (114 mg, 0.45 mmol, 0.15 eq). The reaction mixture was allowed to stir at room temperature for 30 minutes (heat produced from the reaction can be observed) and cooled to room temperature to give a crude zinc reagent, which was used for the next step without further purification.

A mixture of the 3-aminyl-5-bromopyridine (623 mg, 3.6 mmol, 1.2 eq), $Pd_2(dba)_3$ (69 mg, 0.075 mmol, 0.025 eq) and ligand SPhos (123 mg, 0.3 mmol, 0.1 eq) in Schlenk tube was added anhydrous DMF (2 mL) under $N_2$. The mixture was stirred at rt for 5 min. The above prepared zinc reagent (1.0 eq) suspension was added into the mixture under $N_2$. The reaction was heated to 50° C. for 5 hours. It was cooled to room temperature and filtered through a pad of Celite. The filtrate was concentrated and purified by a silica gel column (DCM:MeOH=9:1) to give compound 4.

Preparation of Compound 5

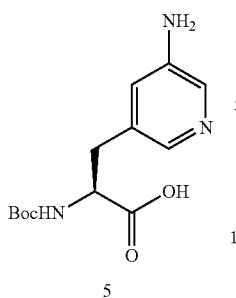

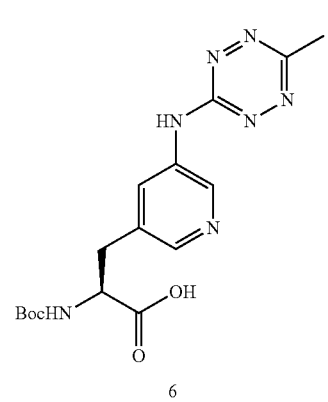

Preparation of the Compound of Formula (3)

To a mixture of compound 4 (containing 3-aminyl-5-bromopyridine) in a mixed solvent of THF (2 mL) and MeOH (5 mL) was added aqueous lithium hydroxide (198 mg, 4.7 mmol, 2.0 eq, in 5 mL of water). The mixture was stirred at rt for 2 h. The solvent was removed and the residue was purified by $C_{18}$ column (MeOH: $H_2O$) to give product 5 (480 mg, 57% yield, two-steps).

Preparation of Compound 6

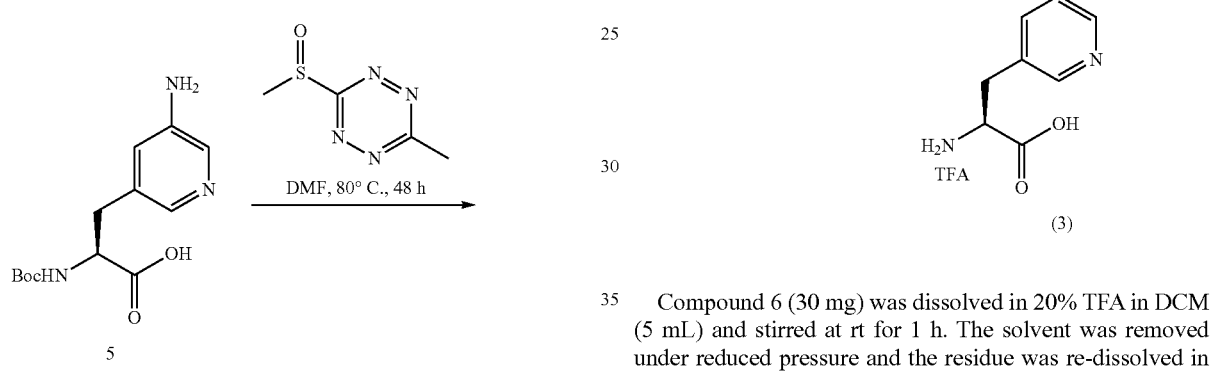

Compound 6 (30 mg) was dissolved in 20% TFA in DCM (5 mL) and stirred at rt for 1 h. The solvent was removed under reduced pressure and the residue was re-dissolved in water, frozen and lyophilized to give a compound of formula (3) (25 mg, TFA salts) as red solid. LC-MS (ESI): 276 (M+1), 274 (M−1). $^1$H NMR (300 MHz, $D_2O$) δ 9.18 (s, 1H), 8.56 (s, 1H), 8.35 (s, 1H), 4.33 (t, 1H), 3.30-3.40 (m, 2H), 2.80 (s, 3H).

Example 3: Preparation of the Compound of Formula (9)

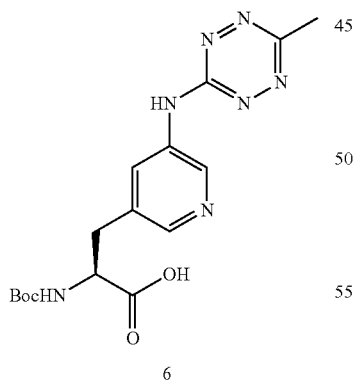

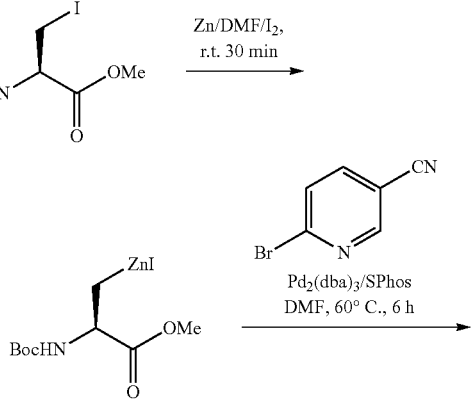

To a solution of compound 5 (281 mg, 1.0 mmol, 1.0 eq) in THF (5 mL) was added 4-methyl tetrazine methyl sulfoxide (316 mg, 2.0 mmol, 2.0 eq, freshly prepared from its sulfide by oxidation with mCPBA) in a sealed tube. The tube was heated at 80° C. for 48 h. The solvent was removed and product was purified by prep-HPLC to give product 6 (30 mg, 8%).

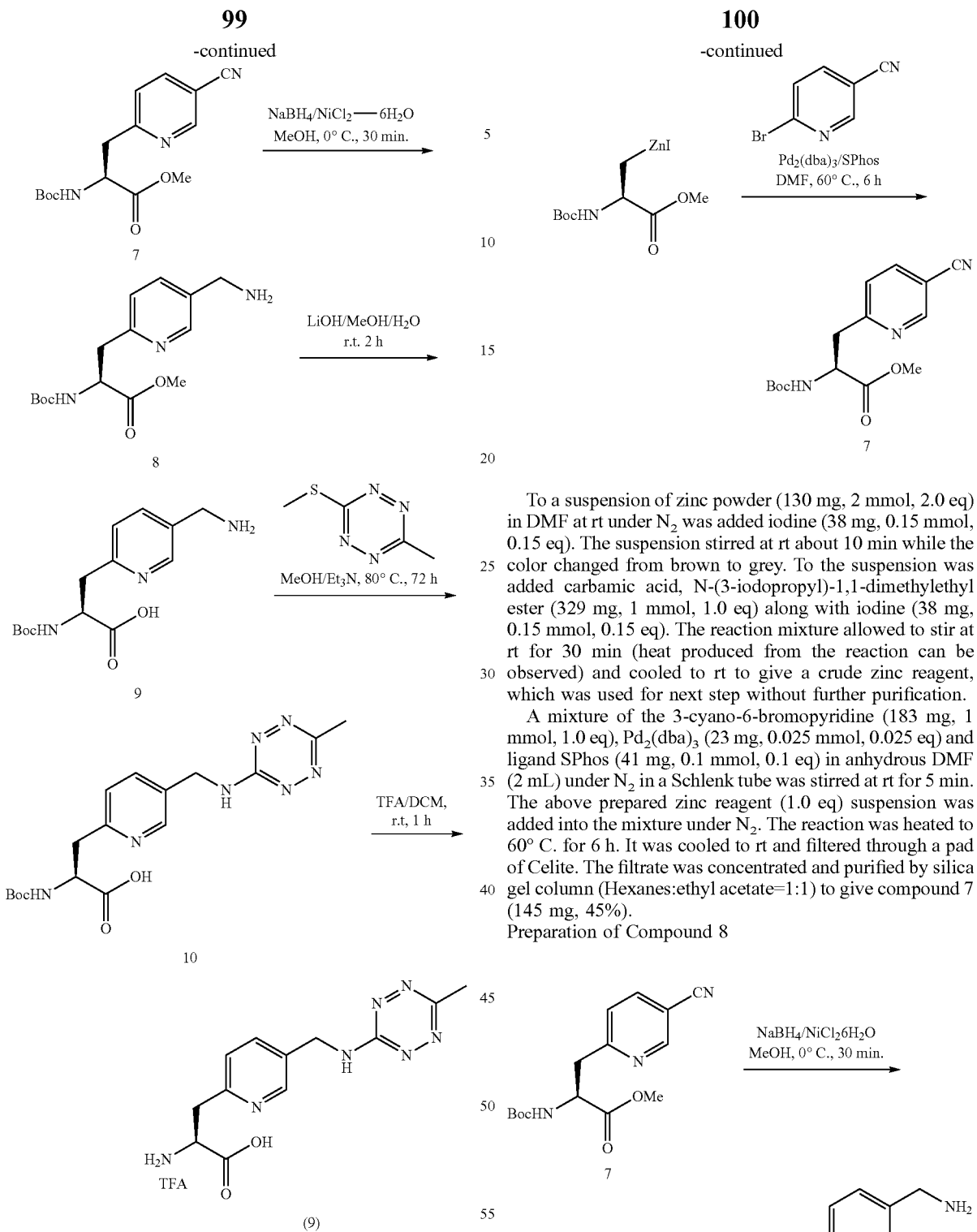

To a suspension of zinc powder (130 mg, 2 mmol, 2.0 eq) in DMF at rt under $N_2$ was added iodine (38 mg, 0.15 mmol, 0.15 eq). The suspension stirred at rt about 10 min while the color changed from brown to grey. To the suspension was added carbamic acid, N-(3-iodopropyl)-1,1-dimethylethyl ester (329 mg, 1 mmol, 1.0 eq) along with iodine (38 mg, 0.15 mmol, 0.15 eq). The reaction mixture allowed to stir at rt for 30 min (heat produced from the reaction can be observed) and cooled to rt to give a crude zinc reagent, which was used for next step without further purification.

A mixture of the 3-cyano-6-bromopyridine (183 mg, 1 mmol, 1.0 eq), $Pd_2(dba)_3$ (23 mg, 0.025 mmol, 0.025 eq) and ligand SPhos (41 mg, 0.1 mmol, 0.1 eq) in anhydrous DMF (2 mL) under $N_2$ in a Schlenk tube was stirred at rt for 5 min. The above prepared zinc reagent (1.0 eq) suspension was added into the mixture under $N_2$. The reaction was heated to 60° C. for 6 h. It was cooled to rt and filtered through a pad of Celite. The filtrate was concentrated and purified by silica gel column (Hexanes:ethyl acetate=1:1) to give compound 7 (145 mg, 45%).

Preparation of Compound 8

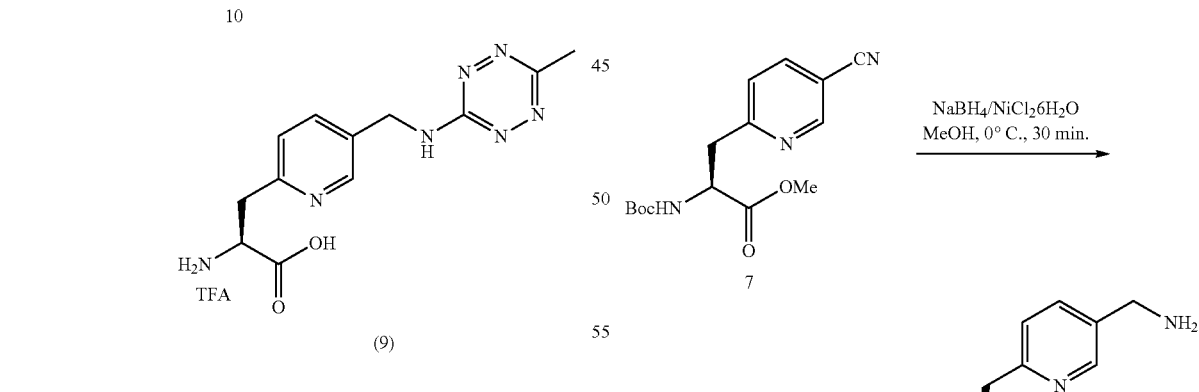

To compound 7 (185 mg, 0.61 mmol, 1.0 eq) in dry MeOH (5 mL) at 0° C. was added $NiCl_2 \cdot 6H_2O$ (71 mg, 0.3 mmol, 0.5 eq), and $NaBH_4$ (229 mg, 6.1 mmol, 10 eq) in portions. The mixture was stirred at rt for 30 min. The reaction mixture was filtered through a pad of Celite, and concentrated to give a crude product, which was purified by silica gel column (DCM:MeOH:Et$_3$N, 9:1:1) to give compound 8 (190 mg).

Preparation of Compound 9

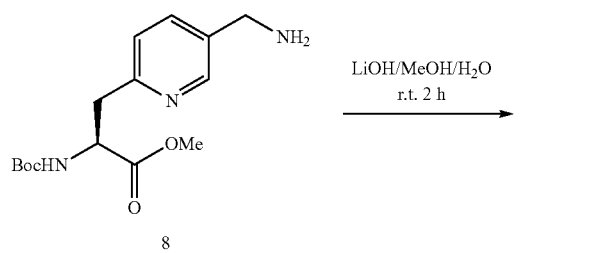

8

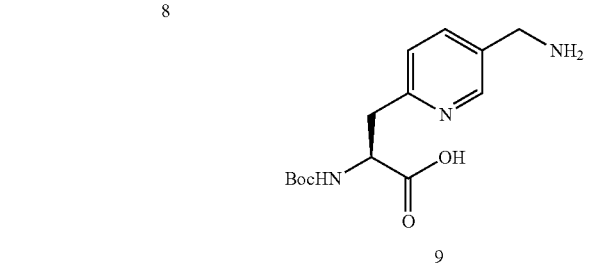

9

To a solution of compound 8 (1.5 g, 5.1 mmol, 1.0 eq) in a mixed solvent of THF (5 mL) and MeOH (10 mL) was added aqueous LiOH (427 mg, 10.2 mmol, 2.0 eq, in 10 mL of water). The mixture was stirred at rt for 2 h. The reaction mixture was concentrated to a small volume and most lithium salts were precipitated out and removed by filtration. The filtrate was concentrated to give product 9 (1.6 g, still containing some lilhiuiii salt).

Preparation of Compound 10

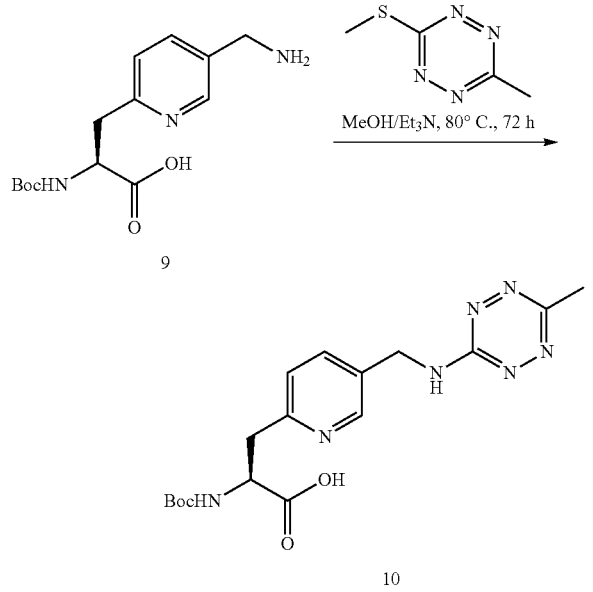

10

To a product 9 (800 mg, 2.85 mmol, 1.0 eq) in MeOH (10.0 mL) was added 4-methyltetrazine methyl sulfide (808 mg, 5.7 mmol, 2.0 eq) and triethylamine (0.792 mL, 5.7 mmol, 2.0 eq) in a sealed tube. The tube was heated to 80° C. for 72 h. The reaction mixture was cooled and purified by prep-HPLC to give product 10 (460 mg, 43%).

Preparation of Compound a Compound of Formula (9)

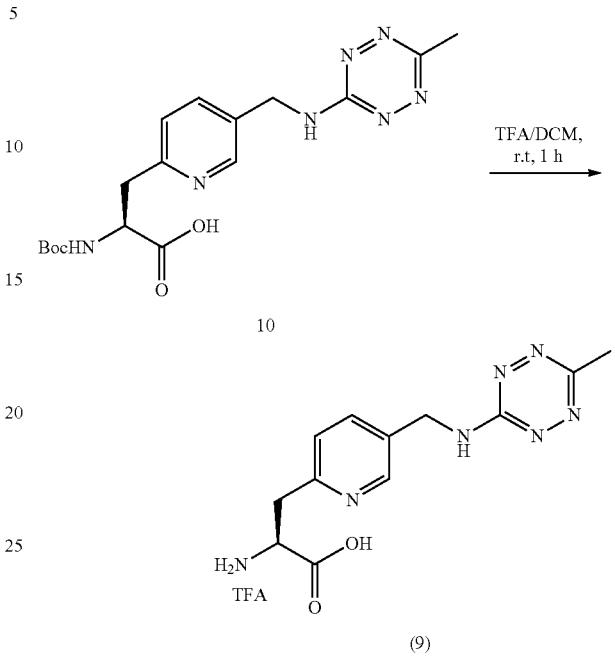

(9)

Compound 10 (470 mg, 1.21 mmol) was dissolved in 20% TFA in DCM (8 mL) and stirred at rt for 1 h. The solvent was removed under reduced pressure, and the residue was re-dissolved in water, frozen and lyophilized to give a compound of formula (9) (660 mg, TFA salts) as red solid. LC-MS (ESI): 290 (M+1), 288 (M−1). $^1$H NMR (300 MHz, CD$_3$OD) δ 8.61 (d, =1.8 Hz, 1H), 7.93 (dd, J=2.4 and 8.1 Hz, 1H), 7.42 (d, J=8.1 Hz, 1H), 4.73 (s, 2H), 4.44 (m, 1H), 3.35-3.50 (m, 2H), 2.74 (s, 3H).

Example 4: Preparation of Green Fluorescent Protein Comprising a Compound of Formula 9 or a Compound of Formula 6

This example provides two novel tRNA synthetases useful with tetrazine-containing amino acids described herein. These two synthetases, designated "2A2" (SEQ ID NO: 4) and "2A9" (SEQ ID NO: 5) were produced by mutagenesis of wild-type tyrosyl-tRNA synthetase (TyrRS) from *Methanococcus jannaschii* (SEQ ID NO:3). Mutagenesis was performed by assembling overlapping oligonucleotides encoding the mutations by polymerase chain reaction (PCR). Mutants were screened utilizing the green fluorescent protein expression assay described below.

The ability of the novel tRNA synthetases to incorporate modified amino acids into a polypeptide was evaluated in cell-free protein synthesis reactions comprising DNA encoding SUPERFOLDER green fluorescent protein (GFP). The codon encoding position 49 of the GFP polypeptide, which normally encodes a lysine residue, was substituted with an amber stop codon (TAG). Full-length GFP is expressed only if the novel tRNA synthetases incorporate s modified amino acid into the polypeptide chain. The level of expression of full-length GFP can be evaluated by measuring fluorescence.

The GFP DNA containing the TAG stop codon was expressed in cell-free protein synthesis reactions as described in Zawada et al., 2011, Biotechnol. Bioeng. 108 (7)1570-1578 with the following modifications: the cell-free extracts were prepared from an OmpT sensitive RF-1 attenuated strain that was also engineered to overexpress *E. coli* DsbC, and a similar RF-1 attenuated *E. coli* strain that was engineered to produce an orthogonal CUA-encoding tRNA for insertion of a non-natural amino acid at an amber stop codon. The cell-free extracts were blended (at a ratio of 85:15, respectively), and then added to a premix containing all other components of a cell-free protein synthesis system except for DNA encoding GFP (K49TAG).

The final cell-free protein synthesis reactions contained 30% cell extract, with or without 2 mM non-natural amino acid (either a compound of formula 6 or a compound of formula 9), a novel tRNA synthetase (2A2 or 2A9 at a concentration of 4 µM, 2 uM, 1 uM or zero), 8 mM magnesium glutamate, 10 mM ammonium glutamate, 130 mM potassium glutamate, 35 mM sodium pyruvate, 1.2 mM AMP, 0.86 mM each of GMP, UMP, and CMP, 2 mM amino acids (except 0.5 mM for tyrosine and phenylalanine), 4 mM sodium oxalate, 1 mM putrescine, 1.5 mM spermidine, 15 mM potassium phosphate, 100 nM T7 RNA polymerase, and 10 µg/mL GFP (K49TAG) expression template plasmid. The cell-free synthesis reactions were initiated by the addition of the plasmid DNA encoding GFP (K49TAG). The reactions were incubated at 30° C. for 12 h on a shaker at 650 rpm. After 12 hours of expression, the GFP fluorescence signal was measured at an excitation wavelength of 476 nm, and an emission wavelength of 510 nm, on a SPECTRAMAX M5 fluorescence plate reader.

FIG. 1 shows the results for the combination of tRNA synthetase 2A2 without a compound of formula 9 and with a compound of formula 9 at 4 mM. At a 4 µM concentration of 2A2, the amount of fluorescence is approximately equivalent to that of native GFP ("GFP") positive control, indicating that GFP comprising a compound of formula 9 is produced at approximately the same level as native GFP (without K49TAG). In FIG. 1, the y-axis shows fluorescence, in relative fluorescence units (RFU); "aaRS" is 2A2; "GFP" is native GFP (without K49TAG); and "negative control" is a cell-free protein synthesis reaction without a DNA template.

Figure 2:
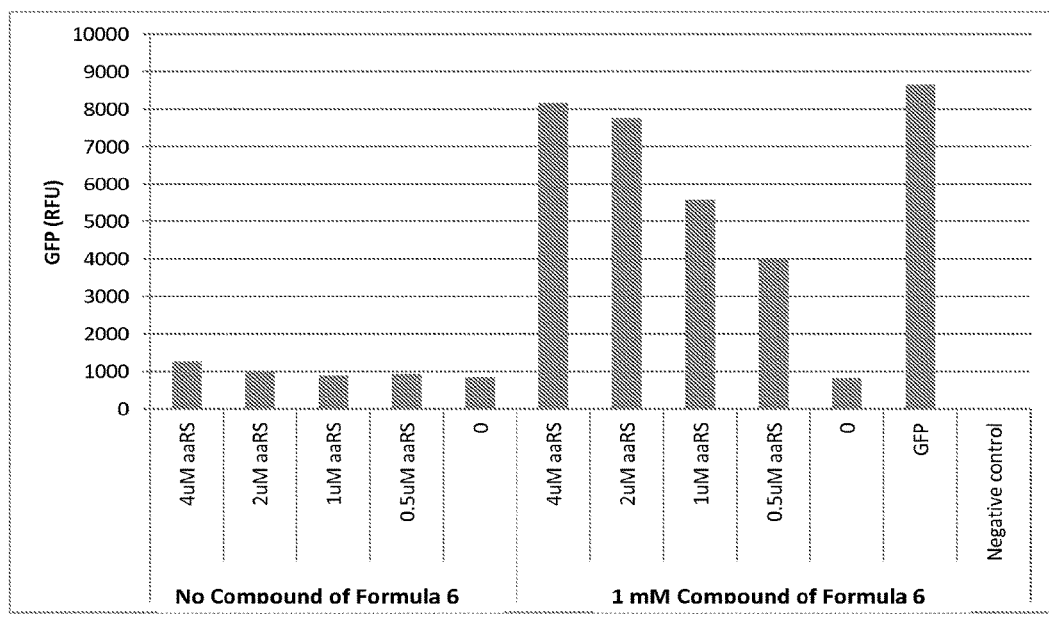
FIG. 2 provides results demonstrating that tRNA synthetase 2A9 incorporates a compound of formula 6 into a GFP polypeptide, as described in Example 4.

FIG. 2 shows the results for the combination of tRNA synthetase 2A9 without a compound of formula 6 and with a compound of formula 6 at 1 mM. At a 2-4 µM concentration of 2A9, the amount of fluorescence approaches that of native GFP ("GFP") positive control, indicating that GFP comprising a compound of formula 6 is produced at a level approaching that of native GFP (without K49TAG). In FIG. 2, the y-axis shows fluorescence, in relative fluorescence units (RFU); "aaRS" is 2A9; "GFP" is native GFP (without K49TAG); and "negative control" is a cell-free protein synthesis reaction without a DNA template.

Example 5: Solubility of Selected Non-Natural Amino Acids Comprising Tetrazine Functionality This example describes the solubility of three non-natural amino acids comprising tetrazine functional groups in phosphate buffered saline solution, with a pH of 7.4 (PBS). The example also illustrates and discusses the useful increased solubility of the pyridyl tetrazine amino acids provided herein when compared to a phenyl tetrazine-comprising non-natural amino acid of the art.

The three compounds tested were AB 4091, compound (9), and compound (6). The structures of these compounds are provided below:

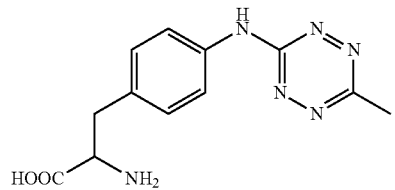
AB 4091

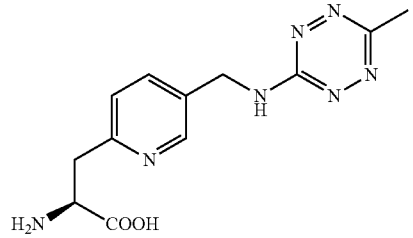
(9)

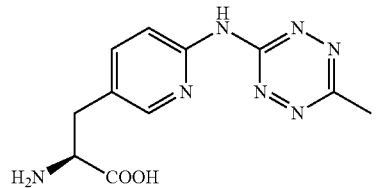
(6)

As described below, AB 4091 has poor aqueous solubility. To address this issue, novel pyridyl tetrazine compounds (e.g., compound (9) and compound (6)) were designed and synthesized. In the novel compounds, the phenyl moiety of AB 4091 was replaced with a pyridine group, to improve the molecular surface polarity and to reduce the lattice energy of the solid form, while conserving the structure of the compound for recognition by the appropriate tRNA during tRNA charging.

Solubility of AB 4091 at Room Temperature

A suspension of AB 4091 was formed by adding 1.8 mg of AB 4091 to 5 mL of PBS. The suspension was vortexed for five minutes and sonicated for two minutes. Suspended particles remained. Additional PBS was added to the suspension in small portions, with vortexing, to reach a total volume of 25 mL of PBS. This mixture remained cloudy after shaking overnight at room temperature and turned clear following the addition of 2 mL of PBS with vortexing. Clarity of the solution was determined by visual inspection. The solubility of AB 4091 is about 215 µM at room temperature.

Solubility of Compound (9) at Room Temperature

A solution of compound (9) was formed by adding 8.3 mg of compound (9) to 200 of PBS to form a homogeneous solution. An additional 11.5 mg of compound (9) was added to this solution, in small portions, over a period of 20 minutes, with vortexing. The solution remained clear after vortexing, with no particulates or cloudiness observed. The maximum solubility of compound (9) was not reached, due to its high solubility and the limited amount of the compound available. The final concentration achieved was 342 mM at room temperature, over 1600-fold greater than the solubility of AB 4091.

Solubility of Compound (6) at Room Temperature

A solution of compound (6) was formed by adding 8.7 mg of compound (6) to 200 µL of PBS to form a homogenous solution. An additional 26.9 mg of compound (6) was added to this solution, in small portions, over a period of 25 minutes, with vortexing. The solution remained clear after vortexing, with no particulates or cloudiness observed. The maximum solubility of compound (6) was not reached, due to its high solubility and the limited amount of the compound available. The final concentration achieved was 647 mM at room temperature, over 3000-fold greater than the solubility of AB 4091.

Pyridyl Compounds Exhibit Greater than Expected Solubility

The calculated log P (c Log P) value is a calculated measure of the partition coefficient of a compound between n-octanol and water. The value is a generally accepted measure of a compound's hydrophilicity, with lower c Log P values indicating higher solubility in aqueous media. This correlation is illustrated by the empirical equation Log S=0.5-log P-0.01(TM-25), where S is the solubility and TM is the melting point of the molecule and an indicator of lattice energy of the solid.

The c Log P value was calculated for compounds AB 4091, (9), and (6), according to the methods described in Leo AJ, "Methods of calculating partition coefficients," in *Comprehensive Medicinal Chemistry: The Rational Design, Mechanistic Study & Therapeutic Application of Chemical Compounds*, volume 4. New York: Pergamon Press. Chapter 18.7, pp. 295-617, incorporated by reference in its entirety, as implemented in ChemDraw software.

The c Log P values were 1.68, 0.36, and 1.06 for AB 4091, compound (9), and compound (6), respectively. The moderate reduction in the c Log P values alone, between AB 4091 and the pyridyl compounds, does not explain the significant increase in solubility observed in the pyridyl compounds (over 1600-fold for compound (9) and over 3000-fold for compound (6)).

Without being bound by theory, it is possible that the nitrogen substitution in the pyridyl compounds influences their solid-state stability by changing their crystal lattice energy. The fact that AB 4091 is a solid powder at room temperature, while compound (6) is an oil, suggests a difference in the crystal lattice energy of the two compounds. Moreover, the pyridyl moiety is capable of forming hydrogen bonds with water upon solvation, while the phenyl moiety does not. These factors, in addition to the changes in surface polarity realized by introducing the nitrogen, may contribute to the enhanced solubility of the pyridyl compounds provided herein.

The novel pyridyl tetrazine amino acids provided herein are particularly useful when incorporated into proteins in a cell-free protein synthesis reaction. Prior compounds, i.e., the phenyl tetrazine amino acids such as AB 4091, were very difficult to use in such reactions because of their poor solubility. Thus, the reactions required very careful introduction of the phenyl tetrazine compounds into the cell-free protein synthesis reaction so that the amino acid did not immediately precipitate, and further required extensive vortexing to re-dissolve any precipitated material. Without taking such care, the effective concentration of the amino acid in the cell-free protein synthesis reaction would be much lower than expected, which then would result in a low concentration of tRNA charged with the amino acid, leading to poor suppression of the amber codon and premature termination of protein synthesis, which ultimately results in poor yields of full length, properly folded protein containing the desired amino acid. In addition, the lower than expected phenyl tetrazine concentration can also lead to increased misincorporation of wild type amino acids instead of the desired phenyl tetrazine at the amber codon site.

In contrast, the novel pyridyl tetrazine compounds provided herein readily mix into the cell-free protein synthesis reaction mixture without precipitation and reliably yield full length properly-folded protein products without demonstrating excessive premature termination of protein synthesis or misincorporation of undesired wild type amino acids.

Example 6: Incorporation of Tetrazine and Azide Functional Groups into an IgG Antibody This example demonstrates the incorporation of two non-natural amino acids (nnAAs) into a trastuzumab parent antibody. The nnAAs were incorporated into the antibody by placing an amber codon at the desired position for nnAA incorporation in a plasmid encoding the trastuzumab heavy chain and in a plasmid encoding a trastuzumab light chain. nnAA1, para-azido-methyl phenylalanine (pAMF) was incorporated at position S7 of the trastuzumab light chain. AB 4091, described above, was incorporated at position F404 of the trastuzumab heavy chain.

Both the heavy chain and the light chain were synthesized by cell-free protein synthesis. The light chain was synthesized first. The cell-free reaction mix comprised an 85%: 15% blend of cell-free extracts made from an OmpT sensitive RF-1 attenuated *E. coli* strain that was engineered to overexpress DsbC (DsbC extract), and an OmpT sensitive RF-1 attenuated *E. coli* strain which was engineered to produce an orthogonal CUA-encoding tRNA (tRNA extract) for insertion of a non-natural amino acid at an amber stop codon. Cell-free extracts were treated with 50 µM iodoacetamide for 30 min at RT (20° C.) and added to a premix containing all other components except for DNA encoding the light chain variant. The final concentration in the protein synthesis reaction was 30% cell extract, 2 mM pAMF (RSP Amino Acids), 0.37 mg/mL pAzMeF-specific amino-acyl tRNA synthetase (FRS), 2 mM oxidized glutathione (GSSG), 8 mM magnesium glutamate, 10 mM ammonium glutamate, 130 mM potassium glutamate, 35 mM sodium pyruvate, 1.2 mM AMP, 0.86 mM each of GMP, UMP, and CMP, 2 mM amino acids (except 0.5 mM for tyrosine and phenylalanine), 4 mM sodium oxalate, 1 mM putrescine, 1.5 mM spermidine, 15 mM potassium phosphate, 100 nM T7 RNA polymerase, and 10 µg/mL trastuzumab light chain variant DNA. The FRS was the p-cyanophenylalanine-specific aminoacyl tRNA synthetase described in Young et al., *Biochem.*, 2011, 50:1894-1900, incorporated by reference in its entirety. After addition of the DNA template, cell-free reactions were incubated at 30° C. for 12 h. The synthesized light chains were purified with a protein L column.

Figure 3:
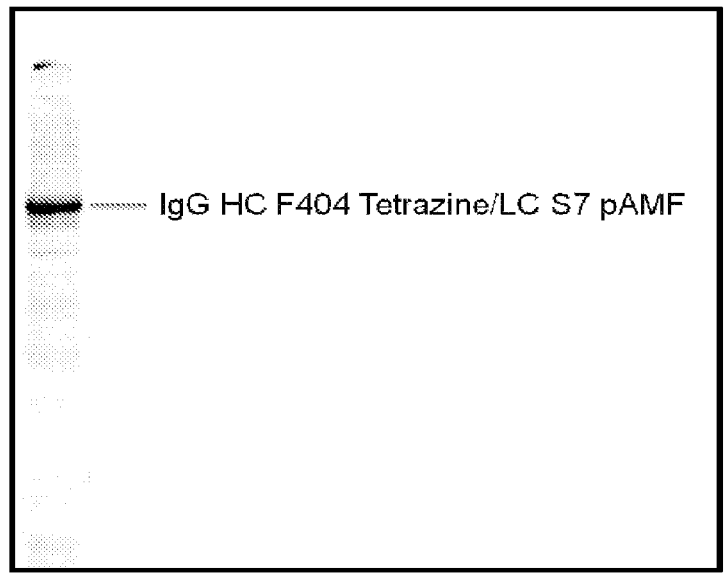
FIG. 3 provides an autoradiogram of an antibody incorporating para-azido methyl phenylalanine (pAMF) at position S7 of the light chain and a tetrazine-containing non-natural amino acid (AB 4091) at position F404 of the heavy chain.

The second nnAA, AB 4091, was incorporated into the heavy chain in the presence of prefabricated light chain containing pAMF, using the same reaction conditions described above, with the following changes: the nnAA was changed to AB 4091; the synthetase was changed to an AB 4091-specific aminoacyl tRNA synthetase; and the reaction was performed in the presence of 10 µg/mL of DNA encoding the trastuzumab heavy chain with an amber stop codon at position F404 and 500 µg/mL of prefabricated LC. The aminoacyl tRNA synthetase used in this reaction was the mtaF synthetase disclosed in Seitchik et al., *J. Am. Chem. Soc.*, 2012, 134:2898-2901, incorporated by reference in its entirety. Autoradiography (FIG. 3) suggests that about 1 mg/mL IgG containing two nnAAs was produced.

This example demonstrates production of assembled IgG having pAMF in the light chain and a tetrazine-containing amino acid (AB 4091) in the heavy chain. Alternatively, one can incorporate a tetrazine-containing amino acid in the light chain and an azide-containing amino acid in the heavy chain by substituting the appropriate amino acid and aminoacyl tRNA synthetase during transcription and translation of each template DNA. Additionally, this approach can be used with any of the nnAAs known in the art or described herein. One of ordinary skill in the art will also recognize that incorporation of multiple nnAAs may be achieved in a single reaction by utilizing orthogonal tRNAs, as described below.

Example 7: Simultaneous Site-Specific Incorporation of Two Different Non-Natural Amino Acids, Enabling Mutually Orthogonal Conjugation Chemistries This example describes the site-specific incorporation of different non-natural amino acid residues into antibodies in a single reaction mixture, and the subsequent mutually orthogonal conjugation of drugs to these non-natural amino acids.

Cell-free protein synthesis reactions were carried out essentially as described in Example 6, with the following variations to enable site-specific incorporation of nnAAs using two different stop codons. Aminoacyl tRNA synthetases PyrTetRS (SEQ ID NO: 6) and PylRS (SEQ ID NO: 7) were expressed and purified separately and added as exogenous components to the cell free expression reactions. Reactions also contained orthogonal suppressor tRNAs recognized exclusively by PyrTetRS or PylRS. In this embodiment, PyrTetRS charges an opal codon (TGA) suppressor tRNA (SEQ ID NO: 8) with compound (6) and PylRS charges an amber codon (TAG) suppressor tRNA (SEQ ID NO: 9) with compound A19 and the ochre codon (TAA) is used to terminate protein translation. Plasmid DNA templates encoding product proteins possessed TAG or TGA codons at the codon position corresponding to the desired site of nnAA incorporation. This may include incorporation of two different nnAAs into a single polypeptide (e.g., the heavy chain or the light chain) or into different polypeptides (e.g., one compound on the heavy chain and one compound on the light chain).

Non-natural amino acid compounds were incorporated into the heavy and light chains of three antibodies: trastuzumab (HC: SEQ ID NO: 1; LC: SEQ ID NO: 2); brentuximab (HC: SEQ ID NO: 10; LC: SEQ ID NO: 11); and anti-CD74 (HC: SEQ ID NO: 12; LC: SEQ ID NO: 13). These antibodies were then conjugated to either DBCO-Gemcitabine, or DBCO-DM1 and to TCO-MMAF in a single pot reaction under the essentially same reaction conditions as described in Example 6. The chemical structures of DBCO-Gemcitabine and TCO-MMAF are provided below.

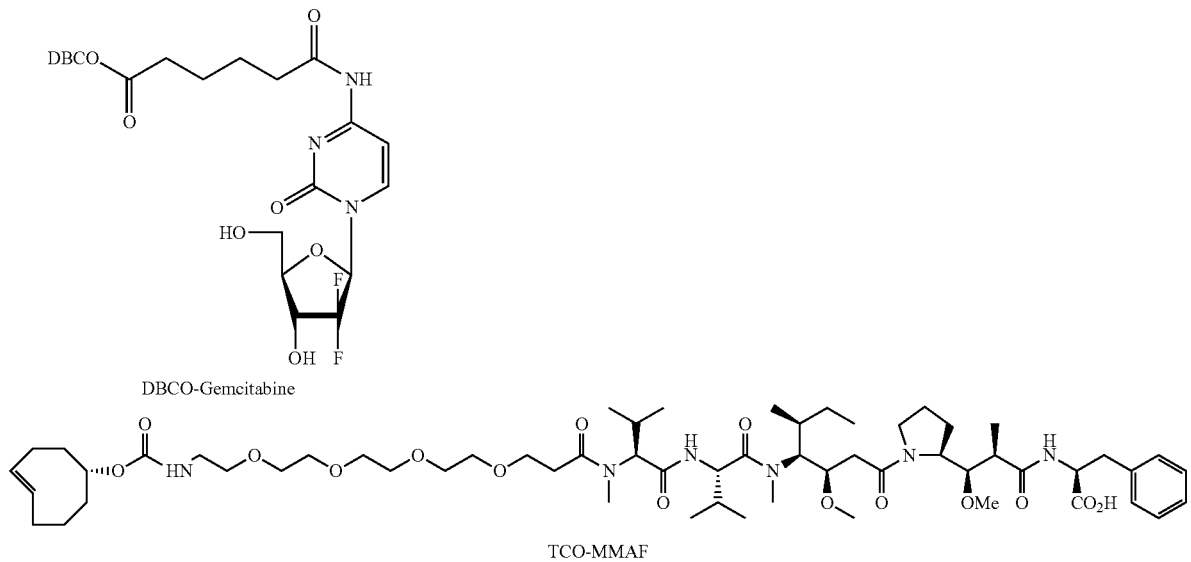

DBCO-Gemcitabine

TCO-MMAF

Drug-to-antibody (DAR) ratios were determined by liquid chromatography mass spectrometry.

Samples were run on a Waters Aquity UPLC system attached a Xevo QTOF. Proteins were separated on an Agilent PLRP-S column (2.3×50 mm, 5 μm, 4000 Å) at 80° C. Mobile phases: A: 0.1% formic acid water; B: 20:80 isopropanol:acetonitrile, 0.1% formic acid. Samples were desalted on column for 0.4 minutes at 10% B followed by a step gradient from 30% B to 40% B over 7 minutes, 40% B to 60% B over 3 minutes. Data was acquired over the whole LC elution using a cone voltage of 35V. Spectra were analyzed using MassLynx software. DAR values were calculated as a weighted average using the peak intensity of the matching peaks in the deconvoluted spectra. Where a defined peak was not observed the baseline intensity at the theoretical mass of the conjugate was used in the DAR calculation.

Table 4 shows the resulting DARs for various combinations of antibody, sites of incorporation of nnAAs, and drugs conjugated to the incorporated nnAAs.

TABLE 10

Drug-to-Antibody Ratios for Antibodies Produced in a Single Reaction Mixture

| Antibody | nnAA Site 1 | nnAA Site 2 | Drug 1 | Drug 2 | DAR |
|---|---|---|---|---|---|
| Trastuzumab | HC S136 AEK | LC S7 PyrTet | DBCO-Gemcitabine | TCO-MMAF | 2.6 |
| Trastuzumab | HC K147 AEK | LC S7 PyrTet | DBCO-DM1 | TCO-MMAF | 3.3 |
| Trastuzumab | HC S25 PyrTet | LC K45 AEK | TCO-MMAF | DBCO-DM1 | 3.6 |
| Trastuzumab | HC S25 PyrTet | HC K147 AEK | TCO-MMAF | DBCO-DM1 | 3.0 |
| Trastuzumab | LC S7 PyrTet | LC K39 AEK | TCO-MMAF | DBCO-DM1F | 1.8 |
| Trastuzumab | LC S7 PyrTet | LC S77 AEK | TCO-MMAF | DBCO-DM1 | 2.6 |
| Trastuzumab | LC S7 PyrTet | LC R142 AEK | TCO-MMAF | DBCO-DM1 | 2.6 |
| Brentuximab | HC K147 AEK | LC S7 PyrTet | DBCO-DM1 | TCO-MMAF | 2.7 |
| Brentuximab | LC S27 PyrTet | LC R147 AEK | TCO-MMAF | DBCO-DM1 | 1.6 |
| Brentuximab | HC S25 PyrTet | HC K147 AEK | TCO-MMAF | DBCO-DM1 | 2.1 |
| Anti-CD74 | HC K147 AEK | LC S7 PyrTet | DBCO-DM1 | TCO-MMAF | 2.0 |
| Anti-CD74 | LC S7 PyrTet | LC R143 AEK | TCO-MMAF | DBCO-DM1 | 2.8 |
| Anti-CD74 | HC S25 PyrTet | HC K147 AEK | TCO-MMAF | DBCO-DM1 | 2.0 |

PyrTet = compound of formula (A6);
AEK = compound of formula (A19);
DAR = total drug-to-antibody ratio (scale: 0 to 4).

In all instances, species were identified in the deconvoluted mass spectra that corresponded to an IgG conjugated to both drugs simultaneously in ratios of 1:1, 2:1, 1:2, and/or 2:2 indicating successful incorporation of both nnAAs and simultaneous conjugation to at least one molecule of each drug.

All publications and patent applications cited in this specification are herein incorporated by reference as if each individual publication or patent application were specifically and individually indicated to be incorporated by reference. While the claimed subject matter has been described in terms of various embodiments, the skilled artisan will appreciate that various modifications, substitutions, omissions, and changes may be made without departing from the spirit thereof. Accordingly, it is intended that the scope of the subject matter limited solely by the scope of the following claims, including equivalents thereof

TABLE 1

Positions in SEQ ID NOs: 1 (heavy chain) and 2 (light chain) and corresponding Kabat, Chothia, and EU residue numbers.

| HEAVY CHAIN | | | | | LIGHT CHAIN | | | | |
|---|---|---|---|---|---|---|---|---|---|
| Pos. in SEQ ID NO: 1 | Residue | Kabat | Chothia | EU | Pos. in SEQ ID NO: 2 | Residue | Kabat | Chothia | EU |
| 1 | E | H1 E | H1 E | | 1 | D | L1 D | L1 D | |
| 2 | V | H2 V | H2 V | | 2 | I | L2 I | L2 I | |
| 3 | Q | H3 Q | H3 Q | | 3 | Q | L3 Q | L3 Q | |
| 4 | L | H4 L | H4 L | | 4 | M | L4 M | L4 M | |
| 5 | V | H5 V | H5 V | | 5 | T | L5 T | L5 T | |
| 6 | E | H6 E | H6 E | | 6 | Q | L6 Q | L6 Q | |
| 7 | S | H7 S | H7 S | | 7 | S | L7 S | L7 S | |
| 8 | G | H8 G | H8 G | | 8 | P | L8 P | L8 P | |
| 9 | G | H9 G | H9 G | | 9 | S | L9 S | L9 S | |
| 10 | G | H10 G | H10 G | | 10 | S | L10 S | L10 S | |
| 11 | L | H11 L | H11 L | | 11 | L | L11 L | L11 L | |
| 12 | V | H12 V | H12 V | | 12 | S | L12 S | L12 S | |
| 13 | Q | H13 Q | H13 Q | | 13 | A | L13 A | L13 A | |
| 14 | P | H14 P | H14 P | | 14 | S | L14 S | L14 S | |
| 15 | G | H15 G | H15 G | | 15 | V | L15 V | L15 V | |
| 16 | G | H16 G | H16 G | | 16 | G | L16 G | L16 G | |
| 17 | S | H17 S | H17 S | | 17 | D | L17 D | L17 D | |
| 18 | L | H18 L | H18 L | | 18 | R | L18 R | L18 R | |
| 19 | R | H19 R | H19 R | | 19 | V | L19 V | L19 V | |
| 20 | L | H20 L | H20 L | | 20 | T | L20 T | L20 T | |
| 21 | S | H21 S | H21 S | | 21 | I | L21 I | L21 I | |
| 22 | C | H22 C | H22 C | | 22 | T | L22 T | L22 T | |
| 23 | A | H23 A | H23 A | | 23 | C | L23 C | L23 C | |
| 24 | A | H24 A | H24 A | | 24 | R | L24 R | L24 R | |
| 25 | S | H25 S | H25 S | | 25 | A | L25 A | L25 A | |
| 26 | G | H26 G | H26 G | | 26 | S | L26 S | L26 S | |
| 27 | F | H27 F | H27 F | | 27 | Q | L27 Q | L27 Q | |
| 28 | N | H28 N | H28 N | | 28 | D | L28 D | L28 D | |
| 29 | I | H29 I | H29 I | | 29 | V | L29 V | L29 V | |
| 30 | K | H30 K | H30 K | | 30 | N | L30 N | L30 N | |
| 31 | D | H31 D | H31 D | | 31 | T | L31 T | L31 T | |
| 32 | T | H32 T | H32 T | | 32 | A | L32 A | L32 A | |
| 33 | Y | H33 Y | H33 Y | | 33 | V | L33 V | L33 V | |

TABLE 1-continued

Positions in SEQ ID NOs: 1 (heavy chain) and 2 (light chain) and corresponding Kabat, Chothia, and EU residue numbers.

| HEAVY CHAIN | | | | LIGHT CHAIN | | | | |
|---|---|---|---|---|---|---|---|---|
| Pos. in SEQ ID NO: 1 | Residue | Kabat | Chothia | EU | Pos. in SEQ ID NO: 2 | Residue | Kabat | Chothia | EU |
| 34 | I | H34 I | H34 I | | 34 | A | L34 A | L34 A | |
| 35 | H | H35 H | H35 H | | 35 | W | L35 W | L35 W | |
| 36 | W | H36 W | H36 W | | 36 | Y | L36 Y | L36 Y | |
| 37 | V | H37 V | H37 V | | 37 | Q | L37 Q | L37 Q | |
| 38 | R | H38 R | H38 R | | 38 | Q | L38 Q | L38 Q | |
| 39 | Q | H39 Q | H39 Q | | 39 | K | L39 K | L39 K | |
| 40 | A | H40 A | H40 A | | 40 | P | L40 P | L40 P | |
| 41 | P | H41 P | H41 P | | 41 | G | L41 G | L41 G | |
| 42 | G | H42 G | H42 G | | 42 | K | L42 K | L42 K | |
| 43 | K | H43 K | H43 K | | 43 | A | L43 A | L43 A | |
| 44 | G | H44 G | H44 G | | 44 | P | L44 P | L44 P | |
| 45 | L | H45 L | H45 L | | 45 | K | L45 K | L45 K | |
| 46 | E | H46 E | H46 E | | 46 | L | L46 L | L46 L | |
| 47 | W | H47 W | H47 W | | 47 | L | L47 L | L47 L | |
| 48 | V | H48 V | H48 V | | 48 | I | L48 I | L48 I | |
| 49 | A | H49 A | H49 A | | 49 | Y | L49 Y | L49 Y | |
| 50 | R | H50 R | H50 R | | 50 | S | L50 S | L50 S | |
| 51 | I | H51 I | H51 I | | 51 | A | L51 A | L51 A | |
| 52 | Y | H52 Y | H52 Y | | 52 | S | L52 S | L52 S | |
| 53 | P | H52A P | H52A P | | 53 | F | L53 F | L53 F | |
| 54 | T | H53 T | H53 T | | 54 | L | L54 L | L54 L | |
| 55 | N | H54 N | H54 N | | 55 | Y | L55 Y | L55 Y | |
| 56 | G | H55 G | H55 G | | 56 | S | L56 S | L56 S | |
| 57 | Y | H56 Y | H56 Y | | 57 | G | L57 G | L57 G | |
| 58 | T | H57 T | H57 T | | 58 | V | L58 V | L58 V | |
| 59 | R | H58 R | H58 R | | 59 | P | L59 P | L59 P | |
| 60 | Y | H59 Y | H59 Y | | 60 | S | L60 S | L60 S | |
| 61 | A | H60 A | H60 A | | 61 | R | L61 R | L61 R | |
| 62 | D | H61 D | H61 D | | 62 | F | L62 F | L62 F | |
| 63 | S | H62 S | H62 S | | 63 | S | L63 S | L63 S | |
| 64 | V | H63 V | H63 V | | 64 | G | L64 G | L64 G | |
| 65 | K | H64 K | H64 K | | 65 | S | L65 S | L65 S | |
| 66 | G | H65 G | H65 G | | 66 | R | L66 R | L66 R | |
| 67 | R | H66 R | H66 R | | 67 | S | L67 S | L67 S | |
| 68 | F | H67 F | H67 F | | 68 | G | L68 G | L68 G | |
| 69 | T | H68 T | H68 T | | 69 | T | L69 T | L69 T | |
| 70 | I | H69 I | H69 I | | 70 | D | L70 D | L70 D | |
| 71 | S | H70 S | H70 S | | 71 | F | L71 F | L71 F | |
| 72 | A | H71 A | H71 A | | 72 | T | L72 T | L72 T | |
| 73 | D | H72 D | H72 D | | 73 | L | L73 L | L73 L | |
| 74 | T | H73 T | H73 T | | 74 | T | L74 T | L74 T | |
| 75 | S | H74 S | H74 S | | 75 | I | L75 I | L75 I | |
| 76 | K | H75 K | H75 K | | 76 | S | L76 S | L76 S | |
| 77 | N | H76 N | H76 N | | 77 | S | L77 S | L77 S | |
| 78 | T | H77 T | H77 T | | 78 | L | L78 L | L78 L | |
| 79 | A | H78 A | H78 A | | 79 | Q | L79 Q | L79 Q | |
| 80 | Y | H79 Y | H79 Y | | 80 | P | L80 P | L80 P | |
| 81 | L | H80 L | H80 L | | 81 | E | L81 E | L81 E | |
| 82 | Q | H81 Q | H81 Q | | 82 | D | L82 D | L82 D | |
| 83 | M | H82 M | H82 M | | 83 | F | L83 F | L83 F | |
| 84 | N | H82A N | H82A N | | 84 | A | L84 A | L84 A | |
| 85 | S | H82B S | H82B S | | 85 | T | L85 T | L85 T | |
| 86 | L | H82C L | H82C L | | 86 | Y | L86 Y | L86 Y | |
| 87 | R | H83 R | H83 R | | 87 | Y | L87 Y | L87 Y | |
| 88 | A | H84 A | H84 A | | 88 | C | L88 C | L88 C | |
| 89 | E | H85 E | H85 E | | 89 | Q | L89 Q | L89 Q | |
| 90 | D | H86 D | H86 D | | 90 | Q | L90 Q | L90 Q | |
| 91 | T | H87 T | H87 T | | 91 | H | L91 H | L91 H | |
| 92 | A | H88 A | H88 A | | 92 | Y | L92 Y | L92 Y | |
| 93 | V | H89 V | H89 V | | 93 | T | L93 T | L93 T | |
| 94 | Y | H90 Y | H90 Y | | 94 | T | L94 T | L94 T | |
| 95 | Y | H91 Y | H91 Y | | 95 | P | L95 P | L95 P | |
| 96 | C | H92 C | H92 C | | 96 | P | L96 P | L96 P | |
| 97 | S | H93 S | H93 S | | 97 | T | L97 T | L97 T | |
| 98 | R | H94 R | H94 R | | 98 | F | L98 F | L98 F | |
| 99 | W | H95 W | H95 W | | 99 | G | L99 G | L99 G | |
| 100 | G | H96 G | H96 G | | 100 | Q | L100 Q | L100 Q | |
| 101 | G | H97 G | H97 G | | 101 | G | L101 G | L101 G | |
| 102 | D | H98 D | H98 D | | 102 | T | L102 T | L102 T | |
| 103 | G | H99 G | H99 G | | 103 | K | L103 K | L103 K | |
| 104 | F | H100 F | H100 F | | 104 | V | L104 V | L104 V | |

TABLE 1-continued

Positions in SEQ ID NOs: 1 (heavy chain) and 2 (light chain) and corresponding Kabat, Chothia, and EU residue numbers.

| HEAVY CHAIN | | | | | LIGHT CHAIN | | | | |
|---|---|---|---|---|---|---|---|---|---|
| Pos. in SEQ ID NO: 1 | Residue | Kabat | Chothia | EU | Pos. in SEQ ID NO: 2 | Residue | Kabat | Chothia | EU |
| 105 | Y | H100A Y | H100A Y | | 105 | E | L105 E | L105 E | |
| 106 | A | H100B A | H100B A | | 106 | I | L106 I | L106 I | |
| 107 | M | H100C M | H100C M | | 107 | K | L107 K | L107 K | |
| 108 | D | H101 D | H101 D | | 108 | R | | | 108 |
| 109 | Y | H102 Y | H102 Y | | 109 | T | | | 109 |
| 110 | W | H103 W | H103 W | | 110 | V | | | 110 |
| 111 | G | H104 G | H104 G | | 111 | A | | | 111 |
| 112 | Q | H105 Q | H105 Q | | 112 | A | | | 112 |
| 113 | G | H106 G | H106 G | | 113 | P | | | 113 |
| 114 | T | H107 T | H107 T | | 114 | S | | | 114 |
| 115 | L | H108 L | H108 L | | 115 | V | | | 115 |
| 116 | V | H109 V | H109 V | | 116 | F | | | 116 |
| 117 | T | H110 T | H110 T | | 117 | I | | | 117 |
| 118 | V | H111 V | H111 V | | 118 | F | | | 118 |
| 119 | S | H112 S | H112 S | | 119 | P | | | 119 |
| 120 | S | H113 S | H113 S | | 120 | P | | | 120 |
| 121 | A | | | 118 | 121 | S | | | 121 |
| 122 | S | | | 119 | 122 | D | | | 122 |
| 123 | T | | | 120 | 123 | E | | | 123 |
| 124 | K | | | 121 | 124 | Q | | | 124 |
| 125 | G | | | 122 | 125 | L | | | 125 |
| 126 | P | | | 123 | 126 | K | | | 126 |
| 127 | S | | | 124 | 127 | S | | | 127 |
| 128 | V | | | 125 | 128 | G | | | 128 |
| 129 | F | | | 126 | 129 | T | | | 129 |
| 130 | P | | | 127 | 130 | A | | | 130 |
| 131 | L | | | 128 | 131 | S | | | 131 |
| 132 | A | | | 129 | 132 | V | | | 132 |
| 133 | P | | | 130 | 133 | V | | | 133 |
| 134 | S | | | 131 | 134 | C | | | 134 |
| 135 | S | | | 132 | 135 | L | | | 135 |
| 136 | K | | | 133 | 136 | L | | | 136 |
| 137 | S | | | 134 | 137 | N | | | 137 |
| 138 | T | | | 135 | 138 | N | | | 138 |
| 139 | S | | | 136 | 139 | F | | | 139 |
| 140 | G | | | 137 | 140 | Y | | | 140 |
| 141 | G | | | 138 | 141 | P | | | 141 |
| 142 | T | | | 139 | 142 | R | | | 142 |
| 143 | A | | | 140 | 143 | E | | | 143 |
| 144 | A | | | 141 | 144 | A | | | 144 |
| 145 | L | | | 142 | 145 | K | | | 145 |
| 146 | G | | | 143 | 146 | V | | | 146 |
| 147 | C | | | 144 | 147 | Q | | | 147 |
| 148 | L | | | 145 | 148 | W | | | 148 |
| 149 | V | | | 146 | 149 | K | | | 149 |
| 150 | K | | | 147 | 150 | V | | | 150 |
| 151 | D | | | 148 | 151 | D | | | 151 |
| 152 | Y | | | 149 | 152 | N | | | 152 |
| 153 | F | | | 150 | 153 | A | | | 153 |
| 154 | P | | | 151 | 154 | L | | | 154 |
| 155 | E | | | 152 | 155 | Q | | | 155 |
| 156 | P | | | 153 | 156 | S | | | 156 |
| 157 | V | | | 154 | 157 | G | | | 157 |
| 158 | T | | | 155 | 158 | N | | | 158 |
| 159 | V | | | 156 | 159 | S | | | 159 |
| 160 | S | | | 157 | 160 | Q | | | 160 |
| 161 | W | | | 158 | 161 | E | | | 161 |
| 162 | N | | | 159 | 162 | S | | | 162 |
| 163 | S | | | 160 | 163 | V | | | 163 |
| 164 | G | | | 161 | 164 | T | | | 164 |
| 165 | A | | | 162 | 165 | E | | | 165 |
| 166 | L | | | 163 | 166 | Q | | | 166 |
| 167 | T | | | 164 | 167 | D | | | 167 |
| 168 | S | | | 165 | 168 | S | | | 168 |
| 169 | G | | | 166 | 169 | K | | | 169 |
| 170 | V | | | 167 | 170 | D | | | 170 |
| 171 | H | | | 168 | 171 | S | | | 171 |
| 172 | T | | | 169 | 172 | T | | | 172 |
| 173 | F | | | 170 | 173 | Y | | | 173 |
| 174 | P | | | 171 | 174 | S | | | 174 |
| 175 | A | | | 172 | 175 | L | | | 175 |

TABLE 1-continued

Positions in SEQ ID NOs: 1 (heavy chain) and 2 (light chain) and corresponding Kabat, Chothia, and EU residue numbers.

| HEAVY CHAIN | | | | | LIGHT CHAIN | | | | |
|---|---|---|---|---|---|---|---|---|---|
| Pos. in SEQ ID NO: 1 | Residue | Kabat | Chothia | EU | Pos. in SEQ ID NO: 2 | Residue | Kabat | Chothia | EU |
| 176 | V | | | 173 | 176 | S | | | 176 |
| 177 | L | | | 174 | 177 | S | | | 177 |
| 178 | Q | | | 175 | 178 | T | | | 178 |
| 179 | S | | | 176 | 179 | L | | | 179 |
| 180 | S | | | 177 | 180 | T | | | 180 |
| 181 | G | | | 178 | 181 | L | | | 181 |
| 182 | L | | | 179 | 182 | S | | | 182 |
| 183 | Y | | | 180 | 183 | K | | | 183 |
| 184 | S | | | 181 | 184 | A | | | 184 |
| 185 | L | | | 182 | 185 | D | | | 185 |
| 186 | S | | | 183 | 186 | Y | | | 186 |
| 187 | S | | | 184 | 187 | E | | | 187 |
| 188 | V | | | 185 | 188 | K | | | 188 |
| 189 | V | | | 186 | 189 | H | | | 189 |
| 190 | T | | | 187 | 190 | K | | | 190 |
| 191 | V | | | 188 | 191 | V | | | 191 |
| 192 | P | | | 189 | 192 | Y | | | 192 |
| 193 | S | | | 190 | 193 | A | | | 193 |
| 194 | S | | | 191 | 194 | C | | | 194 |
| 195 | S | | | 192 | 195 | E | | | 195 |
| 196 | L | | | 193 | 196 | V | | | 196 |
| 197 | G | | | 194 | 197 | T | | | 197 |
| 198 | T | | | 195 | 198 | H | | | 198 |
| 199 | Q | | | 196 | 199 | Q | | | 199 |
| 200 | T | | | 197 | 200 | G | | | 200 |
| 201 | Y | | | 198 | 201 | L | | | 201 |
| 202 | I | | | 199 | 202 | S | | | 202 |
| 203 | C | | | 200 | 203 | S | | | 203 |
| 204 | N | | | 201 | 204 | P | | | 204 |
| 205 | V | | | 202 | 205 | V | | | 205 |
| 206 | N | | | 203 | 206 | T | | | 206 |
| 207 | H | | | 204 | 207 | K | | | 207 |
| 208 | K | | | 205 | 208 | S | | | 208 |
| 209 | P | | | 206 | 209 | F | | | 209 |
| 210 | S | | | 207 | 210 | N | | | 210 |
| 211 | N | | | 208 | 211 | R | | | 211 |
| 212 | T | | | 209 | 212 | G | | | 212 |
| 213 | K | | | 210 | 213 | E | | | 213 |
| 214 | V | | | 211 | 214 | C | | | 214 |
| 215 | D | | | 212 | | | | | |
| 216 | K | | | 213 | | | | | |
| 217 | K | | | 214 | | | | | |
| 218 | V | | | 215 | | | | | |
| 219 | E | | | 216 | | | | | |
| 220 | P | | | 217 | | | | | |
| 221 | K | | | 218 | | | | | |
| 222 | S | | | 219 | | | | | |
| 223 | C | | | 220 | | | | | |
| 224 | D | | | 221 | | | | | |
| 225 | K | | | 222 | | | | | |
| 226 | T | | | 223 | | | | | |
| 227 | H | | | 224 | | | | | |
| 228 | T | | | 225 | | | | | |
| 229 | C | | | 226 | | | | | |
| 230 | P | | | 227 | | | | | |
| 231 | P | | | 228 | | | | | |
| 232 | C | | | 229 | | | | | |
| 233 | P | | | 230 | | | | | |
| 234 | A | | | 231 | | | | | |
| 235 | P | | | 232 | | | | | |
| 236 | E | | | 233 | | | | | |
| 237 | L | | | 234 | | | | | |
| 238 | L | | | 235 | | | | | |
| 239 | G | | | 236 | | | | | |
| 240 | G | | | 237 | | | | | |
| 241 | P | | | 238 | | | | | |
| 242 | S | | | 239 | | | | | |
| 243 | V | | | 240 | | | | | |
| 244 | F | | | 241 | | | | | |
| 245 | L | | | 242 | | | | | |
| 246 | F | | | 243 | | | | | |

TABLE 1-continued

Positions in SEQ ID NOs: 1 (heavy chain) and 2 (light chain) and corresponding Kabat, Chothia, and EU residue numbers.

| HEAVY CHAIN | | | | | LIGHT CHAIN | | | | |
|---|---|---|---|---|---|---|---|---|---|
| Pos. in SEQ ID NO: 1 | Residue | Kabat | Chothia | EU | Pos. in SEQ ID NO: 2 | Residue | Kabat | Chothia | EU |
| 247 | P | | | 244 | | | | | |
| 248 | P | | | 245 | | | | | |
| 249 | K | | | 246 | | | | | |
| 250 | P | | | 247 | | | | | |
| 251 | K | | | 248 | | | | | |
| 252 | D | | | 249 | | | | | |
| 253 | T | | | 250 | | | | | |
| 254 | L | | | 251 | | | | | |
| 255 | M | | | 252 | | | | | |
| 256 | I | | | 253 | | | | | |
| 257 | S | | | 254 | | | | | |
| 258 | R | | | 255 | | | | | |
| 259 | T | | | 256 | | | | | |
| 260 | P | | | 257 | | | | | |
| 261 | E | | | 258 | | | | | |
| 262 | V | | | 259 | | | | | |
| 263 | T | | | 260 | | | | | |
| 264 | C | | | 261 | | | | | |
| 265 | V | | | 262 | | | | | |
| 266 | V | | | 263 | | | | | |
| 267 | V | | | 264 | | | | | |
| 268 | D | | | 265 | | | | | |
| 269 | V | | | 266 | | | | | |
| 270 | S | | | 267 | | | | | |
| 271 | H | | | 268 | | | | | |
| 272 | E | | | 269 | | | | | |
| 273 | D | | | 270 | | | | | |
| 274 | P | | | 271 | | | | | |
| 275 | E | | | 272 | | | | | |
| 276 | V | | | 273 | | | | | |
| 277 | K | | | 274 | | | | | |
| 278 | F | | | 275 | | | | | |
| 279 | N | | | 276 | | | | | |
| 280 | W | | | 277 | | | | | |
| 281 | Y | | | 278 | | | | | |
| 282 | V | | | 279 | | | | | |
| 283 | D | | | 280 | | | | | |
| 284 | G | | | 281 | | | | | |
| 285 | V | | | 282 | | | | | |
| 286 | E | | | 283 | | | | | |
| 287 | V | | | 284 | | | | | |
| 288 | H | | | 285 | | | | | |
| 289 | N | | | 286 | | | | | |
| 290 | A | | | 287 | | | | | |
| 291 | K | | | 288 | | | | | |
| 292 | T | | | 289 | | | | | |
| 293 | K | | | 290 | | | | | |
| 294 | P | | | 291 | | | | | |
| 295 | R | | | 292 | | | | | |
| 296 | E | | | 293 | | | | | |
| 297 | E | | | 294 | | | | | |
| 298 | Q | | | 295 | | | | | |
| 299 | Y | | | 296 | | | | | |
| 300 | N | | | 297 | | | | | |
| 301 | S | | | 298 | | | | | |
| 302 | T | | | 299 | | | | | |
| 303 | Y | | | 300 | | | | | |
| 304 | R | | | 301 | | | | | |
| 305 | V | | | 302 | | | | | |
| 306 | V | | | 303 | | | | | |
| 307 | S | | | 304 | | | | | |
| 308 | V | | | 305 | | | | | |
| 309 | L | | | 306 | | | | | |
| 310 | T | | | 307 | | | | | |
| 311 | V | | | 308 | | | | | |
| 312 | L | | | 309 | | | | | |
| 313 | H | | | 310 | | | | | |
| 314 | Q | | | 311 | | | | | |
| 315 | D | | | 312 | | | | | |
| 316 | W | | | 313 | | | | | |
| 317 | L | | | 314 | | | | | |

TABLE 1-continued

Positions in SEQ ID NOs: 1 (heavy chain) and 2 (light chain) and corresponding Kabat, Chothia, and EU residue numbers.

| HEAVY CHAIN | | | | | LIGHT CHAIN | | | | |
|---|---|---|---|---|---|---|---|---|---|
| Pos. in SEQ ID NO: 1 | Residue | Kabat | Chothia | EU | Pos. in SEQ ID NO: 2 | Residue | Kabat | Chothia | EU |
| 318 | N | | | 315 | | | | | |
| 319 | G | | | 316 | | | | | |
| 320 | K | | | 317 | | | | | |
| 321 | E | | | 318 | | | | | |
| 322 | Y | | | 319 | | | | | |
| 323 | K | | | 320 | | | | | |
| 324 | C | | | 321 | | | | | |
| 325 | K | | | 322 | | | | | |
| 326 | V | | | 323 | | | | | |
| 327 | S | | | 324 | | | | | |
| 328 | N | | | 325 | | | | | |
| 329 | K | | | 326 | | | | | |
| 330 | A | | | 327 | | | | | |
| 331 | L | | | 328 | | | | | |
| 332 | P | | | 329 | | | | | |
| 333 | A | | | 330 | | | | | |
| 334 | P | | | 331 | | | | | |
| 335 | I | | | 332 | | | | | |
| 336 | E | | | 333 | | | | | |
| 337 | K | | | 334 | | | | | |
| 338 | T | | | 335 | | | | | |
| 339 | I | | | 336 | | | | | |
| 340 | S | | | 337 | | | | | |
| 341 | K | | | 338 | | | | | |
| 342 | A | | | 339 | | | | | |
| 343 | K | | | 340 | | | | | |
| 344 | G | | | 341 | | | | | |
| 345 | Q | | | 342 | | | | | |
| 346 | P | | | 343 | | | | | |
| 347 | R | | | 344 | | | | | |
| 348 | E | | | 345 | | | | | |
| 349 | P | | | 346 | | | | | |
| 350 | Q | | | 347 | | | | | |
| 351 | V | | | 348 | | | | | |
| 352 | Y | | | 349 | | | | | |
| 353 | T | | | 350 | | | | | |
| 354 | L | | | 351 | | | | | |
| 355 | P | | | 352 | | | | | |
| 356 | P | | | 353 | | | | | |
| 357 | S | | | 354 | | | | | |
| 358 | R | | | 355 | | | | | |
| 359 | E | | | 356 | | | | | |
| 360 | E | | | 357 | | | | | |
| 361 | M | | | 358 | | | | | |
| 362 | T | | | 359 | | | | | |
| 363 | K | | | 360 | | | | | |
| 364 | N | | | 361 | | | | | |
| 365 | Q | | | 362 | | | | | |
| 366 | V | | | 363 | | | | | |
| 367 | S | | | 364 | | | | | |
| 368 | L | | | 365 | | | | | |
| 369 | T | | | 366 | | | | | |
| 370 | C | | | 367 | | | | | |
| 371 | L | | | 368 | | | | | |
| 372 | V | | | 369 | | | | | |
| 373 | K | | | 370 | | | | | |
| 374 | G | | | 371 | | | | | |
| 375 | F | | | 372 | | | | | |
| 376 | Y | | | 373 | | | | | |
| 377 | P | | | 374 | | | | | |
| 378 | S | | | 375 | | | | | |
| 379 | D | | | 376 | | | | | |
| 380 | I | | | 377 | | | | | |
| 381 | A | | | 378 | | | | | |
| 382 | V | | | 379 | | | | | |
| 383 | E | | | 380 | | | | | |
| 384 | W | | | 381 | | | | | |
| 385 | E | | | 382 | | | | | |
| 386 | S | | | 383 | | | | | |
| 387 | N | | | 384 | | | | | |
| 388 | G | | | 385 | | | | | |

TABLE 1-continued

Positions in SEQ ID NOs: 1 (heavy chain) and 2 (light chain) and corresponding Kabat, Chothia, and EU residue numbers.

| HEAVY CHAIN | | | | | LIGHT CHAIN | | | | |
|---|---|---|---|---|---|---|---|---|---|
| Pos. in SEQ ID NO: 1 | Residue | Kabat | Chothia | EU | Pos. in SEQ ID NO: 2 | Residue | Kabat | Chothia | EU |
| 389 | Q | | | 386 | | | | | |
| 390 | P | | | 387 | | | | | |
| 391 | E | | | 388 | | | | | |
| 392 | N | | | 389 | | | | | |
| 393 | N | | | 390 | | | | | |
| 394 | Y | | | 391 | | | | | |
| 395 | K | | | 392 | | | | | |
| 396 | T | | | 393 | | | | | |
| 397 | T | | | 394 | | | | | |
| 398 | P | | | 395 | | | | | |
| 399 | P | | | 396 | | | | | |
| 400 | V | | | 397 | | | | | |
| 401 | L | | | 398 | | | | | |
| 402 | D | | | 399 | | | | | |
| 403 | S | | | 400 | | | | | |
| 404 | D | | | 401 | | | | | |
| 405 | G | | | 402 | | | | | |
| 406 | S | | | 403 | | | | | |
| 407 | F | | | 404 | | | | | |
| 408 | F | | | 405 | | | | | |
| 409 | L | | | 406 | | | | | |
| 410 | Y | | | 407 | | | | | |
| 411 | S | | | 408 | | | | | |
| 412 | K | | | 409 | | | | | |
| 413 | L | | | 410 | | | | | |
| 414 | T | | | 411 | | | | | |
| 415 | V | | | 412 | | | | | |
| 416 | D | | | 413 | | | | | |
| 417 | K | | | 414 | | | | | |
| 418 | S | | | 415 | | | | | |
| 419 | R | | | 416 | | | | | |
| 420 | W | | | 417 | | | | | |
| 421 | Q | | | 418 | | | | | |
| 422 | Q | | | 419 | | | | | |
| 423 | G | | | 420 | | | | | |
| 424 | N | | | 421 | | | | | |
| 425 | V | | | 422 | | | | | |
| 426 | F | | | 423 | | | | | |
| 427 | S | | | 424 | | | | | |
| 428 | C | | | 425 | | | | | |
| 429 | S | | | 426 | | | | | |
| 430 | V | | | 427 | | | | | |
| 431 | M | | | 428 | | | | | |
| 432 | H | | | 429 | | | | | |
| 433 | E | | | 430 | | | | | |
| 434 | A | | | 431 | | | | | |
| 435 | L | | | 432 | | | | | |
| 436 | H | | | 433 | | | | | |
| 437 | N | | | 434 | | | | | |
| 438 | H | | | 435 | | | | | |
| 439 | Y | | | 436 | | | | | |
| 440 | T | | | 437 | | | | | |
| 441 | Q | | | 438 | | | | | |
| 442 | K | | | 439 | | | | | |
| 443 | S | | | 440 | | | | | |
| 444 | L | | | 441 | | | | | |
| 445 | S | | | 442 | | | | | |
| 446 | L | | | 443 | | | | | |
| 447 | S | | | 444 | | | | | |
| 448 | P | | | 445 | | | | | |
| 449 | G | | | 446 | | | | | |

TABLE 2

Exemplary site-specific heavy chain modifications. The left-most column refers to the Kabat Chothia number (if less than 118) or the EU number (if 118 or greater.) The columns numbered 1-27 refer to SSHC-1 to SSHC-27, as recited in this disclosure.

| HC Residue No. | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 |
|---|---|---|---|---|---|---|---|---|---|---|---|---|---|---|---|---|---|---|---|---|---|---|---|---|---|---|---|
| 3 | | | | | | | | | | | | | | | | | | | | | | x | x | x | | | |
| 5 | x | x | x | | | | | | | | | x | x | | | x | x | | | | | | | | | | |
| 7 | | | | | | | | | | | | | | | | | | | | | | x | x | x | x | | |
| 14 | | | | | | | | | | | | | | | | | | | | | | x | x | x | x | | |
| 16 | | | | | | | | | | | | | | | | | | | | | | x | x | x | | | |
| 19 | | | | | | | x | x | | | x | | | | | | | | | | | x | x | x | x | x | x |
| 23 | x | x | | x | | | | | | | | x | x | x | | | x | x | x | x | x | | | | | | |
| 25 | | | | | | | x | x | x | | x | | | | | | | | | | | x | x | x | x | x | |
| 40 | | | | | | | x | x | x | | x | | | | | | | | | | | x | x | x | x | | |
| 42 | x | | | | x | | | | | | | x | | | x | | | | | | | x | x | x | x | | |
| 43 | | | | | | | | | | | | | | | | | | | | | | x | x | x | x | | |
| 51 | | | | | | | | | | | | | | | | | | | | | | x | | | | x | x |
| 52 | | | | | | | x | x | | | x | | | | | | | | | | | x | x | x | x | | |
| 53 | | | | | | | | | | | | | | | | | | | | | | x | x | | | | |
| 56 | | | | | | | | | | | | | | | | | | | | | | x | x | | | | |
| 65 | x | | | | x | | | | | | | x | | | x | | | | | | | | | | | | |
| 70 | | | | | | | | x | | | x | | | | | | | | | | | x | x | x | x | x | |
| 71 | | | | | | | x | | | | | | | | | | | | | | | | | | | | |
| 74 | x | x | | x | | | | | | | | x | x | x | | | | | | | | | | | | | |
| 77 | | | | | | | | | | | | | | | | | | | | | | | | | | | x |
| 79 | | | | | | | | | | | | | | | | | | | | | | | | | | | x |
| 82A | | | | | | | | | | | | | | | | | | | | | | x | x | x | | | |
| 84 | x | x | x | | | | | | | | | x | x | | | x | x | x | x | x | x | | | | | | |
| 98 | | | | | | | | | | | | | | | | | | | | | | x | | | | x | x |
| 100 | | | | | | | | | | | | | | | | | | | | | | x | x | x | x | | |
| 110 | | | | | | | | | | | x | | | | | | | | | | | x | x | x | x | x | |
| 112 | | | | | | | | | | | | | | | | | | | | | | x | x | x | x | x | |
| 117 | | | | | | | x | | | | | | | | | | | | | | | | | | | | |
| 118 | x | x | x | | | | | | | | | x | x | | | x | x | x | x | x | x | | | | | | |
| 119 | x | x | | x | | | x | x | x | | x | x | x | x | | | x | x | x | x | | x | x | x | x | x | x |
| 121 | | | | | | | | x | x | x | x | | | | | | | | | | | x | x | x | x | x | |
| 124 | | | | | | | x | | | | | | | | | | | | | | | | | | | | |
| 132 | x | x | x | | | | | | | | | x | x | | | x | x | | | | | | | | | | |
| 134 | x | x | | x | | | | | | | | x | x | x | | | x | | | | | | | | | | |
| 135 | x | x | | x | | | | | | | | x | x | x | | | | x | x | x | x | | | | | | |
| 136 | x | x | x | | | | x | x | x | | | x | x | | | x | x | x | | x | x | | | | | x | x |
| 137 | x | x | | x | | | | | | | | x | x | x | | | x | x | x | x | | | | | | | |
| 138 | x | | | | x | | | | | | | x | | | x | | | | | | | | | | | | |
| 139 | x | x | | x | x | | | | | | | x | x | x | | | | | | | | | | | | | |
| 155 | x | | | | x | | | | | | | x | | | x | | | | | | | | | | | | |
| 160 | x | x | | x | | | | | | | | x | x | x | | | x | x | x | x | | | | | | | |
| 161 | | | | | | | | | | | | | | | | | x | x | x | | | | | | | | |
| 162 | x | x | | x | | | | | | | | x | x | x | | | x | x | x | x | | | | | | | |
| 164 | | | | | | | | | | | | | | | | | x | x | | | | | | | | | |
| 165 | x | x | | x | | | | | | | | x | x | x | | | | | | | | | | | | | |
| 172 | x | x | | x | | | | | | | | x | x | x | | | x | | | | | | | | | | |
| 174 | x | | | | x | | | | | | | x | | | x | | | | | | | | | | | | |
| 176 | x | | | | x | | | | | | | x | | | x | | | | | | | | | | | | |
| 177 | x | | | | x | | | | | | | x | | | x | | | | | | | | | | | | |
| 180 | | | | | | | x | x | x | x | | | | | | | | | | | | x | x | x | x | x | x |
| 183 | | | | | | | x | | | | | | | | | | | | | | | | | | | | |
| 184 | | | | | | | | | | | | | | | | | | | | | | x | | | | | |
| 187 | | | | | | | | | | | | | | | | | | | | | | | | | | x | x |
| 190 | | | | | | | x | x | | | x | | | | | | | | | | | x | x | x | | x | x |
| 191 | x | x | | x | | | | | | | | x | x | x | | | | | | | | | | | | | |
| 192 | | | | | | | | | | | | | | | | | | | | | | x | x | x | | | |
| 193 | | | | | | | x | | | | | | | | | | | | | | | | | | | | |
| 194 | x | x | | x | | | | | | | | x | x | x | | | | | | | | | | | | | |
| 195 | | | | | | | | | | | | | | | | | x | x | x | x | | | | | | | |
| 197 | | | | | | | | | | | | | | | | | x | x | x | | | | | | | | |
| 214 | | | | | | | | | | | | | | | | | | | | | | x | x | x | x | x | |
| 216 | | | | | | | | | | | | | | | | | | | | | | x | x | x | x | | x |
| 219 | x | | | | x | | | | | | | x | | | x | | x | x | x | | | | | | | | |
| 221 | | | | | | | | | | x | | | | | | | | | | | | x | x | x | | x | x |
| 222 | | | | | | | | x | x | | x | | | | | | | | | | | x | x | x | x | x | x |
| 224 | | | | | x | | | | | | | | | | | | | | | | | | | | | | |
| 225 | | | | | x | | | | | | | | | | | | | | | | | x | x | x | | | |
| 227 | | | | | | | | | | | | | | | | | | | | | | x | x | x | | | |
| 230 | | | | | | | | | | | | | | | | | | | | | | x | x | x | x | | |
| 231 | | | | | | | | | | | | | | | | | | | | | | x | x | x | x | | |
| 232 | | | | | | | | | | | | | | | | | | | | | | x | x | x | x | | |
| 236 | | | | | | | | | | | | | | | | | | | | | | x | x | x | x | | |
| 238 | x | | | | x | | | | | | | x | | | x | | | | | | | | | | | | |

TABLE 2-continued

Exemplary site-specific heavy chain modifications. The left-most column refers to the Kabat Chothia number (if less than 118) or the EU number (if 118 or greater.) The columns numbered 1-27 refer to SSHC-1 to SSHC-27, as recited in this disclosure.

| HC Residue No. | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 |
|---|---|---|---|---|---|---|---|---|---|---|---|---|---|---|---|---|---|---|---|---|---|---|---|---|---|---|---|
| 239 | x | x | x | | | | | | | | | x | x | | | x | x | | | | | | | | | | |
| 241 | x | x | | x | | | | x | x | x | | x | x | x | | | x | | | | | | | | | | |
| 243 | x | | | | x | | | | | | | x | | | x | | | | | | | | | | | | |
| 246 | x | x | | x | | | | | | | | x | x | x | | | | | | | | | | | | | |
| 260 | | | | | | | | | | | | | | | | | | x | | | | | | | | | |
| 262 | x | | | | x | | | | | | | x | | | x | | | | | | | | | | | | |
| 264 | x | | | | x | | | | | | | x | | | x | | | | | | | | | | | | |
| 265 | x | | | | x | | | | | | | x | | | x | | | | | | | | | | | | |
| 267 | x | x | | x | | | | | | | | x | x | x | | | x | x | x | x | x | | | | | | |
| 268 | x | x | | x | | | | | | | | x | x | x | | | | x | | | | | | | | | |
| 269 | x | x | | x | | | | | | | | x | x | x | | | x | | | | | | | | | | |
| 270 | x | x | | x | | | | | | | | x | x | x | | | x | | | | | | | | | | |
| 271 | x | x | | x | | | | | | | | x | x | x | | | x | | | | | | | | | | |
| 272 | x | x | | x | | | | | | | | x | x | x | | | x | x | x | x | | | | | | | |
| 274 | x | x | | x | | | | | | | | x | x | x | | | | x | x | | | | | | | | |
| 275 | x | x | | x | | | | | | | | x | x | x | | | | | | | | | | | | | |
| 278 | x | | | | x | | | | | | | x | | | x | | | | | | | | | | | | |
| 280 | x | x | | x | | | | | | | | x | x | x | | | | | | | | | | | | | |
| 281 | x | x | | x | | | | | | | | x | x | x | | | | | | | | | | | | | |
| 282 | x | x | | x | | | | | | | | x | x | x | | | x | x | x | x | x | | | | | | |
| 283 | x | x | | x | | | | | | | | x | x | x | | | | | | | | | | | | | |
| 286 | x | x | | x | | | | | | | | x | x | x | | | x | | | | | | | | | | |
| 289 | x | x | | x | | | | | | | | x | x | x | | | | x | | | | | | | | | |
| 292 | x | x | | x | | x | | | | | | x | x | x | | | x | x | | | | | | | | | |
| 293 | x | x | x | | | x | | | | | | x | x | | | x | x | x | x | x | | | | | | | |
| 294 | x | x | | x | | x | | | | | | x | x | x | | | | | | | | | | | | | |
| 295 | x | x | | x | | x | | | | | | x | x | x | | | | | | | | | | | | | |
| 296 | x | x | | x | | x | | | | | | x | x | x | | | | x | x | x | x | | | | | | |
| 297 | x | x | | x | | x | | | | | | x | x | x | | | | | x | x | x | | | | | | |
| 298 | x | x | | x | | x | | | | | | x | x | x | | | | x | x | x | x | | | | | | |
| 299 | x | x | | x | | x | | | | | | x | x | x | | | | | | | | | | | | | |
| 300 | x | x | | x | | x | | | | | | x | x | x | | | | | | | | | | | | | |
| 301 | x | x | | x | | x | | | | | | x | x | x | | | | | | | | | | | | | |
| 303 | x | x | | x | | x | | | | | | x | x | x | | | | | x | x | x | x | | | | | |
| 305 | x | x | | x | | x | | | | | | x | x | x | | | | | x | x | x | x | | | | | |
| 317 | x | x | | x | | | | | | | | x | x | x | | | | | | | | | | | | | |
| 320 | x | x | | x | | | | | | | | x | x | x | | | | | | | | | | | | | |
| 324 | x | x | | x | | | | | | | | x | x | x | | | | | | | | | | | | | |
| 326 | x | x | | x | | | | | | | | x | x | x | | | | | | | | | | | | | |
| 327 | x | x | | x | | | | | | | | x | x | x | | | | | | | | | | | | | |
| 329 | x | x | | x | | | | | | | | x | x | x | | | | x | | | | | | | | | |
| 330 | x | x | | x | | | | | | | | x | x | x | | | | x | x | | | | | | | | |
| 332 | x | x | | x | | | | | | | | x | x | x | | | | | x | | | | | | | | |
| 333 | x | x | | x | | | | | | | | x | x | x | | | | | x | | | | | | | | |
| 334 | x | x | x | | | | | | | | | x | x | | | x | x | x | x | x | x | | | | | | |
| 335 | x | x | | x | | | | | | | | x | x | x | | | x | x | x | x | | | | | | | |
| 337 | x | x | | x | | | | | | | | x | x | x | | | | | | | | | | | | | |
| 339 | x | x | | x | | | | | | | | x | x | x | | | | | | | | | | | | | |
| 340 | x | x | | x | | | | | | | | x | x | x | | | | x | x | x | x | | | | | | |
| 341 | | | | | | | | | | | | | | | | | | x | x | x | x | | | | | | |
| 342 | | | | | | | | | | | | x | x | x | x | x | x | x | x | x | | | | | | | |
| 343 | | | | | | | | | | | | | | | | | | x | x | | | | | | | | |
| 344 | x | x | | x | | | | | | | | x | x | x | | | | | | | | | | | | | |
| 355 | x | x | x | x | | | | | | | | x | x | x | | x | x | x | x | x | | | | | | | |
| 356 | x | | | | x | | | | | | | x | | | x | | | | | | | | | | | | |
| 358 | x | | | | x | | | | | | | x | | | x | | | | | | | | | | | | |
| 359 | x | x | x | | | | | | | | | x | x | | | x | x | | | | | | | | | | |
| 360 | x | | | | x | | | | | | | x | | | x | | | | | | | | | | | | |
| 361 | | | | | | | | | | | | | | | | | | | x | x | | | | | | | |
| 362 | | | | | | | | | | | | | | | | | | | x | x | | | | | | | |
| 375 | x | x | | x | | | | | | | | x | x | x | | | | | | | | | | | | | |
| 383 | x | | | | x | | | | | | | x | | | x | | | | | | | | | | | | |
| 384 | x | | | | x | | | | | | | x | | | x | | | | | | | | | | | | |
| 386 | x | x | | x | | | | | | | | x | x | x | | | x | x | | | | | | | | | |
| 389 | x | x | x | | | | | | | | | x | x | | | x | x | | | | | | | | | | |
| 392 | x | x | | x | | | | | | | | x | x | x | | | | | x | x | x | | | | | | |
| 398 | x | x | | x | | | | | | | | x | x | x | | | | | | | | | | | | | |
| 400 | | | | | | | | | | | | | | | | | | x | | | | | | | | | |
| 404 | | | | | | x | x | x | x | x | x | x | x | x | x | x | x | x | | | | | | | | | |
| 407 | | | | | x | | | | | | | | | | | | | | | | | | | | | | |
| 420 | x | x | | x | | | | | | | | x | x | x | | | x | | | | | | | | | | |
| 421 | x | x | | x | | | | | | | | x | x | x | | | x | | | | | | | | | | |
| 422 | | | | | | | | | | | | | | | | | | x | x | x | | | | | | | |

TABLE 2-continued

Exemplary site-specific heavy chain modifications. The left-most column refers to the Kabat Chothia number (if less than 118) or the EU number (if 118 or greater.) The columns numbered 1-27 refer to SSHC-1 to SSHC-27, as recited in this disclosure.

| HC Residue No. | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 |
|---|---|---|---|---|---|---|---|---|---|---|---|---|---|---|---|---|---|---|---|---|---|---|---|---|---|---|---|
| 424 | | | | | | | | | | | | | | | | | | x | x | x | | | | | | | |
| 436 | x | | | | x | | | | | | | x | | | x | | | | | | | | | | | | |
| 438 | x | x | | x | | | | | | | | x | x | x | | | x | x | x | x | x | | | | | | |
| 440 | | | | | | | | | | | | | | | | | | x | x | x | | | | | | | |
| 442 | | | | | | | | | | | | | | | | | | x | x | x | x | | | | | | |
| 443 | | | | | | | | | | | | | | | | | | x | x | x | | | | | | | |

TABLE 3

Exemplary site-specific light chain modifications. The left-most column refers to the Kabat or Chothia number (if less than 108) or the EU number (if 108 or greater). The columns numbered 1-22 to SSLC-1 to SSLC-27, as recited in this disclosure.

| LC Residue No. | 1 | 2 | 3 | 4 | 5 | 6 | 7 | 8 | 9 | 10 | 11 | 12 | 13 | 14 | 15 | 16 | 17 | 18 | 19 | 20 | 21 | 22 |
|---|---|---|---|---|---|---|---|---|---|---|---|---|---|---|---|---|---|---|---|---|---|---|
| −1 | | | | | | x | x | x | x | x | x | x | x | x | x | x | x | x | | | | |
| 3 | | | | | | x | x | x | | | | | x | x | | | | | | | | |
| 5 | | | | | | x | x | x | x | | | | x | x | x | | | | | | | |
| 7 | x | | | | | x | x | x | x | | x | x | x | x | x | | x | x | | | | |
| 8 | | | | | | x | x | x | x | | x | x | x | x | x | | x | x | | | | |
| 9 | | | | | | x | x | x | | | | | x | x | | | | | | | | |
| 10 | | | | | | x | x | | | | | | x | | | | | | | | | |
| 14 | | | | | | | | | | | x | | | | | | x | | | | | |
| 16 | | | | | | x | x | x | x | x | x | x | x | x | x | x | x | x | | | | |
| 17 | | | | | | x | x | x | x | | | | x | x | x | | | | | | | |
| 18 | | | | | | x | x | x | x | | | | x | x | x | | | | | | | |
| 20 | | | | | | x | x | x | x | | | | x | x | x | | | | | | | |
| 22 | x | | | | | x | x | x | x | | x | x | x | x | x | | x | x | | | | |
| 26 | | | | | | x | x | x | | | | | x | x | | | | | | | | |
| 27 | | | | | | x | x | x | x | | | | x | x | x | | | | | | | |
| 43 | | x | x | x | | | | | | | | | | | | | | | x | x | x | |
| 45 | | | | | | x | x | x | x | | | | x | x | x | | | | | | | |
| 49 | | x | x | x | x | | | | | | | | | | | | | | x | x | x | x |
| 56 | | x | x | x | x | | | | | | | | | | | | | | x | x | x | x |
| 57 | | x | x | x | x | | | | | | | | | | | | | | x | x | x | x |
| 58 | | | | | | x | x | x | x | | | | x | x | x | | | | | | | |
| 60 | | x | x | x | x | | | | | | | | | | | | | | x | x | x | x |
| 63 | | | | | | x | x | x | x | x | x | x | x | x | x | x | x | x | | | | |
| 65 | | | | | | x | x | x | | | | | x | x | | | | | | | | |
| 66 | | | | | | x | x | x | | | | | x | x | | | | | | | | |
| 67 | | x | x | x | x | | | | | | | | | | | | | | x | x | x | x |
| 68 | | x | x | x | | | | | | | | | | | | | | | x | x | x | |
| 70 | | | | | | x | x | x | | | x | x | x | x | | | x | x | | | | |
| 77 | | | | | | x | x | x | x | | | | x | x | x | | | | | | | |
| 79 | | | | | | x | x | x | x | | | | x | x | x | | | | | | | |
| 107 | | | | | | x | x | x | x | | | | x | x | x | | | | | | | |
| 109 | | x | x | x | x | | | | | | | | | | | | | | x | x | x | x |
| 112 | | x | x | | | | | | | | | | | | | | | | x | x | | |
| 114 | | x | x | | | | | | | | | | | | | | | | x | | | |
| 138 | | | | | | x | | | | | x | x | x | | | | x | x | | | | |
| 142 | | | | | | x | x | x | x | | x | x | x | x | x | | x | x | | | | |
| 143 | | | | | | x | x | | | | x | x | x | | | | x | x | | | | |
| 144 | | x | x | x | | | | | | | | | | | | | | | x | x | x | |
| 152 | x | | | | | x | x | x | | | x | x | x | x | x | | x | x | | | | |
| 153 | | x | x | x | x | | | | | | | | | | | | | | x | x | x | x |
| 156 | | x | x | x | | | | | | | | | | | | | | | x | x | x | |
| 157 | | x | | | | | | | | | | | | | | | | | x | | | |
| 168 | | x | x | | | | | | | | | | | | | | | | x | x | | |
| 171 | | | | | | x | x | x | | | | | x | x | | | | | | | | |
| 182 | | | | | | x | x | x | x | | | | x | x | x | | | | | | | |
| 184 | | x | x | x | | | | | | | | | | | | | | | x | x | x | |
| 188 | | | | | | x | x | x | | | | | x | x | | | | | | | | |
| 199 | | | | | | x | x | x | x | x | | | x | x | x | x | | | x | | | |
| 201 | | | | | | x | x | | | | | x | | | | | | x | | | | |
| 202 | | x | x | x | x | | | | | | | | | | | | | | x | x | x | x |
| 203 | | x | x | x | x | | | | | | | | | | | | | | x | x | x | x |
| 206 | | x | | | | | | | | | | | | | | | | | x | | | |

What is claimed is:

1. A polypeptide comprising at least one amino acid residue according to the following formula:

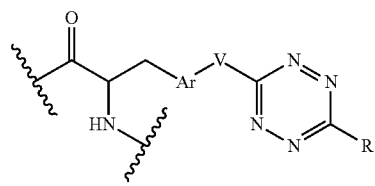

wherein:

Ar is

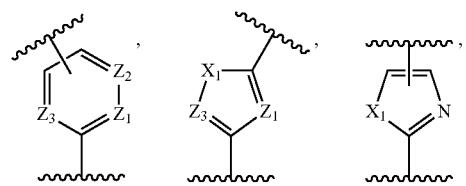

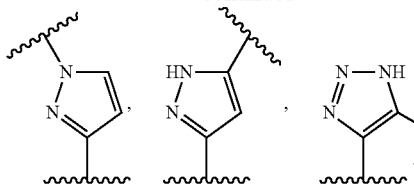, or

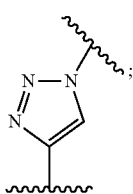;

V is a single bond, lower alkylene, or —W₁—W₂—;
one of W₁ and W₂ is absent or lower alkylene, and the other is —NH—, —O—, or —S—;
X₁ is —NH—, —O—, or —S—;
one of Z₁, Z₂, and Z₃ is —N— and the others of Z₁, Z₂, and Z₃ are each —CH—; and
R is lower alkyl.

2. The polypeptide of claim 1 comprising at least two amino acid residues according to the following formula:

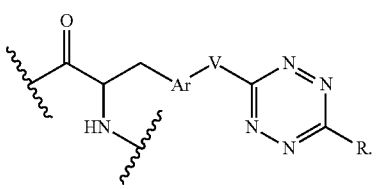

3. The polypeptide of claim 1, further comprising at least one amino acid residue comprising an azide functional group.

4. The polypeptide of claim 1, further comprising at least one amino acid residue comprising an azide functional group, selected from the group consisting of:

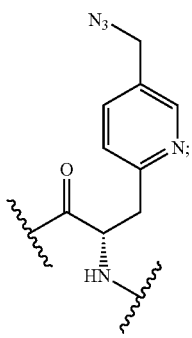

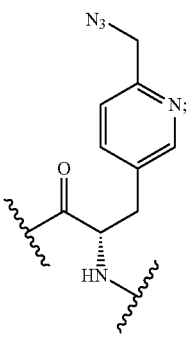

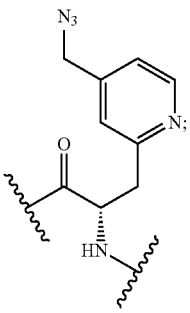

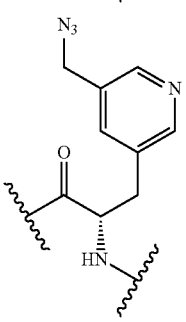

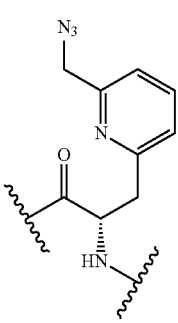

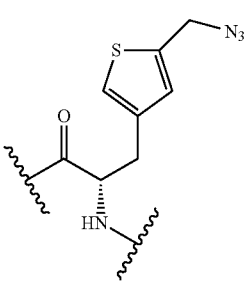

-continued
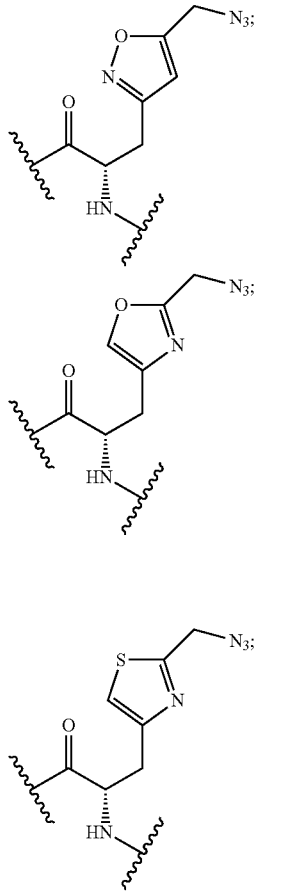
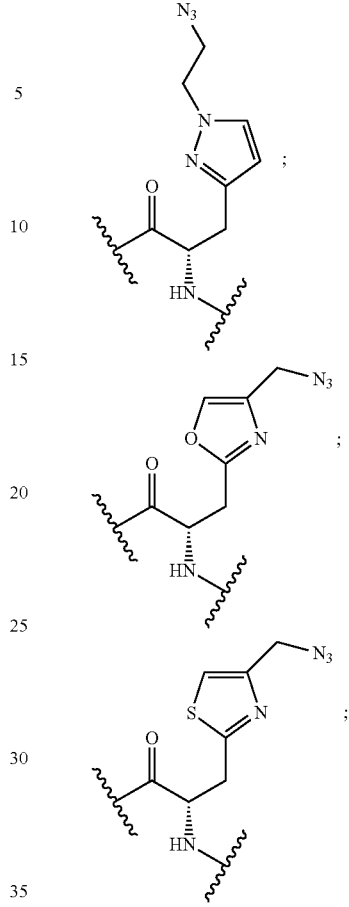
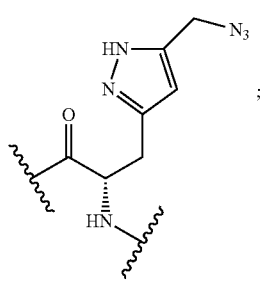
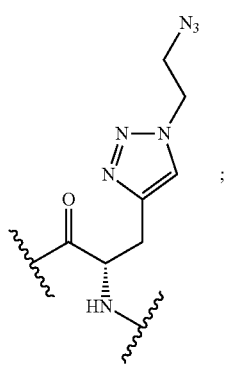

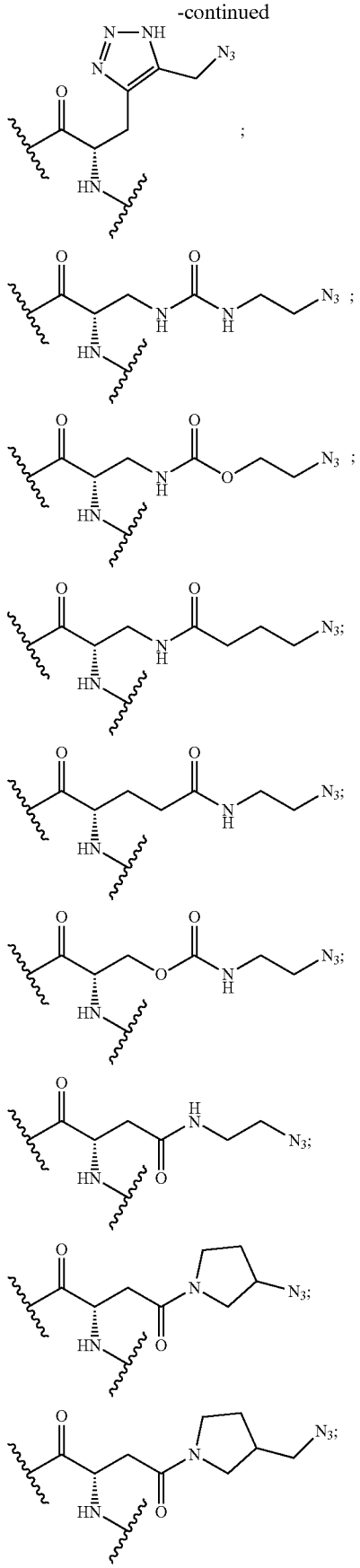

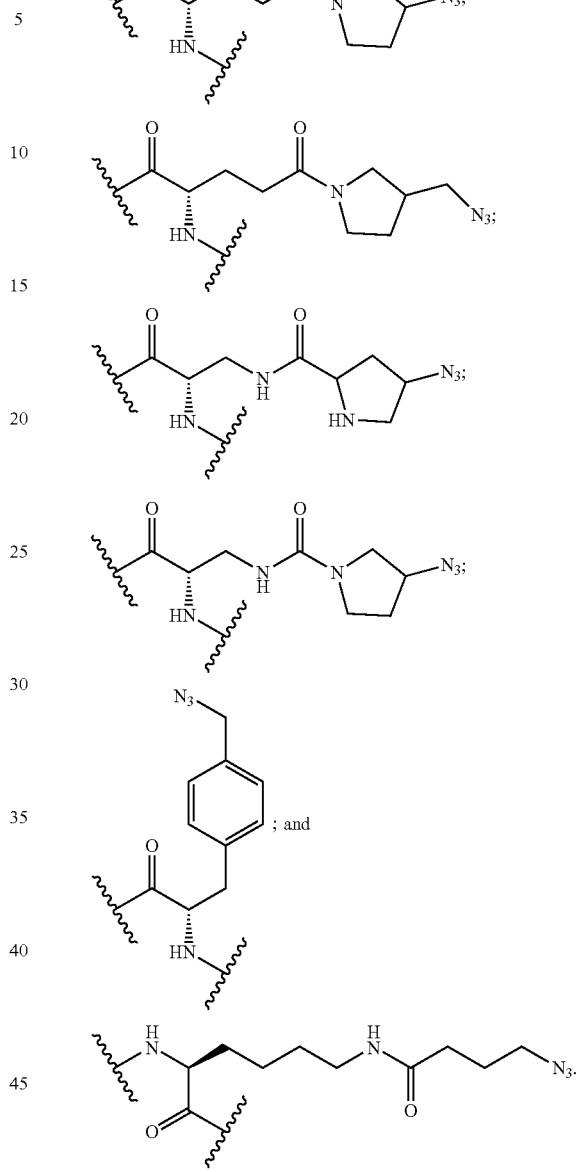

5. A conjugate comprising the polypeptide of claim 1 linked to a payload, where the link is formed by a reaction of the tetrazine of the at least one amino acid residue, with a payload comprising a strained alkene, and optionally comprising a linking moiety between the polypeptide and the payload.

6. The polypeptide of claim 1, wherein the polypeptide is an antibody.

7. The conjugate of claim 5, wherein the polypeptide is an antibody.

8. The conjugate of claim 5, wherein V is a single bond, —NH—, or
—CH$_2$NH—.

9. The conjugate of claim 5, wherein the at least one amino acid residue is according to:

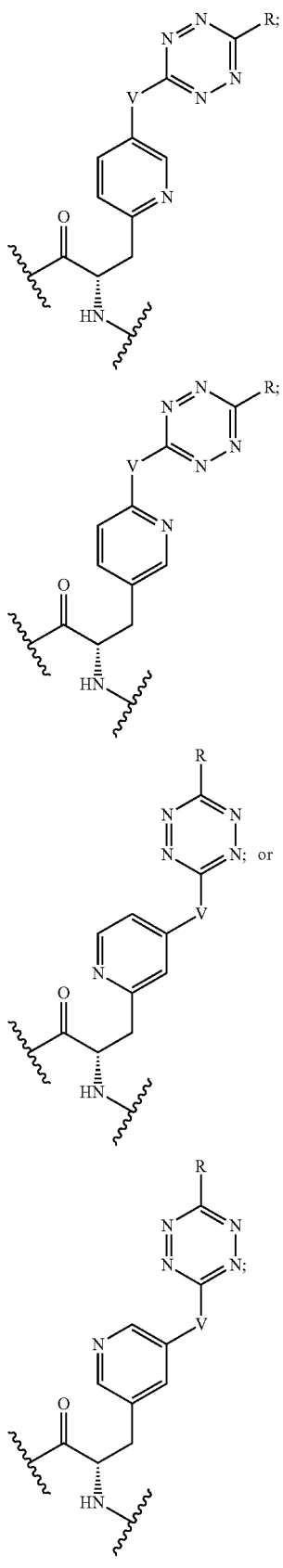
wherein V is a single bond, —NH—, or —CH₂NH—.
10. The conjugate of claim 5, wherein the at least one amino acid residue is according to:
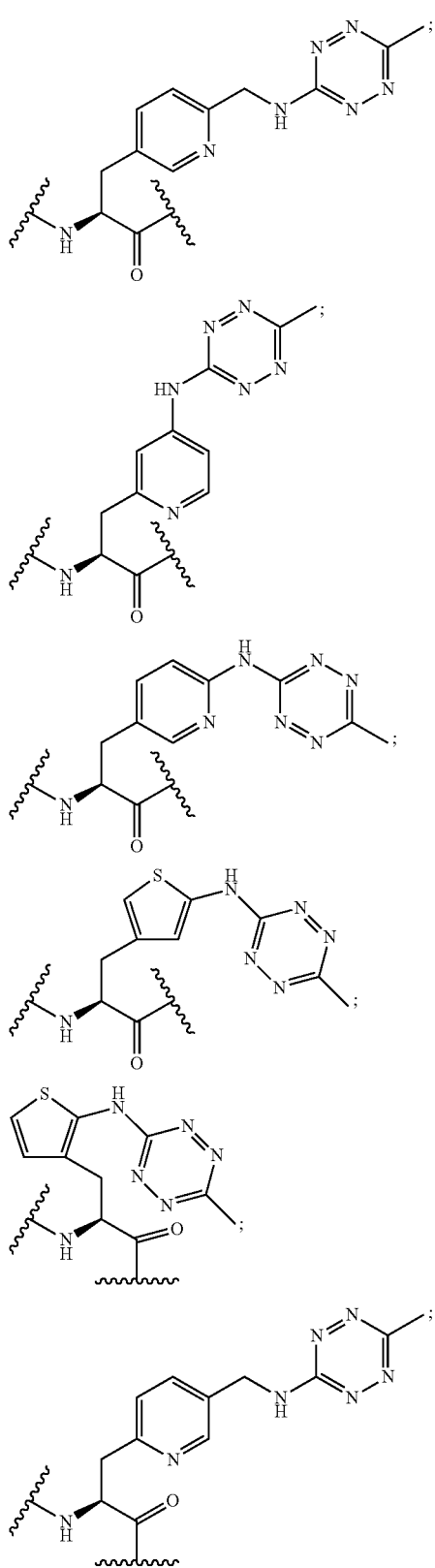

-continued
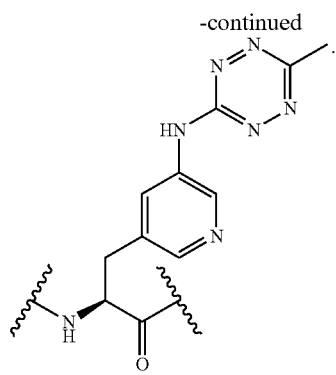
11. The conjugate of claim 5, wherein the strained alkene is selected from the group consisting of trans-cyclooctene, (E)-cyclooct-4-enol, (E)-cyclooct-4-enyl 2,5-dioxo-1-pyrrolidinyl carbonate, 5-norbornene-2-acetic acid succinimidyl ester, and 5-norbornene-2-endo-acetic acid.
* * * * *